US010550091B2

(12) United States Patent
Chen et al.

(10) Patent No.: US 10,550,091 B2
(45) Date of Patent: Feb. 4, 2020

(54) 1,4,5-SUBSTITUTED 1,2,3-TRIAZOLE ANALOGUES AS ANTAGONISTS OF THE PREGNANE X RECEPTOR

(71) Applicant: ST. JUDE CHILDREN'S RESEARCH HOSPITAL, Memphis, TN (US)

(72) Inventors: Taosheng Chen, Germantown, TN (US); Wenwei Lin, Memphis, TN (US); Yueming Wang, Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 16/085,972

(22) PCT Filed: Mar. 10, 2017

(86) PCT No.: PCT/US2017/021949
§ 371 (c)(1),
(2) Date: Sep. 17, 2018

(87) PCT Pub. No.: WO2017/165139
PCT Pub. Date: Sep. 28, 2017

(65) Prior Publication Data
US 2019/0077770 A1 Mar. 14, 2019

Related U.S. Application Data

(60) Provisional application No. 62/313,603, filed on Mar. 25, 2016.

(51) Int. Cl.
| | | |
|---|---|---|
| C07D 249/06 | (2006.01) |
| A61K 9/20 | (2006.01) |
| A61K 47/02 | (2006.01) |
| A61K 9/00 | (2006.01) |
| A61K 47/10 | (2017.01) |
| A61K 47/36 | (2006.01) |
| A61P 35/00 | (2006.01) |

(52) U.S. Cl.
CPC .......... *C07D 249/06* (2013.01); *A61K 9/0019* (2013.01); *A61K 9/0095* (2013.01); *A61K 9/205* (2013.01); *A61K 9/2018* (2013.01); *A61K 9/2054* (2013.01); *A61K 47/02* (2013.01); *A61K 47/10* (2013.01); *A61K 47/36* (2013.01); *A61P 35/00* (2018.01)

(58) Field of Classification Search
CPC .................................................. C07D 249/06
See application file for complete search history.

(56) References Cited

U.S. PATENT DOCUMENTS

| 6,100,398 A | 8/2000 | Hartwig et al. |
| 2013/0274298 A1 | 10/2013 | Boechat et al. |

FOREIGN PATENT DOCUMENTS

| WO | WO-2007/115058 A2 | 10/2007 |
| WO | WO-2010/045188 A1 | 4/2010 |
| WO | WO-2014/134232 A1 | 9/2014 |
| WO | WO-2015/058160 A1 | 4/2015 |
| WO | WO-2015/078949 A1 | 6/2015 |
| WO | WO-2017/165139 A1 | 9/2017 |

OTHER PUBLICATIONS

U.S. Appl. No. 62/313,603, filed Mar. 25, 2016, Taosheng Chen.
PCT, PCT/US2017/021949, Mar. 20, 2017, (Sep. 28, 2017, St Jude Children's Research Hospital.
Aalten, H. L. et al., The copper catalyzed reaction of sodium methoxide with aryl bromides. A mechanistic study leading to a facile synthesis of anisole derivatives. Tetrahedron 1989, 45, 5565-78.
Beattie, D. et al., An investigation into the structure-activity relationships associated with the systematic modification of the β2-adrenoceptor agonist indacaterol. Bioorg. Med Chem. Lett. 2012, 22, 6280-6285.
Bouhlel, A. et al., Synthesis and evaluation of original amidoximes as antileishmanial agents. Bioorg. Med. Chem. 2010, 18, 7310-7320.
Carotti, A et al. Beyond Bile Acids: Targeting Farnesoid X Receptor (FXR) with Natural and Synthetic Ligands. Current Topics in Medicinal Chemistry, vol. 14, pp. 2129-2142; p. 2131, col. 2, paragraph 2; p. 2137, figure 14 (2014).
Chakrabarty, M. et al., An expedient synthesis of 5,11-dimethylindolo[3,2-b]carbazole, a potent ligand and the receptor for TCDD. Synth. Commun. 1996, 26, 3015-3023.
Chen, J.; et al., Synthesis and crystal structure of isomerized butadiene (dicarbonyl)(ethoxyarylcarbene)iron complexes. J. Organomet. Chem. 1985, 286, 55-67.
Doyle, M. P. et al., Alkyl nitrite-metal halide deamination reactions. 2. Substitutive deamination of arylamines by alkyl nitrites and copper(II) halides. A direct and remarkably efficient conversion of arylamines to aryl halides. J. Org. Chem. 1977, 42, 2426-31.
El-Ayache, N. C. et al., Novel bis-arylsulfonamides and aryl sulfonimides as inactivators of plasminogen activator inhibitor-1 (PAI-1). Bioorg. Med. Chem. Lett. 2010, 20, 966-970.
Furuya, T. et al., Palladium-mediated fluorination of arylboronic acids. Angew. Chem., Int. Ed. 2008, 47, 5993-5996, S5993/1-S5993/78.
Ikemoto, N. et al., Practical routes to the triarylsulfonyl chloride intermediate of a 133 adrenergic receptor agonist. Tetrahedron 2003, 59, 1317-1325.

(Continued)

*Primary Examiner* — Brian E McDowell
(74) *Attorney, Agent, or Firm* — Ballard Spahr LLP

(57) ABSTRACT

In an aspect, the invention relates to 1,4,5-substituted 1,2,3-triazole and 1,2,4,5-substituted imidazoles, which are modulators the pregnane X receptor ("PXR"); synthesis methods for making the compounds; pharmaceutical compositions comprising the compounds; and methods of modulating an adverse drug reaction in a mammal using the compounds and pharmaceutical compositions; methods of treatment of a disorder of uncontrolled cellular proliferation, such as a cancer, using the compounds and pharmaceutical compositions; methods of modulating pregnane X receptor activity in a mammal using the compounds and pharmaceutical compositions. This abstract is intended as a scanning tool for purposes of searching in the particular art and is not intended to be limiting of the present invention.

15 Claims, 7 Drawing Sheets

(56) References Cited

OTHER PUBLICATIONS

Ito, Y. et al., The absolute stereochemistry of anachelins, siderophores from the cyanobacterium Anabaena cylindrica. Tetrahedron 2004, 60, 9075-9080.
Korwar, S. et al., Preparation and evaluation of deconstruction analogues of 7-deoxykalafungin as AKT kinase inhibitors. Bioorg. Med Chem. Lett. 2014, 24, 271-274.
Kruse, L. I. Synthesis of 4-Substituted Indoles from o-Nitrotoluenes. Heterocycles 1981, 16(7): 1119-24.
Maligres, P. E. et al., A highly catalytic robust palladium catalyzed cyanation of aryl bromides. Tetrahedron Lett. 1999, 40, 8193-8195.
McKean, D. R. et al., Synthesis of functionalized styrenes via palladium-catalyzed coupling of aryl bromides with vinyl tin reagents. J. Org. Chem. 1987, 52, 422-4.
Mo, J. et al., Ionic liquid-promoted regioselective catalysis by palladium. Proc.—Electrochem. Soc. 2006, 2004-24, 564-571.
Nahm, S. et al., N-Methoxy-N-methylamides as effective acylating agents. Tetrahedron Lett. 1981, 22, 3815-18.
O'Connell, J. F. et al., Convenient synthesis of methyl 1-methyl-2,4-dibromo-5-imidazolecarboxylate. Synthesis 1988, 767-71.
Ortiz-Marciales, M. et al., N-tert-Butyldimethylsilyl imines as intermediates for the synthesis of amines and ketones. Synth. Commun. 1998, 28, 4067-4075.
Pascussi, JM et al. Interleukin-6 Negatively Regulates the Expression of Pregnane X Receptor and Constitutively Activated Receptor in Primary Human Hepatocytes. Biochemical and Biophysical Research Communications, vol. 274, pp. 707-713; abstract (2000).
Peng, Y. Cu(I)-catalyzed coupling of arylsulfinic salts with aryl bromides. J. Chem. Res. 2014, 38, 447-449.
Pokhodylo, N. T et al., (Arylsulfonyl)acetones and—acetonitriles: new activated methylenic building blocks for synthesis of 1,2,3-triazoles. Synthesis 2009, 2321-2323.
PUBCHEM CID) 20865737,(2007), pp. 1-11 [online], [retrieved on Dec. 23, 2013].Retrieved from the Internet <URL:https://pubchem.ncbi.nlm.nih.gov/compound/20865737#section=Top>, pp. 1, 3, 10.
PUBCHEM. AKOS001822451. (2007), pp. 1-10 [online], [retrieved on Dec. 23, 2013]. Retrieved from the Internet <URL:https://pubchem.ncbi.nlm.nih.gov/compound/20865722#section=ChemicalVendors>: pp. 3-5,9.
PUBCHEM. MolPort-005-282-644. (2007), pp. 1-10 [online], [retrieved on Dec. 23, 2013]. Retrieved from the Internet <URL:https://pubchem.ncbi.nlm.nih.gov/compound/18591996#section=2DStructure>, pp. 3-5, 9.
PUBCHEM. MolPort-007-647-768. (2007), pp. 1-11 [online], [retrieved on Dec. 23, 2010]. Retrieved from tho Internet URL:https://pubchem.ncbi.nlm.nih.gov/compound/20865733#section=ChemicalandPhysicalProperties>; pp. 3-5, 10.
Rao, B. N. et al., PdCl2(PPh3)2 catalysed carboalkoxylation of aryl bromides. Journal of Molecular Catalysis1989, 50(3), L27-L29.
Recnik, L.-M. et al. Selective sequential cross-coupling reactions on imidazole towards neurodazine and analogues. Synthesis 2013, 45, 1387-1405.
Rosenmund, K. W. et al., Halogen attached to a ring carbon atom and its replacement by other substituents. I. Replacement of the halogen by the carboxyl group. Ber. Dtsch. Chem. Ges. B 1919, 52B, 1749-56.
Shaginian, A. et al., Design, Synthesis, and Evaluation of an a-Helix Mimetic Library Targeting Protein-Protein Interactions. J. Am. Chem. Soc. 2009, 131, 5564-5572.
Shrestha, J. P. et al., Synthesis and anticancer structure activity relationship investigation of cationic anthraquinone analogs. Eur. J. Med. Chem. 2014, 77, 96-102.
Slocum, D. et al., Metalations utilizing aryllithiums; ortho-functionalization of p-bromoanisole (pBrA). Tetrahedron Lett. 2009, 50, 1593-1595.
Sutherland, H. S. et al. Synthesis and Structure-activity Relationships of Antitubercular 2-Nitroimidazooxazines Bearing Heterocyclic Side Chains. J. Med. Chem. 2010, 53, 855-866.
International Search Report and Written Opinion dated May 25, 2017 by the International Searching Authority for International Application No. PCT/US2017/021949, filed on Mar. 10, 2017 and published as WO/2017/165139 on Sep. 28, 2017 (Applicant—St. Jude Children's Research Hospital) (10 Pages).
International Preliminary Report on Patentability dated Sep. 25, 2018 by the International Searching Authority for International Application No. PCT/US2017/021949, filed on Mar. 10, 2017 and published as WO/2017/165139 on Sep. 28, 2017 (Applicant—St. Jude Children's Research Hospital) (7 Pages).

1,4,5-SUBSTITUTED 1,2,3-TRIAZOLE ANALOGUES AS ANTAGONISTS OF THE PREGNANE X RECEPTOR

CROSS-REFERENCE TO RELATED APPLICATIONS

This is a U.S. National Phase Application of International Application No. PCT/US2017/021949, filed Mar. 10, 2017, which claims the benefit of U.S. Provisional Application No. 62/313,603, filed Mar. 25, 2016, which are incorporated herein by reference in their entireties.

BACKGROUND

The pregnane X receptor (PXR) regulates the metabolism and excretion of xenobiotics and endobiotics by regulating the expression of drug-metabolizing enzymes and drug transporters. By affecting drug metabolism, changes in the expression levels of PXR target genes can influence the therapeutic and toxicologic response to drugs and cause adverse drug-drug interactions. The activity of PXR is largely regulated by direct ligand binding, and the unique structure of PXR allows the binding of a variety of drugs and prospective drugs. That is, a drug or prospective drug molecule can directly modulate the activity of PXR. As such, PXR is associated with multiple undesired drug-drug interactions.

Treatment of multiple diseases and disorders could be improved if there were available a specific and non-toxic antagonist of PXR is desired. A PXR antagonist would be expected to prevent drug-induced adverse drug effects associated with therapeutic agents that induce the expression of PXR target genes. In particular, a specific and non-toxic PXR antagonist could be used as a co-therapeutic agent to prevent therapy-related toxicities, drug-drug interactions, and drug resistance, and improve therapeutic efficacy and safety. However, due to the "promiscuous" nature of receptor binding (i.e., many drugs bind to and activate PXR) it has been considered extremely difficult to design a PXR antagonist based on structure, and equally difficult to perform SAR studies. As a result, there are currently no specific and non-toxic PXR antagonist exists.

Despite in understanding the biochemistry of PXR, there remains a need for specific and non-toxic antagonists of PXR. These needs and other needs are satisfied by the present invention.

SUMMARY

In accordance with the purpose(s) of the invention, as embodied and broadly described herein, the invention, in an aspect, relates to 1,4,5-substituted 1,2,3-triazole and 1,2,4,5-substituted imidazoles that are useful as antagonists of the pregnane X receptor ("PXR"). In a further aspect, the disclosed compounds are useful for modulating an adverse drug reaction in a mammal. In a still further aspect, the disclosed compounds are useful for treatment of a disorder of uncontrolled cellular proliferation, such as a cancer. In an aspect, the disclosed compounds can be used for treatment of a disorder of uncontrolled cellular proliferation alone or in combination with either an anticancer agent or a treatment scheme using a combination of multiple anticancer agents. In a yet further aspect, the disclosed compounds are useful for modulating pregnane X receptor activity in a mammal.

Disclosed are compounds having a structure represented by a formula:

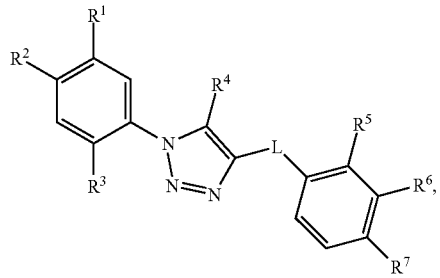

wherein L is $SO_2$, C=O. or $NR^{10}$; wherein $R^{10}$ is hydrogen or C1-C3 alkyl; wherein $R^1$ is hydroxy, halogen, C1-C6 alkyl, C1-C6 alkoxy, and —(C1-C6)-OH; wherein $R^2$ is hydrogen or halogen; wherein $R^3$ is hydroxy, halogen, C1-C6 alkyl, C1-C6 alkoxy, and —(C1-C6)-OH; wherein $R^4$ is hydrogen, cyano, halogen, C1-C6 alkyl, C1-C6 monohaloalkyl, C1-C6 polyhaloalkyl, —(C=O)—(C1-C6 alkyl), —(C=O)—O(C1-C6 alkyl), —(C1-C6 alkyl)-(C=O)—(C1-C6 alkyl), —(C1-C6 alkyl)-(C=O)—OH, —(C1-C6 alkyl)-(C=O)—O(C1-C6 alkyl), $Ar^1$, or $Cy^1$; wherein $Ar^1$ is monocyclic aryl or monocyclic heteroaryl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein $Cy^1$ is C3-C8 cycloalkyl or C2-C7 heterocycloalkyl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein $R^5$ is hydrogen, halogen, hydroxy, C1-C3 alkyl; wherein $R^6$ is hydrogen, halogen, hydroxy, C1-C3 alkyl; wherein $R^7$ is C1-C6 alkyl; or a pharmaceutically acceptable salt thereof, and wherein the compound does not have the structure:

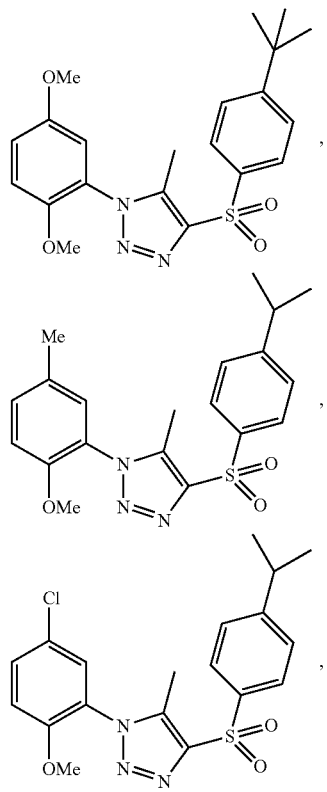

-continued

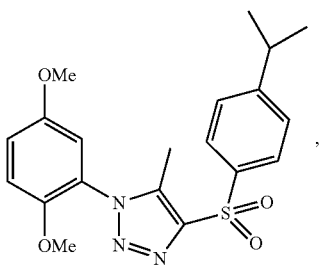,

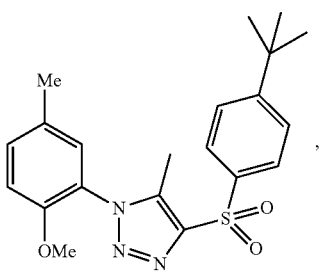,

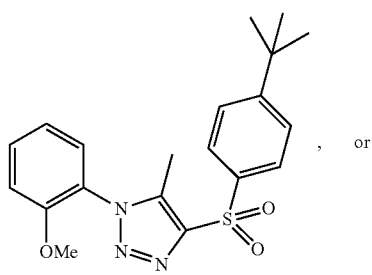, or

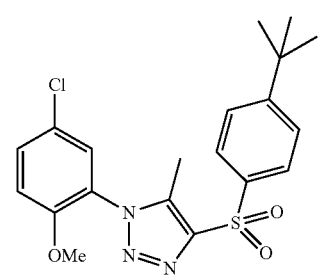.

Also disclosed are compounds having a structure represented by a formula:

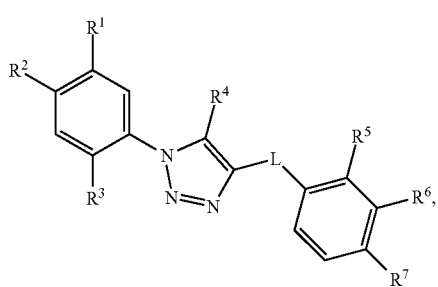

wherein L is C=O or NR$^{10}$; wherein R$^{10}$ is hydrogen or C1-C3 alkyl; wherein R$^1$ is hydroxy, halogen, C1-C6 alkyl, C1-C6 alkoxy, and —(C1-C6)-OH; wherein R$^2$ is hydrogen, halogen, cyano, C1-C6 alkyl, C1-C6 alkoxy, C1-C6 monohaloalkyl, C1-C6 polyhaloalkyl, —CO$_2$H, —(C=O)H, —(C=O)—(C1-C6 alkyl), —(C=O)—O(C1-C6 alkyl); wherein R$^3$ is hydroxy, halogen, C1-C6 alkyl, C1-C6 alkoxy, and —(C1-C6)-OH; wherein R$^4$ is hydrogen, cyano, halogen, C1-C6 alkyl, C1-C6 monohaloalkyl, C1-C6 polyhaloalkyl, —(C=O)—(C1-C6 alkyl), —(C=O)—O(C1-C6 alkyl), —(C1-C6 alkyl)-(C=O)—(C1-C6 alkyl), —(C1-C6 alkyl)-(C=O)—OH, —(C1-C6 alkyl)-(C=O)—O(C1-C6 alkyl), Ar$^1$, or Cy$^1$; wherein Ar$^1$ is monocyclic aryl or monocyclic heteraryl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein Cy$^1$ is C3-C8 cycloalkyl or C2-C7 heterocycloalkyl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein R$^5$ is hydrogen, halogen, hydroxy, C1-C3 alkyl; wherein R$^6$ is hydrogen, halogen, hydroxy, C1-C3 alkyl; wherein R$^7$ is C1-C6 alkyl; or a pharmaceutically acceptable salt thereof.

Also disclosed are compounds having a structure represented by a formula:

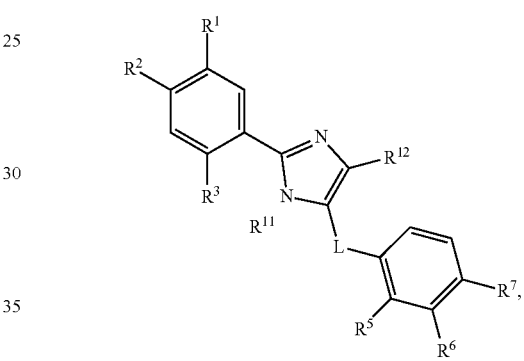

wherein L is SO$_2$, C=O, or NR$^{10}$; wherein R$^{10}$ is hydrogen or C1-C3 alkyl; wherein R$^1$ is hydroxy, halogen, C1-C6 alkyl, C1-C6 alkoxy, and —(C1-C6)-OH; wherein R$^2$ is hydrogen, halogen, cyano, C1-C6 alkyl, C1-C6 alkoxy, C1-C6 monohaloalkyl, C1-C6 polyhaloalkyl, —CO$_2$H, —(C=O)H, —(C=O)—(C1-C6 alkyl), —(C=O)—O(C1-C6 alkyl); wherein R$^3$ is hydroxy, halogen, C1-C6 alkyl, C1-C6 alkoxy, and —(C1-C6)-OH; wherein R$^5$ is hydrogen, halogen, hydroxy, C1-C3 alkyl; wherein R$^6$ is hydrogen, halogen, hydroxy, C1-C3 alkyl; wherein R$^7$ is C1-C6 alkyl; wherein R$^{11}$ is hydrogen or C1-C6 alkyl; wherein R$^{12}$ is hydrogen, cyano, halogen, C1-C6 alkyl, C1-C6 monohaloalkyl, C1-C6 polyhaloalkyl, —(C=O)—(C1-C6 alkyl), —(C=O)—O(C1-C6 alkyl), —(C1-C6 alkyl)-(C=O)—(C1-C6 alkyl), —(C1-C6 alkyl)-(C=O)—OH, —(C1-C6 alkyl)-(C=O)—O(C1-C6 alkyl), Ar$^1$, or Cy$^1$; wherein Ar$^1$ is monocyclic aryl or monocyclic heteraryl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein Cy$^1$ is C3-C8 cycloalkyl or C2-C7 heterocycloalkyl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; or a pharmaceutically acceptable salt thereof.

Also disclosed are compounds having a structure represented by a formula:

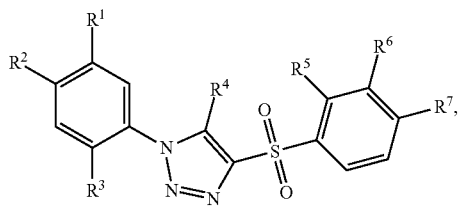

wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —CO$_2$H, —(C═O)H, —(C═O)—(C1-C6 alkyl), —(C═O)—O(C1-C6 alkyl); wherein $R^3$ is hydroxy, halogen, C1-C6 alkyl, C1-C6 alkoxy, and —(C1-C6)-OH; wherein $R^4$ is hydrogen, cyano, halogen, C2-C6 alkyl, C1-C6 monohaloalkyl, C1-C6 polyhaloalkyl, —(C═O)—(C1-C6 alkyl), —(C═O)—O(C1-C6 alkyl), —(C1-C6 alkyl)-(C═O)—(C1-C6 alkyl), —(C1-C6 alkyl)-(C═O)—O(C1-C6 alkyl), Ar$^1$, or Cy$^1$; wherein Ar$^1$ is monocyclic aryl or monocyclic heteraryl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein Cy$^1$ is C3-C8 cycloalkyl or C2-C7 heterocycloalkyl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein $R^5$ is hydrogen, halogen, hydroxy, C1-C3 alkyl; wherein $R^6$ is hydrogen, halogen, hydroxy, C1-C3 alkyl; wherein $R^7$ is C1-C6 alkyl; or a pharmaceutically acceptable salt thereof.

Also disclosed are compounds having a structure represented by a formula:

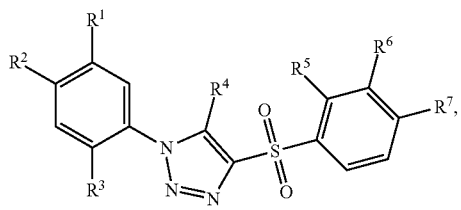

wherein $R^1$ is hydroxy, halogen, C1-C6 alkyl, C1-C6 alkoxy, and —(C1-C6)-OH; wherein $R^2$ is halogen, cyano, C1-C6 alkyl, C1-C6 alkoxy, C1-C6 monohaloalkyl, C1-C6 polyhaloalkyl, —CO$_2$H, —(C═O)H, —(C═O)—(C1-C6 alkyl), —(C═O)—O(C1-C6 alkyl); wherein $R^3$ is hydroxy, halogen, C1-C6 alkyl, C1-C6 alkoxy, and —(C1-C6)-OH; wherein $R^4$ is hydrogen, cyano, halogen, C1-C6 alkyl, C1-C6 monohaloalkyl, C1-C6 polyhaloalkyl, —(C═O)—(C1-C6 alkyl), —(C═O)—O(C1-C6 alkyl), —(C1-C6 alkyl)-(C═O)—(C1-C6 alkyl), —(C1-C6 alkyl)-(C═O)—O(C1-C6 alkyl), Ar$^1$, or Cy$^1$; wherein Ar$^1$ is monocyclic aryl or monocyclic heteraryl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein Cy$^1$ is C3-C8 cycloalkyl or C2-C7 heterocycloalkyl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein $R^5$ is hydrogen, halogen, hydroxy, C1-C3 alkyl; wherein $R^6$ is hydrogen, halogen, hydroxy, C1-C3 alkyl; wherein $R^7$ is C1-C6 alkyl; or a pharmaceutically acceptable salt thereof.

Also disclosed are compounds having a structure represented by a formula:

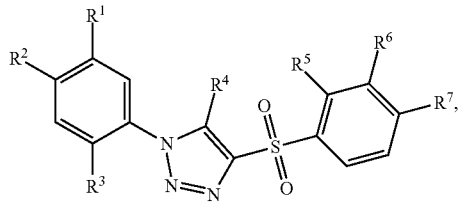

wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —CO$_2$H, —(C═O)H, —(C═O)—(C1-C6 alkyl), —(C═O)—O(C1-C6 alkyl); wherein $R^3$ is hydroxy, halogen, C1-C6 alkyl, C1-C6 alkoxy, and —(C1-C6)-OH; wherein $R^4$ is hydrogen, cyano, halogen, C1-C6 alkyl, C1-C6 monohaloalkyl, C1-C6 polyhaloalkyl, —(C═O)—(C1-C6 alkyl), —(C═O)—O(C1-C6 alkyl), —(C1-C6 alkyl)-(C═O)—(C1-C6 alkyl), —(C1-C6 alkyl)-(C═O)—O(C1-C6 alkyl), Ar$^1$, or Cy$^1$; wherein Ar$^1$ is monocyclic aryl or monocyclic heteraryl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein Cy$^1$ is C3-C8 cycloalkyl or C2-C7 heterocycloalkyl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein $R^5$ is hydrogen, halogen, hydroxy, C1-C3 alkyl; wherein $R^6$ is hydrogen, halogen, hydroxy, C1-C3 alkyl; wherein at least one of $R^5$ or $R^6$ is not hydrogen; wherein $R^7$ is C1-C6 alkyl; or a pharmaceutically acceptable salt thereof.

Also disclosed are compounds having a structure represented by a formula:

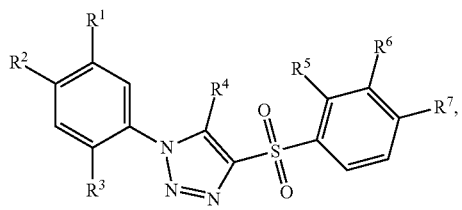

wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —CO$_2$H, —(C═O)H, —(C═O)—(C1-C6 alkyl), —(C═O)—O(C1-C6 alkyl); wherein $R^3$ is hydroxy, halogen, C1-C6 alkyl, C1-C6 alkoxy, and —(C1-C6)-OH; wherein at least one of $R^1$ or $R^3$ is hydroxy; wherein $R^4$ is hydrogen, cyano, halogen, C1-C6 alkyl, C1-C6 monohaloalkyl, C1-C6 polyhaloalkyl, —(C═O)—(C1-C6 alkyl), —(C═O)—O(C1-C6 alkyl), —(C1-C6 alkyl)-(C═O)—(C1-C6 alkyl), —(C1-C6 alkyl)-(C═O)—O(C1-C6 alkyl), Ar$^1$, or Cy$^1$; wherein Ar$^1$ is monocyclic aryl or monocyclic heteraryl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein $Cy^1$ is C3-C8 cycloalkyl or C2-C7 heterocycloalkyl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein $R^5$ is hydrogen, halogen, hydroxy, C1-C3 alkyl; wherein $R^6$ is hydrogen, halogen, hydroxy, C1-C3 alkyl; wherein $R^7$ is C1-C6 alkyl; or a pharmaceutically acceptable salt thereof.

Also disclosed are pharmaceutical compositions comprising a therapeutically effective amount of a disclosed compound or a product of a disclosed method of making and a pharmaceutically acceptable carrier.

Also disclosed are pharmaceutical compositions comprising a therapeutically effective amount of a compound having a structure represented by a formula:

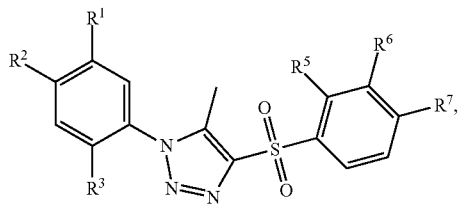

wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —$CO_2H$, —(C=O)H, —(C=O)—(C1-C6 alkyl), —(C=O)—O(C1-C6 alkyl); wherein $R^3$ is hydrogen, hydroxy, halogen, C1-C6 alkyl, C1-C6 alkoxy, and —(C1-C6)-OH; wherein $R^5$ is hydrogen, halogen, hydroxy, C1-C3 alkyl; wherein $R^6$ is hydrogen, halogen, hydroxy, C1-C3 alkyl; wherein $R^7$ is C1-C6 alkyl; or a pharmaceutically acceptable salt thereof; and a pharmaceutically acceptable carrier.

Also disclosed are methods for modulating an adverse drug reaction in a mammal comprising the step of administering to the mammal a therapeutically effective amount of at least one disclosed compound; a disclosed pharmaceutical composition; or a compound having a structure represented by a formula:

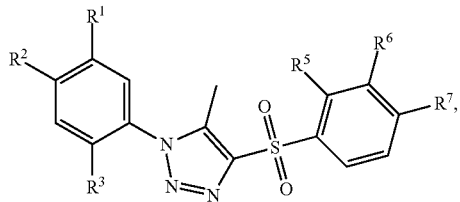

wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —$CO_2H$, —(C=O)H, —(C=O)—(C1-C6 alkyl), —(C=O)—O(C1-C6 alkyl); wherein $R^3$ is hydrogen, hydroxy, halogen, C1-C6 alkyl, C1-C6 alkoxy, and —(C1-C6)-OH; wherein $R^5$ is hydrogen, halogen, hydroxy, C1-C3 alkyl; wherein $R^6$ is hydrogen, halogen, hydroxy, C1-C3 alkyl; and wherein $R^7$ is C1-C6 alkyl; or a pharmaceutically acceptable salt thereof.

Also disclosed are methods for treatment of a disorder of uncontrolled cellular proliferation in a mammal comprising the step of administering to the mammal a therapeutically effective amount of at least one disclosed compound; a disclosed pharmaceutical composition; or a compound having a structure represented by a formula:

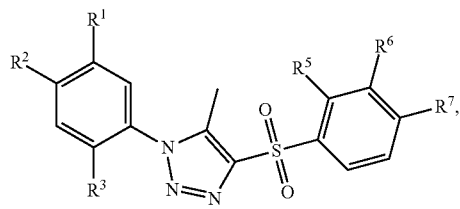

wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —$CO_2H$, —(C=O)H, —(C=O)—(C1-C6 alkyl), —(C=O)—O(C1-C6 alkyl); wherein $R^3$ is hydrogen, hydroxy, halogen, C1-C6 alkyl, C1-C6 alkoxy, and —(C1-C6)-OH; wherein $R^5$ is hydrogen, halogen, hydroxy, C1-C3 alkyl; wherein $R^6$ is hydrogen, halogen, hydroxy, C1-C3 alkyl; and wherein $R^7$ is C1-C6 alkyl; or a pharmaceutically acceptable salt thereof.

Also disclosed are methods for modulating pregnane X receptor activity in a mammal comprising the step of administering to the mammal a therapeutically effective amount of at least disclosed compound; a disclosed pharmaceutical composition; or a compound having a structure represented by a formula:

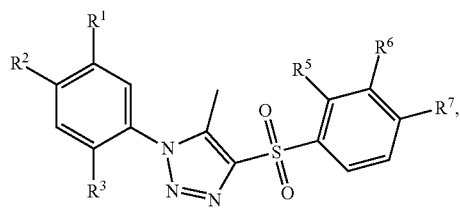

wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —$CO_2H$, —(C=O)H, —(C=O)—(C1-C6 alkyl), —(C=O)—O(C1-C6 alkyl); wherein $R^3$ is hydrogen, hydroxy, halogen, C1-C6 alkyl, C1-C6 alkoxy, and —(C1-C6)-OH; wherein $R^5$ is hydrogen, halogen, hydroxy, C1-C3 alkyl; wherein $R^6$ is hydrogen, halogen, hydroxy, C1-C3 alkyl; and wherein $R^7$ is C1-C6 alkyl; or a pharmaceutically acceptable salt thereof.

Also disclosed are methods for modulating pregnane X receptor activity in at least one cell, comprising the step of contacting the at least one cell with an effective amount of at least one disclosed compound; a disclosed pharmaceutical composition; or a compound having a structure represented by a formula:

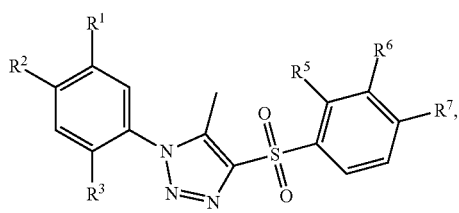

wherein R[1] is hydroxy, halogen, C1-C6 alkyl, C1-C6 alkoxy, and —(C1-C6)-OH; wherein R[2] is hydrogen, halogen, cyano, C1-C6 alkyl, C1-C6 alkoxy, C1-C6 monohaloalkyl, C1-C6 polyhaloalkyl, —CO$_2$H, —(C=O)H, —(C=O)—(C1-C6 alkyl), —(C=O)—O(C1-C6 alkyl); wherein R[3] is hydrogen, hydroxy, halogen, C1-C6 alkyl, C1-C6 alkoxy, and —(C1-C6)-OH; wherein R[5] is hydrogen, halogen, hydroxy, C1-C3 alkyl; wherein R[6] is hydrogen, halogen, hydroxy, C1-C3 alkyl; and wherein R[7] is C1-C6 alkyl; or a pharmaceutically acceptable salt thereof.

Also disclosed are kits comprising at least disclosed one compound; a disclosed pharmaceutical composition; or a compound having a structure represented by a formula:

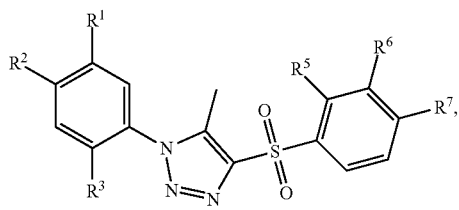

wherein R[1] is hydroxy, halogen, C1-C6 alkyl, C1-C6 alkoxy, and —(C1-C6)-OH; wherein R[2] is hydrogen, halogen, cyano, C1-C6 alkyl, C1-C6 alkoxy, C1-C6 monohaloalkyl, C1-C6 polyhaloalkyl, —CO$_2$H, —(C=O)H, —(C=O)—(C1-C6 alkyl), —(C=O)—O(C1-C6 alkyl); wherein R[3] is hydrogen, hydroxy, halogen, C1-C6 alkyl, C1-C6 alkoxy, and —(C1-C6)-OH; wherein R[5] is hydrogen, halogen, hydroxy, C1-C3 alkyl; wherein R[6] is hydrogen, halogen, hydroxy, C1-C3 alkyl; and wherein R[7] is C1-C6 alkyl; or a pharmaceutically acceptable salt thereof; and one or more of: (a) at least one agent known to increase pregnane X receptor activity; (b) at least one agent known to decrease pregnane X receptor activity; (c) at least one agent known to treat a disorder of uncontrolled cellular proliferation; (d) at least one agent known to treat an infectious disease; (e) at least one agent known to be a non-steroidal anti-inflammatory drug; (f) at least one agent known to be an anticonvulsant agent; or (g) instructions for treating a disorder associated with pregnane X receptor dysfunction.

Also disclosed are methods for the manufacturing a medicament comprising combining at least one disclosed compound or at least one disclosed product with a pharmaceutically acceptable carrier or diluent.

Also disclosed are uses of a disclosed compound or a disclosed product in the manufacture of a medicament for modulating an adverse drug reaction in a mammal.

Also disclosed are uses of a disclosed compound or a disclosed product in the manufacture of a medicament for treatment of a disorder of uncontrolled cellular proliferation in a mammal.

Also disclosed are uses of a disclosed compound or a disclosed product in the manufacture of a medicament for modulating pregnane X receptor activity in a mammal comprising the step of administering to the mammal.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The accompanying figures, which are incorporated in and constitute a part of this specification, illustrate several aspects and together with the description serve to explain the principles of the invention.

FIG. 3A shows data for the expression levels of liver Cyp3a11 mRNA in the mouse model. Briefly, mouse liver Cyp3a11 mRNA was analyzed by real-time PCR in hPXR-tg mice treated with vehicle control (Vehicle), RIF (10 mg/kg) or RIF (10 mg/kg) plus test compound (200 mg/kg) for 72 h. The liver CYP3A protein levels were also determined by Western blotting in hPXR-tg mice with the treatments indicated in FIG. 3A. Each data point represents the level of Cyp3a11 mRNA (FIG. 3A) or protein (FIG. 3B) in an individual mouse; lines indicate the mean value for 3-7 mice per group. Representative Western blots from 3-5 mice in each group are shown in FIG. 3C.

Figure 1A:
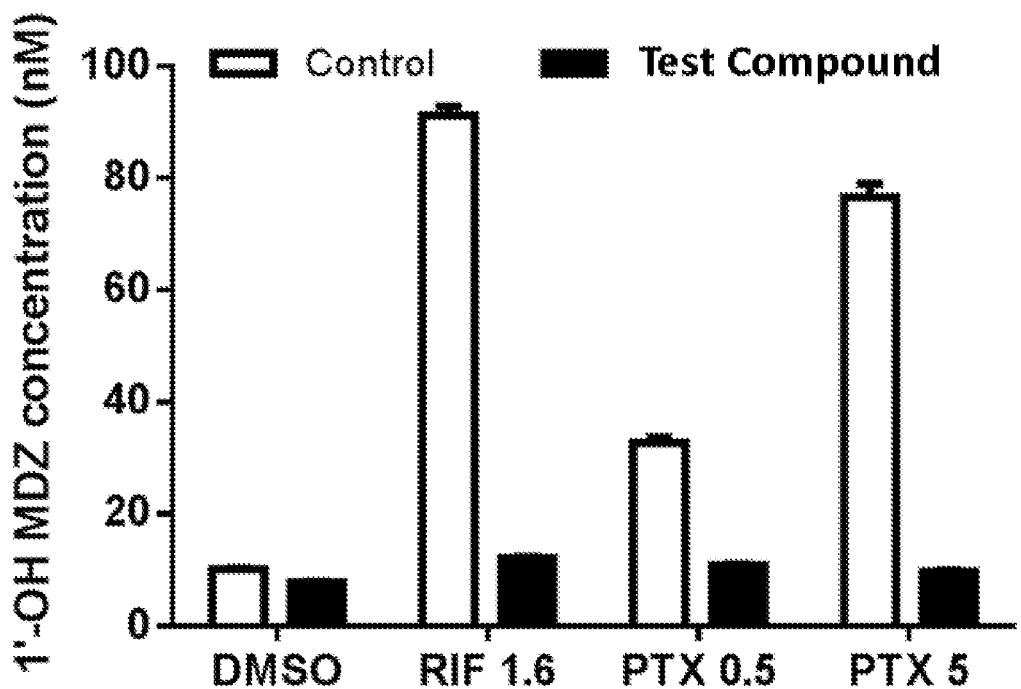
FIGS. 1A-1D show representative data for a representative disclosed compound showing that the tested compound modulates the activity of an hPXR agonist in primary human hepatocytes ("PHHs"). The test compound used in these studies was 4-((4-(tert-butyl)phenyl)sulfonyl)-1-(2,5-dimethoxyphenyl)-5-methyl-1H-1,2,3-triazole, and the structure is shown in FIG. 1D (herein referred to as the "test compound"). PHHs were pretreated with DMSO (0.1%), 1.6 µM of rifampicin (RIF), 0.5 µM of paclitaxel (PTX) or 5 µM of PTX, respectively, in the absence and presence of 10 µM of the test compound. After 72 hr, PHHs then received 3.3 µM of midazolam (MDZ) treatment for 4 h. The concentrations of 1'-OH MDZ (MDZ metabolite) in the media of each pretreatment condition were determined using LC/MS/MS as described in the Examples. The results are shown in FIG. 1A, and the data show that metabolism of MDZ is essentially blocked in the presence of the test compound regardless of the pretreatment condition. PHHs were also treated with 1 µM of PTX in the absence and presence of 10 µM of the test compound, and then the concentrations of major PTX metabolites, 3-OH PTX (by CYP3A4) and 6α-OH PTX (by CYP2C8), were determined using LC/MS/MS at 24 hr and 48 hr of treatment, respectively. The concentrations of 3-OH PTX and 6α-OH PTX are shown in FIGS. 1B and 1C, respectively. The data show that at both 24 and 48 hr of treatment the metabolism of PTX to either of the metabolites examined, 3-OH PTX and 6α-OH PTX, was effectively blocked by treatment with the test compound.
Figure 1B:
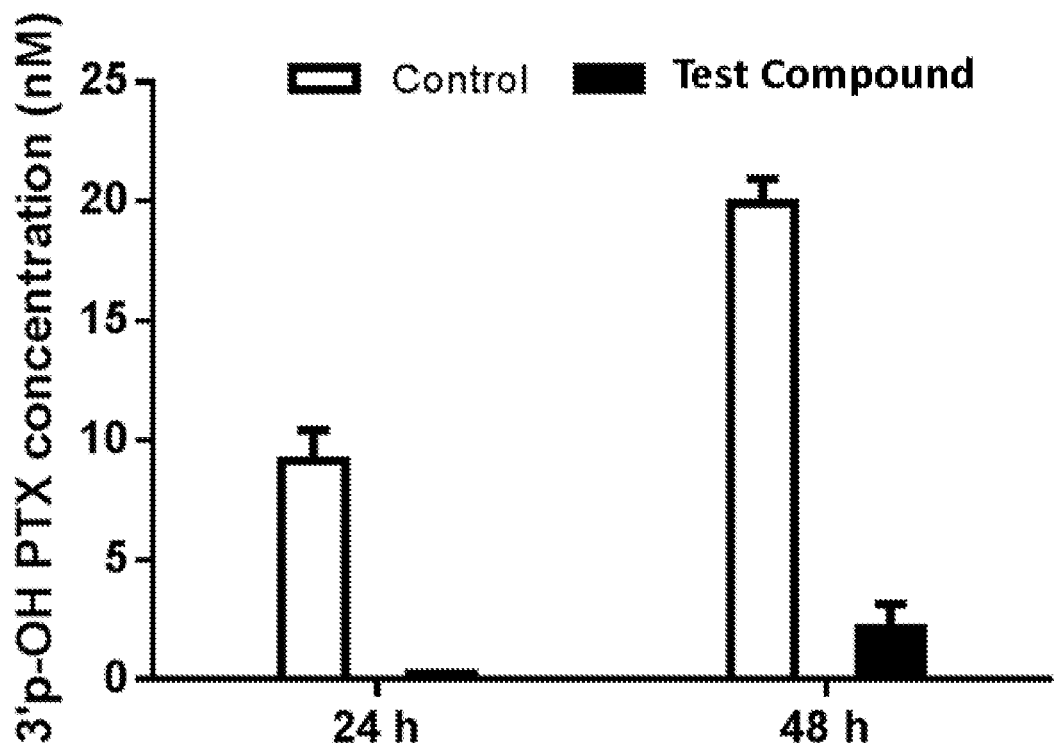
Figure 1C:
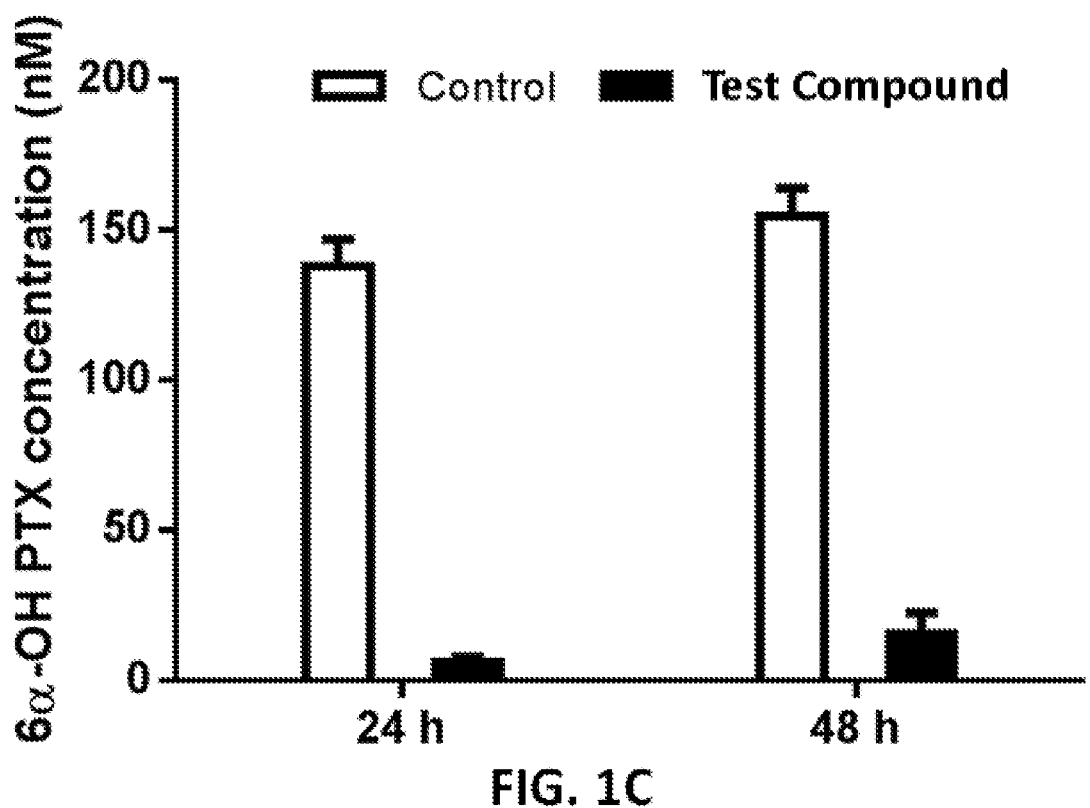
Figure 1D:
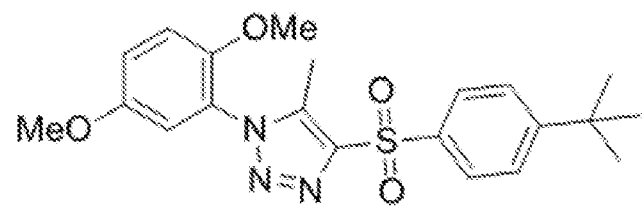
Figure 2A:
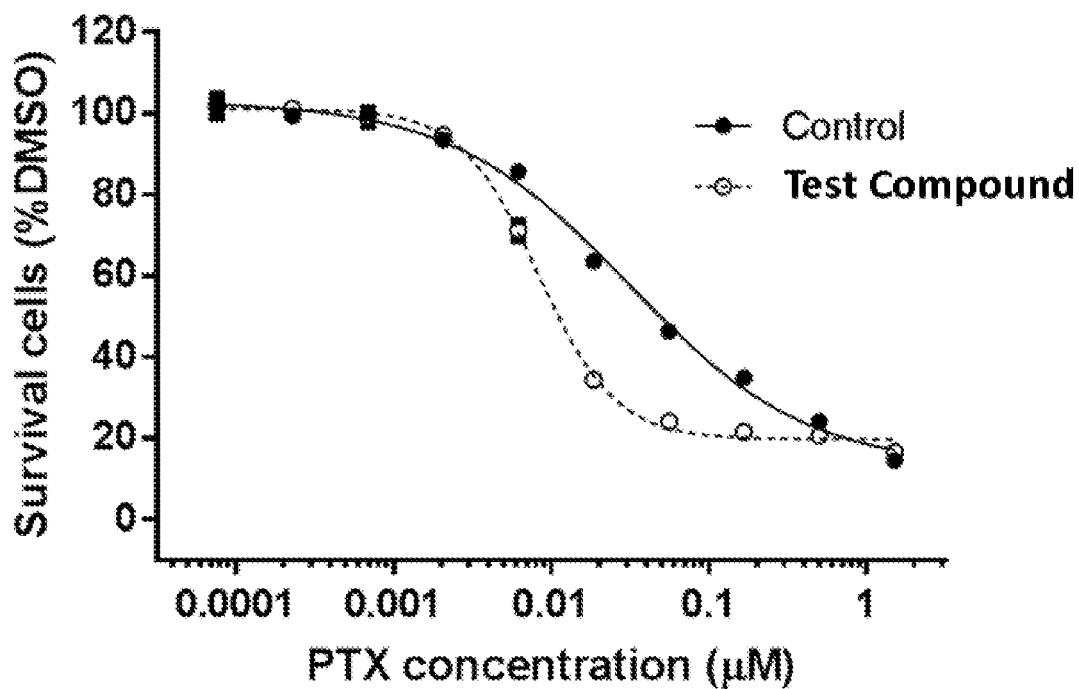
FIGS. 2A-2D show representative data for a representative disclosed compound showing that the tested compound sensitizes colon cancer cells to representative anti-cancer drugs. The test compound used in these studies was 4-((4-(tert-butyl)phenyl)sulfonyl)-1-(2,5-dimethoxyphenyl)-5-methyl-1H-1,2,3-triazole, and the structure is shown in FIG. 1D (herein referred to as the "test compound"). LS 180 cells stably overexpressed hPXR were treated with serial dilutions of paclitaxel (PTX; see FIG. 2A), docetaxel (TXT; see FIG. 2B), vinblastine (VBL; see FIG. 2C), or vincristine (VCR; see FIG. 2D) in the absence and presence of 10 µM of the test compound as indicated for 96 h. Values of the viability of compound-treated cells were expressed as a percentage of that of DMSO-treated cells, and drug concentration is expressed in a log scale. Data at each point represents mean±SEM from quadruplicate measurements. The data shown in FIGS. 2A-2D show that the apparent $IC_{50}$ for PTX, TXT, VBL, or VCR is significantly higher in the absence of the test compound.
Figure 2B:
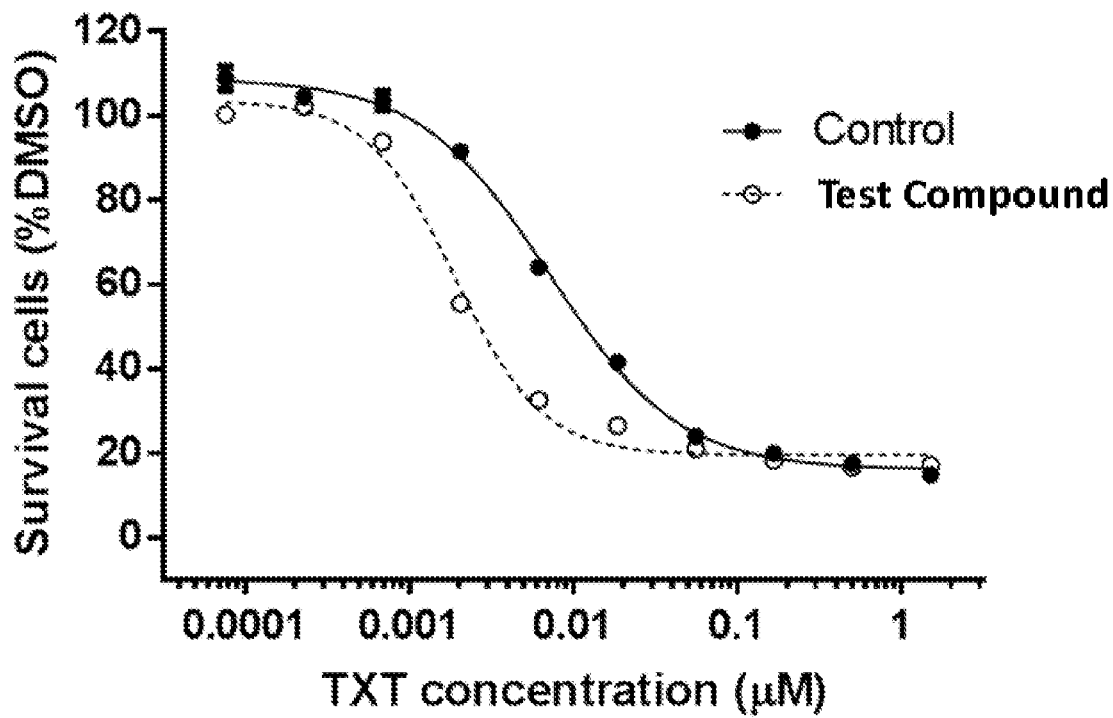
Figure 2C:
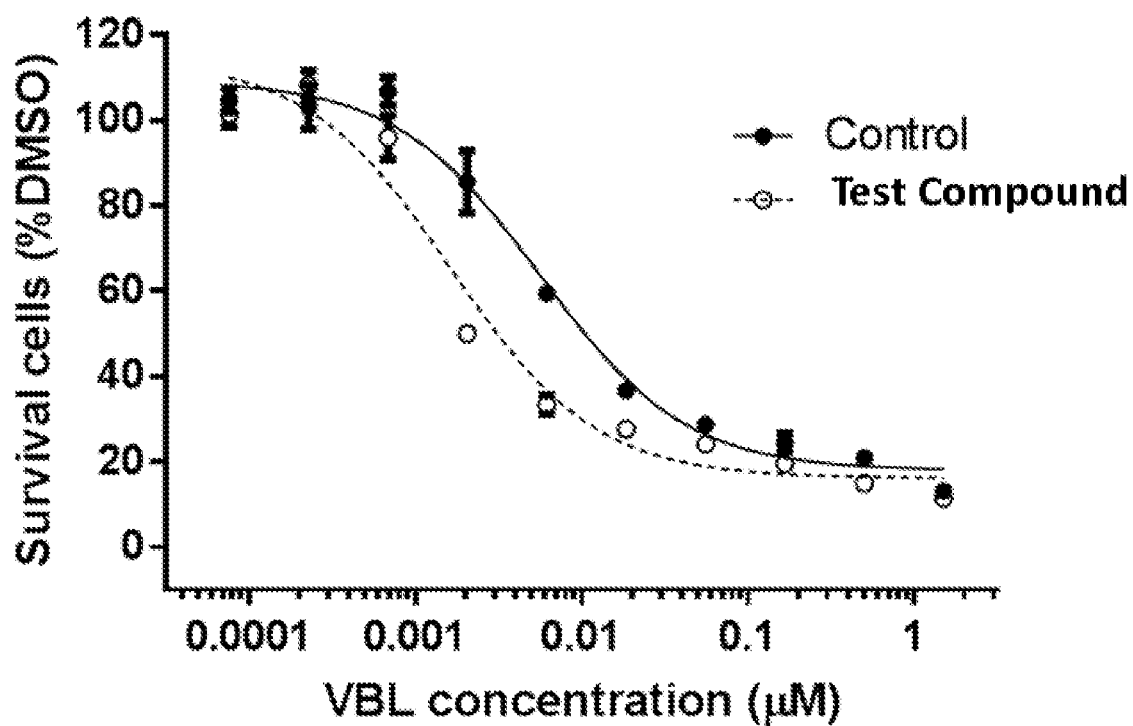
Figure 2D:
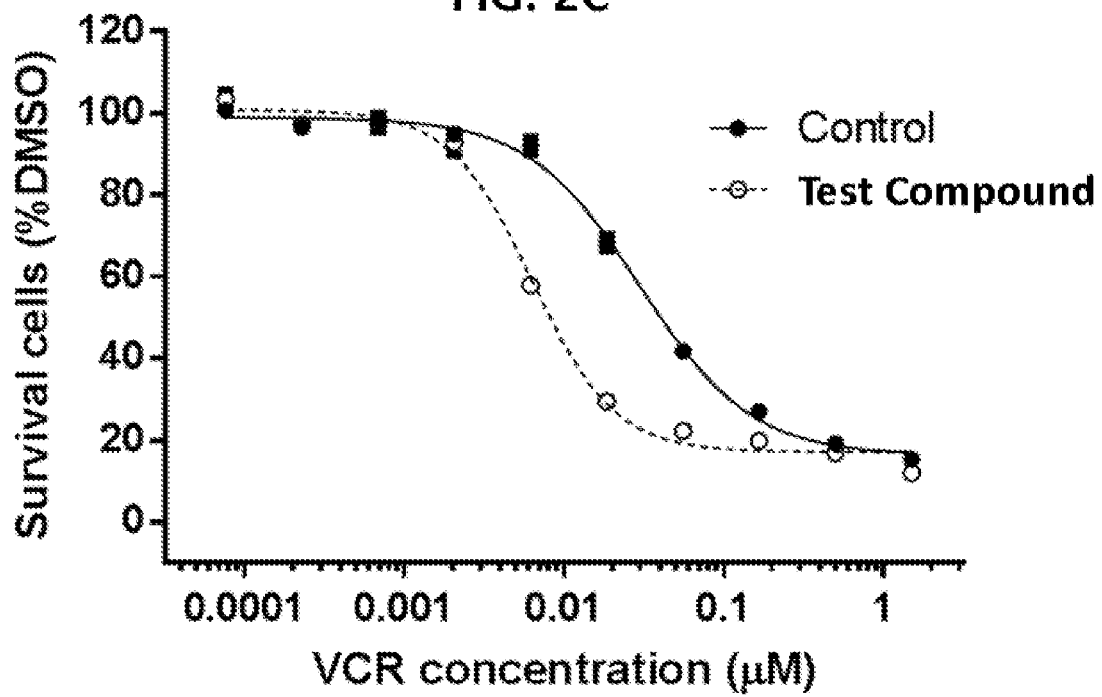
Figure 3A:
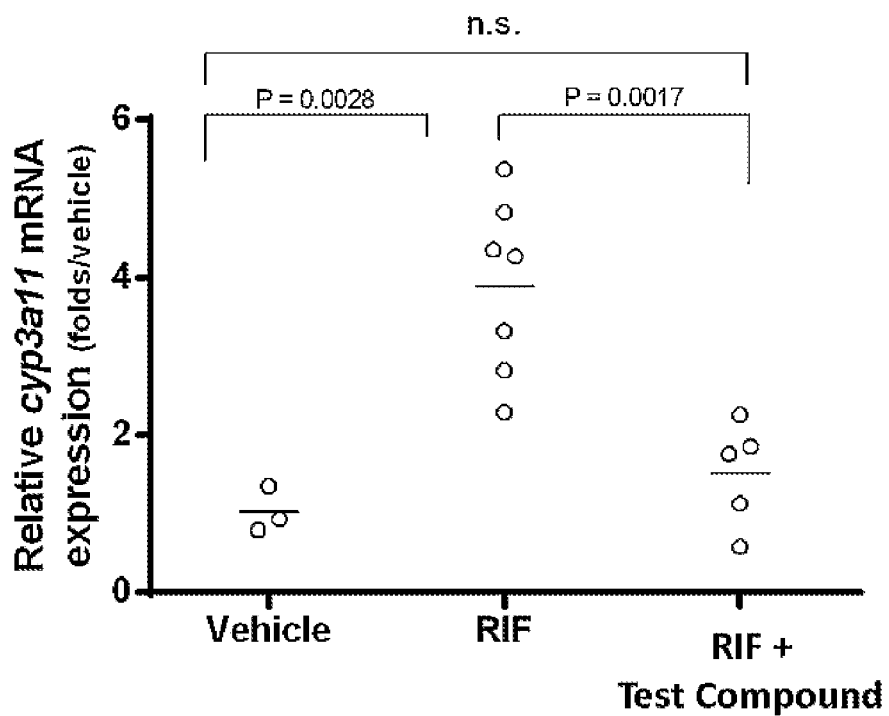
FIGS. 3A-3C show representative data for a representative disclosed compound showing that the tested compound inhibits the hPXR-mediated increase in CYP3A expression. The test compound used in these studies was 4-((4-(tert-butyl)phenyl)sulfonyl)-1-(2,5-dimethoxyphenyl)-5-methyl-1H-1,2,3-triazole, and the structure is shown in FIG. 1D (herein referred to as the "test compound").
Figure 3B:
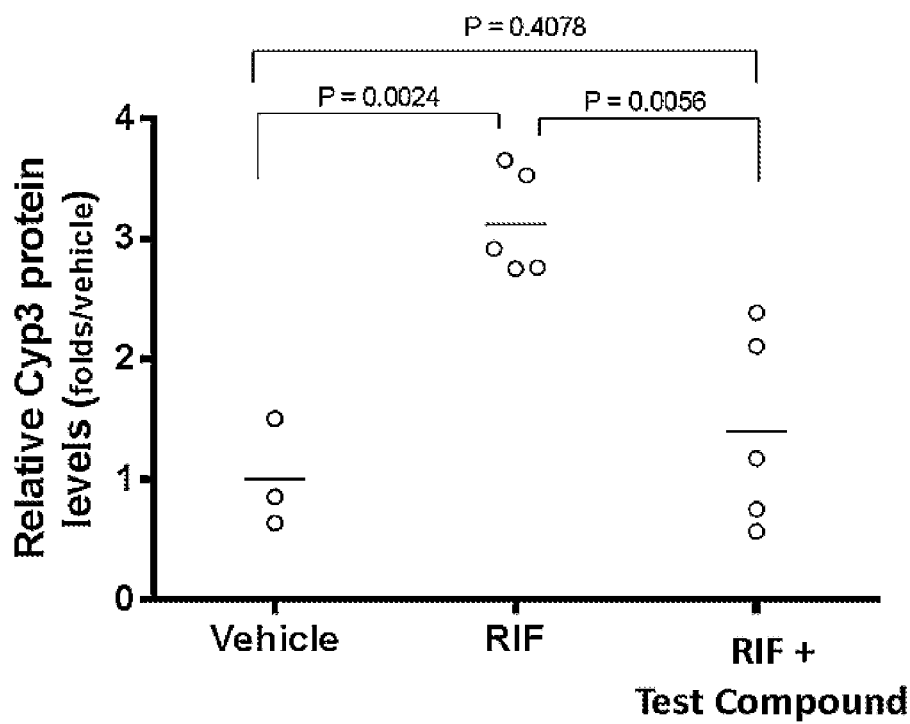
Figure 3C:
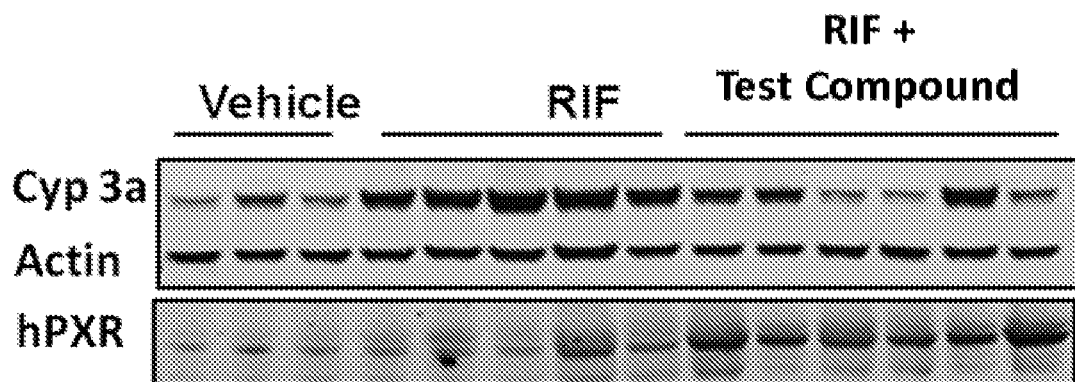
Figure 4:
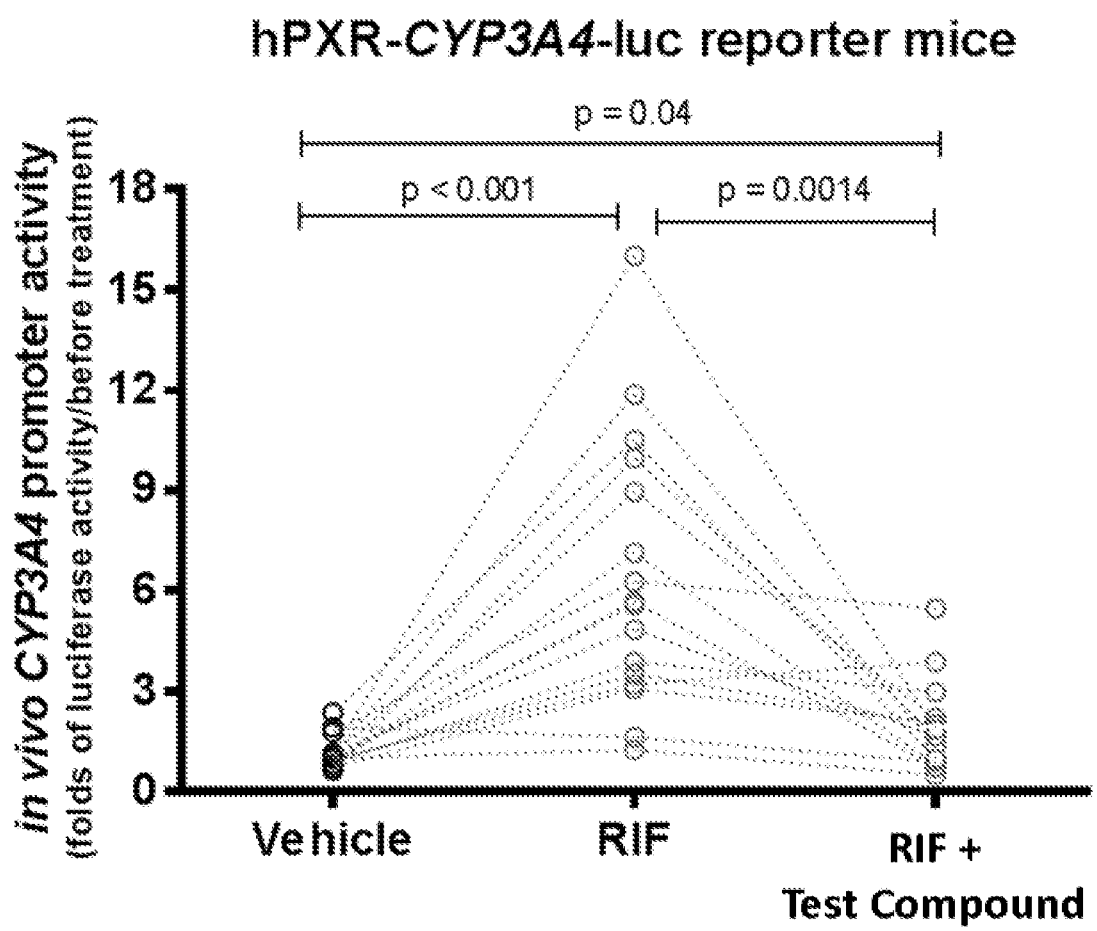
FIG. 4 shows representative data for a representative disclosed compound showing that the tested compound inhibits the hPXR-mediated increase in CYP3A expression. The test compound used in this study was 4-((4-(tert-butyl)phenyl)sulfonyl)-1-(2,5-dimethoxyphenyl)-5-methyl-1H-1,2,3-triazole, and the structure is shown in FIG. 1D (herein referred to as the "test compound"). The hPXR-CYP3A4-luc reporter mice (n=15) were generated by the hydrodynamic injection of the pGL3-CYP3A4-luc reporter in combination with pcDNA3-hPXR. Individual mouse received 3 rounds of sequential treatment of vehicle control (Vehicle), RIF (10 mg/kg) and RIF (10 mg/kg) plus the test compound (150 mg/kg) every 24 h for 2 days, respectively, with a washout period of 72-hour between two rounds of treatment. The luciferase activity in these reporter mice was recorded by bioluminescence imaging 10 h after the last treatment of each round, and the induction of CYP3A4 promoter reporter activity was calculated as described in Examples. Each data point represents the induction of CYP3A4 promoter reporter activity by the treatment in an individual mouse, and dos lines indicate the CYP3A4 promoter reporter activity change in individual mouse after following round of treatment. p values are indicated between the two treatment compared by paired t test. The data show the RIF-induced expression of the reporter under the control of the CYP3A4 promoter is significantly reduced when treatment with RIF occurs in the presence of the test compound.
Figure 5:
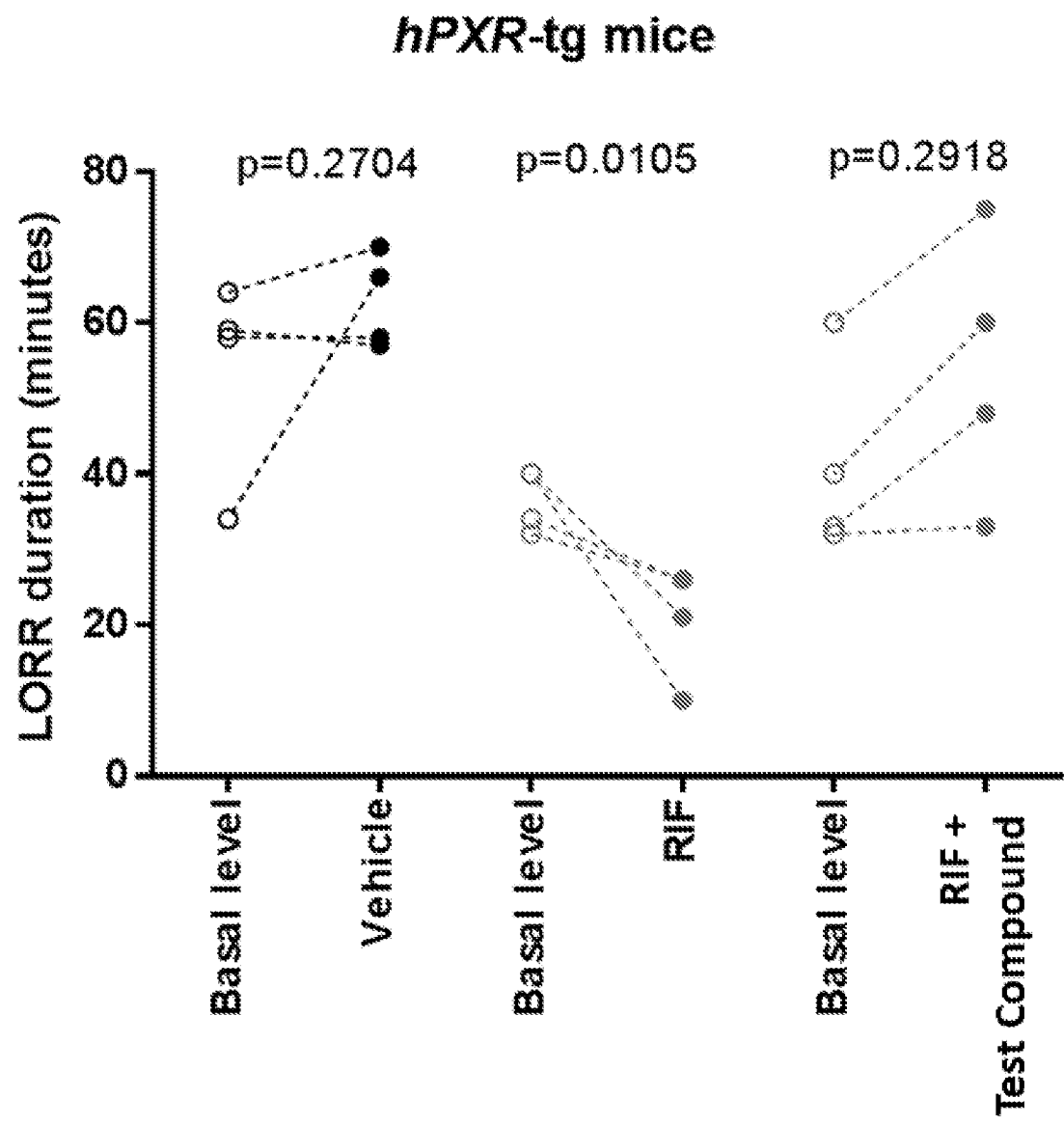
FIG. 5 shows representative data for a representative disclosed compound showing that the tested compound modulates effects of the anesthetic (2,2,2-tribromoethanolamine) in hPXR transgenic mice. The test compound used in this study was 4-((4-(tert-butyl)phenyl)sulfonyl)-1-(2,5-dimethoxyphenyl)-5-methyl-1H-1,2,3-triazole, and the structure is shown in FIG. 1D (herein referred to as the "test compound"). Loss of righting reflex (LORR) duration was recorded as described in Examples to measure metabolism of the anesthetic (2,2,2-tribromoethanolamine) in hPXR-tg, mice before and after treatment with vehicle, RIF, and RIF plus the test compound as indicated. Each data point represents LORR duration in an individual mouse; lines indicate LORR duration change in individual mouse before and after treatment. P values indicate comparison of values by paired t test. The data show that the apparent RIF-induced metabolism of the anesthetic (2,2,2-tribromoethanolamine), as determined by measurement of LORR, is significantly inhibited by treatment of mice in the presence of the test compound.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and in the claims, the term "comprising" can include the aspects "consisting of" and "consisting essentially of." Thus, for example, an aspect such as "a composition comprising A, B, and C" also includes aspects such as "a composition consisting of A, B, and C" and "a composition consisting essentially of A, B, and C."

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about," "approximate," and "at or about" mean that the amount or value in question can be the exact value designated or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the terms "PXR" and "pregnane X receptor" can be used interchangeably and refer to a nuclear receptor protein encoded by the NR1I2 gene, which is a transcriptional regulator of cytochrome P450 genes such as CYP3A4 and CYP3A5. PXR has a human gene map locus given as 3q12-q13.3, 3q13.3, and 3q12-q13.3 by Entrez Gene, Ensembl, and HGNC, respectively. The corresponding rat and mouse genes are given the gene symbol Nr1i2, and the respective gene map loci are 11q21 and 16 B3. The gene and protein have variously been referred to in the scientific literature as ONR1, BXR, SXR, PAR2, Orphan nuclear receptor PAR1, pregnane-activated receptor, steroid and xenobiotic receptor, MGC108643, pregnane X receptor (nuclear receptor sub family 1, group I, member 2), nuclear receptor subfamily 1 group I member 2, NR1I2, orphan nuclear receptor PXR, PXR.1, PXR.2, mPXR, and nuclear receptor subfamily 1, group 1, member 2. It can be appreciated that these terms can also be used to refer to PXR. The term PXR is understood to be inclusive of related homologous proteins in other species. The human form can be specifically designated by the term "hPXR." The PXR protein is characterized by a DNA binding domain and a ligand binding domain (also referred to by the term "LBD"). The PXR protein forms a heterodimer with the 9-cis retinoic acid receptor RXR, and the formation of the heterodimer is required for transcriptional activation of target genes, and the heterodimer binds to the response element of the CYP3A4 or CYP3A5 promoter. The heterodimer is also believed to bind to the response elements of the ABCB1/MDR1 gene.

The major human, rat, and mouse PXR protein isoforms encoded by the PXR gene (NR1I2) are, respectively, 434, 431, and 431 amino acids. However, several major splice variants have been described at least for human encoding different isoforms, some of which have been described as using non-AUG translation initiation codons. For example, a significant human isoform is the "long isoform", that is 473 amino acids comprising 39 additional amino acids added to the N-terminus of the major human isoform which is 434 amino acids. The LBD of the major human isoform is from amino acids 141-434, whereas the LBD of the long isoform is from amino acids 180-473.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In an aspect, the subject is a mammal. A patient refers to a subject afflicted with a disease or disorder. The term "patient" includes human and veterinary subjects.

In some aspects of the disclosed methods, the subject has been diagnosed with a need for treatment of an infectious disease prior to the administering step. In some aspects of the disclosed methods, the subject has been diagnosed with a need for modulating PXR activity prior to the administering step. In some aspects of the disclosed methods, the subject has been diagnosed with having a gram positive or gram negative infection prior to the administering step. In some aspects of the disclosed methods, the subject has been identified with an infectious disease that is treatable by antagonizing the activity of PXR prior to the administering step. In some aspects of the disclosed methods, the subject has been identified with a gram positive bacterial infection prior to the administering step. In various aspects of the disclosed methods, the subject has been identified with a gram negative bacterial infection prior to the administering step. In an aspect, a subject can be treated prophylactically with a compound or composition disclosed herein, as discussed herein elsewhere.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In an aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with an infectious disease treatable by antagonizing PXR activity" means having been subjected to a physical examination by a person of skill, for example, a physician, and found to have a condition that can be diagnosed or treated by a compound or composition that can inhibit PXR activity. As a further example, "diagnosed with a need for treatment of an infectious disease" refers to having been subjected to a physical examination by a person of skill, for example, a physician, and found to have a condition characterized by infection with a pathogenic microbe, such as a gram positive or gram negative bacteria.

As used herein, the phrase "identified to be in need of treatment for an infectious disease," or the like, refers to selection of a subject based upon need for treatment of the infectious disease. For example, a subject can be identified as having a need for treatment of an infectious disease (e.g., an infectious disease related to infection with a pathogenic gram negative or gram positive bacteria) based upon an earlier diagnosis by a person of skill and thereafter subjected to treatment for the infectious disease. It is contemplated that the identification can, In an aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, a target protein (e.g. the PXR protein), or other biological entity together in such a manner that the compound can affect the activity of the target, either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "$EC_{50}$," is intended to refer to the concentration of a substance (e.g., a compound or a drug) that is required for 50% activation or enhancement of a biological process, or component of a process. For example, $EC_{50}$ can refer to the concentration of a compound that provokes a response halfway between the baseline and maximum response in an appropriate assay of the target activity. For example, an $EC_{50}$ for the PXR can be determined in an in vitro assay system. Such in vitro assay systems include assay such as the assays as described herein.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In an aspect, an $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance. For example, an $EC_{50}$ for the PXR can be determined in an in vitro assay system. Such in vitro assay systems include assay such as the assays as described herein.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A2)C=C(A^3A4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the it clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen" or "halide," as used herein can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl" as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl" as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl" as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxy" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula $-N_3$.

The term "nitro" as used herein is represented by the formula $-NO_2$.

The term "nitrile" or "cyano" as used herein is represented by the formula —CN.

The term "silyl" as used herein is represented by the formula $-SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas $-S(O)A^1$, $-S(O)_2A^1$, $-OS(O)_2A^1$, or $-OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula $-S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," ... "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $-(CH_2)_{0-4}R°$; $-(CH_2)_{0-4}OR°$; $-O(CH_2)_{0-4}R°$, $-O-(CH_2)_{0-4}C(O)OR°$; $-(CH_2)_{0-4}CH(OR°)_2$; $-(CH_2)_{0-4}SR°$; $-(CH_2)_{0-4}Ph$, which may be substituted with $R°$; $-(CH_2)_{0-4}O(CH_2)_{0-1}Ph$ which may be substituted with $R°$; —CH=CHPh, which may be substituted with $R°$; $-(CH_2)_{0-4}O(CH_2)_{0-1}$-pyridyl which may be substituted with $R°$; $-NO_2$; —CN; $-N_3$; $-(CH_2)_{0-4}N(R°)_2$; $-(CH_2)_{0-4}N(R°)C(O)R°$; $-N(R°)C(S)R°$; $-(CH_2)_{0-4}N(R°)C(O)NR°_2$; $-N(R°)C(S)NR°_2$; $-(CH_2)_{0-4}N(R°)C(O)OR°$; $-N(R°)N(R°)C(O)R°$; $-N(R°)N(R°)C(O)NR°_2$; $-N(R°)N(R°)C(O)OR°$; $-(CH_2)_{0-4}C(O)R°$; —C(S)R°; $-(CH_2)_{0-4}C(O)OR°$; $-(CH_2)_{0-4}C(O)SR°$; $-(CH_2)_{0-4}C(O)OSiR°_3$; $-(CH_2)_{0-4}OC(O)R°$; —OC(O)(CH_2)_{0-4}SR—, SC(S)SR°; $-(CH_2)_{0-4}SC(O)R°$; $-(CH_2)_{0-4}C(O)NR°_2$; —C(S)NR°_2; —C(S)SR°; $-(CH_2)_{0-4}OC(O)NR°_2$; —C(O)N(OR°)R°; —C(O)C(O)R°; —C(O)CH_2C(O)R°; —C(NOR)R°; $-(CH_2)_{0-4}SSR°$; $-(CH_2)_{0-4}S(O)_2R°$; $-(CH_2)_{0-4}S(O)_2 OR°$; $-(CH_2)_{0-4}OS(O)_2R°$; —S(O)_2NR°_2; $-(CH_2)_{0-4}S(O)R°$; —N(R°)S(O)_2NR°_2; —N(R°)S(O)_2R°$; —N(OR°)R°; —C(NH)NR°_2; —P(O)_2R°; —P(O)R°_2; —OP(O)R°_2; —OP(O)(OR°)_2; SiR°_3; $-(C_{1-4}$ straight or branched alkylene)O—N(R°)_2; or $-(C_{1-4}$ straight or branched alkylene)C(O)O—N(R°)_2, wherein each R° may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR°$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR°$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

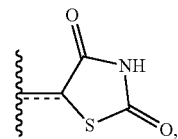

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as $^2$H, $^3$H, $^{13}$C, $^{14}$C, $^{15}$N, $^{18}$O, $^{17}$O, $^{35}$S, $^{18}$F, and $^{36}$Cl, respectively. Compounds further comprise prodrugs thereof and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through noncovalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

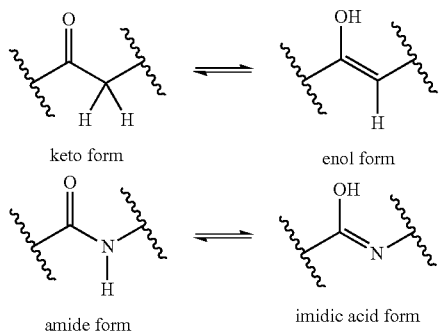

keto form             enol form amide form            imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

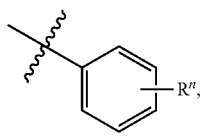

which is understood to be equivalent to a formula:

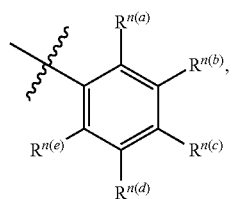

wherein n is typically an integer. That is, $R^n$ is understood to represent five independent substituents, $R^{n(a)}$, $R^{n(b)}$, $R^{n(c)}$, $R^{n(d)}$, and $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental Volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In an aspect, disclosed are compounds useful as antagonists of the pregnane X receptor ("PXR"). In a further aspect, the disclosed compounds are useful for modulating an adverse drug reaction in a mammal. In a still further aspect, the disclosed compounds are useful for treatment of a disorder of uncontrolled cellular proliferation, such as a cancer. In an aspect, the disclosed compounds can be used for treatment of a disorder of uncontrolled cellular proliferation alone or in combination with an anticancer agent or a treatment scheme using a combination of multiple anticancer agents. In a yet further aspect, the disclosed compounds are useful for modulating pregnane X receptor activity in a mammal.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In an aspect, disclosed are compounds having a structure represented by a formula:

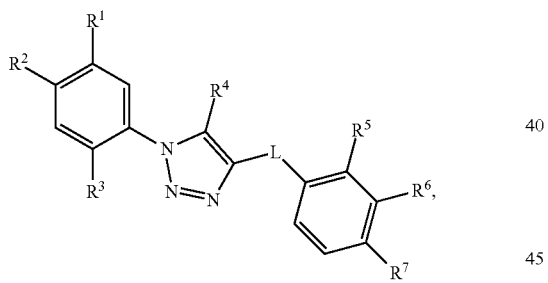

wherein L is $SO_2$, C=O. or $NR^{10}$; wherein $R^{10}$ is hydrogen or C1-C3 alkyl; wherein $R^1$ is hydroxy, halogen, C1-C6 alkyl, C1-C6 alkoxy, and —(C1-C6)-OH; wherein $R^2$ is hydrogen or halogen; wherein $R^3$ is hydroxy, halogen, C1-C6 alkyl, C1-C6 alkoxy, and —(C1-C6)-OH; wherein $R^4$ is hydrogen, cyano, halogen, C1-C6 alkyl, C1-C6 monohaloalkyl, C1-C6 polyhaloalkyl, —(C=O)—(C1-C6 alkyl), —(C=O)—O(C1-C6 alkyl), —(C1-C6 alkyl)-(C=O)— (C1-C6 alkyl), —(C1-C6 alkyl)-(C=O)—OH, —(C1-C6 alkyl)-(C=O)—O(C1-C6 alkyl), $Ar^1$, or $Cy^1$; wherein $Ar^1$ is monocyclic aryl or monocyclic heteraryl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein $Cy^1$ is C3-C8 cycloalkyl or C2-C7 heterocycloalkyl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein $R^5$ is hydrogen, halogen, hydroxy, C1-C3 alkyl; wherein $R^6$ is hydrogen, halogen, hydroxy, C1-C3 alkyl; and wherein $R^7$ is C1-C6 alkyl; or a pharmaceutically acceptable salt thereof; and wherein the compound does not have the structure:

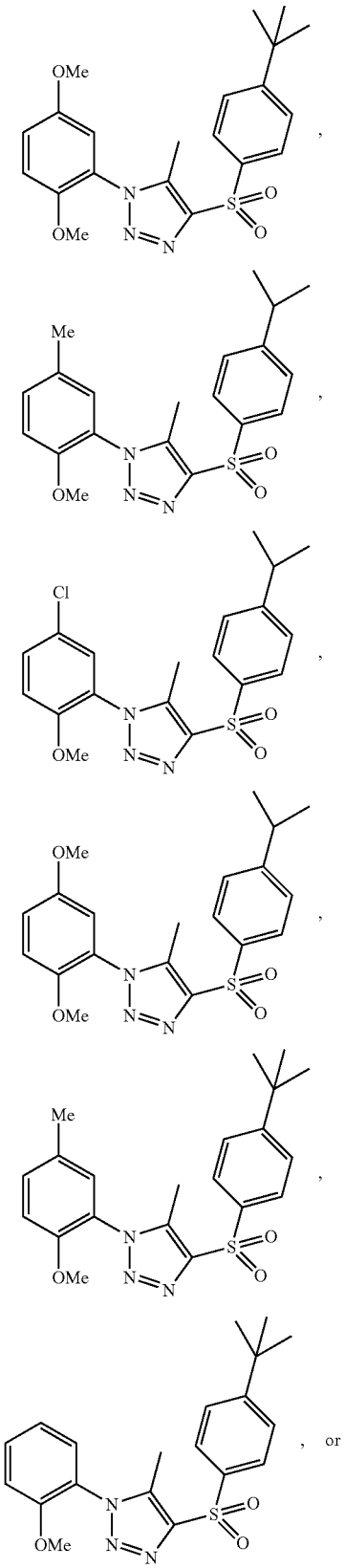

, or

-continued

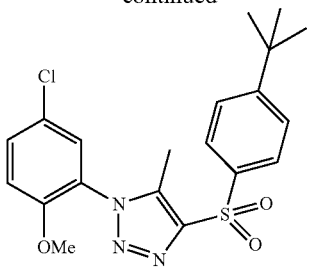

Also disclosed are compounds having a structure represented by a formula:

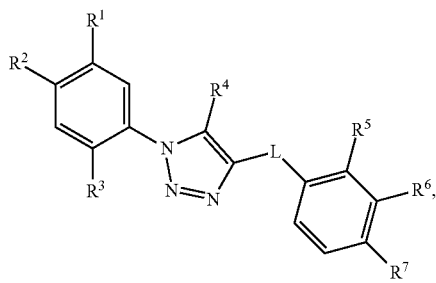

wherein L is C=O or NR$^{10}$; wherein R$^{10}$ is hydrogen or C1-C3 alkyl; wherein R$^1$ is hydroxy, halogen, C1-C6 alkyl, C1-C6 alkoxy, and —(C1-C6)-OH; wherein R$^2$ is hydrogen, halogen, cyano, C1-C6 alkyl, C1-C6 alkoxy, C1-C6 monohaloalkyl, C1-C6 polyhaloalkyl, —CO$_2$H, —(C=O)H, —(C=O)—(C1-C6 alkyl), —(C=O)—O(C1-C6 alkyl); wherein R$^3$ is hydroxy, halogen, C1-C6 alkyl, C1-C6 alkoxy, and —(C1-C6)-OH; wherein R$^4$ is hydrogen, cyano, halogen, C1-C6 alkyl, C1-C6 monohaloalkyl, C1-C6 polyhaloalkyl, —(C=O)—(C1-C6 alkyl), —(C=O)—O(C1-C6 alkyl), —(C1-C6 alkyl)-(C=O)—(C1-C6 alkyl), —(C1-C6 alkyl)-(C=O)—OH, —(C1-C6 alkyl)-(C=O)—O(C1-C6 alkyl), Ar$^1$, or Cy$^1$; wherein Ar$^1$ is monocyclic aryl or monocyclic heteraryl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein Cy$^1$ is C3-C8 cycloalkyl or C2-C7 heterocycloalkyl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein R$^5$ is hydrogen, halogen, hydroxy, C1-C3 alkyl; wherein R$^6$ is hydrogen, halogen, hydroxy, C1-C3 alkyl; and wherein R$^7$ is C1-C6 alkyl; or a pharmaceutically acceptable salt thereof.

Also disclosed are compounds having a structure represented by a formula:

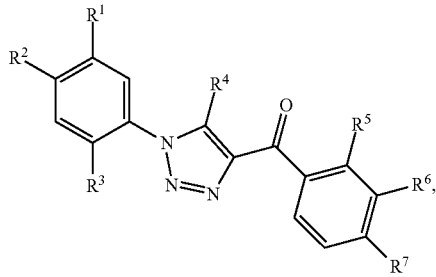

wherein R$^1$ is hydroxy, halogen, C1-C6 alkyl, C1-C6 alkoxy, and —(C1-C6)-OH; wherein R$^2$ is hydrogen, halogen, cyano, C1-C6 alkyl, C1-C6 alkoxy, C1-C6 monohaloalkyl, C1-C6 polyhaloalkyl, —CO$_2$H, —(C=O)H, —(C=O)—(C1-C6 alkyl), —(C=O)—O(C1-C6 alkyl); wherein R$^3$ is hydroxy, halogen, C1-C6 alkyl, C1-C6 alkoxy, and —(C1-C6)-OH; wherein R$^4$ is hydrogen, cyano, halogen, C1-C6 alkyl, C1-C6 monohaloalkyl, C1-C6 polyhaloalkyl, —(C=O)—(C1-C6 alkyl), —(C=O)—O(C1-C6 alkyl), —(C1-C6 alkyl)-(C=O)—(C1-C6 alkyl), —(C1-C6 alkyl)-(C=O)—OH, —(C1-C6 alkyl)-(C=O)—O(C1-C6 alkyl), Ar$^1$, or Cy$^1$; wherein Ar$^1$ is monocyclic aryl or monocyclic heteraryl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein Cy$^1$ is C3-C8 cycloalkyl or C2-C7 heterocycloalkyl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein R$^5$ is hydrogen, halogen, hydroxy, C1-C3 alkyl; wherein R$^6$ is hydrogen, halogen, hydroxy, C1-C3 alkyl; and wherein R$^7$ is C1-C6 alkyl; or a pharmaceutically acceptable salt thereof.

Also disclosed are compounds having a structure represented by a formula:

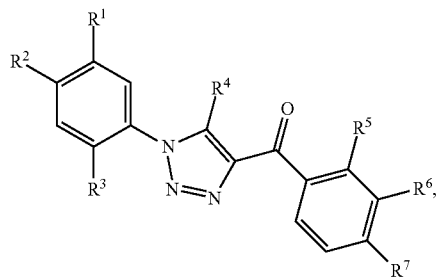

wherein R$^1$ is hydroxy, halogen, methyl, ethyl, methoxy, or ethoxy; wherein R$^2$ is hydrogen, fluoro, or methyl; wherein R$^3$ is hydroxy, halogen, methyl, ethyl, methoxy, or ethoxy; wherein R$^4$ is fluoro, chloro, bromo, cyano, methyl, ethyl, propyl, isopropyl, —CH$_2$F, —CH$_2$Cl, —(C=O)CH$_3$, or —CH$_2$(C=O)OCH$_3$, wherein R$^5$ is hydrogen, hydroxy, or methyl; wherein R$^6$ is hydrogen, hydroxy, or methyl; and wherein R$^7$ is propyl, isopropyl, n-butyl, tert-butyl, or sec-butyl.

Also disclosed are compounds having a structure represented by a formula:

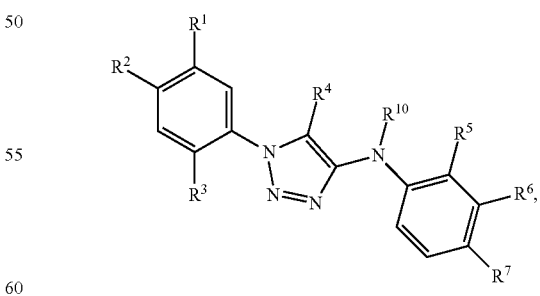

wherein R$^1$ is hydroxy, halogen, C1-C6 alkyl, C1-C6 alkoxy, and —(C1-C6)-OH; wherein R$^2$ is hydrogen, halogen, cyano, C1-C6 alkyl, C1-C6 alkoxy, C1-C6 monohaloalkyl, C1-C6 polyhaloalkyl, —CO$_2$H, —(C=O)H, —(C=O)—(C1-C6 alkyl), —(C=O)—O(C1-C6 alkyl); wherein R$^3$ is hydroxy, halogen, C1-C6 alkyl, C1-C6 alkoxy, and —(C1-

C6)-OH; wherein $R^4$ is hydrogen, cyano, halogen, C1-C6 alkyl, C1-C6 monohaloalkyl, C1-C6 polyhaloalkyl, —(C=O)—(C1-C6 alkyl), —(C=O)—O(C1-C6 alkyl), —(C1-C6 alkyl)-(C=O)—(C1-C6 alkyl), —(C1-C6 alkyl)-(C=O)—OH, —(C1-C6 alkyl)-(C=O)—O(C1-C6 alkyl), $Ar^1$, or $Cy^1$; wherein $Ar^1$ is monocyclic aryl or monocyclic heteraryl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein $Cy^1$ is C3-C8 cycloalkyl or C2-C7 heterocycloalkyl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein $R^5$ is hydrogen, halogen, hydroxy, C1-C3 alkyl; wherein $R^6$ is hydrogen, halogen, hydroxy, C1-C3 alkyl; wherein $R^7$ is C1-C6 alkyl; and wherein $R^{10}$ is hydrogen or C1-C3 alkyl; or a pharmaceutically acceptable salt thereof.

Also disclosed are compounds having a structure represented by a formula:

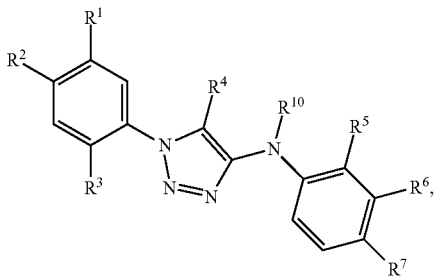

wherein $R^1$ is hydroxy, halogen, methyl, ethyl, methoxy, or ethoxy; wherein $R^2$ is hydrogen, fluoro, or methyl; wherein $R^3$ is hydroxy, halogen, methyl, ethyl, methoxy, or ethoxy; wherein $R^4$ is fluoro, chloro, bromo, cyano, methyl, ethyl, propyl, isopropyl, —CH$_2$F, —CH$_2$Cl, —(C=O)CH$_3$, or —CH$_2$(C=O)OCH$_3$, wherein $R^5$ is hydrogen, hydroxy, or methyl; wherein $R^6$ is hydrogen, hydroxy, or methyl; wherein $R^7$ is propyl, isopropyl, n-butyl, tert-butyl, or sec-butyl; and wherein $R^{10}$ is hydrogen or methyl.

Also disclosed are compounds having a structure represented by a formula:

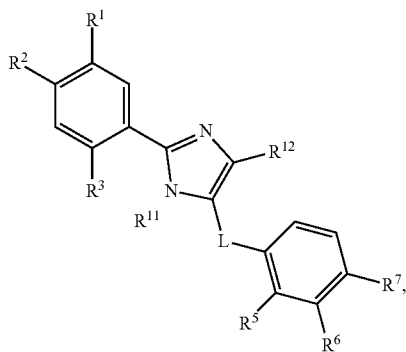

wherein L is SO$_2$, C=O, or NR$^{10}$; wherein $R^{10}$ is hydrogen or C1-C3 alkyl; wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —CO$_2$H, —(C=O)H, —(C=O)—(C1-C6 alkyl), —(C=O)—O(C1-C6 alkyl); wherein $R^3$ is hydroxy, halogen, C1-C6 alkyl, C1-C6 alkoxy, and —(C1-C6)-OH; wherein $R^5$ is hydrogen, halogen, hydroxy, C1-C3 alkyl; wherein $R^6$ is hydrogen, halogen, hydroxy, C1-C3 alkyl; wherein $R^7$ is C1-C6 alkyl; wherein $R^{11}$ is hydrogen or C1-C6 alkyl; and wherein $R^{12}$ is hydrogen, cyano, halogen, C1-C6 alkyl, C1-C6 monohaloalkyl, C1-C6 polyhaloalkyl, —(C=O)—(C1-C6 alkyl), —(C=O)—O(C1-C6 alkyl), —(C1-C6 alkyl)-(C=O)—(C1-C6 alkyl), —(C1-C6 alkyl)-(C=O)—OH, —(C1-C6 alkyl)-(C=O)—O(C1-C6 alkyl), $Ar^1$, or $Cy^1$; wherein $Ar^1$ is monocyclic aryl or monocyclic heteraryl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein $Cy^1$ is C3-C8 cycloalkyl or C2-C7 heterocycloalkyl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; or a pharmaceutically acceptable salt thereof.

Also disclosed are compounds having a structure represented by a formula:

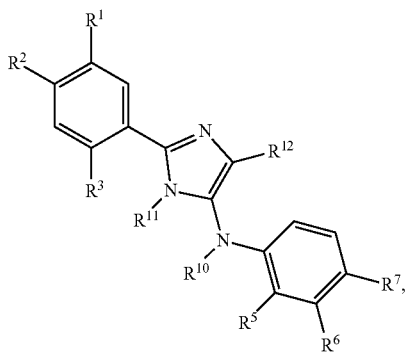

wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —CO$_2$H, —(C=O)H, —(C=O)—(C1-C6 alkyl), —(C=O)—O(C1-C6 alkyl); wherein $R^3$ is hydroxy, halogen, C1-C6 alkyl, C1-C6 alkoxy, and —(C1-C6)-OH; wherein $R^5$ is hydrogen, halogen, hydroxy, C1-C3 alkyl; wherein $R^6$ is hydrogen, halogen, hydroxy, C1-C3 alkyl; wherein $R^7$ is C1-C6 alkyl; wherein $R^{10}$ is hydrogen or C1-C3 alkyl; wherein $R^{11}$ is hydrogen or C1-C6 alkyl; and wherein $R^{12}$ is hydrogen, cyano, halogen, C1-C6 alkyl, C1-C6 monohaloalkyl, C1-C6 polyhaloalkyl, —(C=O)—(C1-C6 alkyl), —(C=O)—O(C1-C6 alkyl), —(C1-C6 alkyl)-(C=O)—(C1-C6 alkyl), —(C1-C6 alkyl)-(C=O)—OH, —(C1-C6 alkyl)-(C=O)—O(C1-C6 alkyl), $Ar^1$, or $Cy^1$; wherein $Ar^1$ is monocyclic aryl or monocyclic heteraryl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein $Cy^1$ is C3-C8 cycloalkyl or C2-C7 heterocycloalkyl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; or a pharmaceutically acceptable salt thereof.

Also disclosed are compounds having a structure represented by a formula:

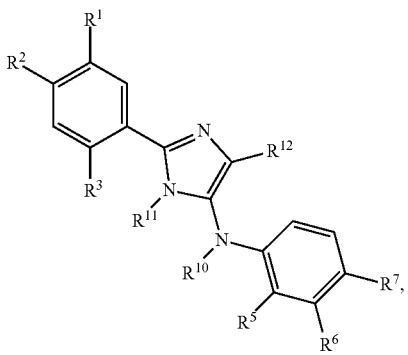

wherein $R^1$ is hydroxy, halogen, methyl, ethyl, methoxy, or ethoxy; wherein $R^2$ is hydrogen, fluoro, or methyl; wherein $R^3$ is hydroxy, halogen, methyl, ethyl, methoxy, or ethoxy; wherein $R^5$ is hydrogen, hydroxy, or methyl; wherein $R^6$ is hydrogen, hydroxy, or methyl; wherein $R^7$ is propyl, isopropyl, n-butyl, tert-butyl, or sec-butyl; wherein $R^{10}$ is hydrogen or methyl; wherein $R^{11}$ is hydrogen or methyl; and wherein $R^{12}$ is fluoro, chloro, bromo, cyano, methyl, ethyl, propyl, isopropyl, —$CH_2F$, —$CH_2Cl$, —(C=O)$CH_3$, or —$CH_2$(C=O)O$CH_3$.

Also disclosed are compounds having a structure represented by a formula:

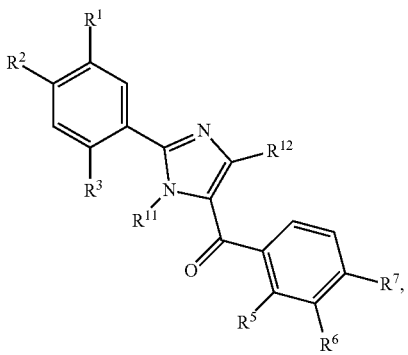

wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —$CO_2H$, —(C=O)H, —(C=O)—(C1-C6 alkyl), —(C=O)—O(C1-C6 alkyl); wherein $R^3$ is hydroxy, halogen, C1-C6 alkyl, C1-C6 alkoxy, and —(C1-C6)-OH; wherein $R^5$ is hydrogen, halogen, hydroxy, C1-C3 alkyl; wherein $R^6$ is hydrogen, halogen, hydroxy, C1-C3 alkyl; wherein $R^7$ is C1-C6 alkyl; wherein $R^{11}$ is hydrogen or C1-C6 alkyl; and wherein $R^{12}$ is hydrogen, cyano, halogen, C1-C6 alkyl, C1-C6 monohaloalkyl, C1-C6 polyhaloalkyl, —(C=O)—(C1-C6 alkyl), —(C=O)—O(C1-C6 alkyl), —(C1-C6 alkyl)-(C=O)—(C1-C6 alkyl), —(C1-C6 alkyl)-(C=O)—OH, —(C1-C6 alkyl)-(C=O)—O(C1-C6 alkyl), $Ar^1$, or $Cy^1$; wherein $Ar^1$ is monocyclic aryl or monocyclic heteraryl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein $Cy^1$ is C3-C8 cycloalkyl or C2-C7 heterocycloalkyl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; or a pharmaceutically acceptable salt thereof.

Also disclosed are compounds having a structure represented by a formula:

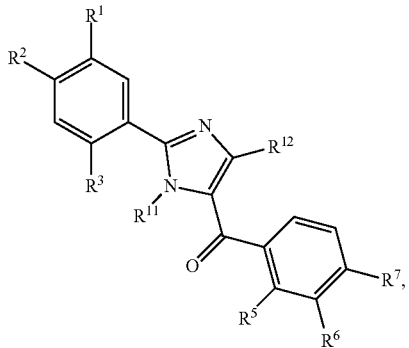

wherein $R^1$ is hydroxy, halogen, methyl, ethyl, methoxy, or ethoxy; wherein $R^2$ is hydrogen, fluoro, or methyl; wherein $R^3$ is hydroxy, halogen, methyl, ethyl, methoxy, or ethoxy; wherein $R^5$ is hydrogen, hydroxy, or methyl; wherein $R^6$ is hydrogen, hydroxy, or methyl; wherein $R^7$ is propyl, isopropyl, n-butyl, tert-butyl, or sec-butyl; wherein $R^{11}$ is hydrogen or methyl; and wherein $R^{12}$ is fluoro, chloro, bromo, cyano, methyl, ethyl, propyl, isopropyl, —$CH_2F$, —$CH_2Cl$, —(C=O)$CH_3$, or —$CH_2$(C=O)O$CH_3$.

Also disclosed are compounds having a structure represented by a formula:

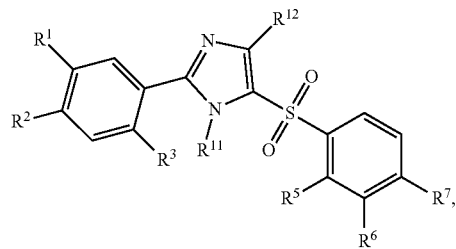

wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —$CO_2H$, —(C=O)H, —(C=O)—(C1-C6 alkyl), —(C=O)—O(C1-C6 alkyl); wherein $R^3$ is hydroxy, halogen, C1-C6 alkyl, C1-C6 alkoxy, and —(C1-C6)-OH; wherein $R^5$ is hydrogen, halogen, hydroxy, C1-C3 alkyl; wherein $R^6$ is hydrogen, halogen, hydroxy, C1-C3 alkyl; wherein $R^7$ is C1-C6 alkyl; wherein $R^{11}$ is hydrogen or C1-C6 alkyl; and wherein $R^{12}$ is hydrogen, cyano, halogen, C1-C6 alkyl, C1-C6 monohaloalkyl, C1-C6 polyhaloalkyl, —(C=O)—(C1-C6 alkyl), —(C=O)—O(C1-C6 alkyl), —(C1-C6 alkyl)-(C=O)—(C1-C6 alkyl), —(C1-C6 alkyl)-(C=O)—OH, —(C1-C6 alkyl)-(C=O)—O(C1-C6 alkyl), $Ar^1$, or $Cy^1$; wherein $Ar^1$ is monocyclic aryl or monocyclic heteraryl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein $Cy^1$ is C3-C8 cycloalkyl or C2-C7 heterocycloalkyl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; or a pharmaceutically acceptable salt thereof.

Also disclosed are compounds having a structure represented by a formula:

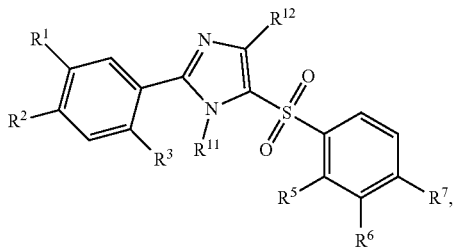

wherein $R^1$ is hydroxy, halogen, methyl, ethyl, methoxy, or ethoxy; wherein $R^2$ is hydrogen, fluoro, or methyl; wherein $R^3$ is hydroxy, halogen, methyl, ethyl, methoxy, or ethoxy; wherein $R^5$ is hydrogen, hydroxy, or methyl; wherein $R^6$ is hydrogen, hydroxy, or methyl; wherein $R^7$ is propyl, isopropyl, n-butyl, tert-butyl, or sec-butyl; wherein $R^{11}$ is hydrogen or methyl; and wherein $R^{12}$ is fluoro, chloro, bromo, cyano, methyl, ethyl, propyl, isopropyl, —CH$_2$F, —CH$_2$Cl, —(C=O)CH$_3$, or —CH$_2$(C=O)OCH$_3$.

Also disclosed are compounds having a structure represented by a formula:

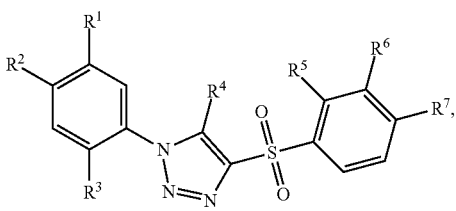

wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —CO$_2$H, —(C=O)H, —(C=O)—(C1-C6 alkyl), —(C=O)—O(C1-C6 alkyl); wherein $R^3$ is hydroxy, halogen, C1-C6 alkyl, C1-C6 alkoxy, and —(C1-C6)-OH; wherein $R^4$ is hydrogen, cyano, halogen, C2-C6 alkyl, C1-C6 monohaloalkyl, C1-C6 polyhaloalkyl, —(C=O)—(C1-C6 alkyl), —(C=O)—O(C1-C6 alkyl), —(C1-C6 alkyl)-(C=O)—(C1-C6 alkyl), —(C1-C6 alkyl)-(C=O)—O(C1-C6 alkyl), Ar$^1$, or Cy$^1$; wherein Ar$^1$ is monocyclic aryl or monocyclic heteraryl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein Cy$^1$ is C3-C8 cycloalkyl or C2-C7 heterocycloalkyl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein $R^5$ is hydrogen, halogen, hydroxy, C1-C3 alkyl; wherein $R^6$ is hydrogen, halogen, hydroxy, C1-C3 alkyl; wherein $R^7$ is C1-C6 alkyl; or a pharmaceutically acceptable salt thereof.

Also disclosed are compounds having a structure represented by a formula:

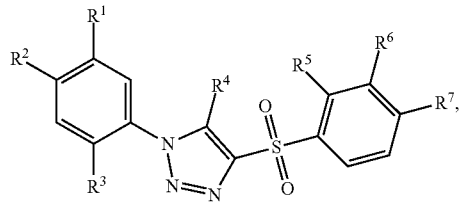

wherein $R^1$ is hydroxy, halogen, methyl, ethyl, methoxy, or ethoxy; wherein $R^2$ is hydrogen, fluoro, or methyl; wherein $R^3$ is hydroxy, halogen, methyl, ethyl, methoxy, or ethoxy; wherein $R^4$ is fluoro, chloro, bromo, cyano, propyl, isopropyl, —CH$_2$F, —CH$_2$Cl, —(C=O)CH$_3$, or —CH$_2$(C=O)OCH$_3$, wherein $R^5$ is hydrogen, hydroxy, or methyl; wherein $R^6$ is hydrogen, hydroxy, or methyl; and wherein $R^7$ is propyl, isopropyl, n-butyl, tert-butyl, or sec-butyl.

Also disclosed are compounds having a structure represented by a formula:

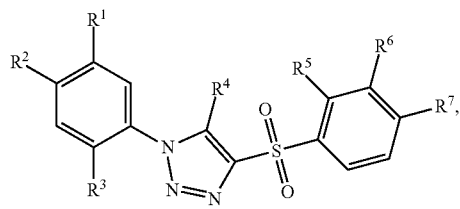

wherein $R^1$ is hydroxy, halogen, C1-C6 alkyl, C1-C6 alkoxy, and —(C1-C6)-OH; wherein $R^2$ is halogen, cyano, C1-C6 alkyl, C1-C6 alkoxy, C1-C6 monohaloalkyl, C1-C6 polyhaloalkyl, —CO$_2$H, —(C=O)H, —(C=O)—(C1-C6 alkyl), —(C=O)—O(C1-C6 alkyl); wherein $R^3$ is hydroxy, halogen, C1-C6 alkyl, C1-C6 alkoxy, and —(C1-C6)-OH; wherein $R^4$ is hydrogen, cyano, halogen, C1-C6 alkyl, C1-C6 monohaloalkyl, C1-C6 polyhaloalkyl, —(C=O)—(C1-C6 alkyl), —(C=O)—O(C1-C6 alkyl), —(C1-C6 alkyl)-(C=O)—(C1-C6 alkyl), —(C1-C6 alkyl)-(C=O)—O(C1-C6 alkyl), Ar$^1$, or Cy$^1$; wherein Ar$^1$ is monocyclic aryl or monocyclic heteraryl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein Cy$^1$ is C3-C8 cycloalkyl or C2-C7 heterocycloalkyl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein $R^5$ is hydrogen, halogen, hydroxy, C1-C3 alkyl; wherein $R^6$ is hydrogen, halogen, hydroxy, C1-C3 alkyl; wherein $R^7$ is C1-C6 alkyl; or a pharmaceutically acceptable salt thereof.

Also disclosed are compounds having a structure represented by a formula:

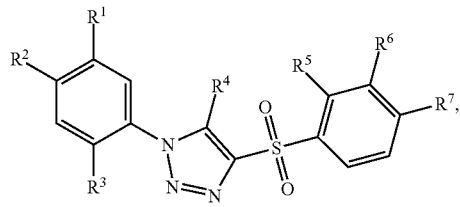

wherein $R^1$ is hydroxy, halogen, methyl, ethyl, methoxy, or ethoxy; wherein $R^2$ is fluoro or methyl; wherein $R^3$ is hydroxy, halogen, methyl, ethyl, methoxy, or ethoxy; wherein $R^4$ is fluoro, chloro, bromo, cyano, methyl, ethyl, propyl, isopropyl, —CH$_2$F, —CH$_2$Cl, —(C═O)CH$_3$, or —CH$_2$(C═O)OCH$_3$, wherein $R^5$ is hydrogen, hydroxy, or methyl; wherein $R^6$ is hydrogen, hydroxy, or methyl; and wherein $R^7$ is propyl, isopropyl, n-butyl, tert-butyl, or sec-butyl.

Also disclosed are compounds having a structure represented by a formula:

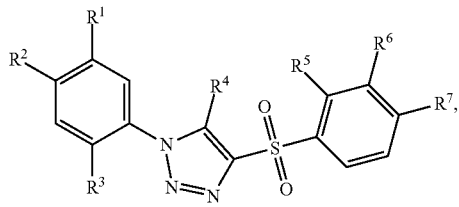

wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —CO$_2$H, —(C═O)H, —(C═O)—(C1-C6 alkyl), —(C═O)—O(C1-C6 alkyl); wherein $R^3$ is hydroxy, halogen, C1-C6 alkyl, C1-C6 alkoxy, and —(C1-C6)-OH; wherein $R^4$ is hydrogen, cyano, halogen, C1-C6 alkyl, C1-C6 monohaloalkyl, C1-C6 polyhaloalkyl, —(C═O)—(C1-C6 alkyl), —(C═O)—O(C1-C6 alkyl), —(C1-C6 alkyl)-(C═O)—(C1-C6 alkyl), —(C1-C6 alkyl)-(C═O)—O(C1-C6 alkyl), Ar$^1$, or Cy$^1$; wherein Ar$^1$ is monocyclic aryl or monocyclic heteroaryl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein Cy$^1$ is C3-C8 cycloalkyl or C2-C7 heterocycloalkyl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein $R^5$ is hydrogen, halogen, hydroxy, C1-C3 alkyl; wherein $R^6$ is hydrogen, halogen, hydroxy, C1-C3 alkyl; wherein at least one of $R^5$ or $R^6$ is not hydrogen; wherein $R^7$ is C1-C6 alkyl; or a pharmaceutically acceptable salt thereof.

Also disclosed are compounds having a structure represented by a formula:

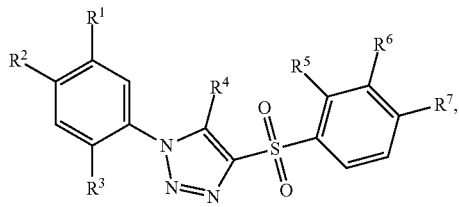

wherein $R^1$ is hydroxy, halogen, methyl, ethyl, methoxy, or ethoxy; wherein $R^2$ is hydrogen, fluoro, or methyl; wherein $R^3$ is hydroxy, halogen, methyl, ethyl, methoxy, or ethoxy; wherein $R^4$ is fluoro, chloro, bromo, cyano, methyl, ethyl, propyl, isopropyl, —CH$_2$F, —CH$_2$Cl, —(C═O)CH$_3$, or —CH$_2$(C═O)OCH$_3$, wherein $R^5$ is hydrogen, hydroxy, or methyl; wherein $R^6$ is hydrogen, hydroxy, or methyl; wherein at least one of $R^5$ or $R^6$ is not hydrogen; and wherein $R^7$ is propyl, isopropyl, n-butyl, tert-butyl, or sec-butyl.

Also disclosed are compounds having a structure represented by a formula:

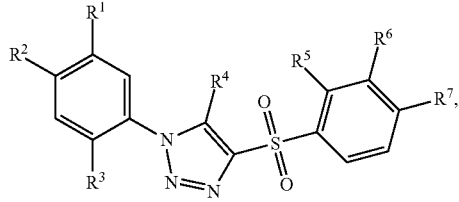

wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —CO$_2$H, —(C═O)H, —(C═O)—(C1-C6 alkyl), —(C═O)—O(C1-C6 alkyl); wherein $R^3$ is hydroxy, halogen, C1-C6 alkyl, C1-C6 alkoxy, and —(C1-C6)-OH; wherein at least one of $R^1$ or $R^3$ is hydroxy; wherein $R^4$ is hydrogen, cyano, halogen, C1-C6 alkyl, C1-C6 monohaloalkyl, C1-C6 polyhaloalkyl, —(C═O)—(C1-C6 alkyl), —(C═O)—O(C1-C6 alkyl), —(C1-C6 alkyl)-(C═O)—(C1-C6 alkyl), —(C1-C6 alkyl)-(C═O)—O(C1-C6 alkyl), Ar$^1$, or Cy$^1$; wherein Ar$^1$ is monocyclic aryl or monocyclic heteroaryl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein Cy$^1$ is C3-C8 cycloalkyl or C2-C7 heterocycloalkyl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; wherein $R^5$ is hydrogen, halogen, hydroxy, C1-C3 alkyl; wherein $R^6$ is hydrogen, halogen, hydroxy, C1-C3 alkyl; wherein $R^7$ is C1-C6 alkyl; or a pharmaceutically acceptable salt thereof.

Also disclosed are compounds having a structure represented by a formula:

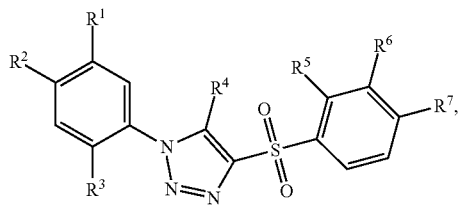

wherein $R^1$ is hydroxy, halogen, methyl, ethyl, methoxy, or ethoxy; wherein $R^2$ is hydrogen, fluoro, or methyl; wherein $R^3$ is hydroxy, halogen, methyl, ethyl, methoxy, or ethoxy; wherein at least one of $R^1$ or $R^3$ is hydroxy; wherein $R^4$ is fluoro, chloro, bromo, cyano, methyl, ethyl, propyl, isopropyl, —CH$_2$F, —CH$_2$Cl, —(C═O)CH$_3$, or —CH$_2$(C═O)OCH$_3$, wherein $R^5$ is hydrogen, hydroxy, or methyl; wherein $R^6$ is hydrogen, hydroxy, or methyl; and wherein $R^7$ is propyl, isopropyl, n-butyl, tert-butyl, or sec-butyl.

a. L Groups

In an aspect, L is SO$_2$, C═O, or NR$^{10}$. In a further aspect, L is C═O or NR$^{10}$. In a still further aspect, L is SO$_2$ or C═O. In a yet further aspect, L is SO$_2$ or NR$^{10}$.

In a further aspect, L is SO$_2$. In a still further aspect, L is C═O. In a yet further aspect, L is NR$^{10}$.

b. $R^1$ Groups

In an aspect, $R^1$ is hydroxy, halogen, C1-C6 alkyl, C1-C6 alkoxy, or —(C1-C6)-OH.

In a further aspect, $R^1$ is hydroxy, —F, —Cl, —Br, methyl, ethyl, propyl, isopropyl, tert-butyl, sec-butyl, isobutyl, —OCH$_3$, —OCH$_2$CH$_3$, —O(CH$_2$)$_2$CH$_3$, —OCH(CH$_3$)$_2$, —(CH$_2$)—OH, —(CH$_2$)$_2$—OH, or —(CH$_2$)$_3$—OH. In a still further aspect, $R^1$ is hydroxy, —F, —Cl, —Br, methyl, —OCH$_3$, or —(CH$_2$)—OH.

In a further aspect, $R^1$ is hydroxy. In a still further aspect, $R^1$ is —F. In a yet further aspect, $R^1$ is —Cl. In an even further aspect, $R^1$ is —Br. In a still further aspect, $R^1$ is methyl. In a yet further aspect, $R^1$ is —OCH$_3$. In an even further aspect, $R^1$ is —(CH$_2$)—OH.

In a further aspect, $R^1$ is hydroxy, halogen, C1-C6 alkyl, C1-C6 alkoxy, or —(C1-C6)-OH; and at least one of $R^1$ or $R^3$ is hydroxy.

In a further aspect, $R^1$ is hydroxy, —F, —Cl, —Br, methyl, ethyl, propyl, isopropyl, tert-butyl, sec-butyl, isobutyl, —OCH$_3$, —OCH$_2$CH$_3$, —O(CH$_2$)$_2$CH$_3$, —OCH(CH$_3$)$_2$, —(CH$_2$)—OH, —(CH$_2$)$_2$—OH, or —(CH$_2$)$_3$—OH, and at least one of $R^1$ or $R^3$ is hydroxy. In a still further aspect, $R^1$ is hydroxy, —F, —Cl, —Br, methyl, —OCH$_3$, or —(CH$_2$)—OH, and at least one of $R^1$ or $R^3$ is hydroxy.

In a further aspect, $R^1$ is hydroxy, and $R^3$ is hydroxy. In a still further aspect, $R^1$ is —F, and $R^3$ is hydroxy. In a yet further aspect, $R^1$ is —Cl, and $R^3$ is hydroxy. In an even further aspect, $R^1$ is —Br, and $R^3$ is hydroxy. In a still further aspect, $R^1$ is methyl, and $R^3$ is hydroxy. In a yet further aspect, $R^1$ is —OCH$_3$, and $R^3$ is hydroxy. In an even further aspect, $R^1$ is —(CH$_2$)—OH, and $R^3$ is hydroxy.

c. $R^2$ Groups

In an aspect, $R^2$ is hydrogen, halogen, cyano, C1-C6 alkyl, C1-C6 alkoxy, C1-C6 monohaloalkyl, C1-C6 polyhaloalkyl, —CO$_2$H, —(C=O)H, —(C=O)—(C1-C6 alkyl), or —(C=O)—O(C1-C6 alkyl).

In a further aspect, $R^2$ is hydrogen. In a still further aspect, In a still further aspect, $R^2$ is hydrogen or halogen. In a yet further aspect, $R^2$ is halogen.

In a further aspect, $R^2$ is halogen, cyano, C1-C6 alkyl, C1-C6 alkoxy, C1-C6 monohaloalkyl, C1-C6 polyhaloalkyl, —CO$_2$H, —(C=O)H, —(C=O)—(C1-C6 alkyl), —(C=O)—O(C1-C6 alkyl).

In a further aspect, $R^2$ is hydrogen, —F, —Cl, —Br, methyl, ethyl, OCH$_3$, —OCH$_2$CH$_3$, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CO$_2$H, —(C=O)H, —(C=O)CH$_3$, —(C=O)CH$_2$CH$_3$, —(C=O)OCH$_3$, or —(C=O)OCH$_2$CH$_3$. In a still further aspect, $R^2$ is hydrogen, —F, —Cl, —Br, methyl, OCH$_3$, —CHF$_2$, —CF$_3$, —CHCl$_2$, —CCl$_3$, —CHBr$_2$, —CBr$_3$, —CO$_2$H, —(C=O)H, —(C=O)CH$_3$, or —(C=O)OCH$_3$. In a yet further aspect, $R^2$ is hydrogen, —F, —Cl, —Br, methyl, OCH$_3$, —CHF$_2$, —CF$_3$, —CHCl$_2$, —CCl$_3$, —CHBr$_2$, or —CBr$_3$. In an even further aspect, $R^2$ is hydrogen, —F, —Cl, or —Br, methyl, —F, —Cl, —Br, methyl, OCH$_3$, —CHF$_2$, —CF$_3$, —CHCl$_2$, —CCl$_3$, —CHBr$_2$, or —CBr$_3$.

In a further aspect, $R^2$ is —F, —Cl, —Br, methyl, ethyl, OCH$_3$, —OCH$_2$CH$_3$, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CO$_2$H, —(C=O)H, —(C=O)CH$_3$, —(C=O)CH$_2$CH$_3$, —(C=O)OCH$_3$, or —(C=O)OCH$_2$CH$_3$. In a still further aspect, $R^2$ is —F, —Cl, —Br, methyl, OCH$_3$, —CHF$_2$, —CF$_3$, —CHCl$_2$, —CCl$_3$, —CHBr$_2$, —CBr$_3$, —CO$_2$H, —(C=O)H, —(C=O)CH$_3$, or —(C=O)OCH$_3$. In a yet further aspect, $R^2$ is —F, —Cl, —Br, methyl, OCH$_3$, —CHF$_2$, —CF$_3$, —CHCl$_2$, —CCl$_3$, —CHBr$_2$, or —CBr$_3$. In an even further aspect, $R^2$ is —F, —Cl, or —Br, methyl, —F, —Cl, —Br, methyl, OCH$_3$, —CHF$_2$, —CF$_3$, —CHCl$_2$, —CCl$_3$, —CHBr$_2$, or —CBr$_3$.

d. $R^3$ Groups

In an aspect, $R^3$ is hydroxy, halogen, C1-C6 alkyl, C1-C6 alkoxy, or —(C1-C6)-OH.

In a further aspect, $R^3$ is hydroxy, —F, —Cl, —Br, methyl, ethyl, propyl, isopropyl, tert-butyl, sec-butyl, isobutyl, —OCH$_3$, —OCH$_2$CH$_3$, —O(CH$_2$)$_2$CH$_3$, —OCH(CH$_3$)$_2$, —(CH$_2$)—OH, —(CH$_2$)$_2$—OH, or —(CH$_2$)$_3$—OH. In a still further aspect, $R^3$ is hydroxy, —F, —Cl, —Br, methyl, —OCH$_3$, or —(CH$_2$)—OH.

In a further aspect, $R^3$ is hydroxy. In a still further aspect, $R^3$ is —F. In a yet further aspect, $R^3$ is —Cl. In an even further aspect, $R^3$ is —Br. In a still further aspect, $R^3$ is methyl. In a yet further aspect, $R^3$ is —OCH$_3$. In an even further aspect, $R^3$ is —(CH$_2$)—OH.

In a further aspect, $R^3$ is hydroxy, halogen, C1-C6 alkyl, C1-C6 alkoxy, or —(C1-C6)-OH; and at least one of $R^1$ or $R^3$ is hydroxy.

In a further aspect, $R^3$ is hydroxy, —F, —Cl, —Br, methyl, ethyl, propyl, isopropyl, tert-butyl, sec-butyl, isobutyl, —OCH$_3$, —OCH$_2$CH$_3$, —O(CH$_2$)$_2$CH$_3$, —OCH(CH$_3$)$_2$, —(CH$_2$)—OH, —(CH$_2$)$_2$—OH, or —(CH$_2$)$_3$—OH, and at least one of $R^1$ or $R^3$ is hydroxy. In a still further aspect, $R^3$ is hydroxy, —F, —Cl, —Br, methyl, —OCH$_3$, or —(CH$_2$)—OH, and at least one of $R^1$ or $R^3$ is hydroxy.

In a further aspect, $R^3$ is hydroxy, and $R^1$ is hydroxy. In a still further aspect, $R^3$ is —F, and $R^1$ is hydroxy. In a yet further aspect, $R^3$ is —Cl, and $R^1$ is hydroxy. In an even further aspect, $R^3$ is —Br, and $R^1$ is hydroxy. In a still further aspect, $R^3$ is methyl, and $R^1$ is hydroxy. In a yet further aspect, $R^3$ is —OCH$_3$, and $R^1$ is hydroxy. In an even further aspect, $R^3$ is —(CH$_2$)—OH, and $R^1$ is hydroxy.

e. $R^4$ Groups

In an aspect, $R^4$ is hydrogen, cyano, halogen, C1-C6 alkyl, C1-C6 monohaloalkyl, C1-C6 polyhaloalkyl, —(C=O)—(C1-C6 alkyl), —(C=O)—O(C1-C6 alkyl), —(C1-C6 alkyl)-(C=O)—(C1-C6 alkyl), —(C1-C6 alkyl)-(C=O)—OH, —(C1-C6 alkyl)-(C=O)—O(C1-C6 alkyl), Ar$^1$, or Cy$^1$.

In a further aspect, $R^4$ is hydrogen, cyano, halogen, C2-C6 alkyl, C1-C6 monohaloalkyl, C1-C6 polyhaloalkyl, —(C=O)—(C1-C6 alkyl), —(C=O)—O(C1-C6 alkyl), —(C1-C6 alkyl)-(C=O)—(C1-C6 alkyl), —(C1-C6 alkyl)-(C=O)—O(C1-C6 alkyl), Ar$^1$, or Cy$^1$.

In a further aspect, $R^4$ is methyl, ethyl, propyl, isopropyl, n-butyl, tert-butyl, sec-butyl, isobutyl, neopentyl, isopentyl, sec-pentyl, or tert-pentyl. In a still further aspect, $R^4$ is methyl, ethyl, propyl, isopropyl, n-butyl, tert-butyl, sec-butyl, or isobutyl. In a yet further aspect, $R^4$ is methyl, ethyl, propyl, or isopropyl. In an even further aspect, $R^4$ is methyl or ethyl. In a still further aspect, $R^4$ is methyl.

In a further aspect, $R^4$ is ethyl, propyl, isopropyl, n-butyl, tert-butyl, sec-butyl, isobutyl, neopentyl, isopentyl, sec-pentyl, or tert-pentyl. In a still further aspect, $R^4$ is ethyl, propyl, isopropyl, n-butyl, tert-butyl, sec-butyl, or isobutyl. In a yet further aspect, $R^4$ is ethyl, propyl, or isopropyl. In an even further aspect, $R^4$ is ethyl.

In a further aspect, $R^4$ is propyl, isopropyl, n-butyl, tert-butyl, sec-butyl, isobutyl, neopentyl, isopentyl, sec-pentyl, or tert-pentyl. In a still further aspect, $R^4$ is propyl, isopropyl, n-butyl, tert-butyl, sec-butyl, or isobutyl. In a yet further aspect, $R^4$ is propyl or isopropyl. In an even further aspect, $R^4$ is propyl. In a still further aspect, $R^4$ is isopropyl.

f. $R^5$ Groups

In an aspect, $R^5$ is hydrogen, halogen, hydroxy, or C1-C3 alkyl. In a further aspect, $R^5$ is hydrogen.

In a further aspect, $R^5$ is hydrogen, —F, —Cl, —Br, hydroxy, methyl, or ethyl. In a still further aspect, $R^5$ is hydrogen, —F, —Cl, —Br, hydroxy, or methyl. In a yet further aspect, $R^5$ is hydrogen, —F, —Cl, —Br, or hydroxy. In an even further aspect, $R^5$ is hydrogen, hydroxy, methyl, or ethyl. In a still further aspect, $R^5$ is —F. In a yet further aspect, $R^5$ is —Cl. In an even further aspect, $R^5$ is —Br. In a still further aspect, $R^5$ is hydroxy. In a yet further aspect, $R^5$ is methyl.

In a further aspect, $R^5$ is hydrogen, halogen, hydroxy, C1-C3 alkyl; and at least one of $R^5$ or $R^6$ is not hydrogen.

In a further aspect, $R^5$ is hydrogen, —F, —Cl, —Br, hydroxy, methyl, or ethyl; and at least one of $R^5$ or $R^6$ is not hydrogen. In a still further aspect, $R^5$ is hydrogen, —F, —Cl, —Br, hydroxy, or methyl; and at least one of $R^5$ or $R^6$ is not hydrogen. In a yet further aspect, $R^5$ is hydrogen, —F, —Cl, —Br, or hydroxy; and at least one of $R^5$ or $R^6$ is not hydrogen. In an even further aspect, $R^5$ is hydrogen, hydroxy, methyl, or ethyl; and at least one of $R^5$ or $R^6$ is not hydrogen.

In a further aspect, $R^5$ is —F, —Cl, —Br, hydroxy, methyl, or ethyl, and $R^6$ is hydrogen. In a still further aspect, $R^5$ is —F, —Cl, —Br, hydroxy, or methyl, and $R^6$ is hydrogen. In a yet further aspect, $R^5$—F, —Cl, —Br, or hydroxy, and $R^6$ is hydrogen. In an even further aspect, $R^5$ is hydroxy, methyl, or ethyl, and $R^6$ is hydrogen. In a still further aspect, $R^5$ is —F, and $R^6$ is hydrogen. In a yet further aspect, $R^5$ is —Cl, and $R^6$ is hydrogen. In an even further aspect, $R^5$ is —Br, and $R^6$ is hydrogen. In a still further aspect, $R^5$ is hydroxy, and $R^6$ is hydrogen. In a yet further aspect, $R^5$ is methyl, and $R^6$ is hydrogen.

g. $R^6$ Groups

In an aspect, $R^6$ is hydrogen, halogen, hydroxy, or C1-C3 alkyl. In a further aspect, $R^6$ is hydrogen.

In a further aspect, $R^6$ is hydrogen, —F, —Cl, —Br, hydroxy, methyl, or ethyl. In a still further aspect, $R^6$ is hydrogen, —F, —Cl, —Br, hydroxy, or methyl. In a yet further aspect, $R^6$ is hydrogen, —F, —Cl, —Br, or hydroxy. In an even further aspect, $R^6$ is hydrogen, hydroxy, methyl, or ethyl. In a still further aspect, $R^6$ is —F. In a yet further aspect, $R^6$ is —Cl. In an even further aspect, $R^6$ is —Br. In a still further aspect, $R^6$ is hydroxy. In a yet further aspect, $R^6$ is methyl.

In a further aspect, $R^6$ is hydrogen, halogen, hydroxy, C1-C3 alkyl; and at least one of $R^6$ or $R^6$ is not hydrogen.

In a further aspect, $R^6$ is hydrogen, —F, —Cl, —Br, hydroxy, methyl, or ethyl; and at least one of $R^6$ or $R^6$ is not hydrogen. In a still further aspect, $R^6$ is hydrogen, —F, —Cl, —Br, hydroxy, or methyl; and at least one of $R^6$ or $R^6$ is not hydrogen. In a yet further aspect, $R^6$ is hydrogen, —F, —Cl, —Br, or hydroxy; and at least one of $R^6$ or $R^6$ is not hydrogen. In an even further aspect, $R^6$ is hydrogen, hydroxy, methyl, or ethyl; and at least one of $R^6$ or $R^6$ is not hydrogen.

In a further aspect, $R^6$ is —F, —Cl, —Br, hydroxy, methyl, or ethyl, and $R^5$ is hydrogen. In a still further aspect, $R^6$ is —F, —Cl, —Br, hydroxy, or methyl, and $R^5$ is hydrogen. In a yet further aspect, $R^6$—F, —Cl, —Br, or hydroxy, and $R^5$ is hydrogen. In an even further aspect, $R^6$ is hydroxy, methyl, or ethyl, and $R^5$ is hydrogen. In a still further aspect, $R^6$ is —F, and $R^5$ is hydrogen. In a yet further aspect, $R^6$ is —Cl, and $R^5$ is hydrogen. In an even further aspect, $R^6$ is —Br, and $R^6$ is hydrogen. In a still further aspect, $R^6$ is hydroxy, and $R^5$ is hydrogen. In a yet further aspect, $R^6$ is methyl, and $R^5$ is hydrogen.

h. $R^7$ Groups

In an aspect, $R^7$ is C1-C6 alkyl. In a further aspect, $R^7$ is methyl, ethyl, propyl, isopropyl, n-butyl, tert-butyl, sec-butyl, isobutyl, neopentyl, isopentyl, sec-pentyl, or tert-pentyl. In a still further aspect, $R^7$ is methyl, ethyl, propyl, isopropyl, n-butyl, tert-butyl, sec-butyl, or isobutyl.

In a further aspect, $R^7$ is n-butyl, tert-butyl, sec-butyl, or isobutyl. In a still further aspect, $R^7$ is n-butyl. In a yet further aspect, $R^7$ is tert-butyl. In an even further aspect, $R^7$ is sec-butyl. In a still further aspect, $R^7$ is isobutyl.

In a further aspect, $R^7$ is methyl. In a still further aspect, $R^7$ is ethyl. In a yet further aspect, $R^7$ is propyl. In an even further aspect, $R^7$ is isopropyl. In a still further aspect, $R^7$ is propyl or isopropyl. In a yet further aspect, $R^7$ is isopropyl or tert-butyl.

i. $R^{10}$ Groups

In an aspect, $R^{10}$ is hydrogen or C1-C3 alkyl. In a further aspect, $R^{10}$ is hydrogen or methyl. In a still further aspect, $R^{10}$ is hydrogen. In a yet further aspect, $R^{10}$ is methyl.

j. $R^{11}$ Groups

In an aspect, $R^{11}$ is hydrogen or C1-C6 alkyl. In a further aspect, $R^{11}$ is hydrogen, methyl, ethyl, propyl, isopropyl, n-butyl, tert-butyl, sec-butyl, isobutyl, neopentyl, isopentyl, sec-pentyl, or tert-pentyl. In a still further aspect, $R^{11}$ is hydrogen, methyl, ethyl, propyl, isopropyl, n-butyl, tert-butyl, sec-butyl, or isobutyl.

In a further aspect, $R^{11}$ is hydrogen, n-butyl, tert-butyl, sec-butyl, or isobutyl. In a still further aspect, $R^{11}$ is hydrogen or n-butyl. In a yet further aspect, $R^{11}$ is hydrogen or tert-butyl. In an even further aspect, $R^{11}$ is hydrogen or sec-butyl. In a still further aspect, $R^{11}$ is hydrogen or isobutyl.

In a further aspect, $R^{11}$ is hydrogen or methyl. In a still further aspect, $R^{11}$ is hydrogen or ethyl. In a yet further aspect, $R^{11}$ is hydrogen or propyl. In an even further aspect, $R^{11}$ is hydrogen or isopropyl. In a still further aspect, $R^{11}$ is hydrogen, propyl or isopropyl. In a yet further aspect, $R^{11}$ is hydrogen, isopropyl or tert-butyl.

In an aspect, $R^{11}$ is C1-C6 alkyl. In a further aspect, $R^{11}$ is methyl, ethyl, propyl, isopropyl, n-butyl, tert-butyl, sec-butyl, isobutyl, neopentyl, isopentyl, sec-pentyl, or tert-pentyl. In a still further aspect, $R^{11}$ is methyl, ethyl, propyl, isopropyl, n-butyl, tert-butyl, sec-butyl, or isobutyl.

In a further aspect, $R^{11}$ is n-butyl, tert-butyl, sec-butyl, or isobutyl. In a still further aspect, $R^{11}$ is n-butyl. In a yet further aspect, $R^{11}$ is tert-butyl. In an even further aspect, $R^{11}$ is sec-butyl. In a still further aspect, $R^{11}$ is isobutyl.

In a further aspect, $R^{11}$ is methyl. In a still further aspect, $R^{11}$ is ethyl. In a yet further aspect, $R^{11}$ is propyl. In an even further aspect, $R^{11}$ is isopropyl. In a still further aspect, $R^{11}$ is propyl or isopropyl. In a yet further aspect, $R^{11}$ is isopropyl or tert-butyl.

k. $R^{12}$ Groups

In an aspect, $R^{12}$ is hydrogen, cyano, halogen, C1-C6 alkyl, C1-C6 monohaloalkyl, C1-C6 polyhaloalkyl, —(C=O)—(C1-C6 alkyl), —(C=O)—O(C1-C6 alkyl), —(C1-C6 alkyl)-(C=O)—(C1-C6 alkyl), —(C1-C6 alkyl)-(C=O)—OH, —(C1-C6 alkyl)-(C=O)—O(C1-C6 alkyl), $Ar^1$, or $Cy^1$.

In a further aspect, $R^{12}$ is hydrogen, cyano, halogen, C2-C6 alkyl, C1-C6 monohaloalkyl, C1-C6 polyhaloalkyl, —(C=O)—(C1-C6 alkyl), —(C=O)—O(C1-C6 alkyl), —(C1-C6 alkyl)-(C=O)—(C1-C6 alkyl), —(C1-C6 alkyl)-(C=O)—O(C1-C6 alkyl), $Ar^1$, or $Cy^1$.

In a further aspect, $R^{12}$ is methyl, ethyl, propyl, isopropyl, n-butyl, tert-butyl, sec-butyl, isobutyl, neopentyl, isopentyl, sec-pentyl, or tert-pentyl. In a still further aspect, $R^{12}$ is methyl, ethyl, propyl, isopropyl, n-butyl, tert-butyl, sec-butyl, or isobutyl. In a yet further aspect, $R^{12}$ is methyl, ethyl, propyl, or isopropyl. In an even further aspect, $R^{12}$ is methyl or ethyl. In a still further aspect, $R^{12}$ is methyl.

In a further aspect, $R^{12}$ is ethyl, propyl, isopropyl, n-butyl, tert-butyl, sec-butyl, isobutyl, neopentyl, isopentyl, sec-pentyl, or tert-pentyl. In a still further aspect, $R^{12}$ is ethyl, propyl, isopropyl, n-butyl, tert-butyl, sec-butyl, or isobutyl. In a yet further aspect, $R^{12}$ is ethyl, propyl, or isopropyl. In an even further aspect, $R^{12}$ is ethyl.

In a further aspect, $R^{12}$ is propyl, isopropyl, n-butyl, tert-butyl, sec-butyl, isobutyl, neopentyl, isopentyl, sec-pentyl, or tert-pentyl. In a still further aspect, $R^{12}$ is propyl, isopropyl, n-butyl, tert-butyl, sec-butyl, or isobutyl. In a yet further aspect, $R^{12}$ is propyl or isopropyl. In an even further aspect, $R^{12}$ is propyl. In a still further aspect, $R^{12}$ is isopropyl.

1. $Ar^1$ Groups

In an aspect, $Ar^1$ is monocyclic aryl or monocyclic heteroaryl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl.

m. $Cy^1$ Groups

In an aspect, $Cy^1$ is C3-C8 cycloalkyl or C2-C7 heterocycloalkyl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl.

2. Example Compounds

In an aspect, a compound can be present as one or more of the following structures:

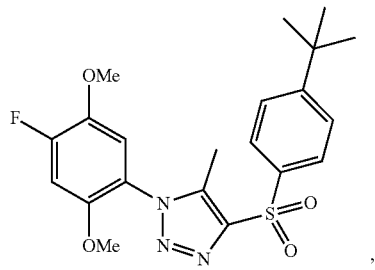
,

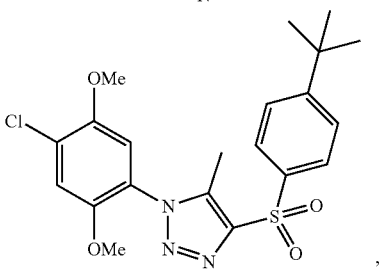
,

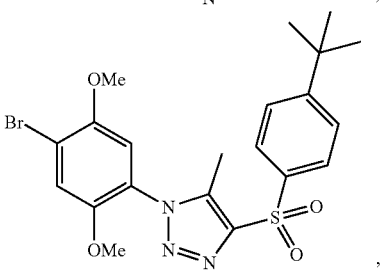
,

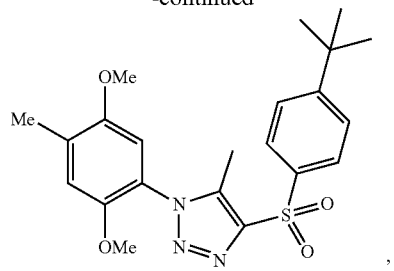
,

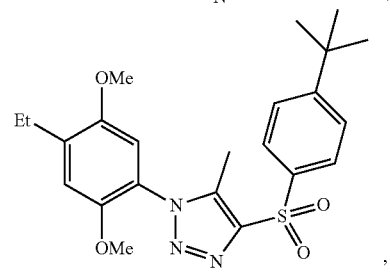
,

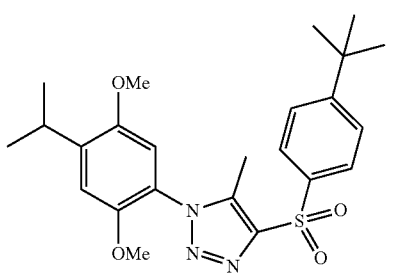
,

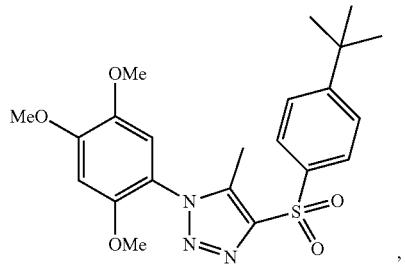
,

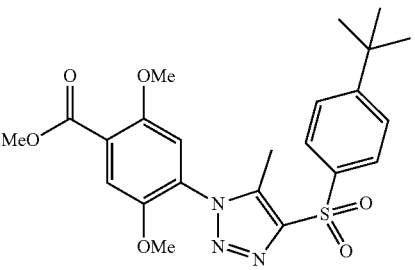
,

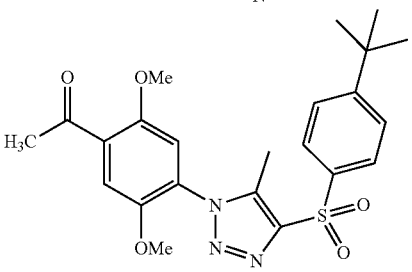
,

51
-continued
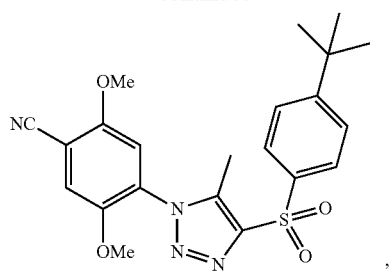
,
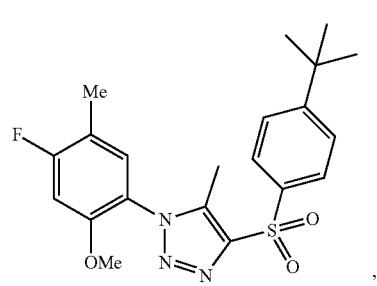
,
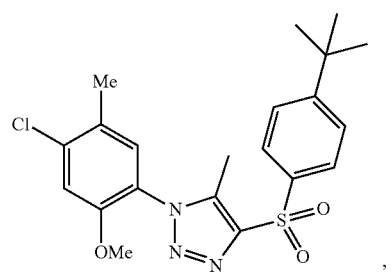
,
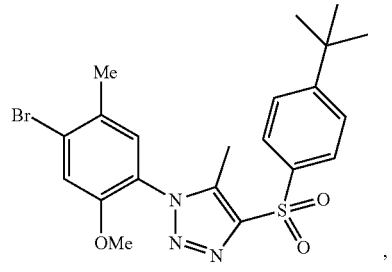
,
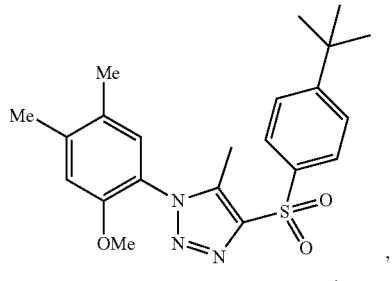
,
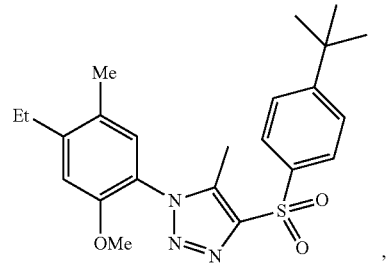
,
52
-continued
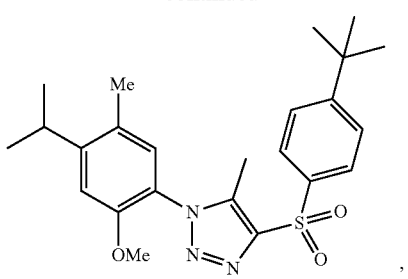
,
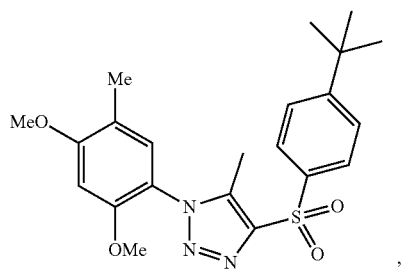
,
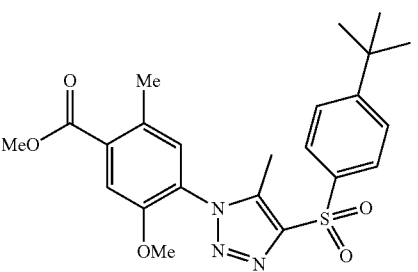
,
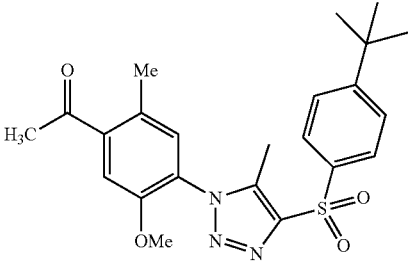
,
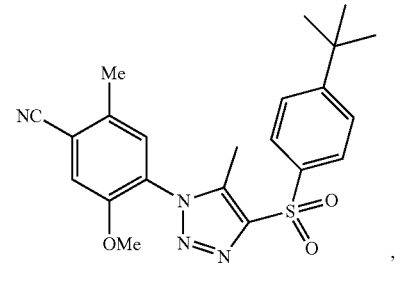
,
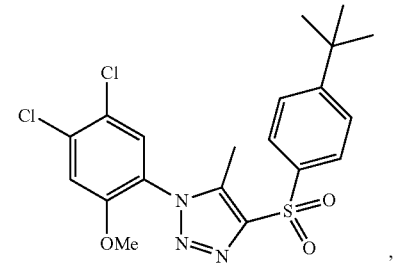
,

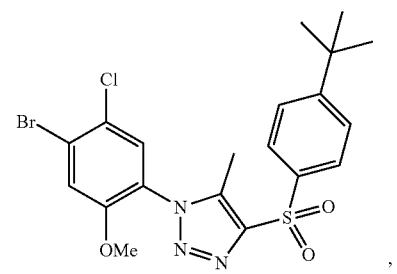,
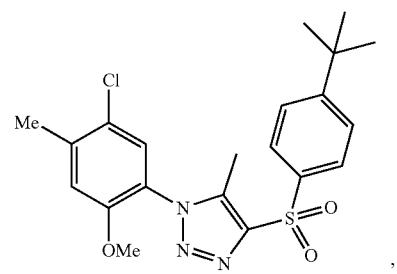,
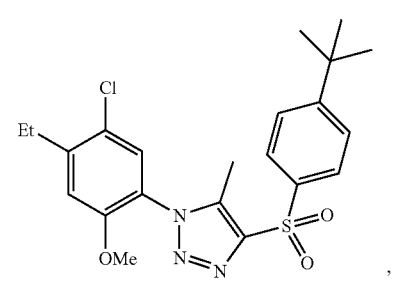,
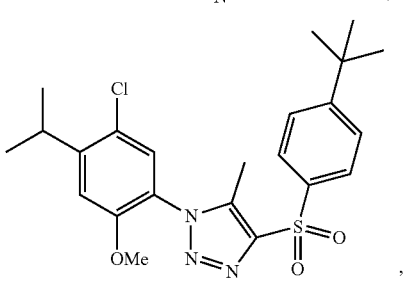,
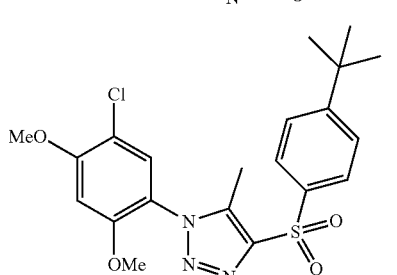,
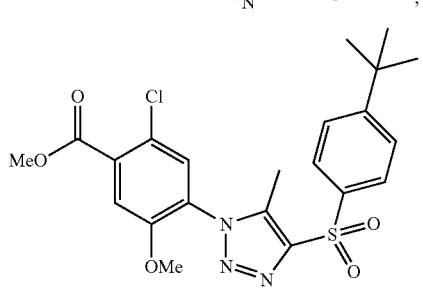,
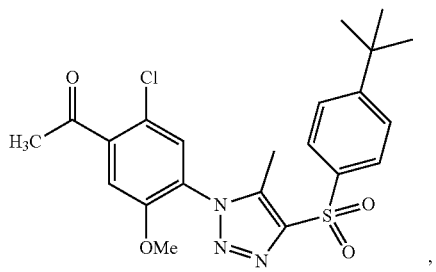,
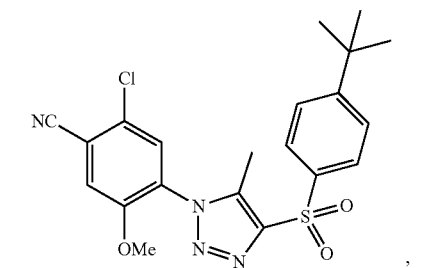,
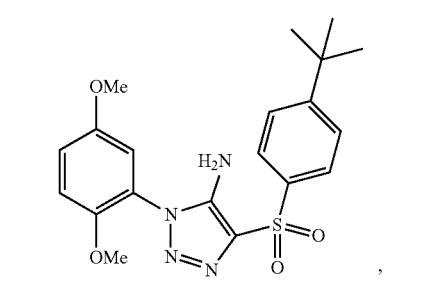,
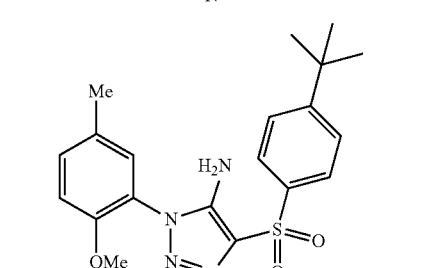,
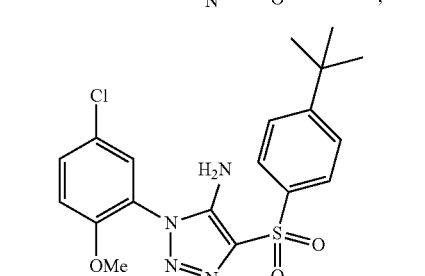,
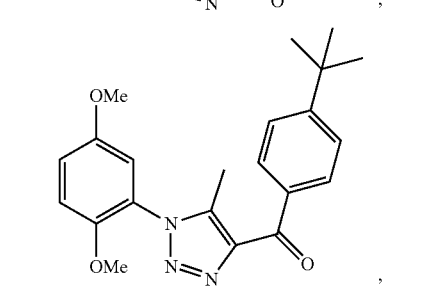,

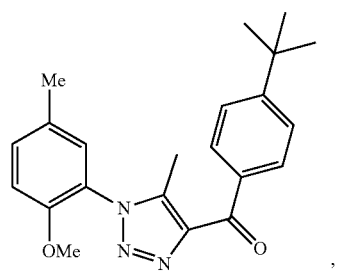,
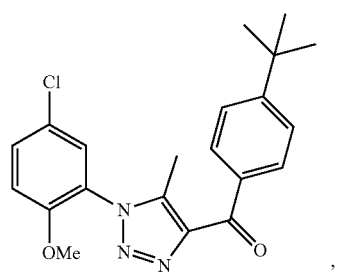,
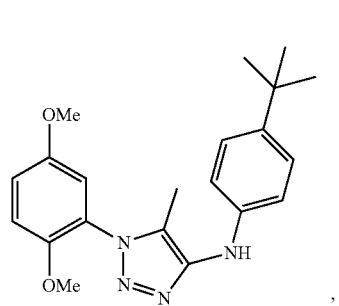,
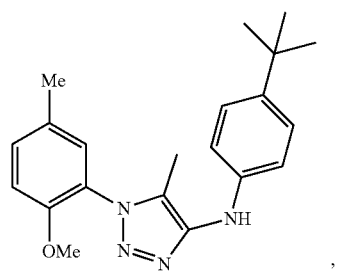,
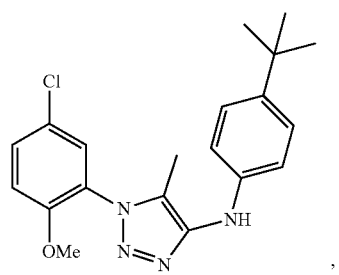,
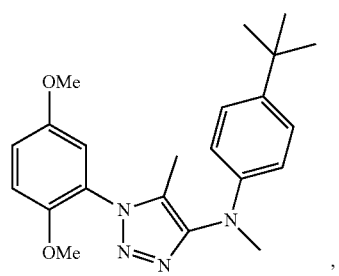,
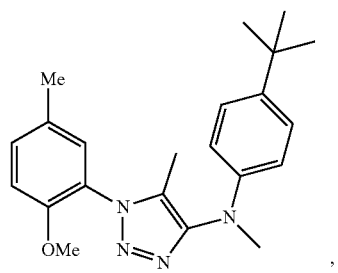,
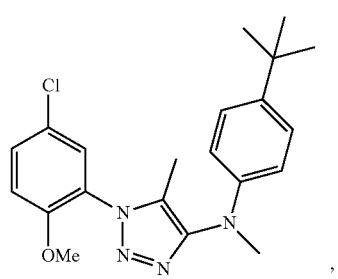,
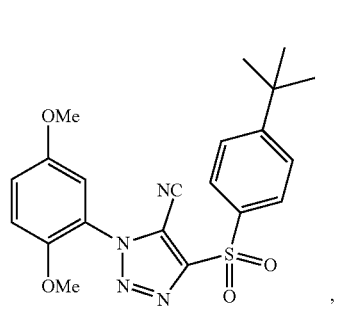,
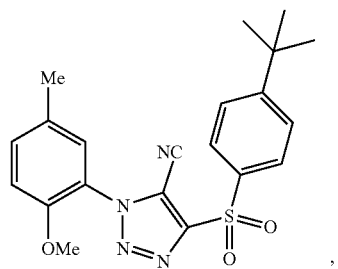,
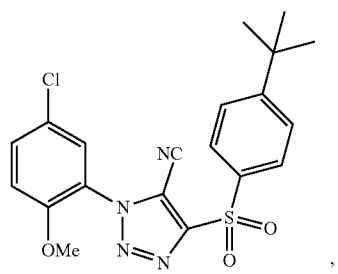,
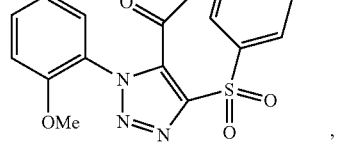, -continued
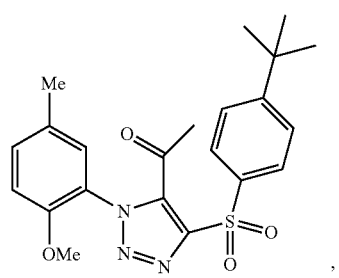
,
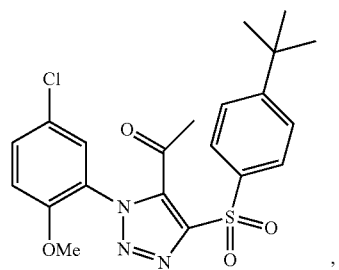
,
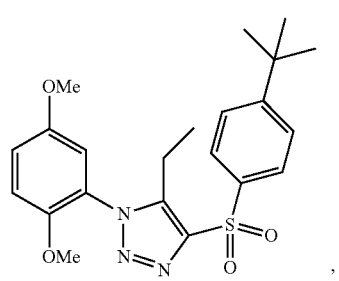
,
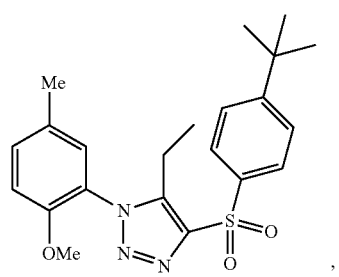
,
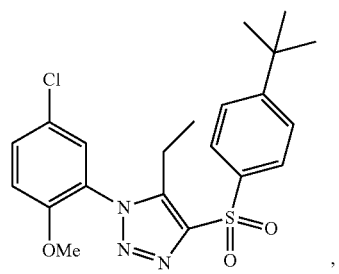
,
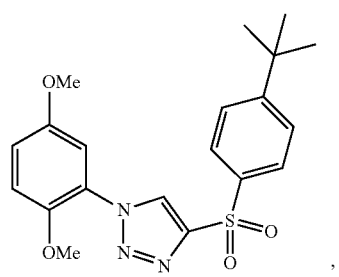
,
-continued
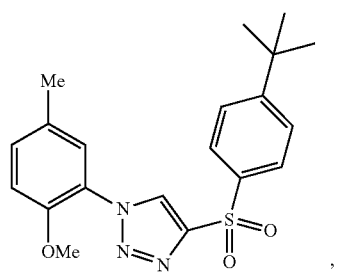
,
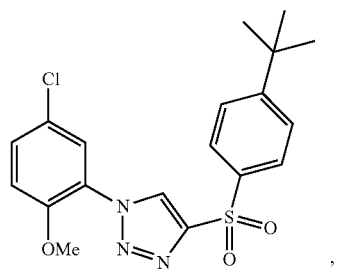
,
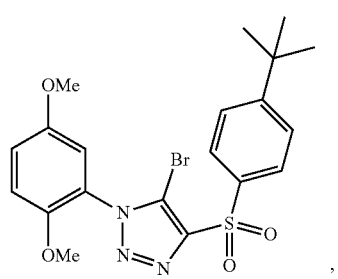
,
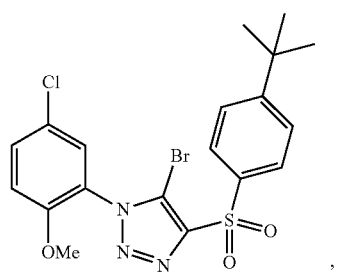
,
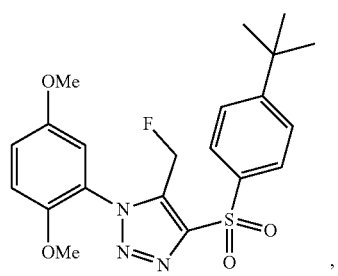
,
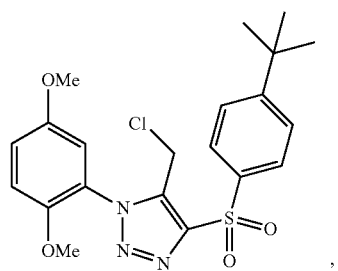
,

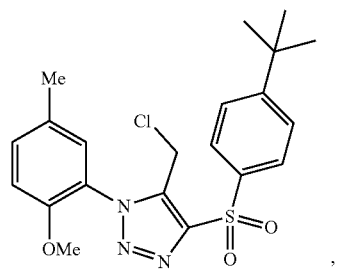,
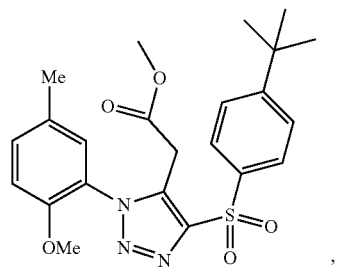,
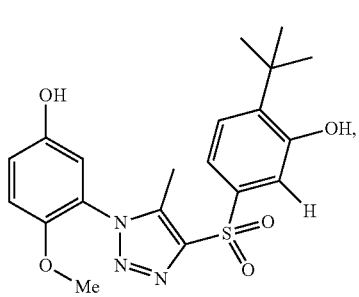,
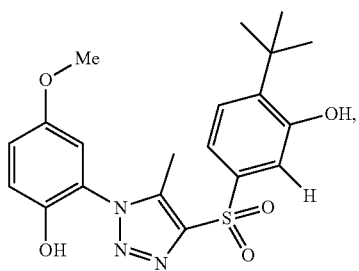,
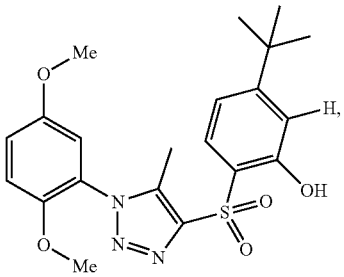,
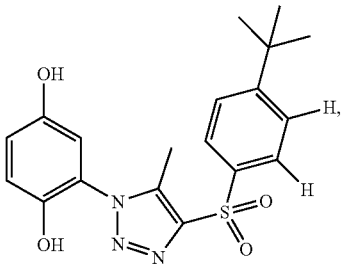,
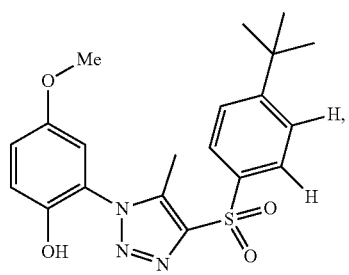,
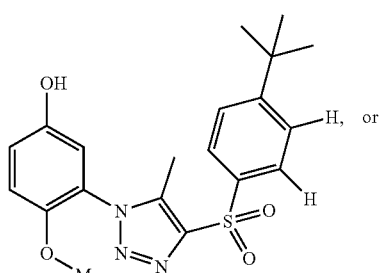, or
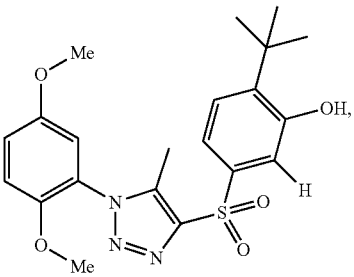,
or a pharmaceutically acceptable salt thereof.
In an aspect, a compound can be present as one or more of the following structures:
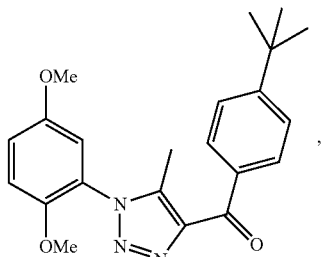,
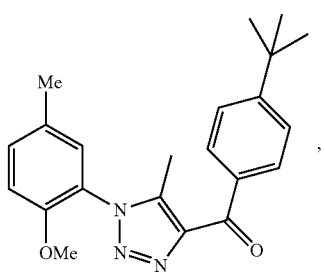, -continued
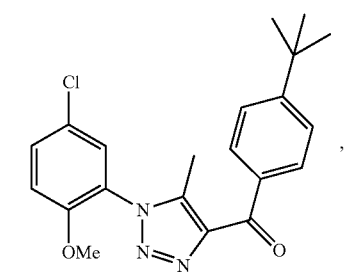
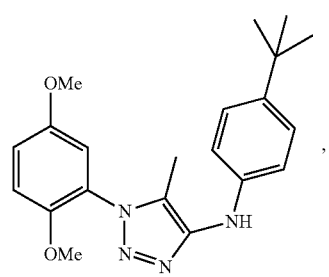
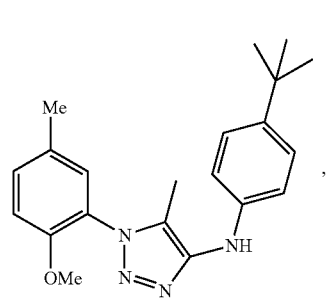
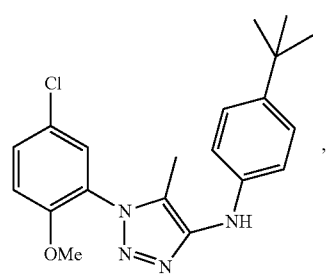
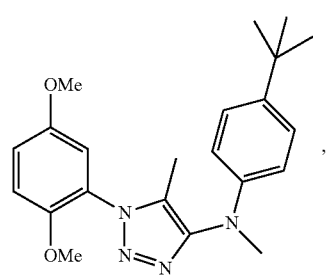
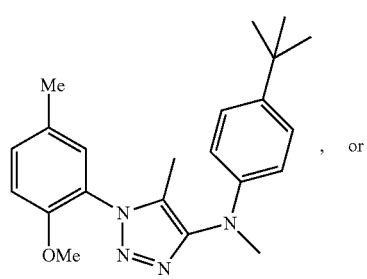, or
-continued
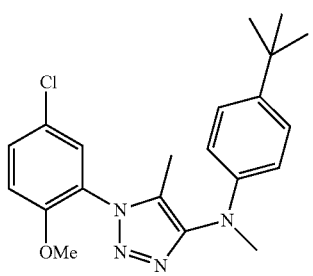
or a pharmaceutically acceptable salt thereof.
In an aspect, a compound can be present as one or more of the following structures:
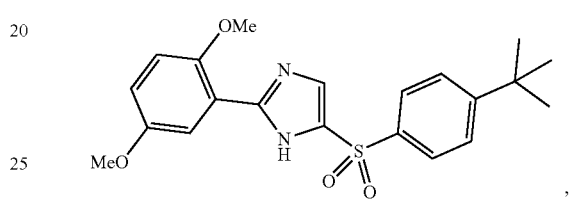
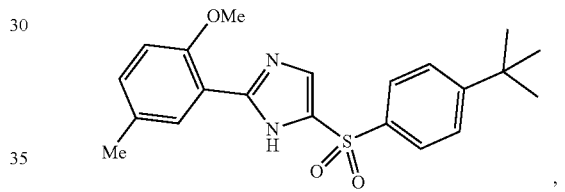
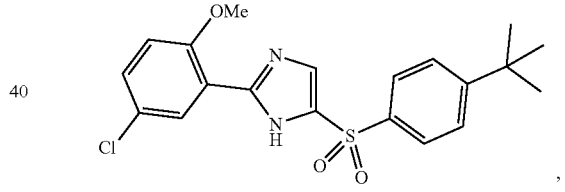
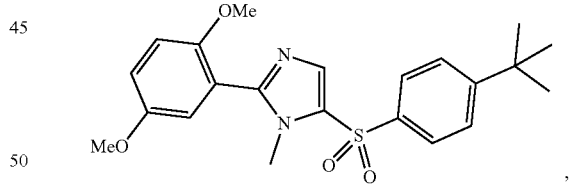
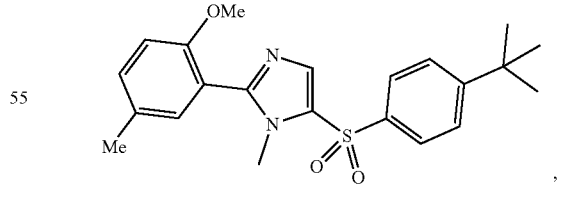
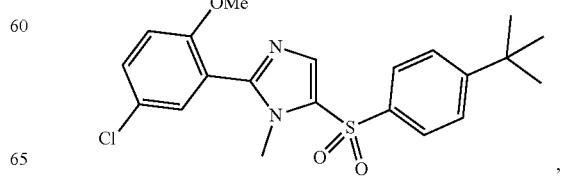

-continued
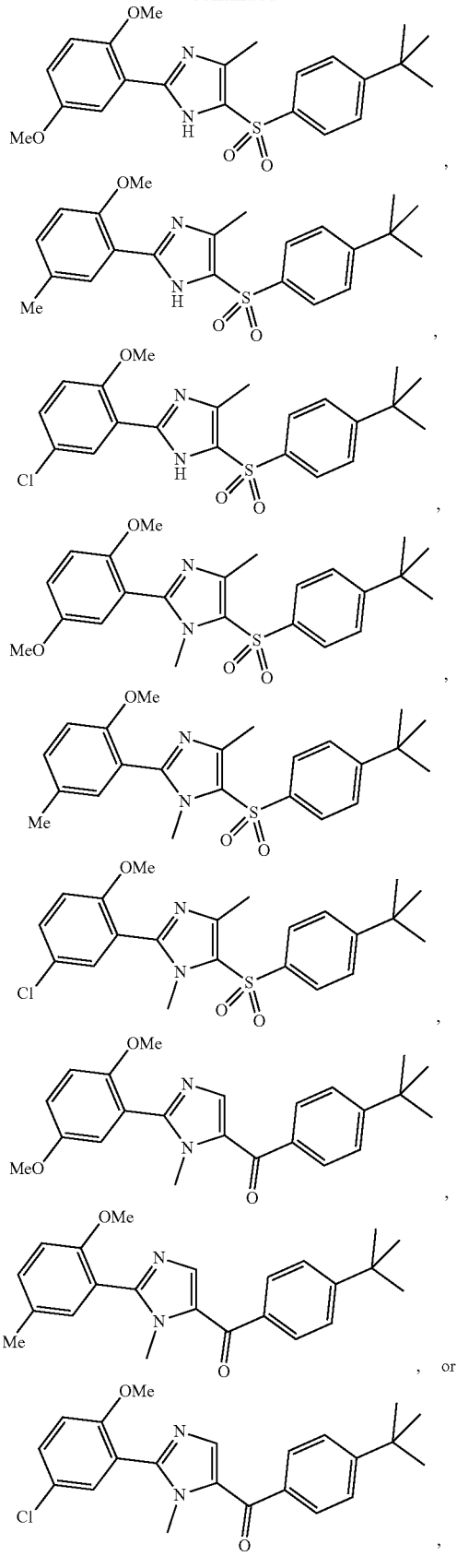
or a pharmaceutically acceptable salt thereof.
In an aspect, a compound can be present as one or more of the following structures:
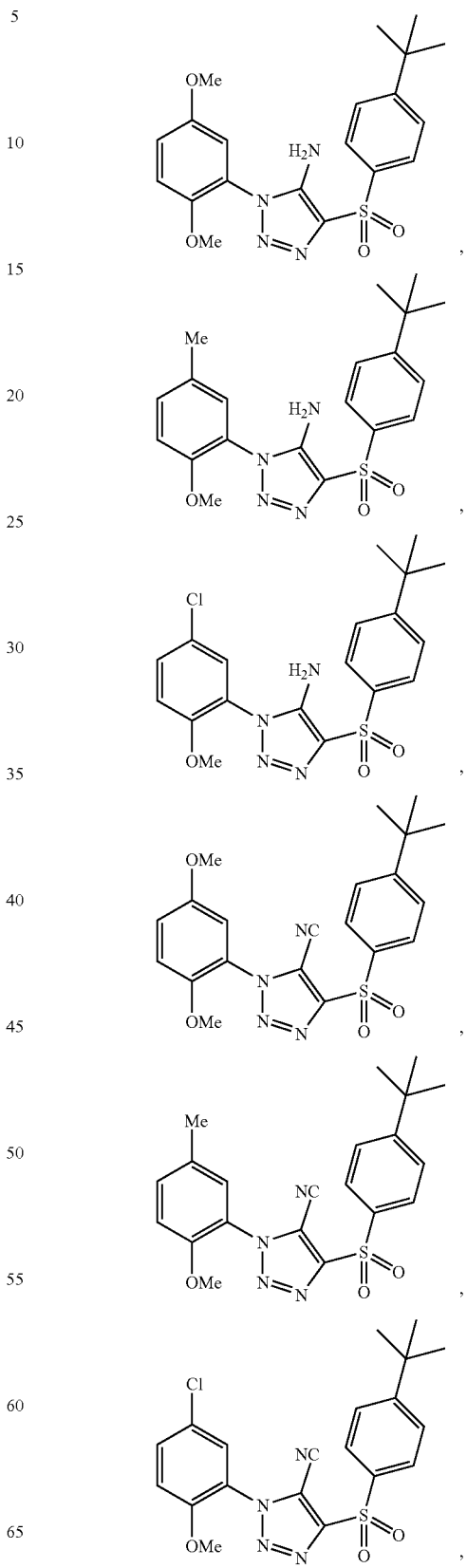

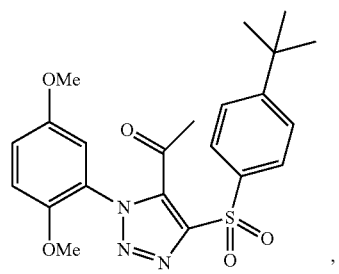
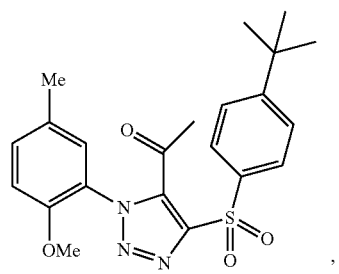
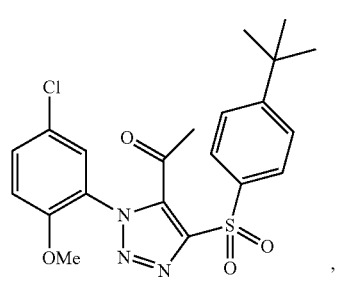
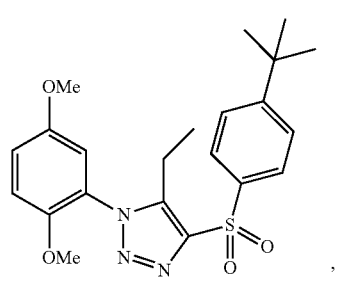
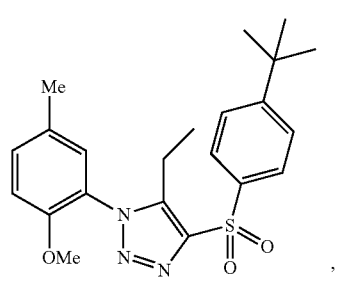
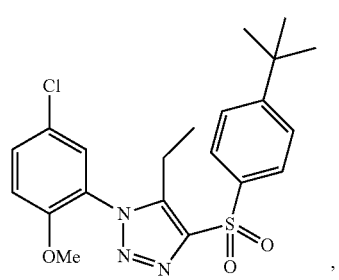
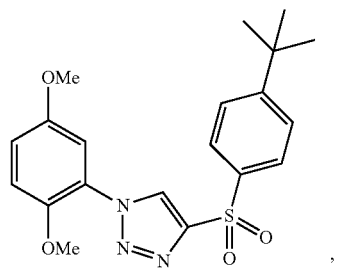
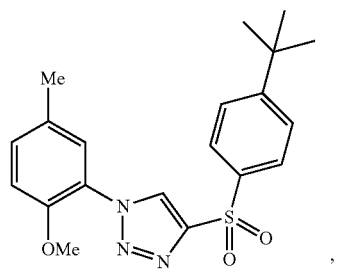
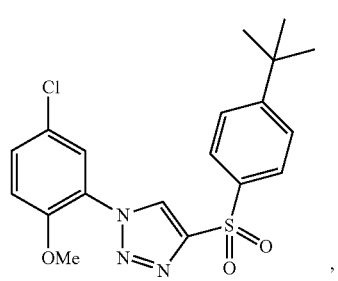
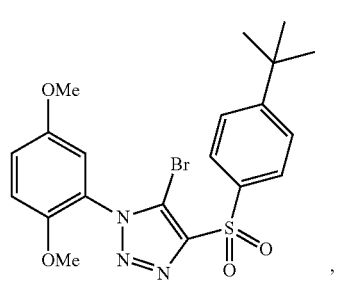
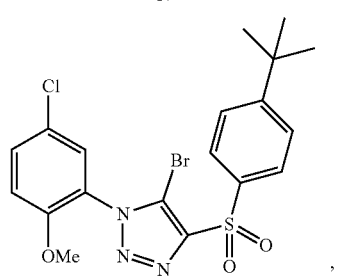
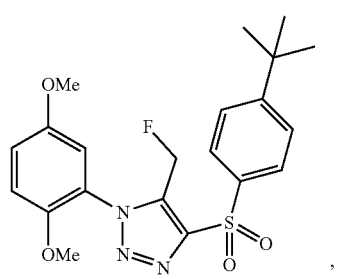

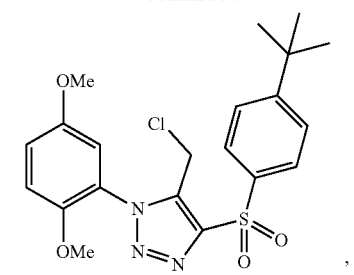
,
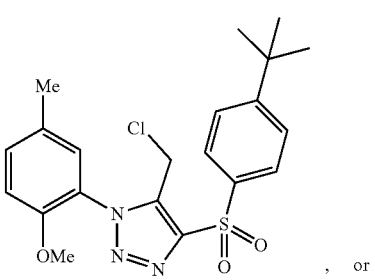
, or
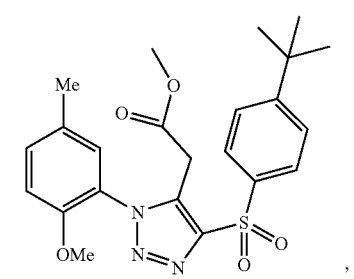
,
or a pharmaceutically acceptable salt thereof.
In an aspect, a compound can be present as one or more of the following structures:
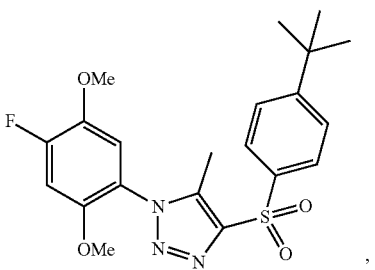
,
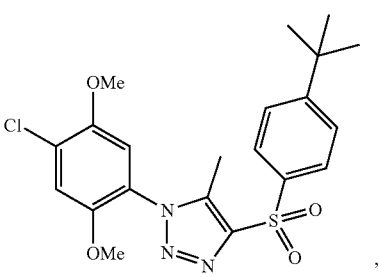
,
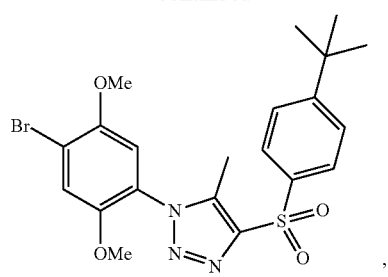
,
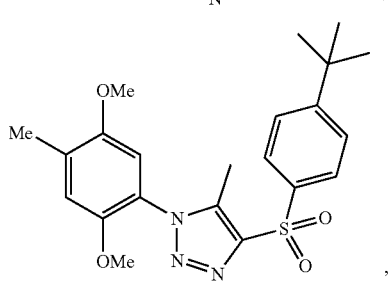
,
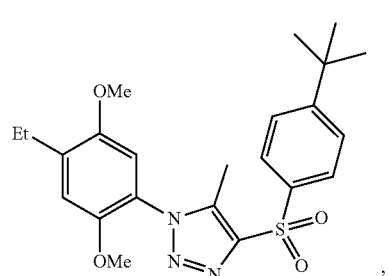
,
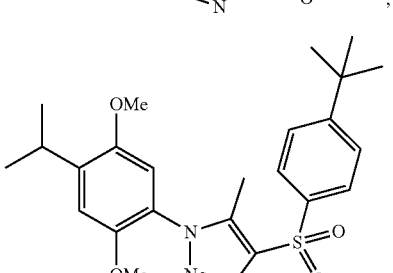
,
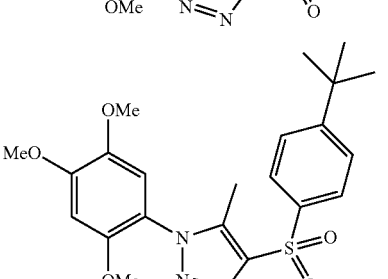
,
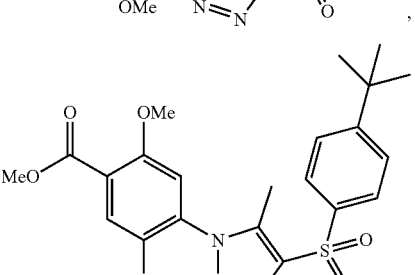
, 69
-continued
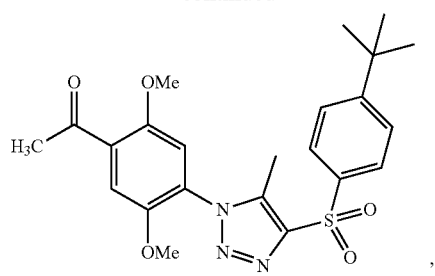,
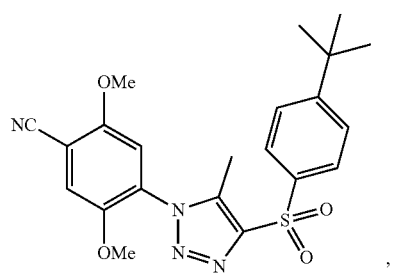,
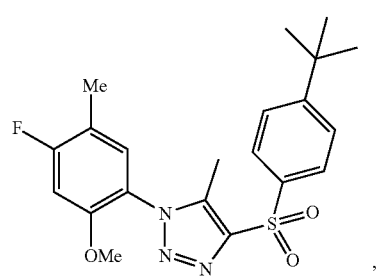,
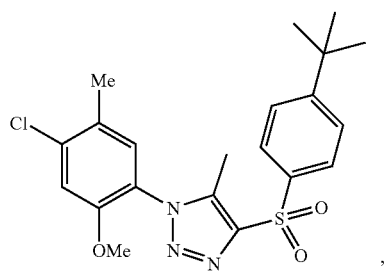,
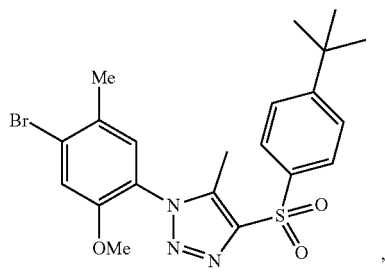,
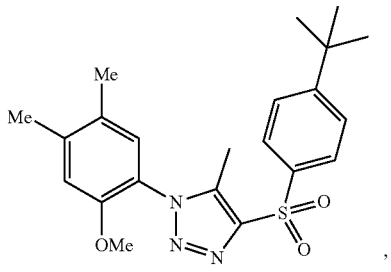,
70
-continued
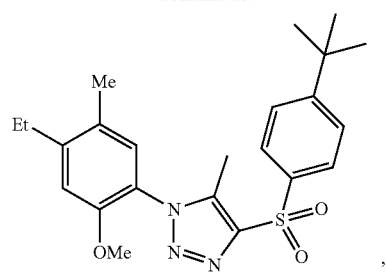,
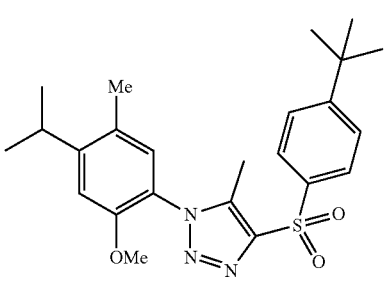,
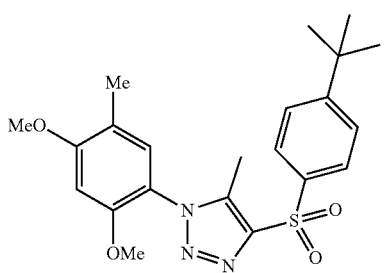,
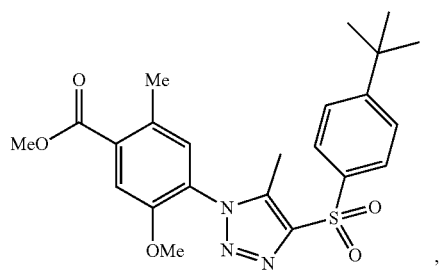,
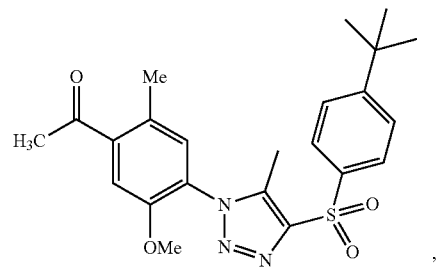,
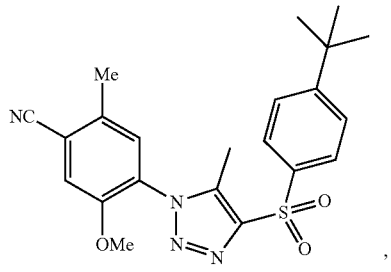, -continued
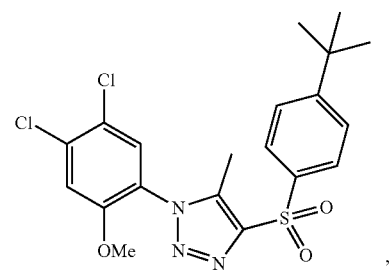
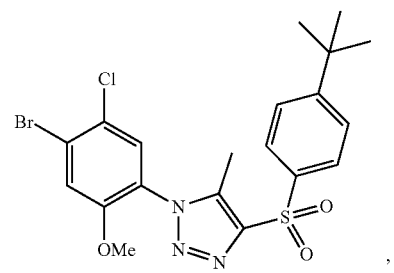
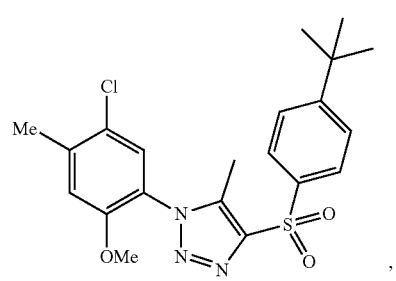
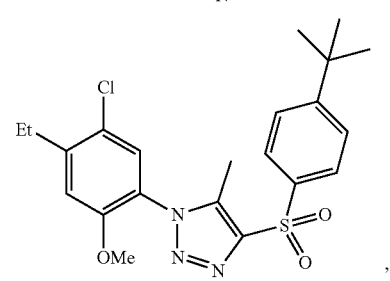
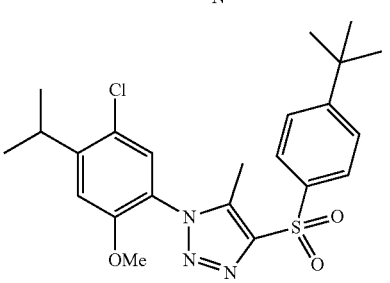
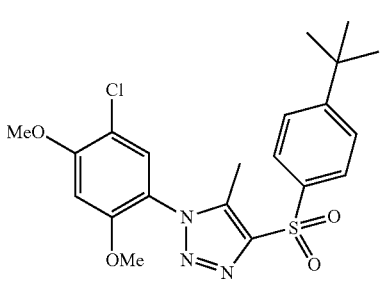
-continued
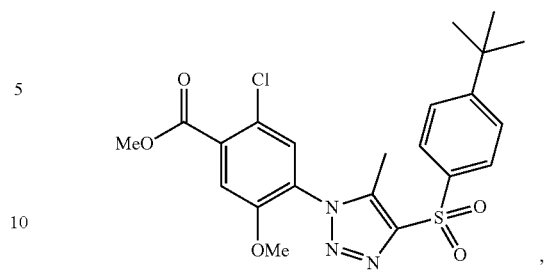
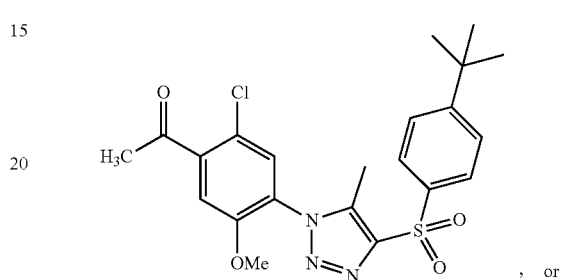
, or
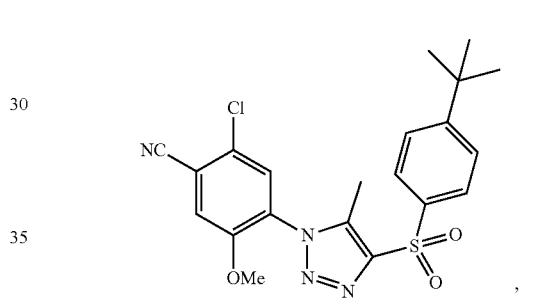
or a pharmaceutically acceptable salt thereof.
In an aspect, a compound can be present as one or more of the following structures:
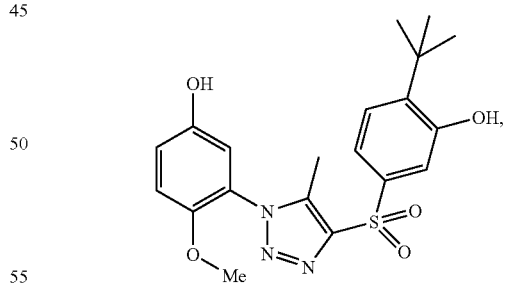
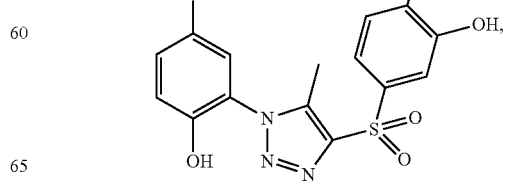

-continued

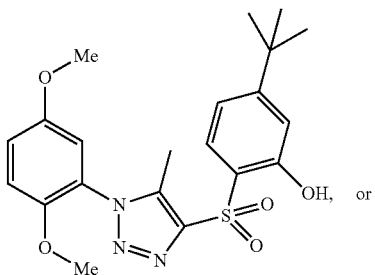

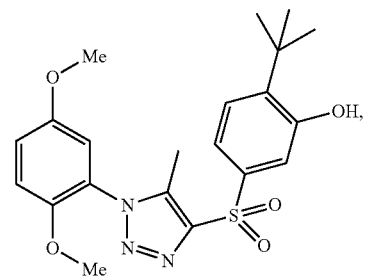

or a pharmaceutically acceptable salt thereof.

In an aspect, a compound can be present as one or more of the following structures:

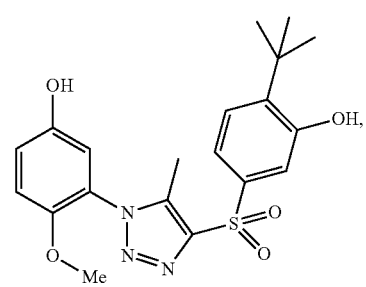

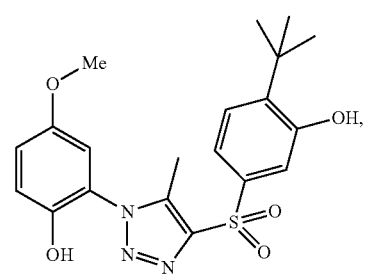

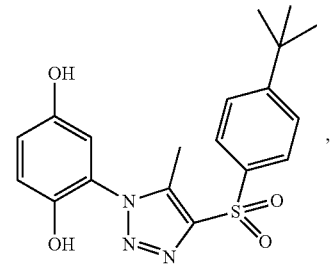

-continued

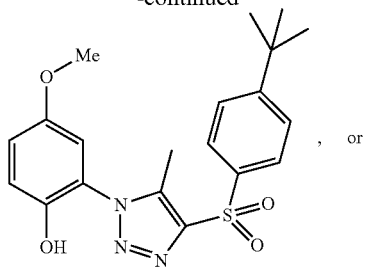

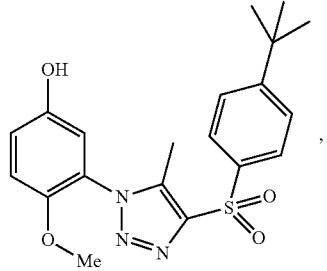

or a pharmaceutically acceptable salt thereof.

C. Pharmaceutical Compositions

In an aspect, the invention relates to pharmaceutical compositions comprising the disclosed compounds and products of disclosed methods. That is, a pharmaceutical composition can be provided comprising an effective amount of at least one disclosed compound, at least one product of a disclosed method, or a pharmaceutically acceptable salt, thereof, and a pharmaceutically acceptable carrier. In an aspect, the invention relates to pharmaceutical compositions comprising a pharmaceutically acceptable carrier and an effective amount of at least one disclosed compound; or a pharmaceutically acceptable salt, thereof.

In a further aspect, the effective amount is a therapeutically effective amount. In a still further aspect, the effective amount is a prophylactically effective amount. In a still further aspect, the pharmaceutical composition comprises a compound that is a product of a disclosed method of making.

In a further aspect, the pharmaceutical composition comprises a therapeutically effective amount of a compound having a structure represented by a formula:

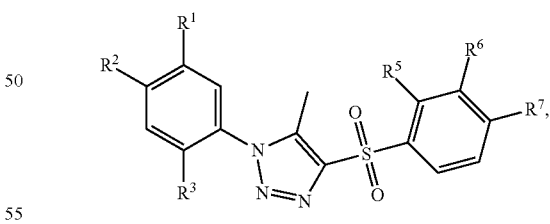

wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —CO$_2$H, —(C=O)H, —(C=O)—(C1-C6 alkyl), —(C=O)—O(C1-C6 alkyl); wherein $R^3$ is hydrogen, hydroxy, halogen, C1-C6 alkyl, C1-C6 alkoxy, and —(C1-C6)-OH; wherein $R^5$ is hydrogen, halogen, hydroxy, C1-C3 alkyl; wherein $R^6$ is hydrogen, halogen, hydroxy, C1-C3 alkyl; and wherein $R^7$ is C1-C6 alkyl; or a pharmaceutically acceptable salt thereof; and a pharmaceutically acceptable carrier.

In a further aspect, the pharmaceutical composition comprises a disclosed compound. In a yet further aspect, the pharmaceutical composition comprises a product of a disclosed method of making.

In a further aspect, the pharmaceutical composition comprises a disclosed compound that exhibits an $IC_{50}$ of less than or equal to about 10 µM as determined in a time-resolved fluorescence resonance transfer (TR-FRET) hPXR competitive binding assay. In a still further aspect, the pharmaceutical composition comprises a disclosed compound that has an $IC_{50}$ of less than or equal to about 5.0 µM as determined in a time-resolved fluorescence resonance transfer (TR-FRET) hPXR competitive binding assay. In a yet further aspect, the pharmaceutical composition comprises a disclosed compound that has an $IC_{50}$ of less than or equal to about 2.5 µM as determined in a time-resolved fluorescence resonance transfer (TR-FRET) hPXR competitive binding assay. In an even further aspect, the pharmaceutical composition comprises a disclosed compound that has an $IC_{50}$ of less than or equal to about 1.0 µM as determined in a time-resolved fluorescence resonance transfer (TR-FRET) hPXR competitive binding assay. In a still further aspect, the pharmaceutical composition comprises a disclosed compound that has an $IC_{50}$ of less than or equal to about 100 nM as determined in a time-resolved fluorescence resonance transfer (TR-FRET) hPXR competitive binding assay. In a yet further aspect, the pharmaceutical composition comprises a disclosed compound that has an $IC_{50}$ of less than or equal to about 1.0 nM as determined in a time-resolved fluorescence resonance transfer (TR-FRET) hPXR competitive binding assay.

In a further aspect, the pharmaceutical composition comprises a disclosed compound that exhibits an $IC_{50}$ of less than or equal to about 10 µM as determined in an hPXR transactivation assay. In a still further aspect, the pharmaceutical composition comprises a disclosed compound that has an $IC_{50}$ of less than or equal to about 5.0 µM as determined in an hPXR transactivation assay. In a yet further aspect, the pharmaceutical composition comprises a disclosed compound that has an $IC_{50}$ of less than or equal to about 2.5 µM as determined in an hPXR transactivation assay. In an even further aspect, the pharmaceutical composition comprises a disclosed compound that has an $IC_{50}$ of less than or equal to about 1.0 µM as determined in an hPXR transactivation assay. In a still further aspect, the pharmaceutical composition comprises a disclosed compound that has an $IC_{50}$ of less than or equal to about 100 nM as determined in an hPXR transactivation assay. In a yet further aspect, the pharmaceutical composition comprises a disclosed compound that has an $IC_{50}$ of less than or equal to about 1.0 nM as determined in an hPXR transactivation assay.

In an aspect, the pharmaceutical composition is used to treat a mammal. In a further aspect, the mammal is a human. In a still further aspect, the mammal has been diagnosed with a need for treatment of an adverse drug reaction associated with PXR activity. In a yet further aspect, the mammal has been diagnosed with a need for treatment of an adverse drug reaction associated with PXR activity prior to the administering step. In an even further aspect, the mammal has been identified to be in need of treatment of an adverse drug reaction. In a still further aspect, the adverse drug reaction is enhanced toxicity, increased metabolism, and/or decreased efficacy. In a yet further aspect, the adverse drug reaction is associated with another therapeutic agent, and the pharmaceutical composition is administered to treat the adverse drug reaction associated with the other therapeutic agent. In an even further aspect, the adverse drug reaction is associated with another therapeutic agent, and the pharmaceutical composition is co-administered the other therapeutic agent in order to treat the adverse drug reaction associated with the other therapeutic agent. In a further aspect, the pharmaceutical composition is used to treat an adverse drug reaction.

In a further aspect, the mammal has been diagnosed with a need for treatment of an infectious disease. In a yet further aspect, the mammal has been diagnosed with a need for treatment of an infectious disease prior to the administering step. In an even further aspect, the mammal has been identified to be in need of treatment of an infectious disease. In a still further aspect, a therapeutic agent known to treat an infectious disease is co-administered with the pharmaceutical composition. In a yet further aspect, the therapeutic agent known to treat an infectious disease that is co-administered with the pharmaceutical composition is isoniazid, isoniazid in combination with rifampin, rifampicin, or flucloxacilline.

In a further aspect, the mammal has been diagnosed with a need for treatment of an inflammatory disease. In a yet further aspect, the mammal has been diagnosed with a need for treatment of an inflammatory disease prior to the administering step. In an even further aspect, the mammal has been identified to be in need of treatment of an inflammatory disease. In a still further aspect, a therapeutic agent known to treat an inflammatory disease is co-administered with the pharmaceutical composition. In a yet further aspect, the therapeutic agent known to treat an inflammatory disease that is co-administered with the pharmaceutical composition is acetaminophen.

In a further aspect, the mammal has been diagnosed with a need for treatment of a seizure or convulsant disorder. In a yet further aspect, the mammal has been diagnosed with a need for treatment of a seizure or convulsant disorder prior to the administering step. In an even further aspect, the mammal has been identified to be in need of treatment of a seizure or convulsant disorder. In a still further aspect, a therapeutic agent known to treat a seizure or convulsant disorder is co-administered with the pharmaceutical composition. In a yet further aspect, the therapeutic agent known to treat a seizure or convulsant disorder that is co-administered with the pharmaceutical composition is phenytoin.

In a further aspect, the mammal has been diagnosed with a need for treatment of a disorder of uncontrolled cellular proliferation, such as a cancer. In a yet further aspect, the mammal has been diagnosed with a need for treatment of a disorder of uncontrolled cellular proliferation prior to the administering step. In an even further aspect, the mammal has been identified to be in need of treatment of a disorder of uncontrolled cellular proliferation. In a still further aspect, a therapeutic agent known to treat a disorder of uncontrolled cellular proliferation is co-administered with the pharmaceutical composition. In a yet further aspect, the therapeutic agent known to treat a disorder of uncontrolled cellular proliferation that is co-administered with the pharmaceutical composition is paclitaxel, irinotecan, leucovorin, dasatinib, or erlotinib.

In various aspects, the pharmaceutical composition of the present invention comprises a pharmaceutically acceptable carrier; an effective amount of at least one disclosed compound; or a pharmaceutically acceptable salt thereof; and an anticancer agent. In a further aspect, the anticancer agent comprises a compound selected from paclitaxel, irinotecan, leucovorin, dasatinib, and erlotinib, or combinations thereof. In a still further aspect, the anticancer agent comprises a compound selected from paclitaxel, docetaxel, vinblastine, vincristine, vinorelbine, camptothecin, topotecan, irinotecan, belotecan, gimatecan, inidimitecan, indotecan, Genz-644282, daunorubicin, epirubicin, etoposide, teniposide, mitoxantrone, ellipticinium, vasaroxin, dexrazoxane, mebarone, 3-hydroxy-2-[(1R)-6-isopropenyl-3-methyl-cyclohex-2-en-1-yl]-5-pentyl-1,4-benzoquinone (HU-331), axitinib, crizotinib, dasatinib, erlotinib, gefitinib, imatinib, lapatinib, nilotinib, pazopanib, regorafenib, ruxolitinib, sorafenib, sunitinib, vandetanib, vemurafenib, doxorubicin, mitoxantrone, bleomycin, daunorubicin, dactinomycin, epirubicin, idarubicin, plicamycin, mitomycin, pentostatin, valrubicin, gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, methotrexate coadministered with leucovorin, thioguanine, carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, streptozocin, etoposide, vincristine, ixabepilone, vinorelbine, vinblastine, teniposide, everolimus, siroliumus, temsirolimus, or combinations thereof.

In various aspects, the pharmaceutical composition of the present invention comprises a pharmaceutically acceptable carrier; an effective amount of at least one disclosed compound; or a pharmaceutically acceptable salt thereof; and an antibacterial agent. In a further aspect, the antibacterial agent comprises a compound selected from isoniazid, isoniazid in combination with rifampin, rifampicin, and flucloxacillin, or combinations thereof.

In various aspects, the pharmaceutical composition of the present invention comprises a pharmaceutically acceptable carrier; an effective amount of at least one disclosed compound; or a pharmaceutically acceptable salt thereof; and a non-steroidal anti-inflammatory drug. In a further aspect, the non-steroidal anti-inflammatory drug comprises acetaminophen.

In various aspects, the pharmaceutical composition of the present invention comprises a pharmaceutically acceptable carrier; an effective amount of at least one disclosed compound; or a pharmaceutically acceptable salt thereof; and an anticonvulsant drug. In a further aspect, the anticonvulsant drug comprises acetaminophen phenytoin.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids," includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require modulation of PXR activity, an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for modulating PXR activity (e.g., modulating adverse reactions or treating a disease of uncontrolled cellular proliferation) in mammals (e.g., humans) comprising combining one or more disclosed compounds, products, or compositions with a pharmaceutically acceptable carrier or diluent. Thus, in an aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

D. Methods of Using the Compounds

Also provided is a method of use of a disclosed compound, composition, or medicament. In an aspect, the method of use is directed to the treatment of an infectious disease. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

In an aspect, the disclosed compounds or products of a disclosed method of making can be coadministered with an anticancer therapeutic agent. In a further aspect, the anticancer therapeutic agent can be paclitaxel, irinotecan, leucovorin, dasatinib, or erlotinib, or combinations thereof. In a still further aspect, anticancer therapeutic agent can be paclitaxel, docetaxel, vinblastine, vincristine, vinorelbine, camptothecin, topotecan, irinotecan, belotecan, gimatecan, inidimitecan, indotecan, Genz-644282, daunorubicin, epirubicin, etoposide, teniposide, mitoxantrone, ellipticinium, vasaroxin, dexrazoxane, mebarone, 3-hydroxy-2-[(1R)-6-isopropenyl-3-methyl-cyclohex-2-en-1-yl]-5-pentyl-1,4-benzoquinone (HU-331), axitinib, crizotinib, dasatinib, erlotinib, gefitinib, imatinib, lapatinib, nilotinib, pazopanib, regorafenib, ruxolitinib, sorafenib, sunitinib, vandetanib, vemurafenib, doxorubicin, mitoxantrone, bleomycin, daunorubicin, dactinomycin, epirubicin, idarubicin, plicamycin, mitomycin, pentostatin, valrubicin, gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, methotrexate coadministered with leucovorin, thioguanine, carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, streptozocin, etopside, vincristine, ixabepilone, vinorelbine, vinblastine, teniposide, everolimus, siroliumus, or temsirolimus, or combinations thereof.

In an aspect, the disclosed compounds or products of a disclosed method of making can be coadministered with an anti-infectious or antibacterial therapeutic agent. In a further aspect, the anti-infectious or antibacterial therapeutic agent can be isoniazid, isoniazid in combination with rifampin, rifampicin, or flucloxacillin, or combinations thereof. In a still further aspect, the anti-infectious or antibacterial therapeutic agent can be amoxicillin, ampicillin, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clavulanic acid, clinafloxacin, clindamycin, clofazimine, cloxacillin, colistin, dalbavancin, dalfopristin, daptomycin, demeclocycline, dicloxacillin, dirithromycin, doxycycline, erythromycin, enrofloxacin, enoxacin, enviomycin, ertepenem, ethambutol, flucloxacillin, fosfomycin, furazolidone, gatifloxacin, gentamicin, imipenem, isoniazid, kanamycin, linezolid, lomefloxacin, loracarbef, mafenide, moxifloxacin, meropenem, metronidazole, mezlocillin, minocycline, mupirocin, nafcillin, nalidixic acid, neomycin, netilmicin, nitrofurantoin, norfloxacin, ofloxacin, oritavancin, oxytetracycline, penicillin, piperacillin, platensimycin, polymixin B, quinupristin, retapamulin, rifabutin, rifampin, rifapentine, roxithromycin, sparfloxacin, spectinomycin, sulbactam, sulfacetamide, sulfamethizole, sulfamethoxazole, teicoplanin, telithromycin, telavancin, temafloxacin, tetracycline, tedolizid, thioacetazone, thioridazine, ticarcillin, tinidazole, tobramycin, torezolid, tosufloxacin, trimethoprim, troleandomycin, trovafloxacin, or vancomycin, or combinations thereof.

In an aspect, the disclosed compounds or products of a disclosed method of making can be coadministered with a non-steroidal anti-inflammatory drug. In a further aspect, the non-steroidal anti-inflammatory drug comprises acetaminophen. In a still further aspect, the non-steroidal anti-inflammatory drug comprises diflusinal, ibuprofen, naproxen, ketoprofen, fenoprofen, flurbiprofen, fenbufen, benoxaprofen, tiaprofenic acid, indoprofen, suprofen, etodolac, zomepirac, indomethacin, alclofenac, sulindac, fenclofenac, diclofenac, tolmetin, mefanamic acid, phenylbutazone, oxyphenbuta, azapropazone, feprazone, or piroxicam, or combinations thereof.

Provided are methods of using of a disclosed compound, pharmaceutical composition, or medicament. In an aspect, the method of use is directed to the treatment of a disease or disorder.

In a further aspect, the disclosed compounds can be used as single agents or in combination with one or more other drugs in the treatment, prevention, control, amelioration, or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of adverse reactions associated with therapeutic agents normally given to treat cancer, infectious disease, seizure or convulsant disorders, and inflammatory diseases. For example, a treatment can include administration of the disclosed compounds to modulate, e.g., inhibition activity of PXR. The activity of PXR can be upregulated by administration of a number of therapeutic agents as discussed herein. Thus, provided is a method of treating or preventing a disorder in a subject comprising the step of administering to the subject at least one disclosed compound; at least one disclosed pharmaceutical composition; and/or at least one disclosed product in a dosage and amount effective to treat an adverse reaction in the subject.

Alternatively, the disclosed compounds can be co-administered with a therapeutic agent that is being administered to treat a disease such as cancer, an infectious disease, an inflammatory disorder, or a seizure or convulsant disorder. It should be understood that "co-administration" can refer to simultaneous administration of the disclosed compounds with another therapeutic agent. Simultaneous administration is understood to comprise administration of two separate dosage forms, such as one dosage form for the disclosed compound and one dosage form for the other therapeutic agent. Alternatively, simultaneous administration can comprise co-formulation or co-packaging of the disclosed compound and the other therapeutic agent. Further, it should be understood that "co-administration" can refer sequential administration of the disclosed compound and the other therapeutic agent. Sequential administration comprises a first administration of the disclosed compound followed by a second administration of the other therapeutic agent, or alternatively, a first administration of the other therapeutic agent followed by administration of the disclosed compound. The time interval between the first and second administration can be as needed to obtain the most efficacious treatment outcomes, e.g., the time interval between the first and second administration can be about one minute, five minutes, ten minutes, fifteen minutes, 20 minutes, 30 minutes, 45 minutes, 60 minutes, 90 minutes, two hours, three hours, four hours, five hours, six hours, eight hours, ten hours, fifteen hours, 20 hours, 24 hours, two days, three days, four days, five days, six days, seven days, two weeks, three week, four weeks, two months, or three months.

In an aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Accordingly, the pharmaceutical compositions include those that contain one or more other active ingredients, in addition to a compound of the present invention.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1;1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the disclosed compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

Also provided are methods for the treatment of one or more disorders associated with dysregulation of PXR in a subject, comprising the step of administering to the subject at least one disclosed compound, at least one disclosed compound with at least one other disclosed therapeutic agent, at least one disclosed pharmaceutical composition, and/or at least one disclosed medicament in a dosage and treatment frequency effective to treat the disorder in the subject.

Also provided are methods for the treatment in a mammal comprising the step of administering to the mammal at least one disclosed compound, at least one disclosed compound with at least one other disclosed therapeutic agent, at least one disclosed pharmaceutical composition, or at least one disclosed medicament.

In the treatment of a disease or disorder or pathological condition, as disclosed herein, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15. 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, In an aspect, the invention relates to a method for inhibiting PXR activity in at least one cell, e.g. a mammalian cell, comprising the step of contacting the at least one cell with at least one disclosed compound, at least one product of a disclosed method, and/or at least one disclosed pharmaceutical composition in an amount effective to inhibit PXR activity in the at least one cell. In a further aspect, the cell is mammalian cell, e.g., a human cell. In a further aspect, the cell has been isolated from a subject prior to the contacting step. In a further aspect, contacting is via administration to a subject.

a. Methods for Modulating an Adverse Drug Reaction in a Mammal

In an aspect, the invention relates to a method for modulating an adverse drug reaction in a mammal comprising the step of administering to the mammal a therapeutically effective amount of at least one disclosed compound, or a pharmaceutically acceptable salt thereof; at least one disclosed pharmaceutical composition; or at least one disclosed medicament; or a compound having a structure represented by a formula:

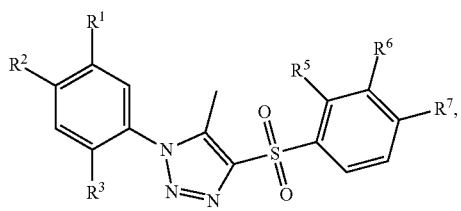

wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —CO$_2$H, —(C=O)H, —(C=O)—(C1-C6 alkyl), —(C=O)—O(C1-C6 alkyl); wherein $R^3$ is hydrogen, hydroxy, halogen, C1-C6 alkyl, C1-C6 alkoxy, and —(C1-C6)-OH; wherein $R^5$ is hydrogen, halogen, hydroxy, C1-C3 alkyl; wherein $R^6$ is hydrogen, halogen, hydroxy, C1-C3 alkyl; and wherein $R^7$ is C1-C6 alkyl; or a pharmaceutically acceptable salt thereof.

In a further aspect, the compound administered is a product of a disclosed method of making. In a still further aspect, an effective amount is a therapeutically effective amount. In a yet further aspect, an effective amount is a prophylactically effective amount.

In a further aspect, the mammal is a human. In a still further aspect, the mammal has been diagnosed with a need for modulating an adverse drug reaction prior to the administering step. In an even further aspect, the method further comprises the step of identifying a mammal in need of modulating an adverse drug reaction. In a still further aspect, modulating an adverse drug reaction is associated with the mammal receiving treatment for a disorder of uncontrolled cellular proliferation. In a yet further aspect, modulating an adverse drug reaction is associated with the mammal receiving treatment for a disorder of uncontrolled cellular proliferation, and the disorder of uncontrolled cellular proliferation is a cancer.

In various aspects, the compound administered exhibits an $IC_{50}$ of less than about μM. In a further aspect, the compound administered exhibits an $IC_{50}$ of less than about 10 μM. In a still further aspect the compound administered exhibits an $IC_{50}$ of less than about 5.0 μM. In a yet further aspect, the compound administered exhibits an $IC_{50}$ of less than about 2.5 μM. In an even further aspect, the compound administered exhibits an $IC_{50}$ of less than about 1.0 μM. In a still further aspect, the compound administered exhibits an $IC_{50}$ of less than about 750 nM. In a yet further aspect, the compound administered exhibits an $IC_{50}$ of less than about 500 nM. In an even further aspect, the compound administered exhibits an $IC_{50}$ of less than about 250 nM. In a still further aspect, the compound administered exhibits an $IC_{50}$ of less than about 100 nM. In a yet further aspect, the compound administered exhibits an $IC_{50}$ of less than about 50 nM. In an even further aspect, the compound administered exhibits an $IC_{50}$ of less than about 25 nM. In a still further aspect, the compound administered exhibits an $IC_{50}$ of less than about 10 nM.

It is understood, that in various aspects, the $IC_{50}$ of the compound administered can be determined by methods disclosed herein, e.g., the time-resolved fluorescence resonance transfer (TR-FRET) hPXR competitive binding assay or the hPXR transactivation assay. That is, in aspects, the $IC_{50}$ should be understood to be the $IC_{50}$ as determined in the time-resolved fluorescence resonance transfer (TR-FRET) hPXR competitive binding assay described herein. Alternatively, in aspects, the $IC_{50}$ should be understood to be the $IC_{50}$ as determined in the hPXR transactivation assay.

In various aspects, the method for modulating an adverse drug reaction in a mammal further comprises administration of the at least one disclosed compound or the pharmaceutical composition with another therapeutic agent. In a further aspect, the administration is co-administration of the at least one disclosed compound or the pharmaceutical composition with another therapeutic agent. In a still further aspect, the administration is sequential administration of the at least one disclosed compound or the pharmaceutical composition with another therapeutic agent.

In a further aspect, the method for modulating an adverse drug reaction in a mammal further comprises administration of the at least one disclosed compound or the pharmaceutical composition with another therapeutic agent, and the other therapeutic agent is an anticancer agent. In a yet further aspect, the anticancer agent administered with the at least one disclosed compound or the disclosed pharmaceutical composition is paclitaxel, irinotecan, leucovorin, dasatinib, or erlotinib.

In a further aspect, the anticancer agent administered with the at least one disclosed compound or the disclosed pharmaceutical composition is a topoisomerase inhibitor. In a still further aspect, the topoisomerase inhibitor is camptothecin, topotecan, irinotecan, belotecan, gimatecan, inidimitecan, indotecan, Genz-644282, daunorubicin, epirubicin, etoposide, teniposide, mitoxantrone, ellipticinium, vasaroxin, dexrazoxane, mebarone, or 3-hydroxy-2-[(1R)-6-isopropenyl-3-methyl-cyclohex-2-en-1-yl]-5-pentyl-1,4-benzoquinone (HU-331). In a yet further aspect, the topoisomerase inhibitor is irinotecan.

In a further aspect, the method for modulating an adverse drug reaction in a mammal further comprises administration of the at least one disclosed compound or the pharmaceutical composition with another therapeutic agent, the other therapeutic agent is an anticancer agent, and the anticancer agent is a tyrosine kinase inhibitor. In a still further aspect, the tyrosine kinase inhibitor is axitinib, crizotinib, dasatinib, erlotinib, gefitinib, imatinib, lapatinib, nilotinib, pazopanib, regorafenib, ruxolitinib, sorafenib, sunitinib, vandetanib, or vemurafenib. In a yet further aspect, the tyrosine kinase inhibitor is dasatinib or erlotinib.

In a further aspect, the method for modulating an adverse drug reaction in a mammal further comprises administration of the at least one disclosed compound or the pharmaceutical composition with another therapeutic agent, the other therapeutic agent is an anticancer agent, and the anticancer agent is a mitotic inhibitor. In a still further aspect, the mitotic inhibitor is paclitaxel, docetaxel, vinblastine, vincristine, or vinorelbine. In a yet further aspect, the mitotic inhibitor is paclitaxel or docetaxel. In an even further aspect, the mitotic inhibitor is paclitaxel.

In a further aspect, the method for modulating an adverse drug reaction in a mammal further comprises administration of the at least one disclosed compound or the pharmaceutical composition with another therapeutic agent, the other therapeutic agent is an anticancer agent, and the anticancer agent is a chemotherapeutic agent. In a still further aspect, the chemotherapeutic agent is an alkylating-like agent, an antimetabolite agent, an antineoplastic antibiotic agent, a mitotic inhibitor agent, an mTor inhibitor agent, or other chemotherapeutic agent.

In a further aspect, the method for modulating an adverse drug reaction in a mammal further comprises administration of the at least one disclosed compound or the pharmaceutical composition with another therapeutic agent, the other therapeutic agent is an anticancer agent, and the anticancer agent is an antineoplastic agent selected from one or more of doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof.

In a further aspect, the method for modulating an adverse drug reaction in a mammal further comprises administration of the at least one disclosed compound or the pharmaceutical composition with another therapeutic agent, the other therapeutic agent is an anticancer agent, and the anticancer agent is an antimetabolite agent selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, methotrexate coadministered with leucovorin, and thioguanine, or a pharmaceutically acceptable salt thereof.

In a further aspect, the method for modulating an adverse drug reaction in a mammal further comprises administration of the at least one disclosed compound or the pharmaceutical composition with another therapeutic agent, the other therapeutic agent is an anticancer agent, and the anticancer agent is an alkylating-like agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt thereof.

In a further aspect, the method for modulating an adverse drug reaction in a mammal further comprises administration of the at least one disclosed compound or the pharmaceutical composition with another therapeutic agent, the other therapeutic agent is an anticancer agent, and the anticancer agent is a mitotic inhibitor agent is selected from one or more of the group consisting of etopside, vincristine, ixabepilone, vinorelbine, vinblastine, and teniposide, or a pharmaceutically acceptable salt thereof.

In a further aspect, the method for modulating an adverse drug reaction in a mammal further comprises administration of the at least one disclosed compound or the pharmaceutical composition with another therapeutic agent, the other therapeutic agent is an anticancer agent, and the anticancer agent is a mTor inhibitor agent is selected from one or more of the group consisting of everolimus, siroliumus, and temsirolimus, or a pharmaceutically acceptable salt thereof.

In a further aspect, the method for modulating an adverse drug reaction in a mammal further comprises administration of the at least one disclosed compound or the pharmaceutical composition with another therapeutic agent, the other therapeutic agent is an antibacterial agent. In a still further aspect, the antibacterial agent is isoniazid, isoniazid in combination with rifampin, rifampicin, or flucloxacillin.

In a further aspect, the method for modulating an adverse drug reaction in a mammal further comprises administration of the at least one disclosed compound or the pharmaceutical composition with another therapeutic agent, the other therapeutic agent is a non-steroidal anti-inflammatory drug. In a still further aspect, the non-steroidal anti-inflammatory drug is acetominophen.

In a further aspect, the method for modulating an adverse drug reaction in a mammal further comprises administration of the at least one disclosed compound or the pharmaceutical composition with another therapeutic agent, the other therapeutic agent is an anticonvulsant drug. In a still further aspect, the anticonvulsant drug is phenytoin.

b. Methods for Treatment of a Disorder of Uncontrolled Cellular Proliferation

In an aspect, the invention relates to a method for treatment of a disorder of uncontrolled cellular proliferation in a mammal comprising the step of administering to the mammal a therapeutically effective amount of at least one disclosed compound, or a pharmaceutically acceptable salt thereof; at least one disclosed pharmaceutical composition; or at least one disclosed medicament; or a compound having a structure represented by a formula:

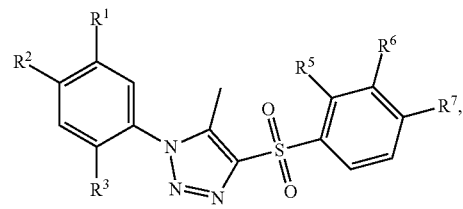

wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —CO$_2$H, —(C=O)H, —(C=O)—(C1-C6 alkyl), —(C=O)—O(C1-C6 alkyl); wherein $R^3$ is hydrogen, hydroxy, halogen, C1-C6 alkyl, C1-C6 alkoxy, and —(C1-C6)-OH; wherein $R^5$ is hydrogen, halogen, hydroxy, C1-C3 alkyl; wherein $R^6$ is hydrogen, halogen, hydroxy, C1-C3 alkyl; and wherein $R^7$ is C1-C6 alkyl; or a pharmaceutically acceptable salt thereof.

In a further aspect, the compound administered is a product of a disclosed method of making. In a still further aspect, an effective amount is a therapeutically effective amount. In a yet further aspect, an effective amount is a prophylactically effective amount.

In a further aspect, the mammal is a human. In a still further aspect, the mammal has been diagnosed with a need for treatment of the disorder of uncontrolled cellular proliferation prior to the administering step. In a yet further aspect, the method for treating a disorder of cellular proliferation further comprises the step of identifying a mammal in need of treatment of the disorder of uncontrolled cellular proliferation.

In a further aspect, the method for treating a disorder of uncontrolled cellular proliferation is a method for treating cancer. In a still further aspect, the cancer is selected from breast cancer, renal cancer, gastric cancer, and colorectal cancer. In a yet further aspect, the cancer is selected from lymphoma, cancers of the brain, genitourinary tract cancer, lymphatic system cancer, stomach cancer, larynx cancer, lung, pancreatic cancer, breast cancer, and malignant melanoma.

In a further aspect, the method for treating a disorder of uncontrolled cellular proliferation further comprises administration of the at least one disclosed compound or the pharmaceutical composition with an anticancer agent. In a further aspect, the administration of the at least one disclosed compound or the pharmaceutical composition with an anticancer agent co-administration of the at least one disclosed compound or the pharmaceutical composition with another therapeutic agent. In a still further aspect, the administration of the at least one disclosed compound or the pharmaceutical composition with an anticancer agent is sequential administration of the at least one disclosed compound or the pharmaceutical composition with another therapeutic agent.

In a further aspect, the method for treating a disorder of uncontrolled cellular proliferation further comprises administration of the at least one disclosed compound or the pharmaceutical composition with paclitaxel, irinotecan, leucovorin, dasatinib, or erlotinib.

In a further aspect, the method for treating a disorder of uncontrolled cellular proliferation further comprises administration of the at least one disclosed compound or the pharmaceutical composition a topoisomerase inhibitor. In a still further aspect, the topoisomerase inhibitor is camptothecin, topotecan, irinotecan, belotecan, gimatecan, inidimitecan, indotecan, Genz-644282, daunorubicin, epirubicin, etoposide, teniposide, mitoxantrone, ellipticinium, vasaroxin, dexrazoxane, mebarone, or 3-hydroxy-2-[(1R)-6-isopropenyl-3-methyl-cyclohex-2-en-1-yl]-5-pentyl-1,4-benzoquinone (HU-331). In a yet further aspect, the topoisomerase inhibitor is irinotecan.

In a further aspect, the method for treating a disorder of uncontrolled cellular proliferation further comprises administration of the at least one disclosed compound or the pharmaceutical composition a tyrosine kinase inhibitor. In a still further aspect, the tyrosine kinase inhibitor is axitinib, crizotinib, dasatinib, erlotinib, gefitinib, imatinib, lapatinib, nilotinib, pazopanib, regorafenib, ruxolitinib, sorafenib, sunitinib, vandetanib, or vemurafenib. In a yet further aspect, the tyrosine kinase inhibitor is dasatinib or erlotinib.

In a further aspect, the method for treating a disorder of uncontrolled cellular proliferation further comprises administration of the at least one disclosed compound or the pharmaceutical composition a mitotic inhibitor. In a still further aspect, the mitotic inhibitor is paclitaxel, docetaxel, vinblastine, vincristine, or vinorelbine. In a yet further aspect, the mitotic inhibitor is paclitaxel or docetaxel. In an even further aspect, the mitotic inhibitor is paclitaxel.

In a further aspect, the method for treating a disorder of uncontrolled cellular proliferation further comprises administration of the at least one disclosed compound or the pharmaceutical composition a chemotherapeutic agent. In a still further aspect, the chemotherapeutic agent is an alkylating-like agent, an antimetabolite agent, an antineoplastic antibiotic agent, a mitotic inhibitor agent, an mTor inhibitor agent, or other chemotherapeutic agent.

In a further aspect, the method for treating a disorder of uncontrolled cellular proliferation further comprises administration of the at least one disclosed compound or the pharmaceutical composition an antineoplastic agent selected from one or more of doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof.

In a further aspect, the method for treating a disorder of uncontrolled cellular proliferation further comprises administration of the at least one disclosed compound or the pharmaceutical composition an antimetabolite agent selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, methotrexate coadministered with leucovorin, and thioguanine, or a pharmaceutically acceptable salt thereof.

In a further aspect, the method for treating a disorder of uncontrolled cellular proliferation further comprises administration of the at least one disclosed compound or the pharmaceutical composition an alkylating-like agent selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt thereof.

In a further aspect, the method for treating a disorder of uncontrolled cellular proliferation further comprises administration of the at least one disclosed compound or the pharmaceutical composition a mitotic inhibitor agent selected from one or more of the group consisting of etopside, vincristine, ixabepilone, vinorelbine, vinblastine, and teniposide, or a pharmaceutically acceptable salt thereof.

In a further aspect the method for treating a disorder of uncontrolled cellular proliferation further comprises administration of the at least one disclosed compound or the pharmaceutical composition a mTor inhibitor agent selected from one or more of the group consisting of everolimus, siroliumus, and temsirolimus, or a pharmaceutically acceptable salt thereof.

c. Method for Modulating Pregnane X Receptor Activity in a Mammal

In an aspect, the invention relates to a method for modulating pregnane X receptor activity in a mammal comprising the step of administering to the mammal a therapeutically effective amount of at least one disclosed compound, or a pharmaceutically acceptable salt thereof; at least one disclosed pharmaceutical composition; or at least one disclosed medicament; or a compound having a structure represented by a formula:

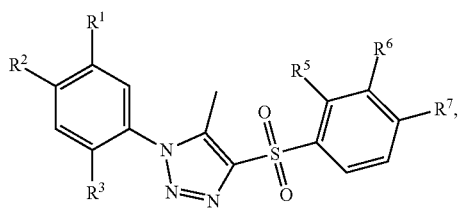

wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —CO$_2$H, —(C=O)H, —(C=O)—(C1-C6 alkyl), —(C=O)—O(C1-C6 alkyl); wherein $R^3$ is hydrogen, hydroxy, halogen, C1-C6 alkyl, C1-C6 alkoxy, and —(C1-C6)-OH; wherein $R^5$ is hydrogen, halogen, hydroxy, C1-C3 alkyl; wherein $R^6$ is hydrogen, halogen, hydroxy, C1-C3 alkyl; and wherein $R^7$ is C1-C6 alkyl; or a pharmaceutically acceptable salt thereof.

In a further aspect, the compound administered in the method for modulating pregnane X receptor activity in a mammal is a product of a disclosed method of making. In a still further aspect, an effective amount is a therapeutically effective amount. In a yet further aspect, an effective amount is a prophylactically effective amount.

In a further aspect, the method for modulating pregnane X receptor activity in a mammal is a method for modulating pregnane X receptor activity in a human.

In a further aspect, the mammal has been diagnosed with a need for modulating pregnane X receptor activity prior to the administering step. In a yet further aspect, the method further comprises the step of identifying a mammal in need of modulating pregnane X receptor activity.

d. Modulating Pregnane X Receptor Activity in at Least One Cell

In an aspect, the invention relates to a method for modulating pregnane X receptor activity in at least one cell, comprising the step of contacting the at least one cell with an effective amount of at least one disclosed compound, or a pharmaceutically acceptable salt thereof; at least one disclosed pharmaceutical composition; or at least one disclosed medicament; or a compound having a structure represented by a formula:

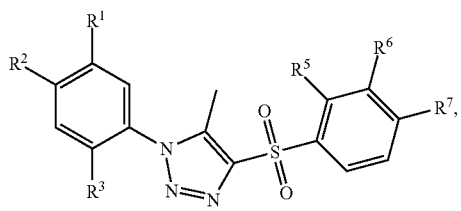

wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —CO$_2$H, —(C=O)H, —(C=O)—(C1-C6 alkyl), —(C=O)—O(C1-C6 alkyl); wherein $R^3$ is hydrogen, hydroxy, halogen, C1-C6 alkyl, C1-C6 alkoxy, and —(C1-C6)-OH; wherein $R^5$ is hydrogen, halogen, hydroxy, C1-C3 alkyl; wherein $R^6$ is hydrogen, halogen, hydroxy, C1-C3 alkyl; and wherein $R^7$ is C1-C6 alkyl; or a pharmaceutically acceptable salt thereof.

In a further aspect, the cell contacted is a mammalian cell. In a still further aspect, the cell contacted is a human cell. In a yet further aspect, the cell contacted has been isolated from a mammal prior to the contacting step. In an even further aspect, the contacting of the cell is ex vivo. In a still further aspect, the contacting of the cell is in vitro.

In a further aspect, the contacting of the cell is via administration to a mammal. In a still further aspect, the mammal has been diagnosed with a need for modulating pregnane X receptor activity prior to the administering step. In a yet further aspect, the mammal has been diagnosed with a need for treatment of a disorder related to pregnane X receptor activity prior to the administering step.

2. Manufacture of a Medicament

In an aspect, the invention relates to a medicament comprising one or more disclosed compounds, a product of a disclosed method of making, a disclosed pharmaceutical composition, or a compound having a structure represented by a formula:

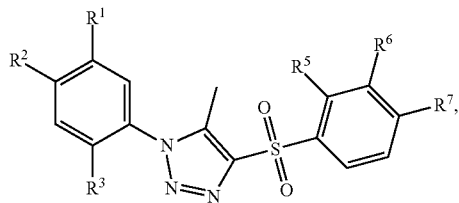

wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —CO$_2$H, —(C=O)H, —(C=O)—(C1-C6 alkyl), —(C=O)—O(C1-C6 alkyl); wherein $R^3$ is hydrogen, hydroxy, halogen, C1-C6 alkyl, C1-C6 alkoxy, and —(C1-C6)-OH; wherein $R^5$ is hydrogen, halogen, hydroxy, C1-C3 alkyl; wherein $R^6$ is hydrogen, halogen, hydroxy, C1-C3 alkyl; wherein $R^7$ is C1-C6 alkyl; or a pharmaceutically acceptable salt thereof. In a further aspect, the medicament is manufactured using a product of a disclosed method of making. In a still further aspect, the medicament is manufactured using a disclosed compound.

In various aspect, the invention relates methods for the manufacture of a medicament for modulating pregnane X receptor activity (e.g., treatment of an adverse drug reaction to a drug used to treat a disease such as a cancer, an infectious disease, an inflammatory disease, or a seizure or convulsant disorder) in mammals (e.g., humans) comprising combining one or more disclosed compounds, products, or compositions or a pharmaceutically acceptable salt, solvate, hydrate, or polymorph thereof, with a pharmaceutically acceptable carrier. It is understood that the disclosed methods can be performed with the disclosed compounds, products, and pharmaceutical compositions. It is also understood that the disclosed methods can be employed in connection with the disclosed methods of using.

In a further aspect, the invention pertains to use of a disclosed compound or a disclosed product in the manufacture of a medicament for modulating an adverse drug reaction in a mammal.

In a further aspect, the invention pertains to use of a disclosed compound or a disclosed product in the manufacture of a medicament for treatment of a disorder of uncontrolled cellular proliferation in a mammal.

In a further aspect, the invention pertains to use of a disclosed compound or a disclosed product in the manufacture of a medicament for modulating pregnane X receptor activity in a mammal comprising the step of administering to the mammal.

In a further aspect, the invention pertains to use of a disclosed compound or a disclosed product in the manufacture of a medicament for modulating pregnane X receptor activity in at least one cell, comprising the step of contacting the cell.

3. Uses of Compounds

Also provided are the uses of the disclosed compounds and products. In one aspect, the invention relates to use of at least one disclosed compound, at least one product of a disclosed method of making, a disclosed pharmaceutical composition, a disclosed medicament, or a compound having a structure represented by a formula:

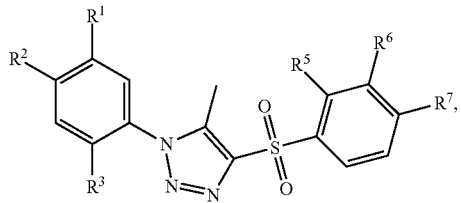

wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —$CO_2$H, —(C=O)H, —(C=O)—(C1-C6 alkyl), —(C=O)—O(C1-C6 alkyl); wherein $R^3$ is hydrogen, hydroxy, halogen, C1-C6 alkyl, C1-C6 alkoxy, and —(C1-C6)-OH; wherein $R^5$ is hydrogen, halogen, hydroxy, C1-C3 alkyl; wherein $R^6$ is hydrogen, halogen, hydroxy, C1-C3 alkyl; wherein $R^7$ is C1-C6 alkyl; or a pharmaceutically acceptable salt thereof. In a further aspect, the compound used is a product of a disclosed method of making. In a further aspect, the compound used is a disclosed compound.

In various aspects, the compound used exhibits an $IC_{50}$ of less than about 15 µM. In a further aspect, the compound used exhibits an $IC_{50}$ of less than about 10 µM. In a still further aspect the compound used exhibits an $IC_{50}$ of less than about 5.0 µM. In a yet further aspect, the compound used exhibits an $IC_{50}$ of less than about 2.5 µM. In an even further aspect, the compound used exhibits an $IC_{50}$ of less than about 1.0 µM. In a still further aspect, the compound used exhibits an $IC_{50}$ of less than about 750 nM. In a yet further aspect, the compound used exhibits an $IC_{50}$ of less than about 500 nM. In an even further aspect, the compound used exhibits an $IC_{50}$ of less than about 250 nM. In a still further aspect, the compound used exhibits an $IC_{50}$ of less than about 100 nM. In a yet further aspect, the compound used exhibits an $IC_{50}$ of less than about 50 nM. In an even further aspect, the compound used exhibits an $IC_{50}$ of less than about 25 nM. In a still further aspect, the compound used exhibits an $IC_{50}$ of less than about 10 nM.

It is understood, that in various aspects, the $IC_{50}$ of the compound used can be determined by methods disclosed herein, e.g., the time-resolved fluorescence resonance transfer (TR-FRET) hPXR competitive binding assay or the hPXR transactivation assay. That is, in aspects, the $IC_{50}$ should be understood to be the $IC_{50}$ as determined in the time-resolved fluorescence resonance transfer (TR-FRET) hPXR competitive binding assay described herein. Alternatively, in aspects, the $IC_{50}$ should be understood to be the $IC_{50}$ as determined in the hPXR transactivation assay.

In a further aspect, the use relates to a process for preparing a pharmaceutical composition comprising a therapeutically effective amount of a disclosed compound or a product of a disclosed method of making, or a pharmaceutically acceptable salt thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt thereof, wherein a pharmaceutically acceptable carrier is intimately mixed with a therapeutically effective amount of the compound or the product of a disclosed method of making.

4. Kits

In an aspect, disclosed are kits comprising at least one disclosed compound, at least one product of a disclosed method of making, a disclosed pharmaceutical composition, a disclosed medicament, or a compound having a structure represented by a formula:

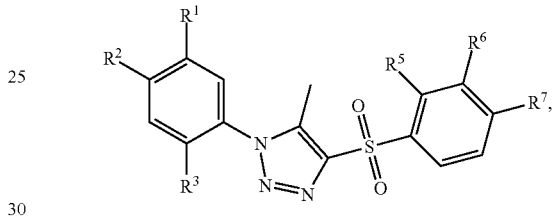

wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —$CO_2$H, —(C=O)H, —(C=O)—(C1-C6 alkyl), —(C=O)—O(C1-C6 alkyl); wherein $R^3$ is hydrogen, hydroxy, halogen, C1-C6 alkyl, C1-C6 alkoxy, and —(C1-C6)-OH; wherein $R^5$ is hydrogen, halogen, hydroxy, C1-C3 alkyl; wherein $R^6$ is hydrogen, halogen, hydroxy, C1-C3 alkyl; wherein $R^7$ is C1-C6 alkyl; or a pharmaceutically acceptable salt thereof; and one or more of: (a) at least one agent known to increase pregnane X receptor activity; (b) at least one agent known to decrease pregnane X receptor activity; (c) at least one agent known to treat a disorder of uncontrolled cellular proliferation; (d) at least one agent known to treat an infectious disease; (e) at least one agent known to be a non-steroidal anti-inflammatory drug; (f) at least one agent known to be an anti-convulsant agent; or (g) instructions for treating a disorder associated with pregnane X receptor dysfunction.

In various aspects, the disclosed compounds, products of a disclosed method of making, a disclosed medicament, the disclosed other therapeutic agents, and the disclosed pharmaceutical compositions described herein can be provided in a kit as described herein. The kit can also include combinations of the disclosed compounds, products of a disclosed method of making, a disclosed medicament, the disclosed other therapeutic agents, and the disclosed pharmaceutical compositions described herein.

In various aspects, the instructions or informational material provided in the kit can be descriptive, instructional, marketing or other material that relates to the methods described herein and/or to the use of the agents for the methods described herein. For example, the informational material may relate to the use of the agents herein to treat a subject who has, or who is at risk for developing, an adverse reaction. The kits can also include paraphernalia for administering the agents of this invention to a cell (in culture or in vivo) and/or for administering a cell to a patient.

In various aspects, the instructions or informational material provided in the kit can include instructions for administering the pharmaceutical composition and/or cell(s) in a suitable manner to treat a human, e.g., in a suitable dose, dosage form, or mode of administration (e.g., a dose, dosage form, or mode of administration described herein). In a further aspect, the informational material can include instructions to administer the pharmaceutical composition to a suitable subject, e.g., a human having, or at risk for developing, an adverse reaction.

In various aspects, the composition of the kit can include other ingredients, such as a solvent or buffer, a stabilizer, a preservative, a fragrance or other cosmetic ingredient. In such aspects, the kit can include instructions for admixing the agent and the other ingredients, or for using one or more compounds together with the other ingredients.

In a further aspect, the at least one compound and the therapeutic agent are co-formulated. In a still further aspect, the at least one compound and the therapeutic agent are co-packaged.

In a further aspect, the kit can further comprise a plurality of dosage forms, the plurality comprising one or more doses; wherein each dose comprises an effective amount of the disclosed compound or product of a disclosed method of making and the at least one agent. In a still further aspect, the effective amount is a therapeutically effective amount. In yet a further aspect, the effective amount is a prophylactically effective amount. In an even further aspect, each dose of the disclosed compound or product of a disclosed method of making and the therapeutic agent are co-packaged. In a still further aspect, each dose of the disclosed compound or product of a disclosed method of making and the therapeutic agent are co-formulated.

In a further aspect, the dosage forms are formulated for topical administration. In a still further aspect, the dosage forms are formulated for oral administration. In a yet further aspect, the dosage forms are formulated for administration via an injection, e.g., intraperitoneal, intravenous, or intramuscular injection.

In a further aspect, the at least one agent in the kit is an anticancer agent. In a still further aspect, the at least one agent in the kit is an anticancer agent, and the anticancer agent is paclitaxel, irinotecan, leucovorin, dasatinib, or erlotinib.

In a further aspect, the at least one agent in the kit is an anticancer agent, and the anticancer agent is a topoisomerase inhibitor. In a still further aspect, the topoisomerase inhibitor is camptothecin, topotecan, irinotecan, belotecan, gimatecan, inidimitecan, indotecan, Genz-644282, daunorubicin, epirubicin, etoposide, teniposide, mitoxantrone, ellipticinium, vasaroxin, dexrazoxane, mebarone, or 3-hydroxy-2-[(1R)-6-isopropenyl-3-methyl-cyclohex-2-en-1-yl]-5-pentyl-1,4-benzoquinone (HU-331). In a yet further aspect, the topoisomerase inhibitor is irinotecan.

In a further aspect, the at least one agent in the kit is an anticancer agent, and the anticancer agent is a tyrosine kinase inhibitor. In a still further aspect, the tyrosine kinase inhibitor is axitinib, crizotinib, dasatinib, erlotinib, gefitinib, imatinib, lapatinib, nilotinib, pazopanib, regorafenib, ruxolitinib, sorafenib, sunitinib, vandetanib, or vemurafenib. In a yet further aspect, the tyrosine kinase inhibitor is dasatinib or erlotinib.

In a further aspect, the at least one agent in the kit is an anticancer agent, and the anticancer agent is a mitotic inhibitor. In a still further aspect, the mitotic inhibitor is paclitaxel, docetaxel, vinblastine, vincristine, or vinorelbine. In a yet further aspect, the mitotic inhibitor is paclitaxel or docetaxel. In an even further aspect, the mitotic inhibitor is paclitaxel.

In a further aspect, the at least one agent in the kit is an anticancer agent, and the anticancer agent is a chemotherapeutic agent. In a still further aspect, the chemotherapeutic agent is an alkylating-like agent, an antimetabolite agent, an antineoplastic antibiotic agent, a mitotic inhibitor agent, an mTor inhibitor agent, or other chemotherapeutic agent.

In a further aspect, the at least one agent in the kit is an anticancer agent, and the anticancer agent is an antineoplastic antibiotic agent selected from one or more of the group consisting of doxorubicin, mitoxantrone, bleomycin, daunorubicin, dactinomycin, epirubicin, idarubicin, plicamycin, mitomycin, pentostatin, or valrubicin, or a pharmaceutically acceptable salt thereof.

In a further aspect, the at least one agent in the kit is an anticancer agent, and the anticancer agent is an antimetabolite agent selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, methotrexate coadministered with leucovorin, and thioguanine, or a pharmaceutically acceptable salt thereof.

In a further aspect, the at least one agent in the kit is an anticancer agent, and the anticancer agent is an alkylating-like agent selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt thereof.

In a further aspect, the at least one agent in the kit is an anticancer agent, and the anticancer agent is a mitotic inhibitor agent selected from one or more of the group consisting of etopside, vincristine, ixabepilone, vinorelbine, vinblastine, and teniposide, or a pharmaceutically acceptable salt thereof.

In a further aspect, the at least one agent in the kit is an anticancer agent, and the anticancer agent is an mTor inhibitor agent selected from one or more of the group consisting of everolimus, siroliumus, and temsirolimus, or a pharmaceutically acceptable salt thereof.

In a further aspect, the at least one agent in the kit is an antibacterial agent. In a still further aspect, the antibacterial agent is isoniazid, isoniazid in combination with rifampin, rifampicin, or flucloxacillin.

In a further aspect, the at least one agent in the kit is a non-steroidal anti-inflammatory drug. In a still further aspect, the non-steroidal anti-inflammatory drug is acetominophen.

In a further aspect, the at least one agent in the kit is an anticonvulsant drug. In a still further aspect, the anticonvulsant drug is phenytoin.

5. Non-Medical Uses

Also provided are the uses of the disclosed compositions and products as pharmacological tools in the development and standardization of in vitro and in vivo test systems for the evaluation of the effect of PXR binding related activity in laboratory animals such as cats, dogs, rabbits, monkeys, rats and mice, as part of the search for new therapeutic agents of preventing undesired drug-drug interactions. In a further aspect, the invention relates to the use of a disclosed compound or a disclosed product as pharmacological tools in the development and standardization of in vitro and in vivo test systems for the evaluation of the effect of PXR binding related activity in laboratory animals such as cats, dogs, rabbits, monkeys, rats and mice, as part of the search for new therapeutic agents of preventing ligand binding interactions with PXR.

E. Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. General Chemistry Experimentals

Organic reagents were purchased from commercial suppliers unless otherwise noted and were used without further purification. All solvents were analytical- or reagent-grade. All reactions were carried out in flame-dried glassware under argon or nitrogen. Flash column chromatography was performed by using Sigma-Aldrich silica gel 60 (200-400 mesh) and carried out under moderate pressure, with columns of an appropriate size packed and eluted with appropriate eluents. All reactions were monitored by performing thin-layer chromatography (TLC) on precoated plates (silica gel HLF). TLC spots were visualized either by exposure to iodine vapor or by irradiation with UV light. Organic solvents were removed under vacuum by a rotary evaporator. The reactions, purities, or identities of final compounds were monitored or determined by performing TLC or using a Waters Acquity UPLC MS system with a C18 column in a 2-min gradient ($H_2O$+0.1% formic acid→Acetonitrile+ 0.1% formic acid) and detectors of PDA (215-400 nm), ELSD, and Acquity SQD ESI Positive MS. Preparative TLC separation was performed by using self-casted preparative TLC plates with Sigma-Aldrich silica gel 60 (200-400 mesh) on 20-cm×20-cm glass plates. The purifications of reaction products were performed by using a Dionex APS 3000 dual purification/analytical LC/PDA/MS system with a C18 column in a 15-min gradient ($H_2O$ with 0.05% $NH_3.H_2O$→Acetonitrile) and ESI Positive MS. High-resolution mass spectra were determined by using a Waters Acquity UPLC system with a C18 column ($H_2O$+0.1% formic acid→acetonitrile+0.1% formic acid gradient over 2.5 min) under Xevo G2Q-TOF ESI in positive, resolution mode. Compounds were internally normalized to leucine-enkephalin lock solution, with a calculated error of <3 ppm. All $^1H$ NMR spectra were recorded on a Bruker ULTRASHIELD 400 plus NMR spectrometer and all $^{13}C$ NMR spectra were recorded on a Bruker Ascend 126 MHz Fourier transform (FT) NMR spectrometer at room temperature. The chemical shift values are expressed in parts per million (ppm) relative to tetramethylsilane as the internal standard. Coupling constants (J) are reported in hertz (Hz).

Abbreviations: PXR, pregnane X receptor; rt, room temperature; THF, tetrahydrofuran; DMF, dimethylformamide; $Pd(dppf)Cl_2$, [1,1'-bis(diphenylphosphino)ferrocene]dichloropalladium(II); NFSI, N-fluorodibenzenesulfonimide; HATU, 1-[bis(dimethylamino)methylene]-1H-1,2,3-triazolo[4,5-b]pyridinium 3-oxid hexafluorophosphate; TEA, triethylolamine; DCM, dichloromethane; DPPA, diphenylphosphoryl azide; AcOH, acetic acid; SEMCl, 2-chloromethoxyethyl)trimethylsilane; NBS, N-bromosuccinimide; AIBN, azobisisobutyronitrile; TBAF, tetra-n-butylammonium fluoride.

2. Chemistry Experimentals a. General Synthesis of Compounds LC-8, LC-10, LC-19, LC-20, and LC-29

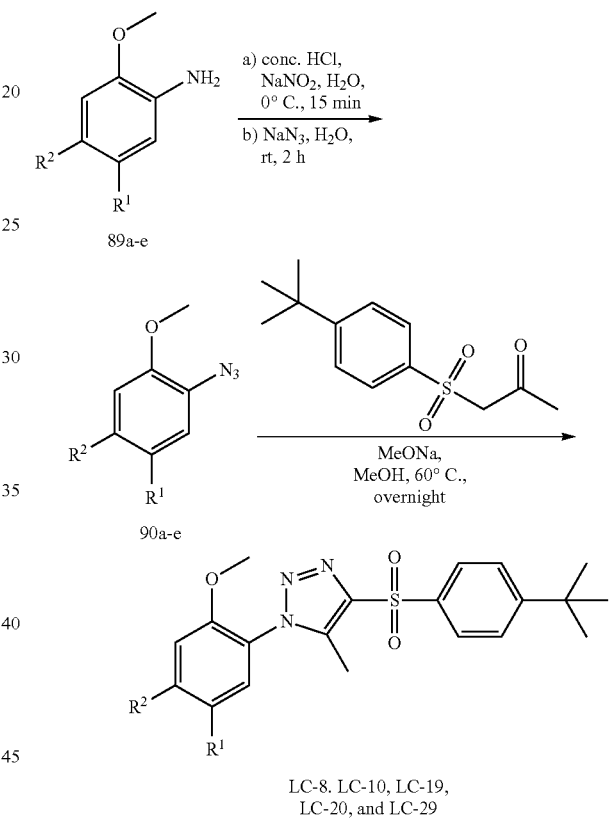

LC-8, LC-10, LC-19, LC-20, and LC-29 i. Preparation of 4-((4-(tert-butyl)phenyl)sulfonyl)-1-(4-fluoro-2,5-dimethoxyphenyl)-5-methyl-1H-1,2,3-triazole (LC-8)

(1) Synthesis of 90a

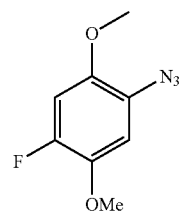

NaNO$_2$ (248 mg, 3.6 mmol) in water (1 mL) was added to a solution of 89a (4-fluoro-2,5-dimethoxyaniline, 513 mg, 3 mmol) in conc. HCl (10 mL) at 0° C. and the reaction mixture was then stirred for 15 minutes at 0° C. A solution of NaN$_3$ (234 mg, 3.6 mmol) in water (1 mL) was added dropwise. The solution was then stirred for 2 hours at ambient temperature. The reaction mixture was extracted with hexane. The hexane layer was washed with water, dried with anhydrous Na$_2$SO$_4$ and concentrated with a Rotavapor to give product 90a (332 mg, 56% yield).

(2) Synthesis of LC-8

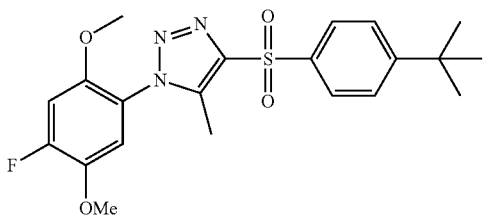 [SMILES: COc1cc(-n2nnc(S(=O)(=O)c3ccc(C(C)(C)C)cc3)c2C)c(OC)cc1F]

MeONa (108 mg, 2 mmol) and 1-((4-(tert-butyl)phenyl)sulfonyl)propan-2-one (254 mg, 1 mmol) were added to a solution of compound 90a (197 mg, 1 mmol) in MeOH. The mixture was stirred at 60° C. overnight. The reaction was then poured into water and extracted with EtOAc. The EtOAc layer was washed with water, dried with anhydrous Na$_2$SO$_4$ and concentrated with a Rotavapor. The residue was purified by preparative HPLC to give product LC-8 (98 mg, 23% yield). $^1$H NMR (CDCl$_3$, 400 MHz): δ (ppm) δ 8.03 (d, 2H, J=8.4 Hz), 7.56 (d, 2H, J=8.4 Hz), 6.94 (d, 1H, J=8.4 Hz), 6.86 (d, 1H, J=12.4 Hz), 3.82 (s, 3H), 3.73 (s, 3H), 2.43 (s, 3H), 1.32 (s, 9H). ESI-MS: m/z 434 (M+H)$^+$.

ii. Preparation of 1-(4-bromo-2,5-dimethoxyphenyl)-4-((4-(tert-butyl)phenyl)sulfonyl)-5-methyl-1H-1,2,3-triazole (LC-10)

(1) Synthesis of 90b

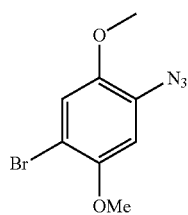

NaNO$_2$ (20 g, 0.29 mol) in water (100 mL) was added to a solution of 89b (4-bromo-2,5-dimethoxyaniline, 50 g, 0.22 mol) in conc. HCl (200 mL) at 0° C. and the reaction mixture was then stirred for 15 minutes at 0° C. A solution of NaN$_3$ (62 g, 0.95 mol) in water (150 mL) was added dropwise. The solution was then stirred for 2 hours at ambient temperature. The formed precipitation was collected by filtration and washed with ice water. The solid was dried to give product 90b (38 g, 68% yield). $^1$H NMR (400 MHz, CDCl$_3$) δ (ppm) 7.00 (s, 1H), 6.47 (s, 1H), 3.76 (s, 6H).

(2) Synthesis of LC-10

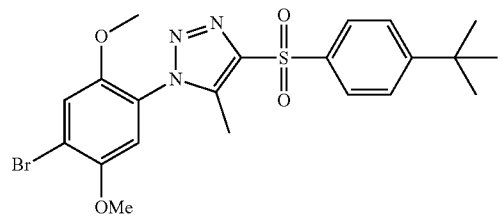 [SMILES: COc1cc(-n2nnc(S(=O)(=O)c3ccc(C(C)(C)C)cc3)c2C)c(OC)cc1Br]

MeONa (15 g, 0.28 mol) and 1-((4-(tert-butyl)phenyl)sulfonyl)propan-2-one (20 g, 79 mmol) were added to a solution of compound 90b (17.5 g, 68 mmol) in MeOH. The mixture was stirred at 60° C. overnight and then poured into water. The precipitation was collected by filtration. The crude product was washed with water, followed by MeOH to give product LC-10 (14 g, 42% yield). $^1$H NMR (CDCl$_3$, 400 MHz): δ (ppm) 8.56 (d, 2H, J=8.8 Hz), 8.03 (d, 2H, J=8.8 Hz), 7.29 (s, 1H), 6.87 (s, 1H), 3.82 (s, 3H), 3.75 (s, 3H), 2.45 (s, 3H), 1.32 (s, 9H). ESI-MS: m/z 494 (M+H)$^+$.

iii. Preparation of 4-((4-(tert-butyl)phenyl)sulfonyl)-1-(4-chloro-2-methoxy-5-methylphenyl)-5-methyl-1-1,2,3-triazole (LC-19)

(1) Synthesis of 90c

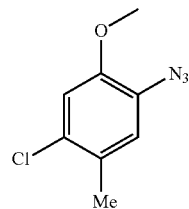

NaNO$_2$ (248 mg, 3.6 mmol) in water (1 mL) was added to a solution of 89c (4-chloro-2-methoxy-5-methylaniline, 513 mg, 3 mmol) in conc. HCl (10 mL) at 0° C. and the reaction mixture was then stirred for 15 minutes at 0° C. A solution of NaN$_3$ (234 mg, 3.6 mmol) in water (1 mL) was added dropwise. The solution was then stirred for 2 hours at ambient temperature. The reaction mixture was extracted with hexane. The hexane layer was washed with water, dried with anhydrous Na$_2$SO$_4$ and concentrated with a Rotavapor to give product 90c (197 mg, 32% yield).

(2) Synthesis of LC-19

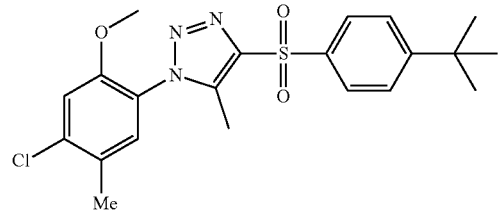

MeONa (108 mg, 2 mmol) and 1-((4-(tert-butyl)phenyl)sulfonyl)propan-2-one (254 mg, 1 mmol) were added to a solution of compound 90c (197 mg, 1 mmol) in MeOH. The mixture was stirred at 60° C. overnight. The reaction was then poured into water and extracted with EtOAc. The EtOAc layer was washed with water, dried with anhydrous Na$_2$SO$_4$ and concentrated with a Rotavapor. The residue was purified by preparative HPLC to give product LC-19 (25 mg, 6% yield). $^1$H NMR (CDCl$_3$, 400 MHz): δ (ppm) 8.02 (d, 2H, J=8.8 Hz), 7.55 (d, 2H, J=8.8 Hz), 7.17 (s, 1H), 7.06 (s, 1H), 3.76 (s, 3H), 2.42 (s, 3H), 2.31 (s, 3H), 1.32 (s, 9H). ESI-MS: m/z 434 (M+H)$^+$.

iv. Preparation of 1-(4-Bromo-2-Methoxy-5-Methylphenyl)-4-((4-(tert-butyl)phenyl)sulfonyl)-5-methyl-1H-1,2,3-triazole (LC-20)

(1) Synthesis of 90d

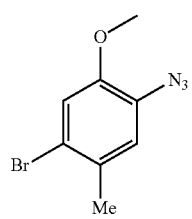

The preparation of compound 90d is similar to the preparation of compound 90b except that compound 89d was used as the starting material to replace compound 89b in the preparation of compound 90b. $^1$H NMR (400 MHz, CDCl$_3$) δ (ppm) 7.01 (s, 1H), 6.83 (s, 1H), 3.82 (s, 3H), 2.28 (s, 3H).

(2) Synthesis of LC-20

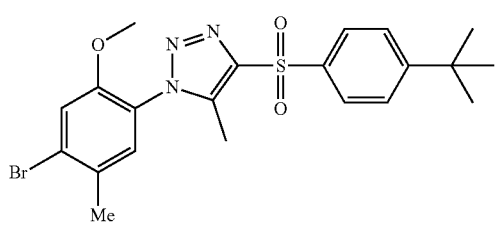 [SMILES: COc1cc(Cl)c(C)cc1-n1nnc(S(=O)(=O)c2ccc(C(C)(C)C)cc2)c1C]

The preparation of LC-20 (70 mg, 14.7% yield) is similar to the preparation of LC-10 except that compound 90d was used as the starting material to replace compound 90b in the preparation of compound LC-10 and the reaction was in a smaller scale (1 mmol scale). $^1$H NMR (CDCl$_3$, 400 MHz): δ (ppm) 8.02 (dd, 2H, J=8.8 Hz, 2 Hz), 8.55 (dd, 2H, J=8.8 Hz, 2 Hz), 7.24 (s, 1H), 7.17 (s, 1H), 3.76 (s, 3H), 2.42 (s, 3H), 2.34 (s, 3H), 1.32 (s, 9H). ESI-MS: m/z 478 (M+H)$^+$.

v. Preparation of 1-(4-bromo-5-chloro-2-methoxyphenyl)-4-((4-(tert-butyl)phenyl)sulfonyl)-5-methyl-1H-1,2,3-triazole (LC-29)

(1) Synthesis of 90e

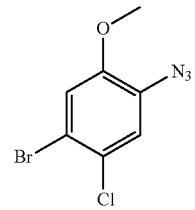

The preparation of 90e is similar to the preparation of 90b except that compound 89e was used as the starting material to replace compound 89b in the preparation of compound 90b. $^1$H NMR (400 MHz, CDCl$_3$) δ (ppm) 7.07 (s, 1H), 7.03 (s, 1H), 3.85 (s, 3H).

(2) Synthesis of LC-29

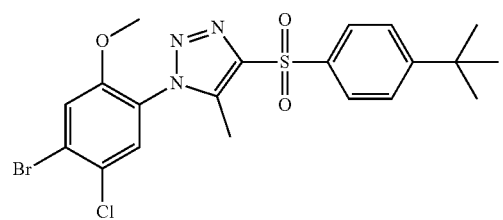 [SMILES: COc1cc(Cl)c(Cl)cc1-n1nnc(S(=O)(=O)c2ccc(C(C)(C)C)cc2)c1C]

The preparation of LC-29 (75 mg, 15.1% yield) is similar to the preparation of LC-10 except that compound 90e was used as the starting material to replace compound 90b in the preparation of compound LC-10 and the reaction was in a smaller scale (1 mmol scale). $^1$H NMR (CDCl$_3$, 400 MHz): δ (ppm) 8.03 (d, 2H, J=8.4 Hz), 8.57 (d, 2H, J=8.4 Hz), 7.43 (s, 1H), 7.34 (s, 1H), 3.82 (s, 3H), 2.45 (s, 3H), 1.34 (s, 9H). ESI-MS: m/z 498 (M+H)$^+$.

b. General Synthesis of Compounds LC-9, LC-28, LC-64, and LC-65

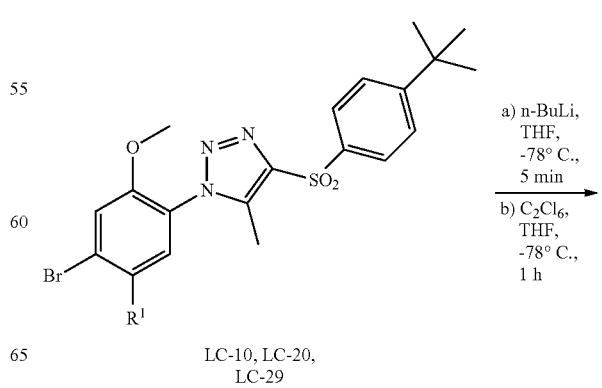

LC-10, LC-20, LC-29

-continued

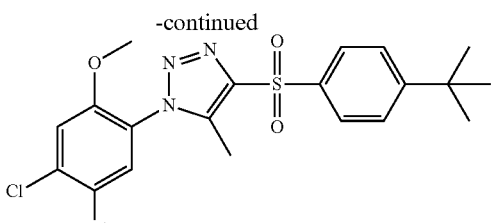

LC-9, LC-28

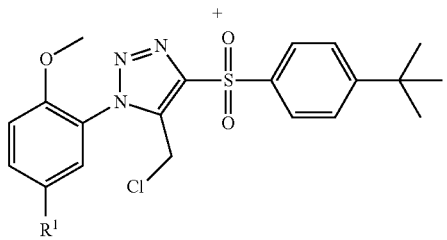

LC-64, LC-65 i. Preparation of 4-((4-(tert-butyl)phenyl)sulfonyl)-1-(4-chloro-2,5-dimethoxyphenyl)-5-methyl-1H-1,2,3-triazole (LC-9) and 4-((4-(tert-butyl)phenyl)sulfonyl)-5-(chloromethyl)-1-(2,5-dimethoxyphenyl)-1H-1,2,3-triazole (LC-64)

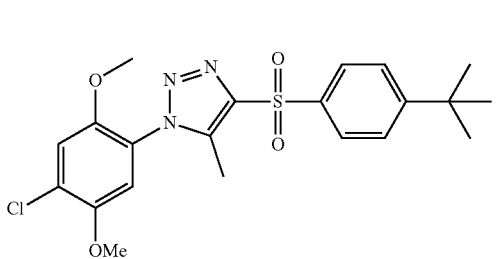

LC-9

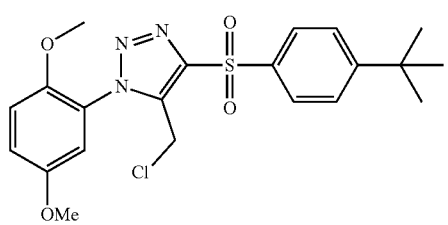

LC-64 n-BuLi (0.24 mL, 0.6 mmol) was added dropwise to solution of compound LC-10 (300 mg, 0.6 mmol) in THF (5 mL) at −78° C. with stirring. The mixture was stirred for 5 min and then $C_2Cl_6$ (430 mg, 1.8 mmol) in THF (2 mL) was added, followed by stirring for 1 more hour. The reaction was quenched with aqueous $NH_4Cl$ and extracted with EtOAc. The EtOAc layer was washed with water, dried with anhydrous $Na_2SO_4$ and concentrated with a Rotavapor. The residue was purified by preparative HPLC to give product LC-9 (30 mg, 11% yield) and LC-64 (25 mg, 4% yield). LC-9 $^1$H NMR (CDCl$_3$, 400 MHz): δ (ppm) 7.98 (d, 2H, J=8.4 Hz), 7.51 (d, 2H, J=8.4 Hz), 7.07 (s, 1H), 6.85 (s, 1H), 3.78 (s, 3H), 3.69 (s, 3H), 2.39 (s, 3H), 1.27 (s, 9H). ESI-MS: m/z 450 (M+H)$^+$. LC-64 $^1$H NMR (CDCl$_3$, 400 MHz): δ (ppm) 8.10 (d, 2H, J=8.8 Hz), 7.59 (d, 2H, J=8.8 Hz), 7.11 (dd, 1H, J=8.8 Hz, 2.8 Hz), 7.03 (d, 1H, J=8.8 Hz), 6.95 (d, 1H, J=2.8 Hz), 3.90 (s, 2H), 3.78 (s, 3H), 3.76 (s, 3H), 1.34 (s, 9H). ESI-MS: m/z 450 (M+H)$^+$.

ii. Preparation of 4-((4-(tert-butyl)phenyl)sulfonyl)-1-(4,5-dichloro-2-methoxyphenyl)-5-methyl-1H-1,2,3-triazole (LC-28)

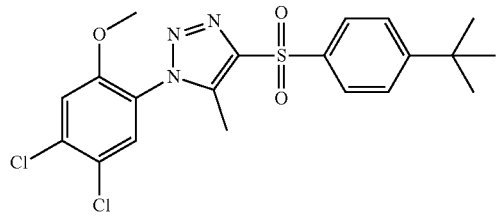

The preparation of LC-28 (38 mg, 14% yield) is similar to the preparation of LC-9 except that LC-29 was used as the starting material to replace LC-10 in the preparation of LC-9. $^1$H NMR (CDCl$_3$, 400 MHz): δ (ppm) 7.96 (d, 2H, J=8.4 Hz), 7.51 (d, 2H, J=8.4 Hz), 7.38 (s, 1H), 7.11 (s, 1H), 3.75 (s, 3H), 2.39 (s, 3H), 1.27 (s, 9H). ESI-MS: m/z 454 (M+H)$^+$.

iii. Preparation of 4-((4-(tert-butyl)phenyl)sulfonyl)-5-(chloromethyl)-1-(2-methoxy-5-methylphenyl)-1H-1,2,3-triazole (LC-65)

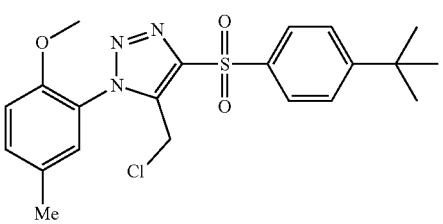 [SMILES: COc1ccc(C)cc1-n1nnc(S(=O)(=O)c2ccc(C(C)(C)C)cc2)c1CCl]

The preparation of LC-65 (80 mg, 30.8% yield) is similar to the preparation of LC-9 except that LC-20 was used as the starting material to replace LC-10 in the preparation of LC-9. $^1$H NMR (CDCl$_3$, 400 MHz): δ (ppm) 8.03 (d, 2H, J=8.8 Hz), 7.52 (d, 2H, J=8.8 Hz), 7.29 (d, 1H, J=8.4 Hz), 7.12 (s, 1H), 6.92 (d, 1H, J=8.4 Hz), 4.81 (s, 2H), 3.70 (s, 3H), 2.27 (s, 3H), 1.28 (s, 9H). ESI-MS: m/z 434 (M+H)$^+$.

a. General Synthesis of Compounds LC-11, LC-21, and LC-30

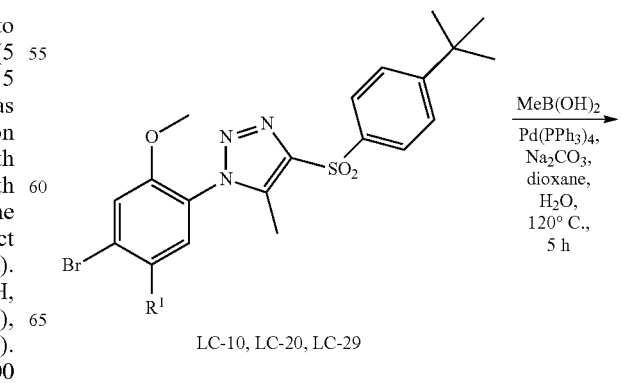

LC-10, LC-20, LC-29

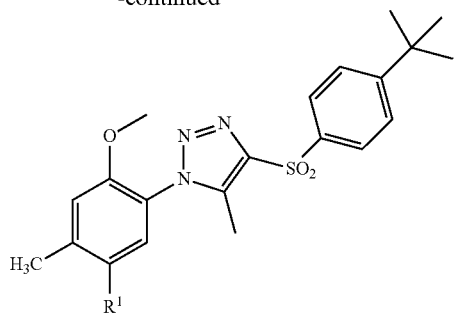

LC-11, LC-21, LC-30 i. Preparation of 4-((4-(tert-butyl)phenyl)sulfonyl)-1-(2,5-dimethoxy-4-methylphenyl)-5-methyl-1H-1,2,3-triazole (LC-11)

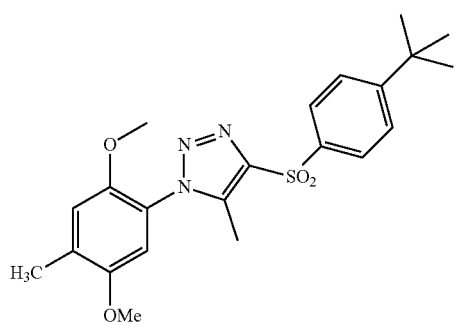 [SMILES: COc1cc(-n2nnc(S(=O)(=O)c3ccc(C(C)(C)C)cc3)c2C)c(OC)cc1C]

MeB(OH)$_2$ (50 mg, 0.8 mmol), Pd(PPh$_3$)$_4$ (30 mg, 0.03 mmol) and aqueous Na$_2$CO$_3$ solution (0.5 mL, 1 mol) were added to a solution of compound LC-10 (0.3 g, 0.6 mmol) in dioxane (5 mL). The reaction was then stirred for 5 hours at 120° C. The reaction was then poured into water and extracted with EtOAc. The EtOAc layer was washed with water, dried with anhydrous Na$_2$SO$_4$ and concentrated with a Rotavapor. The residue was purified by preparative HPLC to give product LC-11 (50 mg, 19% yield). $^1$H NMR (CDCl$_3$, 400 MHz): δ (ppm) 7.98 (d, 2H, J=8.8 Hz), 7.50 (d, 2H, J=8.8 Hz), 6.82 (s, 1H), 6.69 (s, 1H), 3.70 (s, 3H), 3.66 (s, 3H), 2.38 (s, 3H), 2.22 (s, 3H), 1.27 (s, 9H). m/z 430 (M+H)$^+$.

ii. Preparation of 4-((4-(tert-butyl)phenyl)sulfonyl)-1-(2-methoxy-4,5-dimethylphenyl)-5-methyl-1H-1,2,3-triazole (LC-21)

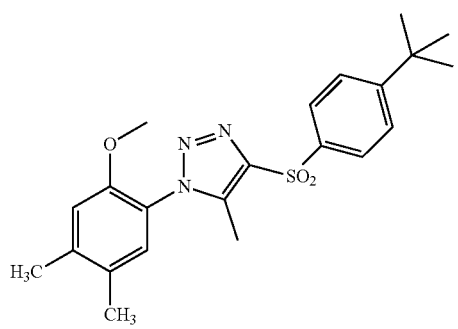 [SMILES: COc1cc(C)c(C)cc1-n1nnc(S(=O)(=O)c2ccc(C(C)(C)C)cc2)c1C]

MeB(OH)$_2$ (50 mg, 0.8 mmol), Pd(PPh$_3$)$_4$ (30 mg, 0.03 mmol) and aqueous Na$_2$CO$_3$ solution (0.5 mL, 1 mol) were added to a solution of compound LC-20 (0.29 g, 0.6 mmol) in dioxane (5 mL). The reaction was then stirred for 5 hours at 120° C. The reaction was then poured into water and extracted with EtOAc. The EtOAc layer was washed with water, dried with anhydrous Na$_2$SO$_4$ and concentrated with a Rotavapor. The residue was purified by preparative HPLC to give product LC-21 (150 mg, 60.5% yield). $^1$H NMR (CDCl$_3$, 400 MHz): δ (ppm) 8.02 (d, 2H, J=8.8 Hz), 7.55 (d, 2H, J=8.8 Hz), 7.03 (s, 1H), 6.82 (s, 1H), 3.73 (s, 3H), 2.41 (s, 3H), 2.31 (s, 3H), 2.19 (s, 3H), 1.32 (s, 9H). m/z 414 (M+H)$^+$.

iii. Preparation of 4-((4-(tert-butyl)phenyl)sulfonyl)-1-(5-chloro-2-methoxy-4-methylphenyl)-5-methyl-1H-1,2,3-triazole (LC-30)

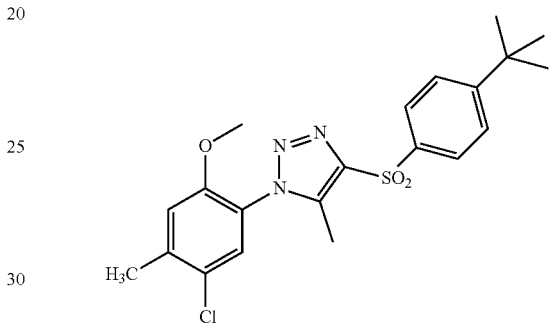

MeB(OH)$_2$ (50 mg, 0.8 mmol), Pd(PPh$_3$)$_4$ (30 mg, 0.03 mmol) and aqueous Na$_2$CO$_3$ solution (0.5 mL, 1 mol) were added to a solution of compound LC-29 (0.3 g, 0.6 mmol) in dioxane (5 mL). The reaction was then stirred for 5 hours at 120° C. The reaction was then poured into water and extracted with EtOAc. The EtOAc layer was washed with water, dried with anhydrous Na$_2$SO$_4$ and concentrated with a Rotavapor. The residue was purified by preparative HPLC to give product LC-30 (135 mg, 51.9% yield). $^1$H NMR (CDCl$_3$, 400 MHz): δ (ppm) 8.01 (d, 2H, J=8.8 Hz), 7.55 (d, 2H, J=8.8 Hz), 7.29 (s, 1H), 6.92 (s, 1H), 3.76 (s, 3H), 2.43 (s, 6H), 1.32 (s, 9H). m/z 434 (M+H)$^+$.

b. General Synthesis of Compounds LC-12, LC-22, and LC-31

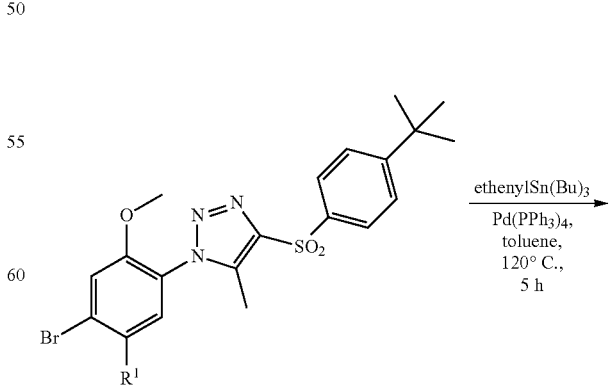

LC-10, LC-20, LC-29

(2) Synthesis of LC-12

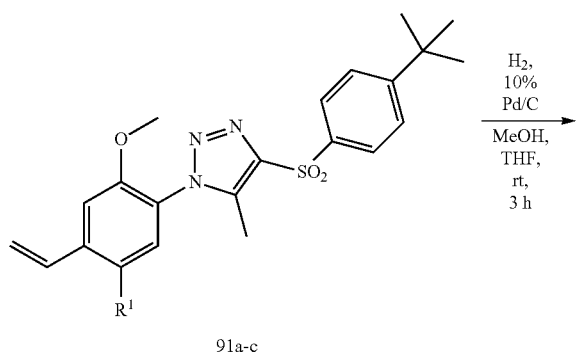

10% Pd/C (10 mg) was added to a solution of compound 91a (85 mg, 0.20 mmol) in MeOH/THF (5 mL/5 mL). Bubbled with $H_2$ gas, the reaction mixture was stirred for 3 hours at room temperature. The reaction mixture was then filtered and the filtrate was concentrated with a Rotavapor. The residue was purified by preparative HPLC to give product LC-12 (65 mg, 76% yield). $^1$H NMR (CDCl$_3$, 400 MHz): δ (ppm) 7.98 (d, 2H, J=8.8 Hz), 7.50 (d, 2H, J=8.8 Hz), 6.81 (s, 1H), 6.70 (s, 1H), 3.69 (s, 3H), 3.67 (s, 3H), 2.65-2.59 (m, 2H), 2.39 (s, 3H), 1.27 (s, 9H), 1.14 (t, 3H, J=7.6 Hz). m/z 444 (M+H)$^+$.

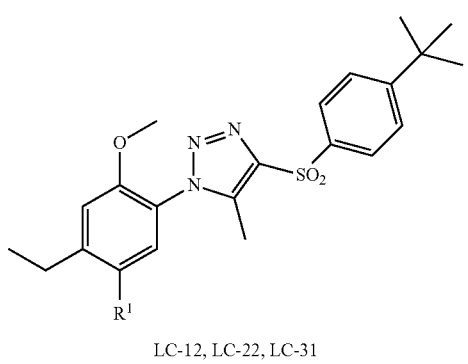

LC-12, LC-22, LC-31 i. Preparation of 4-((4-(tert-butyl)phenyl)sulfonyl)-1-(4-ethyl-2,5-dimethoxyphenyl)-5-methyl-1-1,2,3-triazole (LC-12)

ii. Preparation of 4-((4-(tert-butyl)phenyl)sulfonyl)-1-(4-ethyl-2-methoxy-5-methylphenyl)-5-methyl-1H-1,2,3-triazole (LC-22)

(1) Synthesis of 91a

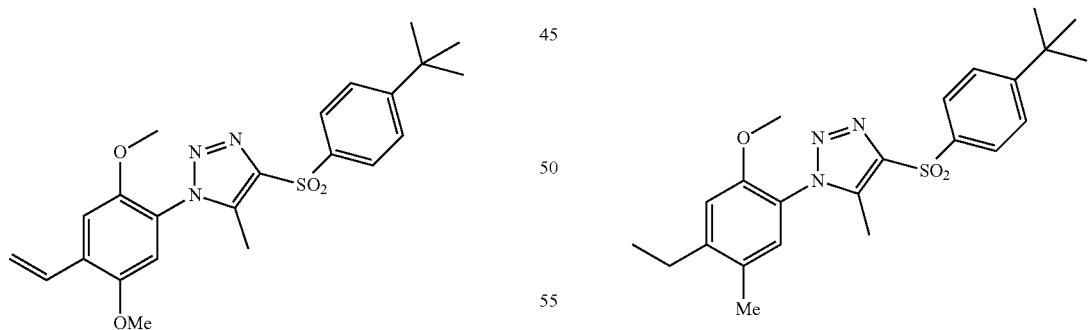

EthenylSn(Bu)$_3$ (385 mg, 1.2 mmol) and Pd(PPh$_3$)$_4$ (70 mg, 0.06 mmol) was added to a solution of compound LC-10 (0.3 g, 0.6 mmol) in toluene (5 mL). The reaction was stirred for 5 hours at 120° C. The reaction was then poured into water and extracted with EtOAc. The EtOAc layer was washed with water, dried with anhydrous Na$_2$SO$_4$ and concentrated with a Rotavapor. The residue was purified by preparative HPLC to give product 91a (85 mg, 32% yield). m/z 442 (M+H)$^+$.

The preparation of compound LC-22 (60 mg, 23.4% yield) was similar to the preparation of compound LC-12 except that compound LC-20 was used as the starting material to replace LC-10 in the preparation of LC-12. $^1$H NMR (CDCl$_3$, 400 MHz): δ (ppm) 7.97 (d, 2H, J=8.4 Hz), 7.49 (d, 2H, J=8.4 Hz), 6.99 (s, 1H), 6.77 (s, 1H), 3.68 (s, 3H), 2.63-2.57 (m, 2H), 2.37 (s, 3H), 2.18 (s, 3H), 1.27 (s, 9H), 1.18 (t, 3H, J=7.2 Hz). m/z 428 (M+H)$^+$.

iii. Preparation of 4-((4-(tert-butyl)phenyl)sulfonyl)-1-(5-chloro-4-ethyl-2-methoxyphenyl)-5-methyl-1H-1,2,3-triazole (LC-31)

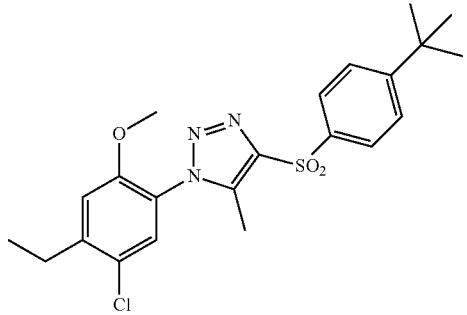 [SMILES: CCc1cc(OC)c(-n2nnc(S(=O)(=O)c3ccc(C(C)(C)C)cc3)c2C)cc1Cl]

The preparation of compound LC-31 (41 mg, 15.3% yield) was similar to the preparation of compound LC-12 except that compound LC-29 was used as the starting material to replace LC-10 in the preparation of LC-12. $^1$H NMR (CDCl$_3$, 400 MHz): δ (ppm) 7.97 (d, 2H, J=8.4 Hz), 7.50 (d, 2H, J=8.4 Hz), 7.25 (s, 1H), 6.86 (s, 1H), 3.73 (s, 3H), 2.77-2.71 (m, 2H), 2.37 (s, 3H), 1.23 (s, 9H), 1.19 (t, 3H, J=6.0 Hz). m/z 448 (M+H)$^+$.

c. General Synthesis of LC-13, LC-23, and LC-32

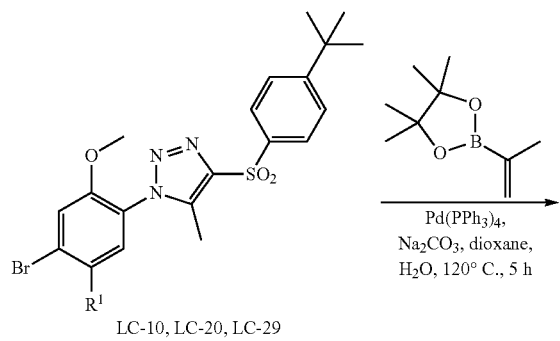

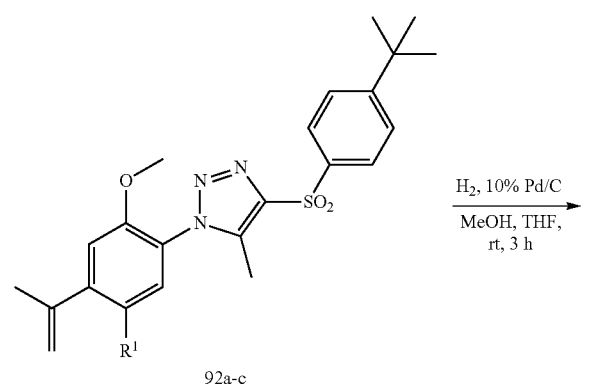

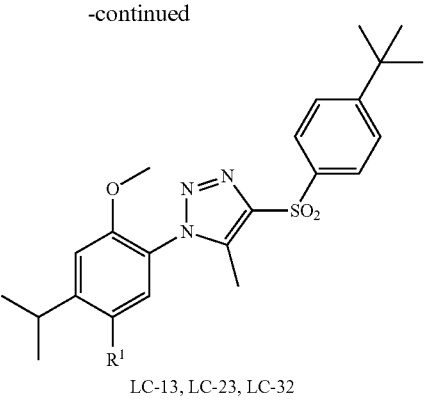

i. Preparation of 4-((4-(tert-butyl)phenyl)sulfonyl)-1-(4-isopropyl-2,5-dimethoxyphenyl)-5-methyl-1H-1,2,3-triazole (LC-13)

(1) Synthesis of 92a

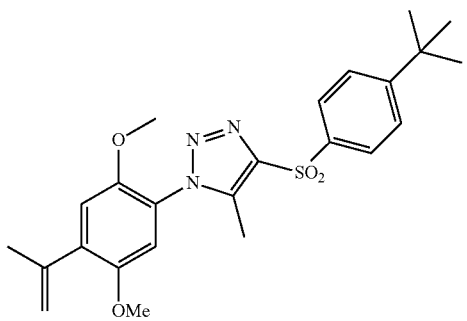 [SMILES: C=C(C)c1cc(OC)c(-n2nnc(S(=O)(=O)c3ccc(C(C)(C)C)cc3)c2C)cc1OC]

4,4,5,5-Tetramethyl-2-(prop-1-en-2-yl)-1,3,2-dioxaborolane (340 mg, 2 mmol), Pd(PPh$_3$)$_4$ (117 mg, 0.1 mmol) and Na$_2$CO$_3$ aq. (0.5 mL, 1 mol) were added to a solution of compound LC-10 (500 mg, 1.0 mmol) and the reaction was stirred for 5 hours at 120° C. The reaction was then poured into water and extracted with EtOAc. The EtOAc layer was washed with water, dried with anhydrous Na$_2$SO$_4$ and concentrated with a Rotavapor. The residue was purified by preparative HPLC to give product 92a (110 mg, 24% yield). m/z 456 (M+H)$^+$.

(2) Synthesis of LC-13

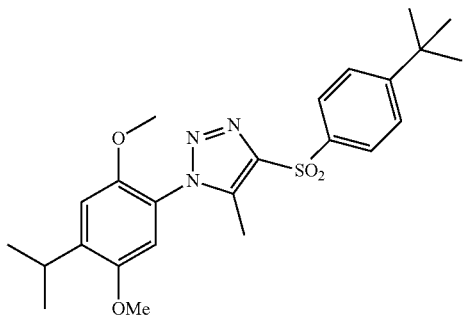 [SMILES: COc1cc(-n2nnc(S(=O)(=O)c3ccc(C(C)(C)C)cc3)c2C)c(OC)cc1C(C)C]

10% Pd/C (10 mg) was added to a solution of compound 92a (110 mg, 0.24 mmol) in MeOH/THF (5 mL/5 mL). Bubbled with H$_2$ gas, the reaction mixture was stirred for 3 hours at room temperature. The reaction mixture was then filtered and the filtrate was concentrated with a Rotavapor. The residue was purified by preparative HPLC to give product LC-13 (100 mg, 91% yield). $^1$H NMR (CDCl$_3$, 400 MHz): δ (ppm) 8.03 (d, 2H, J=8.4 Hz), 7.55 (d, 2H, J=8.4 Hz), 6.90 (s, 1H), 6.75 (s, 1H), 3.74 (s, 3H), 3.72 (s, 3H), 3.38-3.31 (m, 1H), 2.45 (s, 3H), 1.32 (s, 9H), 1.22 (d, 6H, J=6.8 Hz). m/z 458 (M+H)$^+$.

ii. Preparation of 4-((4-(tert-butyl)phenyl)sulfonyl)-1-(4-isopropyl-2-methoxy-5-methylphenyl)-5-methyl-1H-1,2,3-triazole (LC-23)

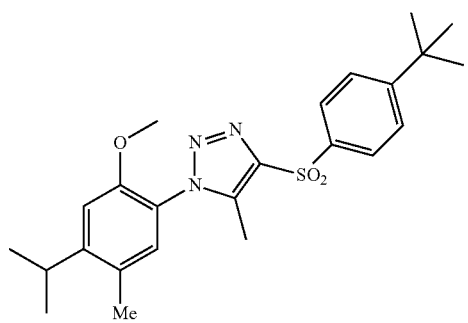 [SMILES: COc1cc(C(C)C)c(C)cc1-n1nnc(S(=O)(=O)c2ccc(C(C)(C)C)cc2)c1C]

The preparation of compound LC-23 (140 mg, 15.9% yield for 2 steps) was similar to the preparation of compound LC-13 except that compound LC-20 was used as the starting material to replace LC-10 in the preparation of LC-13. $^1$H NMR (CDCl$_3$, 400 MHz): δ (ppm) 7.97 (d, 2H, J=8.4 Hz), 7.50 (d, 2H, J=8.4 Hz), 6.98 (s, 1H), 6.89 (s, 1H), 3.74 (s, 3H), 3.41-3.34 (m, 1H), 2.40 (s, 3H), 1.27 (s, 9H), 1.22 (d, 6H, J=6.8 Hz). m/z 442 (M+H)$^+$.

iii. Preparation of 4-((4-(tert-butyl)phenyl)sulfonyl)-1-(5-chloro-4-isopropyl-2-methoxyphenyl)-5-methyl-1H-1,2,3-triazole (LC-32)

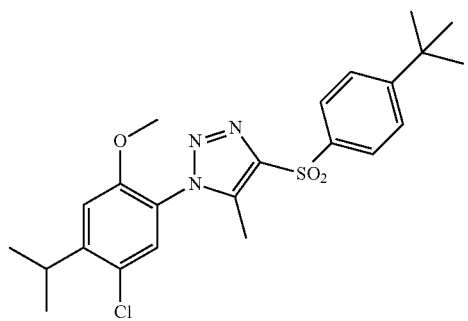 [SMILES: COc1cc(C(C)C)c(Cl)cc1-n1nnc(S(=O)(=O)c2ccc(C(C)(C)C)cc2)c1C]

The preparation of compound LC-32 (31 mg, 3.4% yield for 2 steps) was similar to the preparation of compound LC-13 except that compound LC-29 was used as the starting material to replace LC-10 in the preparation of LC-13. $^1$H NMR (CDCl$_3$, 400 MHz): δ (ppm) 7.97 (d, 2H, J=8.4 Hz), 7.50 (d, 2H, J=8.4 Hz), 7.25 (s, 1H), 6.83 (s, 1H), 3.70 (s, 3H), 3.13-3.06 (m, 1H), 2.38 (s, 3H), 2.21 (s, 3H), 1.27 (s, 9H), 1.19 (d, 6H, J=6.8 Hz). m/z 462 (M+H)$^+$.

d. General Synthesis of LC-14, LC-24, and LC-33

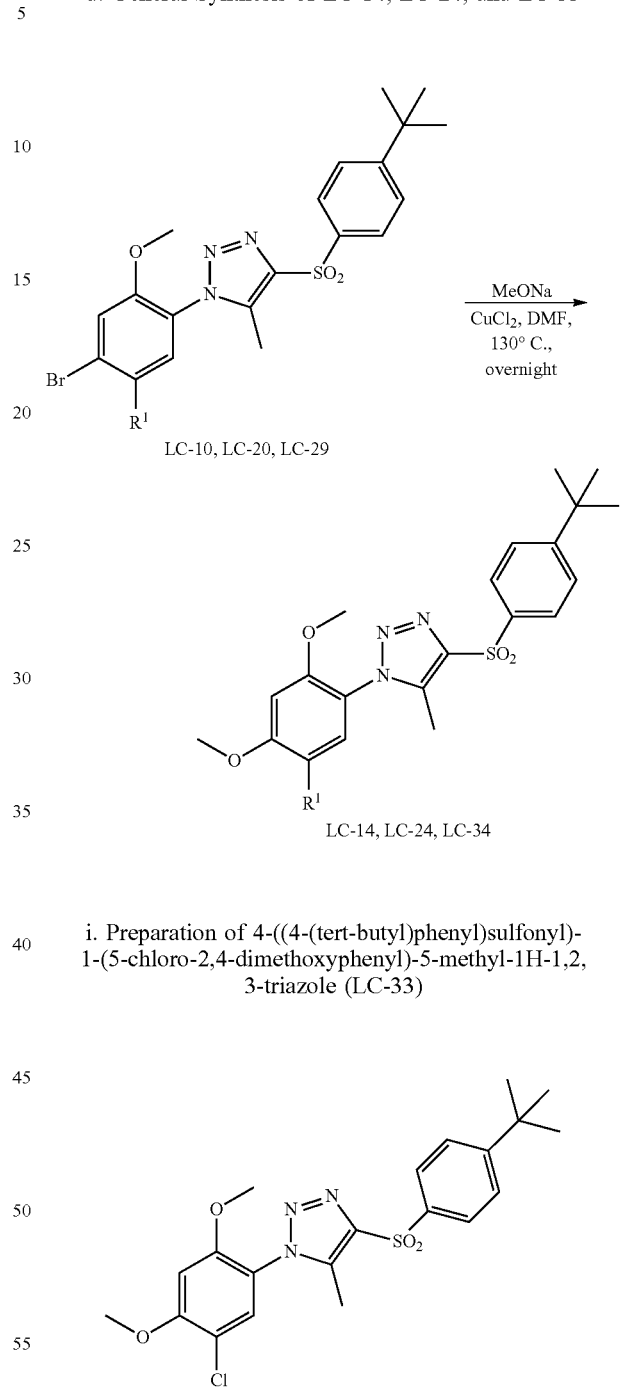

i. Preparation of 4-((4-(tert-butyl)phenyl)sulfonyl)-1-(5-chloro-2,4-dimethoxyphenyl)-5-methyl-1H-1,2,3-triazole (LC-33)

MeONa (130 mg, 2.4 mmol) and CuCl$_2$ (119 mg, 1.2 mmol) were added to a solution of compound LC-29 (300 mg, 0.6 mmol) in DMF (10 mL). The reaction was stirred overnight at 130° C. The reaction was then poured into water and extracted with EtOAc. The EtOAc layer was washed with water, dried with anhydrous Na$_2$SO$_4$ and concentrated with a Rotavapor. The residue was purified by preparative HPLC to give product LC-33 (60 mg, 22% yield). $^1$H NMR (CDCl$_3$, 400 MHz): δ (ppm) 8.01 (d, 2H, J=8.4 Hz), 7.55 (d, 2H, J=8.4 Hz), 7.31 (s, 1H), 6.58 (s, 1H), 3.97 (s, 3H), 3.80 (s, 3H), 2.42 (s, 3H), 1.32 (s, 9H). m/z 450 (M+H)⁺.

ii. Preparation of 4-((4-(tert-butyl)phenyl)sulfonyl)-5-methyl-1-(2,4,5-trimethoxyphenyl)-1H-1,2,3-triazole (LC-14)

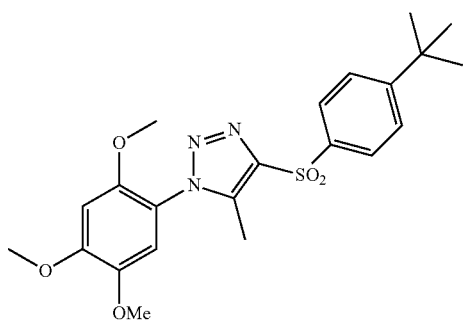 [SMILES: COc1cc(OC)c(-n2nnc(S(=O)(=O)c3ccc(C(C)(C)C)cc3)c2C)cc1OC]

The preparation of compound LC-14 (36 mg, 13.4% yield) was similar to the preparation of compound LC-33 except that compound LC-10 was used as the starting material to replace LC-29 in the preparation of LC-33. ¹H NMR (CDCl₃, 400 MHz): δ (ppm) 7.98 (d, 2H, J=8.4 Hz), 7.50 (d, 2H, J=8.4 Hz), 6.75 (s, 1H), 6.55 (s, 1H), 3.90 (s, 3H), 3.75 (s, 3H), 3.69 (s, 3H), 2.38 (s, 3H), 1.27 (s, 9H). m/z 446 (M+H)⁺.

iii. Preparation of 4-((4-(tert-butyl)phenyl)sulfonyl)-1-(2,4-dimethoxy-5-methylphenyl)-5-methyl-1H-1,2,3-triazole (LC-24)

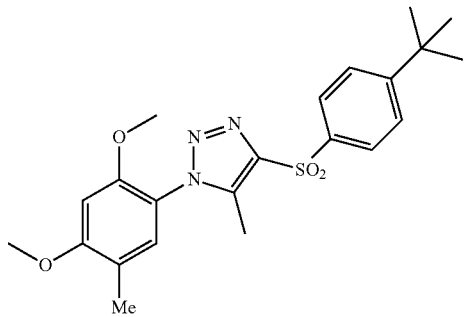 [SMILES: COc1cc(OC)c(-n2nnc(S(=O)(=O)c3ccc(C(C)(C)C)cc3)c2C)cc1C]

The preparation of compound LC-24 (30 mg, 11.7% yield) was similar to the preparation of compound LC-33 except that compound LC-20 was used as the starting material to replace LC-29 in the preparation of LC-33. ¹H NMR (CDCl₃, 400 MHz): δ (ppm) 7.97 (d, 2H, J=8.4 Hz), 7.49 (d, 2H, J=8.4 Hz), 6.97 (s, 1H), 6.44 (s, 1H), 3.84 (s, 3H), 3.71 (s, 3H), 2.36 (s, 3H), 2.08 (s, 3H), 1.27 (s, 9H). m/z 430 (M+H)⁺.

e. General Synthesis of LC-15, LC-25, and LC-34

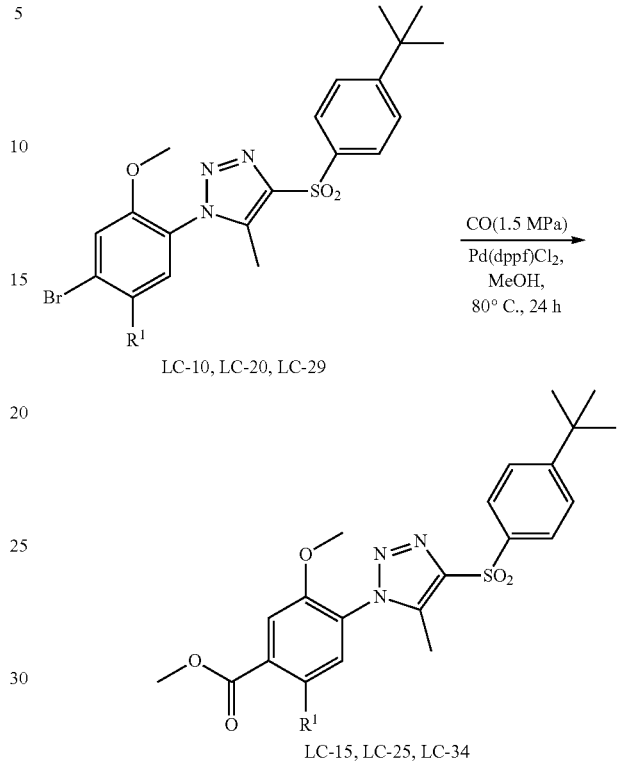

i. Preparation of methyl 4-(4-((4-(tert-butyl)phenyl)sulfonyl)-5-methyl-1H-1,2,3-triazol-1-yl)-2,5-dimethoxybenzoate (LC-15)

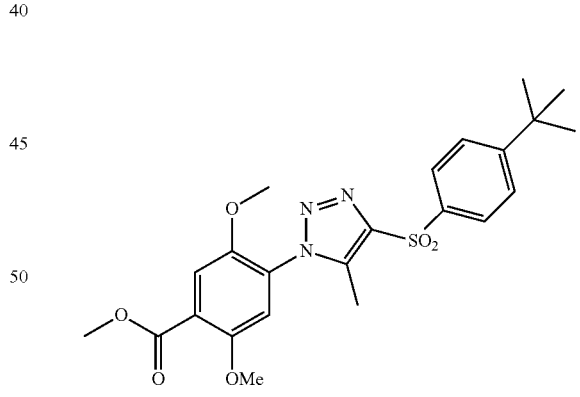

A mixture of compound LC-10 (250 mg, 0.5 mmol) and Pd(dppf)Cl₂ (41 mg, 0.05 mmol) in MeOH (10 mL) was stirred at 80° C. under CO (1.5 MPa) for 24 hours. The reaction was then cooled and the mixture was concentrated with a Rotavapor. The residue was purified by preparative HPLC to give product LC-15 (80 mg, 33% yield). ¹H NMR (CDCl₃, 400 MHz): δ (ppm) 0.98 (d, 2H, J=8.8 Hz), 7.51 (d, 2H, J=8.8 Hz), 7.44 (s, 1H), 6.92 (s, 1H), 3.87 (s, 3H), 3.78 (s, 3H), 3.73 (s, 3H), 2.41 (s, 3H), 1.27 (s, 9H). m/z 474 (M+H)⁺.

ii. Preparation of methyl 4-(4-((4-(tert-butyl)phenyl)sulfonyl)-5-methyl-1H-1,2,3-triazol-1-yl)-5-methoxy-2-methylbenzoate (LC-25)

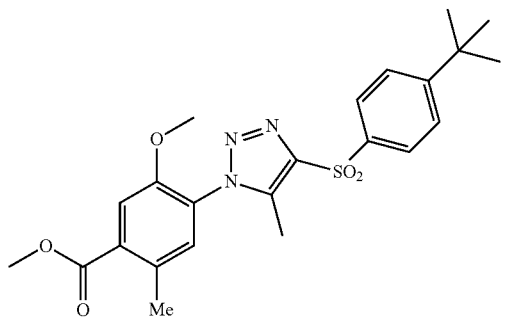 [SMILES: COC(=O)c1cc(OC)c(-n2nnc(S(=O)(=O)c3ccc(C(C)(C)C)cc3)c2C)cc1C]

The preparation of compound LC-25 (54 mg, 23.6% yield) was similar to the preparation of compound LC-15 except that compound LC-20 was used as the starting material to replace LC-10 in the preparation of LC-15. $^1$H NMR (CDCl$_3$, 400 MHz): δ (ppm) 8.02 (d, 2H, J=8.4 Hz), 7.75-7.78 (m, 3H), 7.21 (s, 1H), 3.93 (s, 3H), 3.81 (s, 3H), 2.52 (s, 3H), 2.44 (s, 3H), 1.32 (s, 9H). m/z 458 (M+H)$^+$.

iii. Preparation of methyl 4-(4-((4-(tert-butyl)phenyl)sulfonyl)-5-methyl-1H-1,2,3-triazol-1-yl)-2-chloro-5-methoxybenzoate (LC-34)

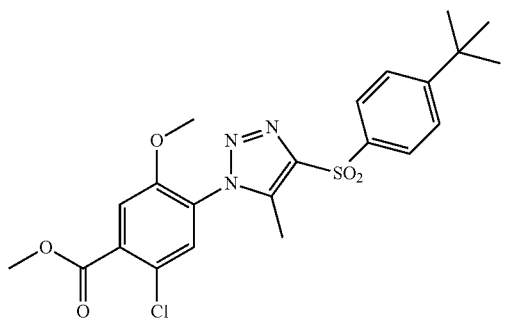 [SMILES: COC(=O)c1cc(OC)c(-n2nnc(S(=O)(=O)c3ccc(C(C)(C)C)cc3)c2C)cc1Cl]

The preparation of compound LC-34 (105 mg, 44% yield) was similar to the preparation of compound LC-15 except that compound LC-29 was used as the starting material to replace LC-10 in the preparation of LC-15. $^1$H NMR (CDCl$_3$, 400 MHz): δ (ppm) 8.01 (d, 2H, J=8.4 Hz), 7.56 (d, 2H, J=8.4 Hz), 7.50 (s, 1H), 7.44 (s, 1H), 3.96 (s, 3H), 3.84 (s, 3H), 2.45 (s, 3H), 1.32 (s, 9H). m/z 478 (M+H)$^+$.

f. General Synthesis of LC-17, LC-27, and LC-36

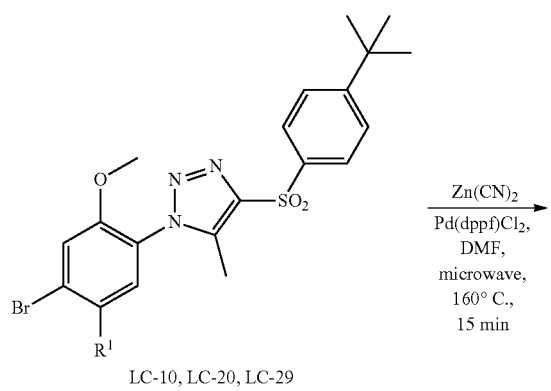

LC-10, LC-20, LC-29

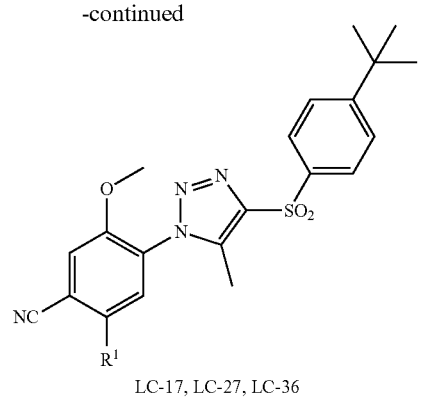

LC-17, LC-27, LC-36 i. Preparation of 4-(4-((4-(tert-butyl)phenyl)sulfonyl)-5-methyl-1H-1,2,3-triazol-1-yl)-2,5-dimethoxybenzonitrile (LC-17)

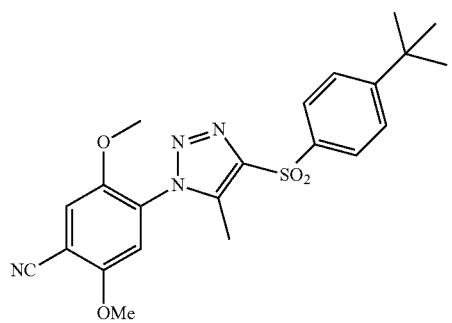 [SMILES: COc1cc(-n2nnc(S(=O)(=O)c3ccc(C(C)(C)C)cc3)c2C)c(OC)cc1C#N]

Zn(CN)$_2$ (423 mg, 3.6 mmol) and Pd(dppf)Cl$_2$ (88 mg, 0.12 mmol) were added to a solution of LC-10 (600 mg, 1.2 mmol) in DMF (10 mL). The reaction was stirred for 15 min at 160° C. under microwave. The reaction was then poured into water and extracted with EtOAc. The EtOAc layer was washed with water, dried with anhydrous Na$_2$SO$_4$ and concentrated with a Rotavapor. The residue was purified by preparative HPLC to give product LC-17 (280 mg, 53% yield). $^1$H NMR (CDCl$_3$, 400 MHz): δ (ppm) 8.63 (d, 2H, J=8.8 Hz), 8.09 (d, 2H, J=8.8 Hz), 7.31 (s, 1H), 7.05 (s, 1H), 3.94 (s, 3H), 3.85 (s, 3H), 2.53 (s, 3H), 1.39 (s, 9H). m/z 441 (M+H)$^+$.

ii. Preparation of 4-(4-((4-(tert-butyl)phenyl)sulfonyl)-5-methyl-1H-1,2,3-triazol-1-yl)-5-methoxy-2-methylbenzonitrile (LC-27)

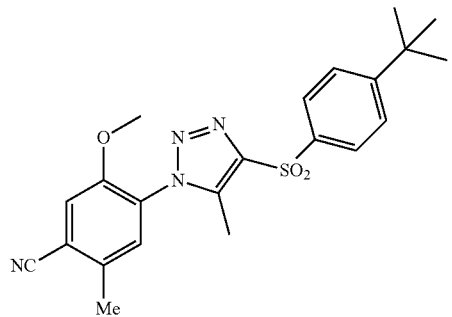 [SMILES: COc1cc(C#N)c(C)cc1-n1nnc(S(=O)(=O)c2ccc(C(C)(C)C)cc2)c1C]

The preparation of compound LC-27 (52 mg, 10.2% yield) was similar to the preparation of compound LC-17 except that compound LC-20 was used as the starting material to replace LC-10 in the preparation of LC-17. ¹H NMR (CDCl₃, 400 MHz): δ (ppm) 7.97 (d, 2H, J=8.4 Hz), 7.51 (d, 2H, J=8.4 Hz), 7.25 (s, 1H), 7.19 (s, 1H), 3.77 (s, 3H), 2.46 (s, 3H), 2.39 (s, 3H), 1.27 (s, 9H). m/z 425 (M+H)⁺.

iii. Preparation of 4-(4-((4-(tert-butyl)phenyl)sulfonyl)-5-methyl-1H-1,2,3-triazol-1-yl)-2-chloro-5-methoxybenzonitrile (LC-36)

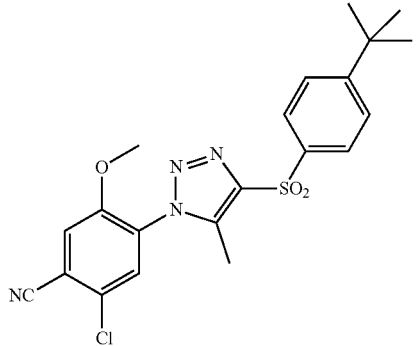 [SMILES: COc1cc(C#N)c(Cl)cc1-n1nnc(S(=O)(=O)c2ccc(C(C)(C)C)cc2)c1C]

The preparation of compound LC-36 (60 mg, 11.3% yield) was similar to the preparation of compound LC-17 except that compound LC-29 was used as the starting material to replace LC-10 in the preparation of LC-17. ¹H NMR (CDCl₃, 400 MHz): δ (ppm) 8.02 (d, 2H, J=8.4 Hz), 7.57 (d, 2H, J=8.4 Hz), 7.53 (s, 1H), 7.34 (s, 1H), 3.87 (s, 3H), 2.47 (s, 3H), 1.33 (s, 9H). m/z 445 (M+H)⁺.

g. General Synthesis of LC-16, LC-26, and LC-35

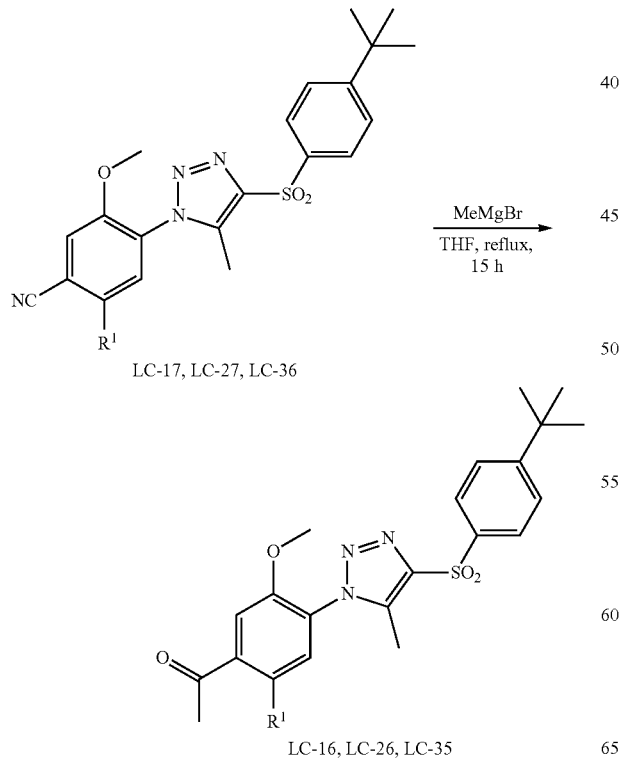

i. Preparation of 1-(4-(4-((4-(tert-butyl)phenyl)sulfonyl)-5-methyl-1H-1,2,3-triazol-1-yl)-2,5-dimethoxyphenyl)ethan-1-one (LC-16)

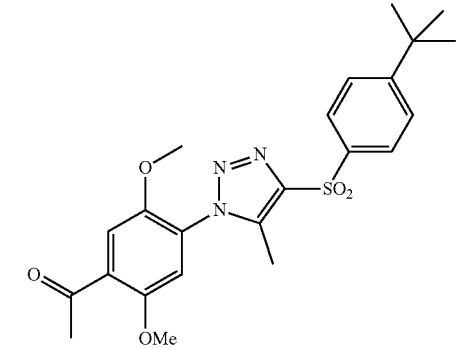 [SMILES: COc1cc(-n2nnc(S(=O)(=O)c3ccc(C(C)(C)C)cc3)c2C)c(OC)cc1C(C)=O]

A solution of MeMgBr (0.2 mL, 1.5 mmol) in THF was added to a solution of compound LC-17 (100 mg, 0.2 mmol) in THF (30 mL). The reaction was under reflux for 15 hours. The reaction was then cooled. HCl (1 mL, 1N) was added and the mixture was stirred for another 2 hours. The reaction was then poured into water and extracted with EtOAc. The EtOAc layer was washed with water, dried with anhydrous Na₂SO₄ and concentrated with a Rotavapor. The residue was purified by preparative HPLC to give product LC-16 (60 mg, 58% yield). ¹H NMR (CDCl₃, 400 MHz): δ (ppm) 7.99 (d, 2H, J=8.8 Hz), 7.52 (d, 2H, J=8.8 Hz), 7.41 (s, 1H), 6.93 (s, 1H), 3.81 (s, 3H), 3.74 (s, 3H), 2.60 (s, 3H), 2.42 (s, 3H), 1.28 (s, 9H). m/z 458 (M+H)⁺.

ii. Preparation of 1-(4-(4-((4-(tert-butyl)phenyl)sulfonyl)-5-methyl-1H-1,2,3-triazol-1-yl)-5-methoxy-2-methylphenyl)ethan-1-one (LC-26)

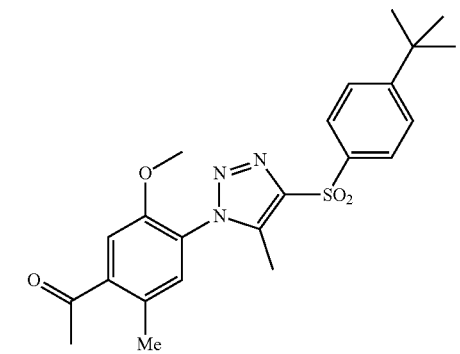 [SMILES: COc1cc(C(C)=O)c(Cl)cc1-n1nnc(S(=O)(=O)c2ccc(C(C)(C)C)cc2)c1C]

The preparation of compound LC-26 (80 mg, 90.7% yield) was similar to the preparation of compound LC-16 except that compound LC-27 was used as the starting material to replace LC-17 in the preparation of LC-16. ¹H NMR (CDCl₃, 400 MHz): δ (ppm) 8.02 (d, J=8.4 Hz, 2H), 7.55 (d, J=8.4 Hz, 2H), 7.20-7.24 (m, 2H), 3.82 (s, 3H), 2.60 (s, 3H), 2.44 (s, 3H), 2.42 (s, 3H), 1.33 (s, 9H). m/z 442 (M+H)⁺.

iii. Preparation of 1-(4-(4-((4-(tert-butyl)phenyl)sulfonyl)-5-methyl-1H-1,2,3-triazol-1-yl)-2-chloro-5-methoxyphenyl)ethan-1-one (LC-35)

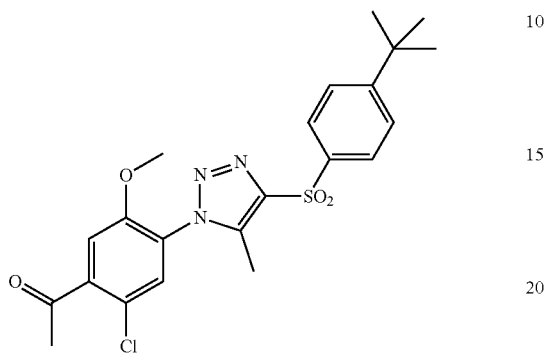

The preparation of compound LC-35 (53 mg, 57.5% yield) was similar to the preparation of compound LC-16 except that compound LC-29 was used as the starting material to replace LC-17 in the preparation of LC-16. $^1$H NMR (CDCl$_3$, 400 MHz): δ (ppm) 8.02 (d, J=8.8 Hz, 2H), 7.56 (d, J=8.8 Hz, 2H), 7.24 (s, 1H), 7.21 (s, 1H), 3.82 (s, 3H), 2.70 (s, 3H), 2.46 (s, 3H), 1.33 (s, 9H). m/z 462 (M+H)$^+$.

h. General Synthesis of LC-18 and LC-63

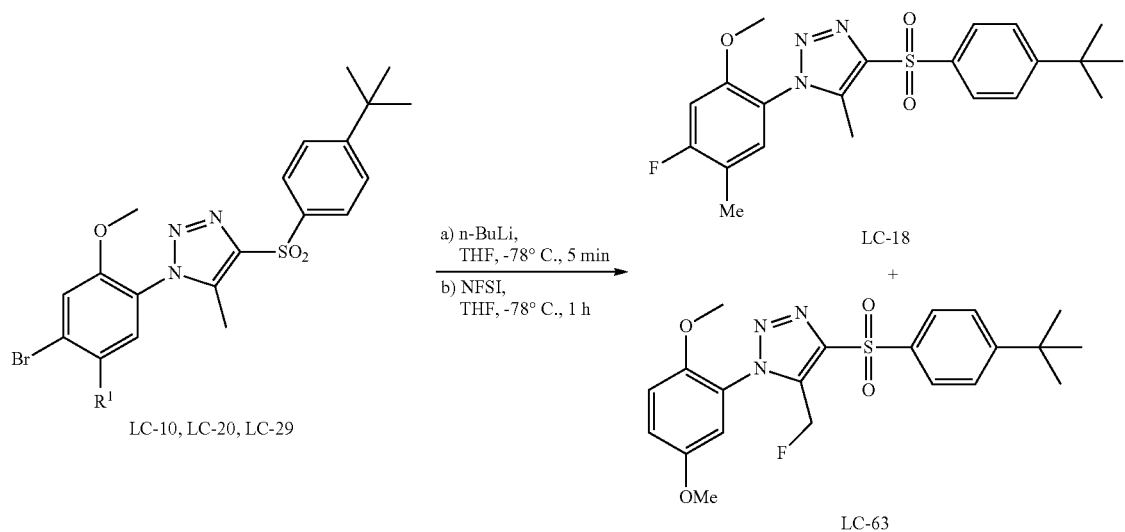

121 i. Preparation of 4-((4-(tert-butyl)phenyl)sulfonyl)-1-(4-fluoro-2-methoxy-5-methylphenyl)-5-methyl-1H-1,2,3-triazole (LC-18)

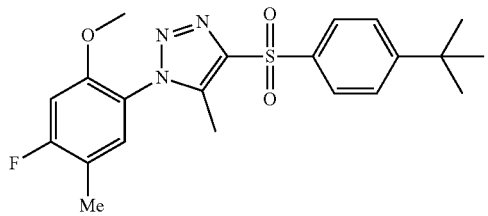 [SMILES: COc1cc(F)c(C)cc1-n1nnc(S(=O)(=O)c2ccc(C(C)(C)C)cc2)c1C]

n-BuLi (0.4 mL, 1 mmol) was added dropwise to solution of compound LC-20 (477 mg, 1 mmol) in THF (5 mL) at −78° C. with stirring. The mixture was stirred for 5 min and then NFSI (409 mg, 1.3 mmol) in THF (2 mL) was added, followed by stirring for 1 more hour. The reaction was quenched with aqueous NH$_4$Cl and extracted with EtOAc. The EtOAc layer was washed with water, dried with anhydrous Na$_2$SO$_4$ and concentrated with a Rotavapor. The residue was purified by preparative HPLC to give product LC-18 (30 mg, 7% yield). $^1$H NMR (CDCl$_3$, 400 MHz): δ (ppm) 8.02 (d, 2H, J=8.4 Hz), 7.55 (d, 2H, J=8.4 Hz), 7.13 (d, 1H, J=7.6 Hz), 6.74 (d, 1H, J=10.4 Hz), 3.74 (s, 3H), 2.42 (s, 3H), 2.21 (d, 3H, J=1.2 Hz), 1.32 (s, 9H). ESI-MS: m/z 418 (M+H)$^+$.

ii. Preparation of 4-((4-(tert-butyl)phenyl)sulfonyl)-1-(2,5-dimethoxyphenyl)-5-(fluoromethyl)-1H-1,2,3-triazole (LC-63)

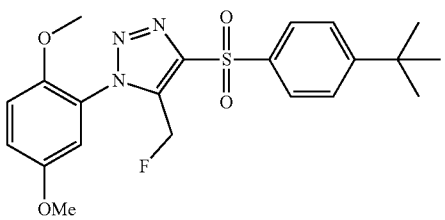 [SMILES: COc1ccc(OC)c(-n2nnc(S(=O)(=O)c3ccc(C(C)(C)C)cc3)c2CF)c1]

n-BuLi (0.4 mL, 1 mmol) was added dropwise to solution of compound LC-10 (493 mg, 1 mmol) in THF (5 mL) at −78° C. with stirring. The mixture was stirred for 5 min and then NFSI (409 mg, 1.3 mmol) in THF (2 mL) was added, followed by stirring for 1 more hour. The reaction was quenched with aqueous NH$_4$Cl and extracted with EtOAc. The EtOAc layer was washed with water, dried with anhydrous Na$_2$SO$_4$ and concentrated with a Rotavapor. The residue was purified by preparative HPLC to give product LC-63 (68 mg, 16% yield). $^1$H NMR (CDCl$_3$, 400 MHz): δ (ppm) 8.06 (d, 2H, J=8.4 Hz), 7.58 (d, 2H, J=8.4 Hz), 7.07-7.10 (m, 1H), 7.00-7.03 (m, 1H), 6.94 (d, 1H, J=2.8 Hz), 5.65 (d, 2H, J=47.2 Hz), 3.76 (s, 3H), 3.73 (s, 3H), 1.33 (s, 9H). ESI-MS: m/z 434 (M+H)$^+$.

122 i. Synthesis of methyl 2-(4-((4-(tert-butyl)phenyl)sulfonyl)-1-(2-methoxy-5-methylphenyl)-1H-1,2,3-triazol-5-yl)acetate (LC-66)

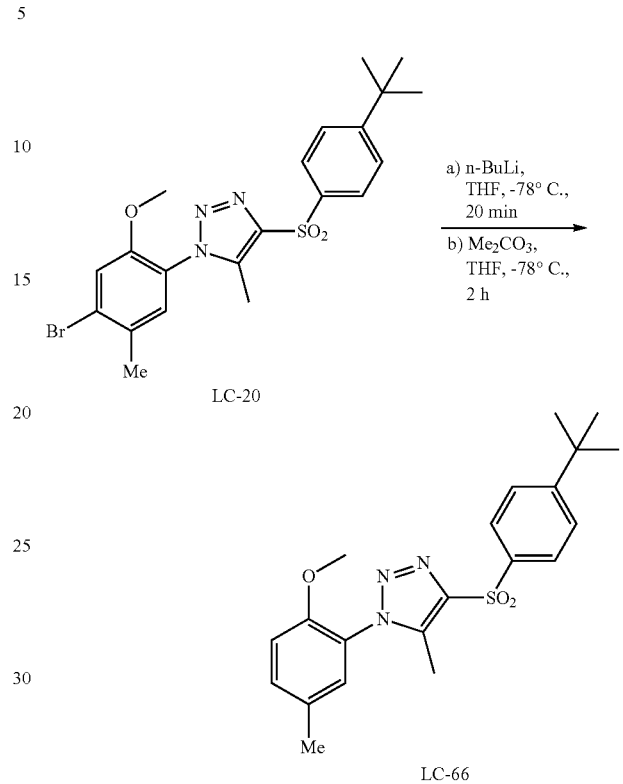

n-BuLi (0.24 mL, 0.6 mmol) was added dropwise to solution of compound LC-20 (300 mg, 0.6 mmol) in THF (5 mL) at −78° C. with stirring. The mixture was stirred for 20 min and then the reaction mixture was poured into a cooled (−78° C.) THF solution of Me$_2$CO$_3$ (113 mg, 1.2 mmol) and stirred for 2 hours at −78° C. The reaction was quenched with aqueous NH$_4$Cl and extracted with EtOAc. The EtOAc layer was washed with water, dried with anhydrous Na$_2$SO$_4$ and concentrated with a Rotavapor. The residue was purified by preparative HPLC to give product LC-66 (10 mg, 3% yield). $^1$H NMR (CDCl$_3$, 400 MHz): δ (ppm) 7.98 (d, 2H, J=8.8 Hz), 7.51 (d, 2H, J=8.8 Hz), 7.25 (d, 1H, J=8.0 Hz), 7.08 (s, 1H), 6.88 (d, 1H, J=8.0 Hz), 3.94 (s, 2H), 3.67 (s, 3H), 3.55 (s, 3H), 2.25 (s, 3H), 1.27 (s, 9H). ESI-MS: m/z 458 (M+H)$^+$.

j. General Synthesis of Compounds LC-37, LC-38, and LC-39

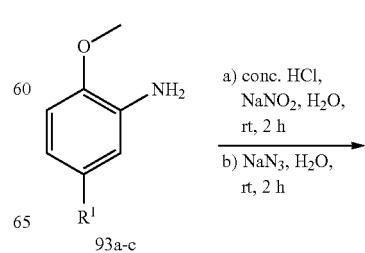

-continued

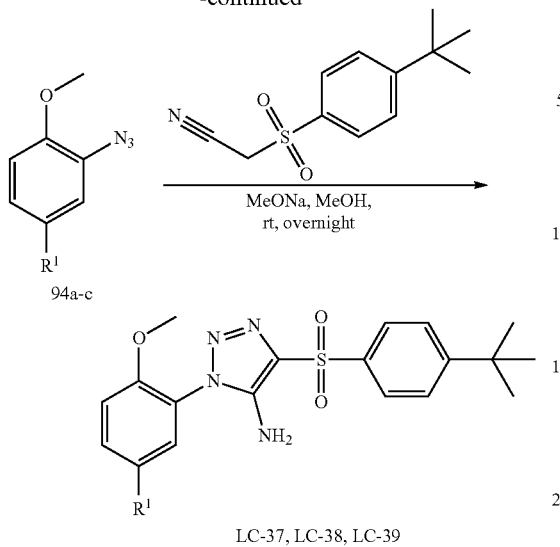

94a-c

LC-37, LC-38, LC-39 i. Preparation of 4-((4-(tert-butyl)phenyl)sulfonyl)-1-(2,5-dimethoxyphenyl)-1H-1,2,3-triazol-5-amine (LC-37)

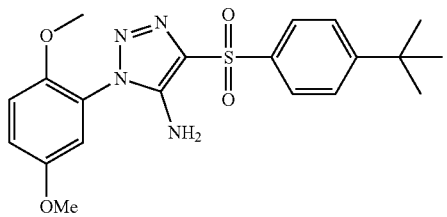

MeONa (2.2 g, 40 mmol) and 94a[32] (4.74 g, 20 mmol) were added to a solution of 2-((4-(tert-butyl)phenyl)sulfonyl)acetonitrile (3.58 g, 20 mmol) in MeOH. The mixture was stirred overnight at room temperature. The formed precipitation was collected by filtration. The crude product was washed with water, MeOH and purified with recrystallization to give product LC-37 (5.12 g, 62% yield). $^1$H NMR (CDCl$_3$, 400 MHz): δ (ppm) 7.98 (d, 2H, J=8.4 Hz), 7.53 (d, 2H, J=8.4 Hz), 7.01 (s, 2H), 6.95 (s, 1H), 5.20 (s, 2H), 3.80 (s, 3H), 3.74 (s, 3H), 1.31 (s, 9H). m/z 417 (M+H)$^+$.

ii. Preparation of 4-((4-(tert-butyl)phenyl)sulfonyl)-1-(2-methoxy-5-methylphenyl)-1H-1,2,3-triazol-5-amine (LC-38)

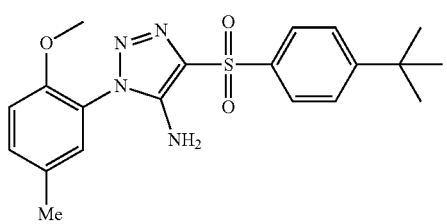

The preparation of compound LC-38 (60 mg, 15% yield) was similar to the preparation of compound LC-37 except that compound 94b[32] was used as the starting material to replace 94a in the preparation of LC-37 and at a smaller scale (1 mmol scale). $^1$H NMR (CDCl$_3$, 400 MHz): δ (ppm) 7.88 (d, 2H, J=8.4 Hz), 7.63 (d, 2H, J=8.4 Hz), 7.33 (d, 1H, J=8.4 Hz), 7.17 (s, 1H), 7.12 (d, 1H, J=8.4 Hz), 6.39 (s, 2H), 3.70 (s, 3H), 2.23 (s, 3H), 1.26 (s, 9H). m/z 401 (M+H)$^+$.

iii. Preparation of 4-((4-(tert-butyl)phenyl)sulfonyl)-1-(5-chloro-2-methoxyphenyl)-1H-1,2,3-triazol-5-amine (LC-39)

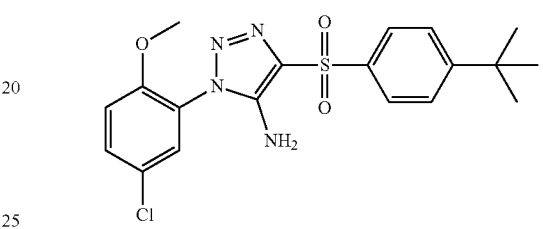

The preparation of compound LC-39 (60 mg, 14.3% yield) was similar to the preparation of compound LC-37 except that compound 94c[32] was used as the starting material to replace 94a in the preparation of LC-37 and at a smaller scale (1 mmol scale). $^1$H NMR (CDCl$_3$, 400 MHz): δ (ppm) 7.96 (d, 2H, J=8.4 Hz), 7.53 (d, 2H, J=8.4 Hz), 7.38-7.45 (m, 2H), 7.02 (d, 1H, J=9.2 Hz), 5.18 (br, 2H), 3.86 (s, 3H), 1.31 (s, 9H). m/z 421 (M+H)$^+$.

k. General Synthesis of 95b, LC-61, and LC-62

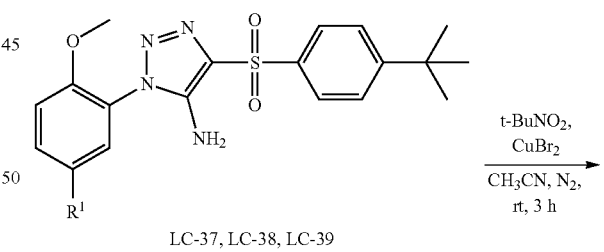

LC-37, LC-38, LC-39

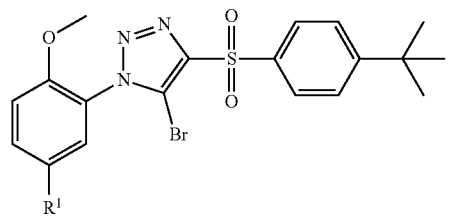

95b, LC-61, LC-62 i. Preparation of 5-bromo-4-((4-(tert-butyl)phenyl)sulfonyl)-1-(2,5-dimethoxyphenyl)-1H-1,2,3-triazole (LC-61, 95a)

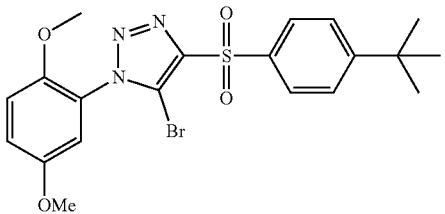

t-BuNO$_2$ (683 mg, 6.64 mmol) was added dropwise to a solution of LC-37 (2.3 g, 5.53 mmol) and CuBr$_2$ (1.85 g, 8.3 mmol) in CH$_3$CN (25 mL) under N$_2$ and room temperature. The reaction was stirred under this condition for 3 hours. H$_2$O (25 mL) was added and the mixture was extracted with EtOAc (25 mL×2). The combined EtOAc layers were dried with anhydrous Na$_2$SO$_4$ and concentrated with a Rotavapor. The residue was purified by silica gel chromatography (Petroleum Ether/EtOAc=10/1 to 6/1) to give product LC-61 (95a, 1.0 g, 37.7% yield). $^1$H NMR (CDCl$_3$, 400 MHz): δ (ppm) 8.06 (d, J=8.0 Hz, 2H), 7.57 (d, J=8.0 Hz, 2H), 6.84-7.00 (m, 3H), 3.77 (s, 3H), 3.74 (s, 3H), 1.33 (s, 9H). m/z 480 (M+H)$^+$.

ii. Preparation of 5-bromo-4-((4-(tert-butyl)phenyl)sulfonyl)-1-(2-methoxy-5-methylphenyl)-1H-1,2,3-triazole (95b)

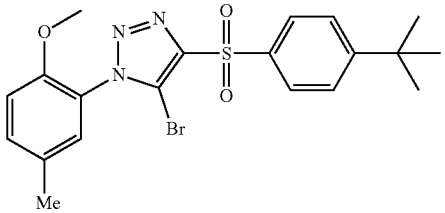 [SMILES: COc1ccc(C)cc1-n1nnc(S(=O)(=O)c2ccc(C(C)(C)C)cc2)c1Br]

t-BuNO$_2$ (683 mg, 6.64 mmol) was added dropwise to a solution of LC-38 (1.9 g, 4.75 mmol) and CuBr$_2$ (1.59 g, 7.12 mmol) in CH$_3$CN (20 mL) under N$_2$ and room temperature. The reaction was stirred under this condition for 2 hours. H$_2$O (20 mL) was added and the mixture was extracted with EtOAc (15 mL×3). The combined EtOAc layers were dried with anhydrous Na$_2$SO$_4$ and concentrated with a Rotavapor. The residue was purified by silica gel chromatography (Petroleum Ether/EtOAc=10/1 to 6/1) to give product 95b (1.0 g, 37.7% yield). m/z 464 (M+H)$^+$.

iii. Preparation of 5-bromo-4-((4-(tert-butyl)phenyl)sulfonyl)-1-(5-chloro-2-methoxyphenyl)-1H-1,2,3-triazole (LC-62, 95c)

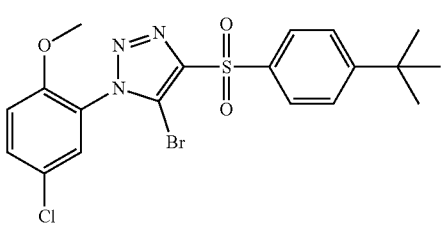 [SMILES: COc1ccc(Cl)cc1-n1nnc(S(=O)(=O)c2ccc(C(C)(C)C)cc2)c1Br]

t-BuNO$_2$ (352 mg, 3.42 mmol) was added dropwise to a solution of LC-39 (1.2 g, 2.85 mmol) and CuBr$_2$ (0.95 g, 4.3 mmol) in CH$_3$CN (15 mL) under N$_2$ and room temperature. The reaction was stirred under this condition for 2 hours. H$_2$O (15 mL) was added and the mixture was extracted with EtOAc (15 mL×3). The combined EtOAc layers were dried with anhydrous Na$_2$SO$_4$ and concentrated with a Rotavapor. The residue was purified by silica gel chromatography (Petroleum Ether/EtOAc=10/1 to 6/1) to give product LC-62 (95c, 0.6 g, 43.8% yield). $^1$H NMR (CDCl$_3$, 400 MHz): δ (ppm) 8.06 (d, J=8.4 Hz, 2H), 7.57 (d, J=8.4 Hz, 2H), 7.52 (d, J=8.4 Hz, 1H), 7.30 (s, 1H), 7.01 (d, J=8.4 Hz, 1H), 3.79 (s, 3H), 1.33 (s, 9H). m/z 484 (M+H)$^+$.

l. General Synthesis of LC-49, LC-50, LC-51, LC-61, and LC-62

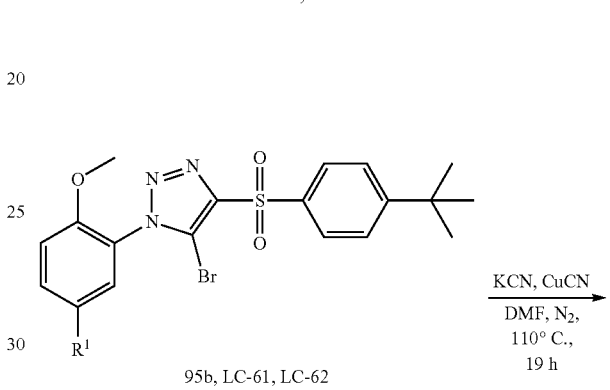

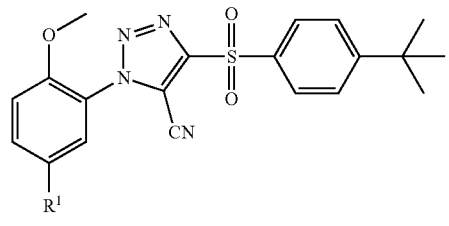

i. Preparation of 4-((4-(tert-butyl)phenyl)sulfonyl)-1-(2,5-dimethoxyphenyl)-1H-1,2,3-triazole-5-carbonitrile (LC-49)

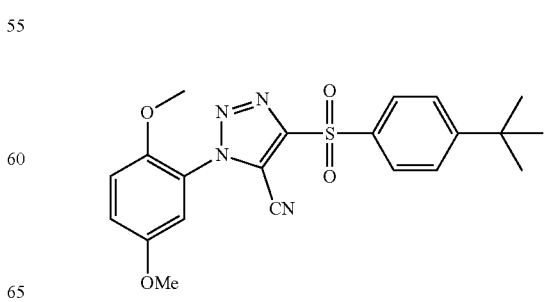

A suspension of compound LC-61 (95a, 1.0 g, 2.1 mmol), KCN (1.36 g, 21 mmol) and CuCN (934 mg, 10.5 mmol) in DMF (15 mL) was heated at 110° C. for 19 hours under $N_2$. EtOAc (30 mL) was then added to the reaction and the mixture was washed with brine, dried with anhydrous $Na_2SO_4$ and concentrated with a Rotavapor. The residue was purified by preparative HPLC to give product LC-49 (180 mg, 20.1% yield). $^1$H NMR (CDCl$_3$, 400 MHz): δ (ppm) 8.11 (d, J=6.8 Hz, 2H), 7.61 (d, J=6.8 Hz, 2H), 7.00-7.13 (m, 3H), 3.85 (s, 3H), 3.78 (s, 3H), 1.34 (s, 9H). m/z 427 (M+H)$^+$.

ii. Preparation of 4-((4-(tert-butyl)phenyl)sulfonyl)-1-(2-methoxy-5-methylphenyl)-1H-1,2,3-triazole-5-carbonitrile (LC-50)

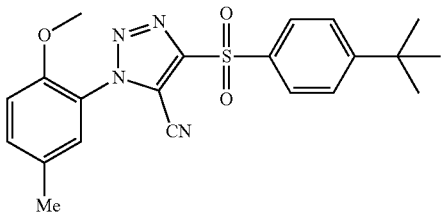

A suspension of compound 95b (400 mg, 0.86 mmol), KCN (559 mg, 8.6 mmol) and CuCN (382 mg, 4.3 mmol) in DMF (6 mL) was heated at 110° C. for 19 hours under $N_2$. EtOAc (15 mL) was then added to the reaction and the mixture was washed with brine, dried with anhydrous $Na_2SO_4$ and concentrated with a Rotavapor. The residue was purified by preparative HPLC to give product LC-50 (53 mg, 15.0% yield). $^1$H NMR (CDCl$_3$, 400 MHz): δ (ppm) 8.09 (d, J=8.4 Hz, 2H), 7.61 (d, J=8.4 Hz, 2H), 7.36 (d, J=8.4 Hz, 1H), 7.24 (s, 1H), 7.01 (d, J=8.4 Hz, 1H), 3.90 (s, 3H), 2.33 (s, 3H), 1.33 (s, 9H). m/z 411 (M+H)$^+$.

iii. Preparation of 4-((4-(tert-butyl)phenyl)sulfonyl)-1-(5-chloro-2-methoxyphenyl)-1H-1,2,3-triazole-5-carbonitrile (LC-51)

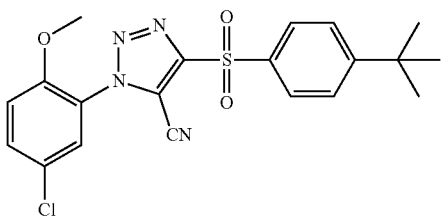 [SMILES: COc1ccc(C)cc1-n1nnc(S(=O)(=O)c2ccc(C(C)(C)C)cc2)c1C#N]

A suspension of compound LC-62 (95c, 600 mg, 1.24 mmol), KCN (807 mg, 12.4 mmol) and CuCN (331 mg, 3.72 mmol) in DMF (7 mL) was heated at 110° C. for 19 hours under $N_2$. EtOAc (30 mL) was then added to the reaction and the mixture was washed with brine, dried with anhydrous $Na_2SO_4$ and concentrated with a Rotavapor. The residue was purified by preparative HPLC to give product LC-51 (160 mg, 30.0% yield). $^1$H NMR (CDCl$_3$, 400 MHz): δ (ppm) 8.10 (d, J=8.4 Hz, 2H), 7.62 (d, J=8.4 Hz, 2H), 7.54 (t, J$_1$=8.8 Hz, J$_2$=2.0 Hz, 1H), 7.46 (d, J=2.0 Hz, 1H), 7.09 (d, J=8.8 Hz, 1H), 3.90 (s, 3H), 1.33 (s, 9H). m/z 431 (M+H)$^+$.

m. General Synthesis of LC-52, LC-53, and LC-54

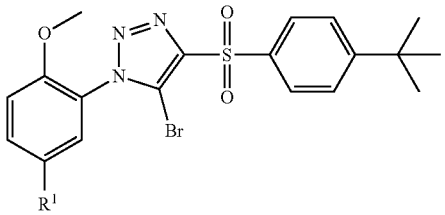

95b, LC-61, LC-62

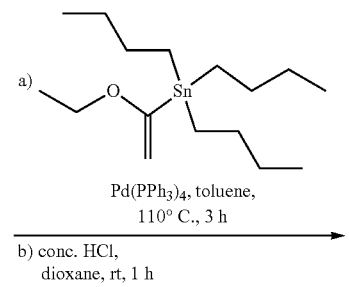

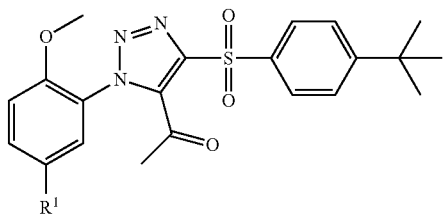

LC-52, LC-53, LC-54 i. Preparation of 1-(4-((4-(tert-butyl)phenyl)sulfonyl)-1-(2,5-dimethoxyphenyl)-1H-1,2,3-triazol-5-yl)ethan-1-one (LC-52)

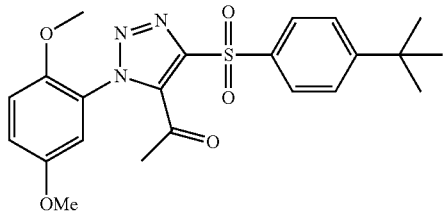

A suspension of compound LC-61 (95a, 400 mg, 0.835 mmol), tributyl(1-ethoxyvinyl)stannane (361 mg, 1.0 mmol), Pd(PPh$_3$)$_4$ (96 mg, 0.0835 mmol) in toluene (8 mL) was heated to 110° C. for 3 hours under N$_2$. After cooled down, concentrated HCl/dioxane (8 mL) was added. The solution was stirred at room temperature for 1 hour. H$_2$O (15 mL) was added and the mixture was extracted with EtOAc (15 mL×3). The combined EtOAc organic layers were dried with anhydrous Na$_2$SO$_4$ and concentrated with a Rotavapor. The residue was purified by preparative HPLC to give the product LC-52 (55 mg, 14.9% yield). $^1$H NMR (CDCl$_3$, 400 MHz): δ (ppm) 8.04 (d, J=8.4 Hz, 2H), 7.58 (d, J=8.4 Hz, 2H), 6.96-7.04 (m, 3H), 3.76 (s, 3H), 3.71 (s, 3H), 2.76 (s, 3H), 1.34 (s, 9H). m/z 444 (M+H)$^+$.

ii. Preparation of 1-(4-((4-(tert-butyl)phenyl)sulfonyl)-1-(2-methoxy-5-methylphenyl)-1H-1,2,3-triazol-5-yl)ethan-1-one (LC-53)

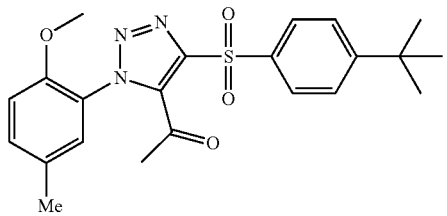 [SMILES: COc1ccc(C)cc1-n1nnc(S(=O)(=O)c2ccc(C(C)(C)C)cc2)c1C(C)=O]

A suspension of compound 95b (300 mg, 0.64 mmol), tributyl(1-ethoxyvinyl)stannane (281 mg, 0.78 mmol), Pd(PPh$_3$)$_4$ (74 mg, 0.064 mmol) in toluene (6 mL) was heated to 110° C. for 3 hours under N$_2$. After cooled down, concentrated HCl/dioxane (7 mL) was added. The solution was stirred at room temperature for 1 hour. H$_2$O (15 mL) was added and the mixture was extracted with EtOAc (10 mL×3). The combined EtOAc organic layers were dried with anhydrous Na$_2$SO$_4$ and concentrated with a Rotavapor. The residue was purified by preparative HPLC to give the product LC-53 (80 mg, 29.3% yield). $^1$H NMR (CDCl$_3$, 400 MHz): δ (ppm) 8.04 (d, J=8.4 Hz, 2H), 7.58 (d, J=8.4 Hz, 2H), 7.23-7.24 (m, 2H), 6.88 (d, J=8.4 Hz, 1H), 3.75 (s, 3H), 2.75 (s, 3H), 2.32 (s, 3H), 1.34 (s, 9H). m/z 428 (M+H)$^+$.

iii. Preparation of 1-(4-((4-(tert-butyl)phenyl)sulfonyl)-1-(5-chloro-2-methoxyphenyl)-1H-1,2,3-triazol-5-yl)ethan-1-one (LC-54)

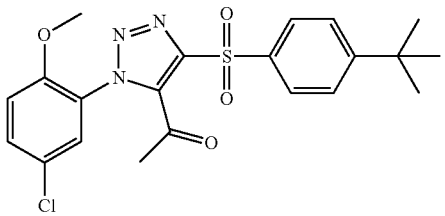 [SMILES: COc1ccc(Cl)cc1-n1nnc(S(=O)(=O)c2ccc(C(C)(C)C)cc2)c1C(C)=O]

A suspension of compound LC-62 (95c, 350 mg, 0.72 mmol), tributyl(1-ethoxyvinyl)stannane (314 mg, 0.87 mmol), Pd(PPh$_3$)$_4$ (83 mg, 0.072 mmol) in toluene (6 mL) was heated to 110° C. for 3 hours under N$_2$. After cooled down, concentrated HCl/dioxane (6 mL) was added. The solution was stirred at room temperature for 1 hour. H$_2$O (15 mL) was added and the mixture was extracted with EtOAc (10 mL×3). The combined EtOAc organic layers were dried with anhydrous Na$_2$SO$_4$ and concentrated with a Rotavapor. The residue was purified by preparative HPLC to give the product LC-54 (35 mg, 10.9% yield). $^1$H NMR (CDCl$_3$, 400 MHz): δ (ppm) 8.02 (d, J=8.4 Hz, 2H), 7.59 (d, J=8.4 Hz, 2H), 7.42-7.49 (m, 2H), 6.93 (d, J=8.4 Hz, 1H), 3.77 (s, 3H), 2.81 (s, 3H), 1.34 (s, 9H). m/z 448 (M+H)$^+$.

n. General Synthesis of LC-55, LC-56, and LC-57

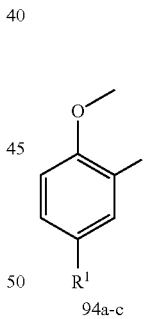

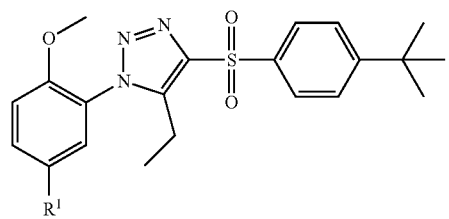 [SMILES: CCc1c(S(=O)(=O)c2ccc(C(C)(C)C)cc2)nnn1-c1cc(Cl)ccc1OC]

LC-55, LC-56, LC-57 i. Preparation of 4-((4-(tert-butyl)phenyl)sulfonyl)-1-(2,5-dimethoxyphenyl)-5-ethyl-1H-1,2,3-triazole (LC-55)

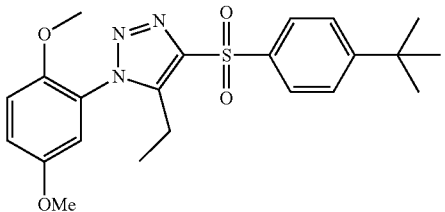

MeONa (108 mg, 2 mmol) and 94a[32] (179 mg, 1 mmol) were added to a solution of 1-((4-(tert-butyl)phenyl)sulfonyl)butan-2-one (268 mg, 1 mmol) in MeOH. The mixture was stirred at 60° C. overnight. H$_2$O (15 mL) was added and the mixture was extracted with EtOAc (15 mL×3). The combined EtOAc organic layers were dried with anhydrous Na$_2$SO$_4$ and concentrated with a Rotavapor. The residue was purified by preparative HPLC to give the product LC-55 (55 mg, 13% yield). $^1$H NMR (CDCl$_3$, 400 MHz): δ (ppm) 8.05 (d, 2H, J=8.4 Hz), 7.57 (d, 2H, J=8.4 Hz), 7.06-7.09 (m, 1H), 6.99-7.01 (m, 1H), 6.84 (d, 1H, J=2.8 Hz), 3.77 (s, 3H), 3.72 (s, 3H), 2.89-2.91 (m, 2H), 1.34 (s, 9H), 1.09 (t, 3H, J=7.6 Hz). m/z 430 (M+H)$^+$.

ii. Preparation of 4-((4-(tert-butyl)phenyl)sulfonyl)-5-ethyl-1-(2-methoxy-5-methylphenyl)-1H-1,2,3-triazole (LC-56)

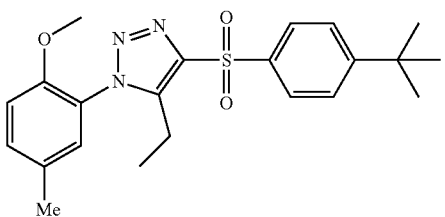

The preparation of compound LC-56 (51 mg, 12.3% yield) was similar to the preparation of compound LC-55 except that compound 94b[32] was used as the starting material to replace 94a in the preparation of LC-55. $^1$H NMR (CDCl$_3$, 400 MHz): δ (ppm) 7.99 (d, 2H, J=8.8 Hz), 7.50 (d, 2H, J=8.8 Hz), 7.25 (d, 1H, J=8.4 Hz), 7.02 (s, 1H), 6.89 (d, 1H, J=8.4 Hz), 3.67 (s, 3H), 2.81 (s, 2H), 2.26 (s, 3H), 1.27 (s, 9H), 1.02 (t, 3H, J=7.6 Hz). m/z 414 (M+H)$^+$.

iii. Preparation of 4-((4-(tert-butyl)phenyl)sulfonyl)-1-(5-chloro-2-methoxyphenyl)-5-ethyl-1H-1,2,3-triazole (LC-57)

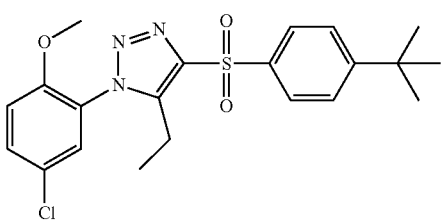

The preparation of compound LC-57 (94 mg, 21.7% yield) was similar to the preparation of compound LC-55 except that compound 94c[32] was used as the starting material to replace 94a in the preparation of LC-55. $^1$H NMR (CDCl$_3$, 400 MHz): δ (ppm) 8.04 (d, 2H, J=8.4 Hz), 7.57 (d, 2H, J=8.4 Hz), 7.49-7.52 (m, 1H), 7.30 (s, 1H), 7.02 (d, 1H, J=8.8 Hz), 3.78 (s, 3H), 2.88-2.90 (m, 2H), 1.34 (s, 9H), 1.09 (t, 3H, J=7.6 Hz). m/z 434 (M+H)$^+$.

o. General Synthesis of Compounds LC-58, LC-59, and LC-60

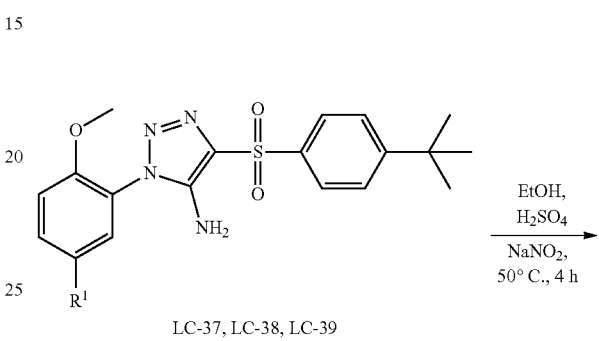

LC-37, LC-38, LC-39

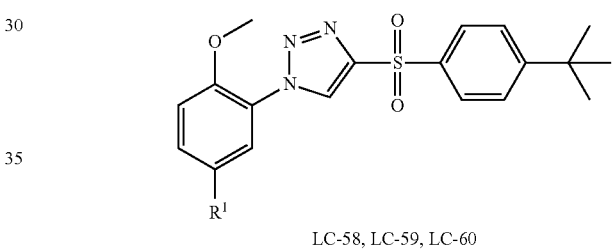

LC-58, LC-59, LC-60 i. Preparation of 4-((4-(tert-butyl)phenyl)sulfonyl)-1-(2,5-dimethoxyphenyl)-1H-1,2,3-triazole (LC-58)

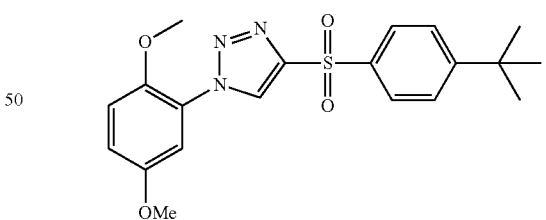

NaNO$_2$ (83 mg, 1.2 mmol) was added to a solution of LC-37 (416 mg, 1 mmol) in 20 mL EtOH and 2 mL H$_2$SO$_4$. The reaction was then stirred at 50° C. for 4 hours. H$_2$O (25 mL) was added and the mixture was extracted with EtOAc (25 mL×3). The combined EtOAc layers were dried with anhydrous Na$_2$SO$_4$ and concentrated with a Rotavapor. The residue was purified by preparative HPLC to give product LC-58 (98 mg, 24% yield). $^1$H NMR (CDCl$_3$, 400 MHz): δ (ppm) 8.74 (s, 1H), 8.03 (d, 2H, J=8.4 Hz), 7.55 (d, 2H, J=8.4 Hz), 7.37 (d, 1H, J=2.8 Hz), 6.95-7.02 (m, 2H), 3.86 (s, 3H), 3.77 (s, 3H), 1.31 (s, 9H). m/z 402 (M+H)$^+$.

ii. Preparation of 4-((4-(tert-butyl)phenyl)sulfonyl)-1-(2-methoxy-5-methylphenyl)-1H-1,2,3-triazole (LC-59)

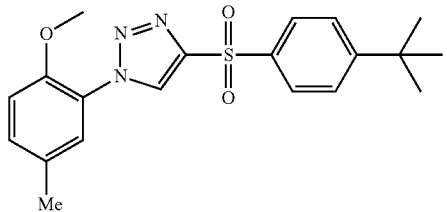

The preparation of compound LC-59 (50 mg, 10.8% yield) was similar to the preparation of compound LC-58 except that compound LC-38 was used as the starting material to replace LC-37 in the preparation of LC-58. $^1$H NMR (CDCl$_3$, 400 MHz): δ (ppm) 8.67 (s, 1H), 8.03 (d, 2H, J=8.8 Hz), 7.53-7.58 (m, 3H), 7.21-7.24 (m, 1H), 6.96 (d, 1H, J=8.4 Hz), 3.86 (s, 3H), 2.32 (s, 3H), 1.31 (s, 9H). m/z 386 (M+H)$^+$.

iii. Preparation of 4-((4-(tert-butyl)phenyl)sulfonyl)-1-(5-chloro-2-methoxyphenyl)-1-1,2,3-triazole (LC-60)

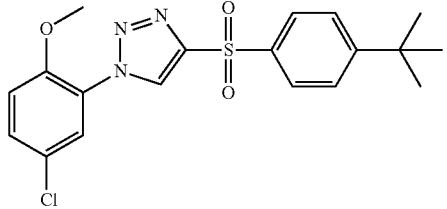 [SMILES: COc1ccc(Cl)cc1-n1cc(S(=O)(=O)c2ccc(C(C)(C)C)cc2)nn1]

The preparation of compound LC-60 (96 mg, 19.8% yield) was similar to the preparation of compound LC-58 except that compound LC-39 was used as the starting material to replace LC-37 in the preparation of LC-58. $^1$H NMR (CDCl$_3$, 400 MHz): δ (ppm) 8.70 (s, 1H), 8.02 (d, 2H, J=8.8 Hz), 7.83 (d, 1H, J=2.4 Hz), 7.55 (d, 2H, J=8.8 Hz), 7.38-7.41 (m, 1H), 7.03 (d, 1H, J=9.2 Hz), 3.92 (s, 3H), 1.31 (s, 9H). m/z 406 (M+H)$^+$.

p. General Synthesis of LC-40, LC-41, and LC-42

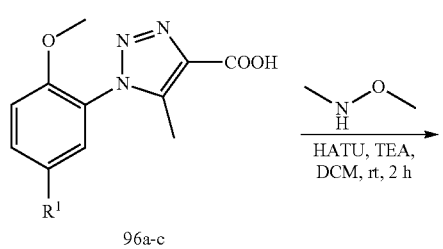

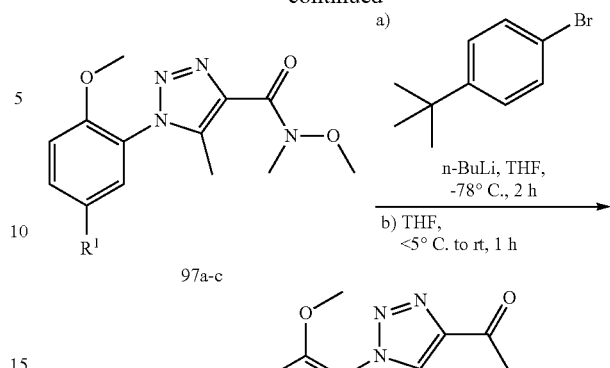

i. Preparation of (4-(tert-butyl)phenyl)(1-(2,5-dimethoxyphenyl)-5-methyl-1-1,2,3-triazol-4-yl)methanone (LC-40)

(1) Synthesis of 97a

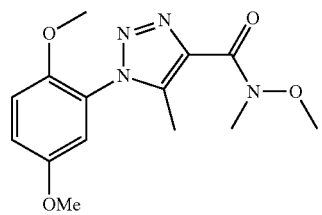 [SMILES: COc1ccc(OC)c(-n2nnc(C(=O)N(C)OC)c2C)c1]

O,N-Dimethyl-hydroxylamine (221 mg, 2.28 mmol) was added to a solution of compound 1-(2,5-dimethoxyphenyl)-5-methyl-1H-1,2,3-triazole-4-carboxylic acid (96a, 500 mg, 1.9 mmol), HATU (866 mg, 2.28 mmol), TEA (767 mg, 7.6 mmol) in DCM (15 mL) and the reaction was stirred at room temperature for 2 hours. The mixture was washed with H$_2$O (15 mL) and organic layer was dried with anhydrous Na$_2$SO$_4$ and concentrated with a Rotavapor. The residue was purified by preparative TLC (Petroleum Ether/EtOAc=1/1) to give the product 97a (500 mg, 86.2% yield). m/z 307 (M+H)$^+$.

(2) Synthesis of LC-40

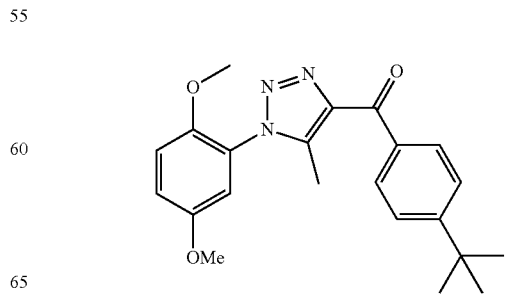

n-BuLi (1.17 mL, 2.94 mmol) was added to 1-bromo-4-tert-butyl-benzene (623 mg, 2.94 mmol) in THF (10 mL) at −78° C. and the solution was then stirred at −70° C. for 2 hours. A solution of compound 97a (500 mg, 0.98 mmol) in THF (6 mL) was added dropwise with the reaction temperature maintained below 5° C. The result mixture was stirred at room temperature for 1 hour. H$_2$O (10 mL) was added and the mixture was extracted with EtOAc (10 mL×2). The combined EtOAc organic layers were dried with anhydrous Na$_2$SO$_4$ and concentrated with a Rotavapor. The residue was purified by preparative HPLC to give the product LC-40 (130 mg, 35% yield). $^1$H NMR (CDCl$_3$, 400 MHz): δ (ppm) 8.32 (d, J=8.4 Hz, 2H), 7.52 (d, J=8.4 Hz, 2H), 7.00-7.01 (m, 2H), 6.96 (s, 1H), 3.80 (s, 3H), 3.75 (s, 3H), 2.50 (s, 3H), 1.35 (s, 9H). m/z 380 (M+H)$^+$.

ii. Preparation of (4-(tert-butyl)phenyl)(1-(2-methoxy-5-methylphenyl)-5-methyl-1-1,2,3-triazol-4-yl)methanone (LC-41)

(1) Synthesis of 97b

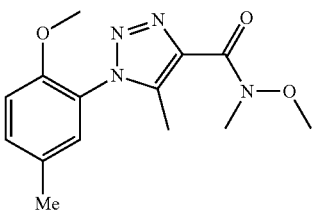

O,N-Dimethyl-hydroxylamine (188 mg, 1.94 mmol) was added to a solution of compound 1-(2-methoxy-5-methyl-phenyl)-5-methyl-1H-1,2,3-triazole-4-carboxylic acid (96b, 400 mg, 1.62 mmol), HATU (862 mg, 2.07 mmol), TEA (0.9 mL, 6.48 mmol) in DCM (15 mL) and the reaction was stirred at room temperature for 2 hours. The mixture was washed with H$_2$O (15 mL) and organic layer was dried with anhydrous Na$_2$SO$_4$ and concentrated with a Rotavapor. The residue was purified by preparative TLC (Petroleum Ether/EtOAc=1/1) to give the product 97b (400 mg, 86.2% yield). m/z 291 (M+H)$^+$.

(2) Synthesis of LC-41

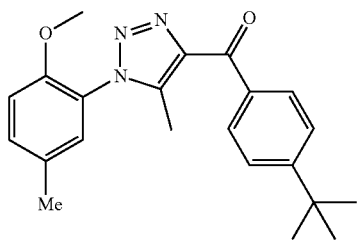 [SMILES: COc1ccc(C)cc1-n1nnc(C(=O)c2ccc(C(C)(C)C)cc2)c1C]

n-BuLi (1.1 mL, 2.76 mmol) was added to 1-bromo-4-tert-butyl-benzene (585 mg, 2.76 mmol) in THF (8 mL) at −78° C. and the solution was then stirred at −70° C. for 1 hour. A solution of compound 97b (400 mg, 1.38 mmol) in THF (8 mL) was added dropwise with the reaction temperature maintained below 5° C. The result mixture was stirred at room temperature for 1 hour. H$_2$O (20 mL) was added and the mixture was extracted with EtOAc (10 mL×3). The combined EtOAc organic layers were dried with anhydrous Na$_2$SO$_4$ and concentrated with a Rotavapor. The residue was purified by preparative HPLC to give the product LC-41 (55 mg, 11% yield). $^1$H NMR (CDCl$_3$, 400 MHz): δ (ppm) 8.30 (d, J=8.0 Hz, 2H), 7.52 (d, J=8.0 Hz, 2H), 7.31 (d, J=8.4 Hz, 1H), 7.21 (S, 1H), 6.97 (d, J=8.4 Hz, 1H), 3.78 (s, 3H), 2.49 (s, 3H), 2.35 (s, 3H), 1.35 (s, 9H). m/z 364 (M+H)$^+$.

iii. Preparation of (4-(tert-butyl)phenyl)(1-(5-chloro-2-methoxyphenyl)-5-methyl-1-1,2,3-triazol-4-yl)methanone (LC-42)

(1) Synthesis of 97c

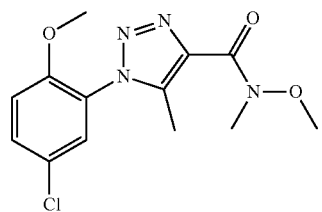 [SMILES: COc1ccc(Cl)cc1-n1nnc(C(=O)N(C)OC)c1C]

O,N-Dimethyl-hydroxylamine (218 mg, 2.24 mmol) was added to a solution of compound 1-(5-chloro-2-methoxy-phenyl)-5-methyl-1H-1,2,3-triazole-4-carboxylic acid (96c, 500 mg, 1.87 mmol), HATU (1.06 g, 2.8 mmol), TEA (1.03 mL, 7.48 mmol) in DCM (15 mL) and the reaction was stirred at room temperature for 2 hours. The mixture was washed with H$_2$O (15 mL) and organic layer was dried with anhydrous Na$_2$SO$_4$ and concentrated with a Rotavapor. The residue was purified by preparative TLC (Petroleum Ether/EtOAc=1/1) to give the product 97c (260 mg, 44.8% yield). m/z 311 (M+H)$^+$.

(2) Synthesis of LC-42

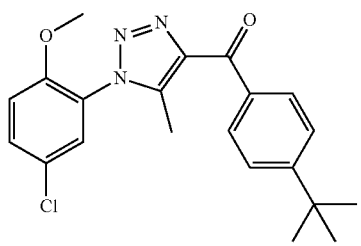 [SMILES: COc1ccc(Cl)cc1-n1nnc(C(=O)c2ccc(C(C)(C)C)cc2)c1C]

n-BuLi (1.0 mL, 2.52 mmol) was added to 1-bromo-4-tert-butyl-benzene (534 mg, 2.52 mmol) in THF (10 mL) at −78° C. and the solution was then stirred at −70° C. for 2 hours. A solution of compound 97c (260 mg, 0.84 mmol) in THF (6 mL) was added dropwise with the reaction temperature maintained below 5° C. The result mixture was stirred at room temperature for 1 hour. H$_2$O (10 mL) was added and the mixture was extracted with EtOAc (10 mL×2). The combined EtOAc organic layers were dried with anhydrous Na$_2$SO$_4$ and concentrated with a Rotavapor. The residue was purified by preparative HPLC to give the product LC-42 (80 mg, 24.9% yield). $^1$H NMR (CDCl$_3$, 400 MHz): δ (ppm) 8.28 (d, J=8.8 Hz, 2H), 7.53 (d, J=8.8 Hz, 2H), 7.43-7.50 (m, 2H), 7.04 (d, J=8.8 Hz, 1H), 3.82 (s, 3H), 2.51 (s, 3H), 1.36 (s, 9H). m/z 384 (M+H)$^+$.

q. General Synthesis of LC-43, LC-44, and LC-45

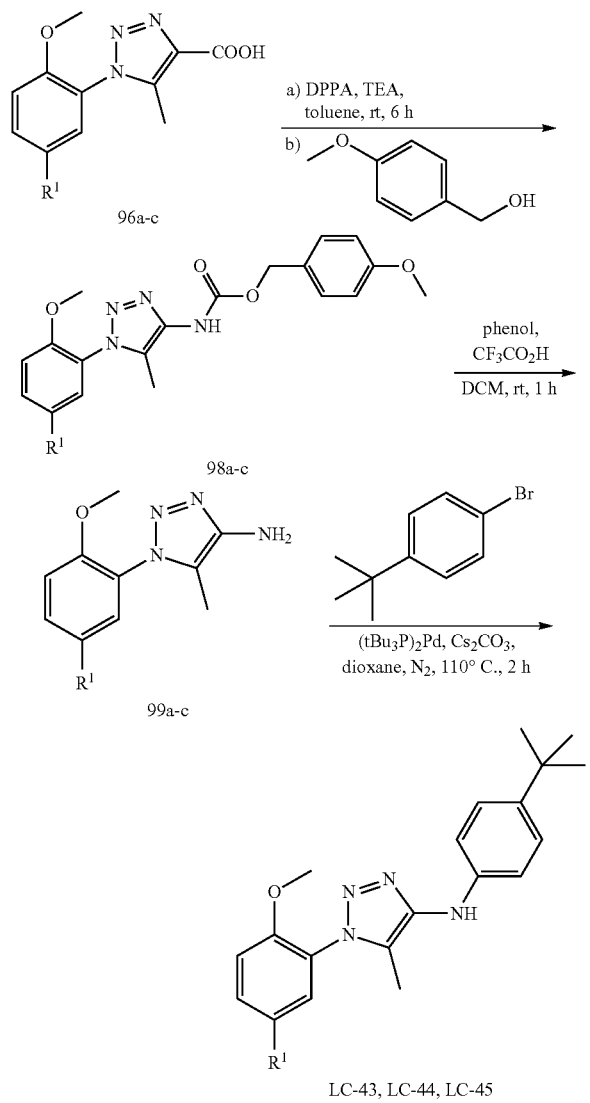

96a-c 98a-c 99a-c

LC-43, LC-44, LC-45 i. Preparation of N-(4-(tert-butyl)phenyl)-1-(2,5-dimethoxyphenyl)-5-methyl-1H-1,2,3-triazol-4-amine (LC-43)

(1) Synthesis of 98a

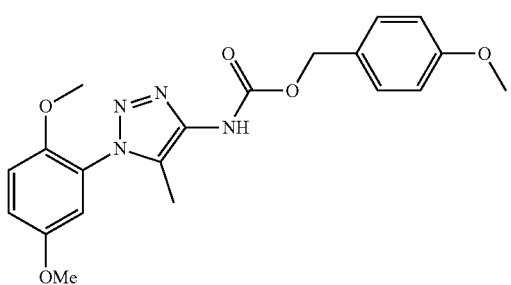 [SMILES: COc1ccc(COC(=O)Nc2nnn(-c3cc(OC)ccc3OC)c2C)cc1]

A solution of compound 96a (3.0 g, 11 mmol), DPPA (2.6 mL, 12 mmol), TEA (3.06 mL, 22 mmol) in toluene (35 mL) was stirred at room temperature for 6 hours. (4-Methoxyphenyl)-methanol (3.8 g, 27.5 mmol) was then added and the reaction was heated to 100° C. for 18 hours. EtOAc (40 mL) was added to the reaction and the mixture was washed with aqueous $NaHCO_3$. The EtOAc organic layer was dried with anhydrous $Na_2SO_4$ and concentrated with a Rotavapor. The residue was purified by silica gel chromatography (Petroleum Ether/EtOAc=10/1 to 2/1) to give product 98a (1.4 g, 31.8% yield). $^1$H NMR ($CDCl_3$, 400 MHz): δ (ppm) 7.28 (d, J=6.8 Hz, 2H), 6.91-6.99 (m, 2H), 6.86-6.88 (m, 1H), 6.82-6.84 (m, 2H), 5.10 (s, 2H), 3.75 (s, 3H), 3.72 (s, 3H), 3.67 (s, 3H), 2.10 (s, 3H). m/z 399 (M+H)$^+$.

(2) Synthesis of 99a

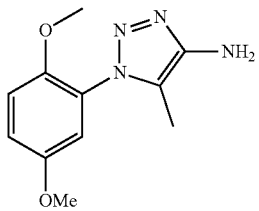 [SMILES: COc1ccc(OC)c(-n2nnc(N)c2C)c1]

A solution of compound 98a (1.4 g, 3.5 mmol) and Phenol (493 mg, 5.25 mmol) in $CF_3COOH$ (3 mL) and DCM (15 mL) was stirred at room temperature for 1 hour. The reaction mixture was then concentrated with a Rotavapor. The residue was basified with aqueous NaOH and then extracted with EtOAc (15 mL×3). The combined organic layers were dried with anhydrous $Na_2SO_4$ and concentrated with a Rotavapor to give crude product 99a (600 mg, 73.2% yield). m/z 235 (M+H)$^+$.

(3) Synthesis of LC-43

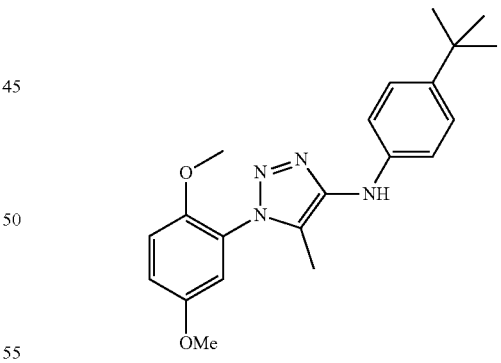

A suspension of compound 99a (500 mg, 2.13 mmol), 1-bromo-4-tert-butyl-benzene (587 mg, 2.52 mmol), $(tBu_3P)_2Pd$ (217 mg, 0.426 mmol) and $Cs_2CO_3$ (1.38 g, 4.26 mmol) in dioxane (15 mL) was heated to 110° C. for 2 hours under $N_2$. The reaction mixture was then filtered and concentrated with a Rotavapor. The residue was purified by preparative HPLC to give product LC-43 (200 mg, 25.6% yield). $^1$H NMR ($CDCl_3$, 400 MHz): δ (ppm) 7.22 (d, J=8.8 Hz, 2H), 6.98-7.02 (m, 3H), 6.72 (d, J=8.8 Hz, 2H), 3.80 (s, 3H), 3.76 (s, 3H), 2.06 (s, 3H), 1.27 (s, 9H). m/z 367 (M+H)$^+$.

ii. Preparation of N-(4-(tert-butyl)phenyl)-1-(2-methoxy-5-methylphenyl)-5-methyl-1H-1,2,3-triazol-4-amine (LC-44)

(1) Synthesis of 98b

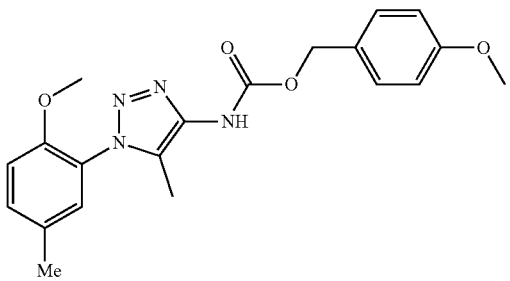 [SMILES: COc1ccc(COC(=O)Nc2nnn(-c3cc(C)ccc3OC)c2C)cc1]

A solution of compound 96b (1.0 g, 4.05 mmol), DPPA (0.93 mL, 4.25 mmol), TEA (1.11 mL, 8.1 mmol) in toluene (15 mL) was stirred at room temperature for 6 hours. (4-Methoxy-phenyl)-methanol (1.4 g, 10.125 mmol) was then added and the reaction was heated to 100° C. for 18 hours. EtOAc (30 mL) was added to the reaction and the mixture was washed with aqueous $NaHCO_3$. The EtOAc organic layer was dried with anhydrous $Na_2SO_4$ and concentrated with a Rotavapor. The residue was purified by silica gel chromatography (Petroleum Ether/EtOAc=20/1 to 2/1) to give product 98b (0.5 g, 32.2% yield). m/z 383 $(M+H)^+$.

(2) Synthesis of 99b

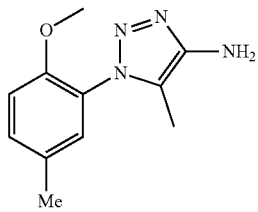 [SMILES: COc1ccc(C)cc1-n1nnc(N)c1C]

A solution of compound 98b (0.5 g, 1.3 mmol) and Phenol (190 mg, 2 mmol) in $CF_3COOH$ (1 mL) and DCM (4 mL) was stirred at room temperature for 1 hour. The reaction mixture was then concentrated with a Rotavapor. The residue was basified with aqueous $K_2CO_3$ and then extracted with DCM (10 mL×2). The combined organic layers were dried with anhydrous $Na_2SO_4$ and concentrated with a Rotavapor to give crude product 99b (190 mg, 66.7% yield). m/z 219 $(M+H)^+$.

(3) Synthesis of LC-44

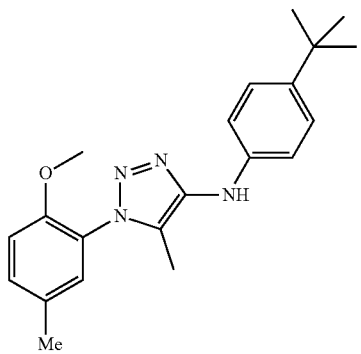 [SMILES: COc1ccc(C)cc1-n1nnc(Nc2ccc(C(C)(C)C)cc2)c1C]

A suspension of compound 99b (190 mg, 0.87 mmol), 1-bromo-4-tert-butyl-benzene (240 mg, 1.33 mmol), $(tBu_3P)_2Pd$ (89 mg, 0.174 mmol) and $Cs_2CO_3$ (567 mg, 1.74 mmol) in dioxane (10 mL) was heated to 110° C. for 2 hours under $N_2$. The reaction mixture was then filtered and concentrated with a Rotavapor. The residue was purified by preparative HPLC to give product LC-44 (75 mg, 23.7% yield). $^1$H NMR ($CDCl_3$, 400 MHz): δ (ppm) 7.24 (d, J=8.8 Hz, 1H), 7.16-7.18 (m, 3H), 6.91 (d, J=8.8 Hz, 1H), 6.66 (d, J=8.8 Hz, 2H), 3.74 (s, 3H), 2.30 (s, 3H), 1.99 (s, 3H), 1.23 (s, 9H). m/z 364 $(M+H)^+$.

iii. Preparation of N-(4-(tert-butyl)phenyl)-1-(5-chloro-2-methoxyphenyl)-5-methyl-1H-1,2,3-triazol-4-amine (LC-45)

(1) Synthesis of 98c

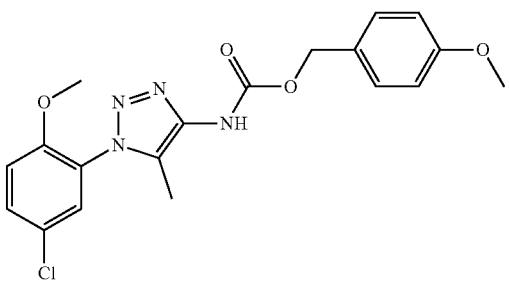 [SMILES: COc1ccc(COC(=O)Nc2nnn(-c3cc(Cl)ccc3OC)c2C)cc1]

A solution of compound 96c (3.0 g, 11.2 mmol), DPPA (2.4 mL, 11.2 mmol), TEA (3.1 mL, 22.4 mmol) in toluene (35 mL) was stirred at room temperature for 6 hours. (4-Methoxy-phenyl)-methanol (3.86 g, 28 mmol) was then added and the reaction was heated to 100° C. for 18 hours. EtOAc (40 mL) was added to the reaction and the mixture was washed with aqueous $NaHCO_3$. The EtOAc organic layer was dried with anhydrous $Na_2SO_4$ and concentrated with a Rotavapor. The residue was purified by silica gel chromatography (Petroleum Ether/EtOAc=10/1 to 2/1) to give product 98c (0.4 g, 8.9% yield). m/z 403 $(M+H)^+$.

(2) Synthesis of 99c

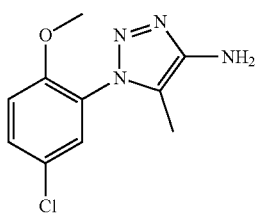 [SMILES: COc1ccc(Cl)cc1-n1nnc(N)c1C]

A solution of compound 98c (0.4 g, 0.99 mmol) and Phenol (140 mg, 1.49 mmol) in $CF_3COOH$ (2 mL) and DCM (10 mL) was stirred at room temperature for 1 hour. The reaction mixture was then concentrated with a Rotavapor. The residue was basified with aqueous NaOH and then extracted with DCM (15 mL×3). The combined organic layers were dried with anhydrous $Na_2SO_4$ and concentrated with a Rotavapor to give crude product 99c (160 mg, 68.1% yield). m/z 239 $(M+H)^+$.

(3) Synthesis of LC-45

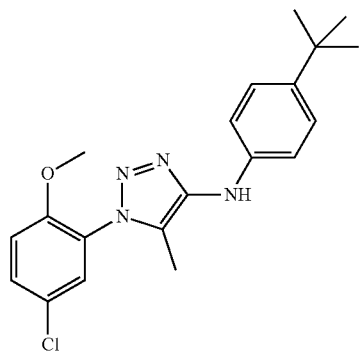 [SMILES: COc1ccc(Cl)cc1-n1nnc(Nc2ccc(C(C)(C)C)cc2)c1C]

A suspension of compound 99c (160 mg, 0.67 mmol), 1-bromo-4-tert-butyl-benzene (185 mg, 0.87 mmol), (tBu$_3$P)$_2$Pd (68 mg, 0.134 mmol) and Cs$_2$CO$_3$ (437 mg, 1.34 mmol) in dioxane (9 mL) was heated to 110° C. for 2 hours under N$_2$. The reaction mixture was then filtered and concentrated with a Rotavapor. The residue was purified by preparative HPLC to give product LC-45 (80 mg, 32.2% yield). $^1$H NMR (CDCl$_3$, 400 MHz): δ (ppm) 7.45-7.49 (m, 2H), 7.22-7.26 (m, 2H), 7.03 (d, J=8.8 Hz, 1H), 6.72 (d, J=8.4 Hz, 2H), 3.83 (s, 3H), 2.07 (s, 3H), 1.28 (s, 9H). m/z 371 (M+H)$^+$.

r. General Synthesis of LC-46, LC-47, and LC-48

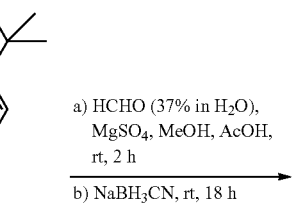

LC-43, LC-44, LC-45 a) HCHO (37% in H$_2$O), MgSO$_4$, MeOH, AcOH, rt, 2 h
b) NaBH$_3$CN, rt, 18 h

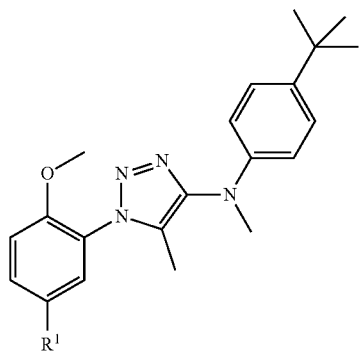

LC-46, LC-47, LC-48 i. Preparation of N-(4-(tert-butyl)phenyl)-1-(2,5-dimethoxyphenyl)-N,5-dimethyl-1H-1,2,3-triazol-4-amine (LC-46)

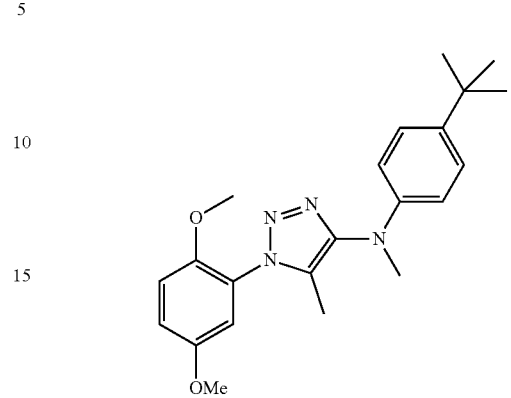

A solution of compound LC-43 (100 mg, 0.27 mmol), HCHO (100 mg, 0.27 mmol, 37% in H$_2$O) and MgSO$_4$ (0.5 g) in methanol (4.2 mL) and AcOH (0.5 mL) was stirred at room temperature for 2 hours. NaBH$_3$CN (34 mg, 0.54 mmol) was then added and the mixture was stirred for another 18 hours at room temperature. The reaction mixture was filtered. The filtrate was concentrated with a Rotavapor and the residue was purified by preparative HPLC to give product LC-46 (90 mg, 88.2% yield). $^1$H NMR (CDCl$_3$, 400 MHz): δ (ppm) 7.24-7.26 (m, 2H), 7.00-7.08 (m, 3H), 6.69 (d, J=8.8 Hz, 2H), 3.82 (s, 3H), 3.79 (s, 3H), 3.40 (s, 3H), 1.99 (s, 3H), 1.27 (s, 9H). m/z 381 (M+H)$^+$.

ii. Preparation of N-(4-(tert-butyl)phenyl)-1-(2-methoxy-5-methylphenyl)-N,5-dimethyl-1H-1,2,3-triazol-4-amine (LC-47)

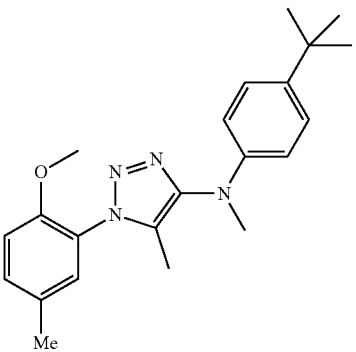 [SMILES: COc1ccc(C)cc1-n1nnc(N(C)c2ccc(C(C)(C)C)cc2)c1C]

A solution of compound LC-44 (200 mg, 0.57 mmol), HCHO (116 mg, 1.43 mmol, 37% in H$_2$O) and MgSO$_4$ (1 g) in methanol (4.9 mL) and AcOH (0.7 mL) was stirred at room temperature for 2 hours. NaBH$_3$CN (72 mg, 1.14 mmol) was then added and the mixture was stirred for another 18 hours at room temperature. The reaction mixture was filtered. The filtrate was concentrated with a Rotavapor and the residue was purified by preparative HPLC to give product LC-47 (180 mg, 86.7% yield). $^1$H NMR (CDCl$_3$, 400 MHz): δ (ppm) 7.28 (d, J=8.8 Hz, 1H), 7.22-7.24 (m, 3H), 6.97 (d, J=8.8 Hz, 1H), 6.67 (d, J=8.8 Hz, 2H), 3.82 (s, 3H), 3.79 (s, 3H), 3.38 (s, 3H), 2.35 (s, 3H), 1.93 (s, 3H), 1.27 (s, 9H). m/z 365 (M+H)$^+$.

iii. Preparation of N-(4-(tert-butyl)phenyl)-1-(5-chloro-2-methoxyphenyl)-N,5-dimethyl-1H-1,2,3-triazol-4-amine (LC-48)

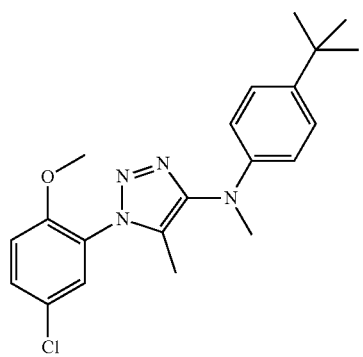 [SMILES: COc1ccc(Cl)cc1-n1nnc(N(C)c2ccc(C(C)(C)C)cc2)c1C]

A solution of compound LC-45 (100 mg, 0.27 mmol), HCHO (44 mg, 0.27 mmol, 37% in H$_2$O) and MgSO$_4$ (0.5 g) in methanol (2.1 mL) and AcOH (0.3 mL) was stirred at room temperature for 2 hours. NaBH$_3$CN (34 mg, 0.54 mmol) was then added and the mixture was stirred for another 18 hours at room temperature. The reaction mixture was filtered. The filtrate was concentrated with a Rotavapor and the residue was purified by preparative HPLC to give product LC-48 (55 mg, 53.0% yield). $^1$H NMR (CDCl$_3$, 400 MHz): δ (ppm) 7.47-7.49 (m, 2H), 7.26-7.27 (m, 2H), 7.02 (d, J=8.4 Hz, 1H), 6.67 (d, J=8.4 Hz, 2H), 3.82 (s, 3H), 3.85 (s, 3H), 3.40 (s, 3H), 1.96 (s, 3H), 1.27 (s, 9H). m/z 385 (M+H)$^+$.

s. General Synthesis of LC-70, LC-71, and LC-72

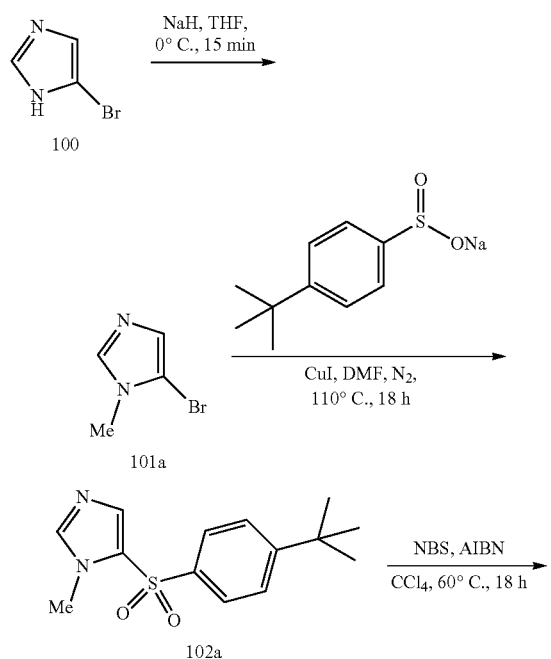

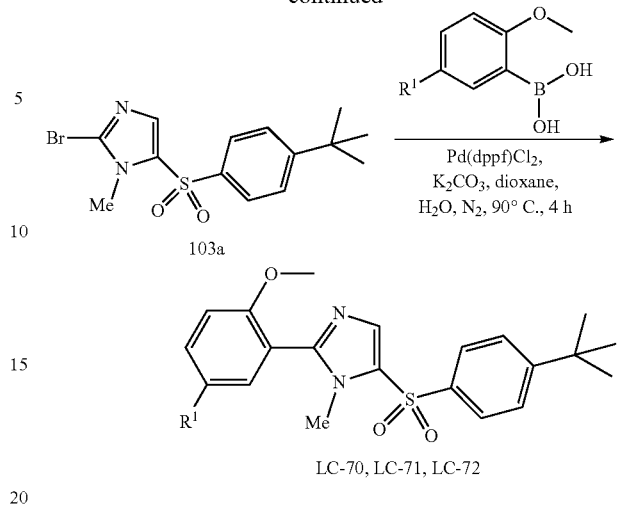

i. Preparation of 5-((4-(tert-butyl)phenyl)sulfonyl)-2-(2,5-dimethoxyphenyl)-1-methyl-1H-imidazole (LC-70, 104a)

(1) Synthesis of 102a

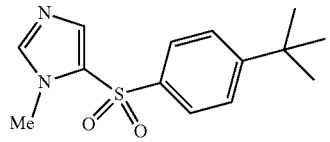 [SMILES: Cn1cncc1S(=O)(=O)c1ccc(C(C)(C)C)cc1]

A solution of compound 101a ((1.6 g, 10 mmol), compound sodium 4-(tert-butyl)benzenesulfinate (3.3 g, 15 mmol) and CuI (1.9 g, 10 mmol) in DMF (20 mL) was heated at 110° C. for 18 hours under N$_2$. The reaction was then cooled down and filtered. H$_2$O (100 mL) was added to the filtrate and the mixture was extracted with EtOAc (100 mL×3). The combined organic layers were dried with anhydrous Na$_2$SO$_4$ and concentrated with a Rotavapor. The residue was purified by silica gel chromatography (Petroleum Ether/EtOAc=10/1 to 2/1) to give the chemical 102a (1.18 g, 42% yield). $^1$H NMR (CDCl$_3$, 400 MHz): δ (ppm) 7.83 (d, 2H, J=8.4 Hz), 7.72 (s, 1H), 7.53 (d, 2H, J=8.4 Hz), 7.48 (s, 1H), 3.71 (s, 3H), 1.31 (s, 9H). m/z 279 (M+H)$^+$.

(2) Synthesis of 103

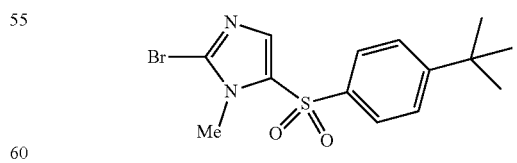

A solution of compound 102a (1.1 g, 4 mmol), NBS (1.06 g, 6 mmol) and AIBN (16.4 mg, 0.1 mmol) in CCl$_4$ (30 mL) was stirred at 60° C. for 18 hours. The mixture was concentrated with a Rotavapor and the residue was purified by preparative TLC (Petroleum Ether/EtOAc=2/1) to give compound 103a (270 mg, 19% yield). m/z 357 (M+H)$^+$.

(3) Synthesis of LC-70 (104a)

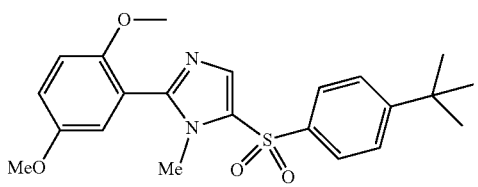 [SMILES: COc1ccc(OC)c(-c2ncc(S(=O)(=O)c3ccc(C(C)(C)C)cc3)n2C)c1]

A solution of compound 103a (72 mg, 0.2 mmol), 2,5-dimethoxyphenylboronic acid (73 mg, 0.4 mmol), Pd(dppf)Cl₂ (8 mg) and K₂CO₃ (138 mg, 1 mmol) in dioxane (3 mL) and H₂O (0.6 mL) was heated at 90° C. for 4 hr under N₂. After the reaction was cooled down to room temperature, H₂O (5 mL) was added and the mixture was extracted with EtOAc (5 mL×3). The combined organic layers were dried with anhydrous Na₂SO₄ and concentrated with a Rotavapor. The residue was purified by preparative HPLC to give compound LC-70 (104a, 30 mg, 36% yield). ¹H NMR (CDCl₃, 400 MHz): δ (ppm) 7.83-7.85 (m, 2H), 7.79 (s, 1H), 7.52-7.54 (m, 2H), 6.97-7.00 (m, 1H), 6.89-6.90 (m, 1H), 6.84-6.87 (m, 1H), 3.70 (s, 3H), 3.66 (s, 3H), 3.54 (s, 3H), 1.28 (s, 9H). m/z 415 (M+H)⁺.

ii. Preparation of 5-((4-(tert-butyl)phenyl)sulfonyl)-2-(2-methoxy-5-methylphenyl)-1-methyl-1H-imidazole (LC-71, 104b)

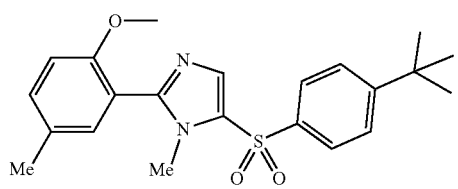 [SMILES: COc1ccc(C)cc1-c1ncc(S(=O)(=O)c2ccc(C(C)(C)C)cc2)n1C]

The preparation of compound LC-71 (20 mg, 25% yield) was similar to the preparation of compound LC-70 except that 2-methoxy-5-methyl-phenylboronic acid was used to replace the 2,5-dimethoxyphenylboronic acid in the preparation of compound LC-70. ¹H NMR (CDCl₃, 400 MHz): δ (ppm) 7.86 (d, 2H, J=8.8 Hz), 7.79 (s, 1H), 7.54 (d, 2H, J=8.8 Hz), 7.19-7.24 (m, 2H), 6.83 (d, 1H, J=8.4 Hz), 3.70 (s, 3H), 3.49 (s, 3H), 2.27 (s, 3H), 1.32 (s, 9H). m/z 399 (M+H)⁺.

iii. Preparation of 5-((4-(tert-butyl)phenyl)sulfonyl)-2-(5-chloro-2-methoxyphenyl)-1-methyl-1H-imidazole (LC-72, 104c)

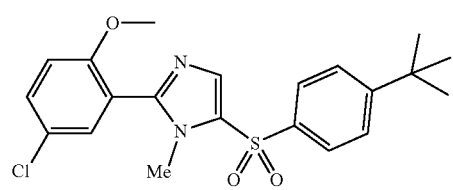 [SMILES: COc1ccc(Cl)cc1-c1ncc(S(=O)(=O)c2ccc(C(C)(C)C)cc2)n1C]

The preparation of compound LC-72 (23 mg, 27.3% yield) was similar to the preparation of compound LC-70 except that 2-methoxy-5-chloro-phenylboronic acid was used to replace the 2,5-dimethoxyphenylboronic acid in the preparation of compound LC-70. ¹H NMR (CDCl₃, 400 MHz): δ (ppm) 7.82-7.85 (m, 3H), 7.55 (d, 2H, J=8.4 Hz), 7.41-7.43 (m, 1H), 7.30 (d, 1H, J=2.0 Hz), 6.89 (d, 1H, J=9.2 Hz), 3.73 (s, 3H), 3.57 (s, 3H), 1.29 (s, 9H). m/z 419 (M+H)⁺.

t. General Synthesis of LC-67, LC-68, and LC-69

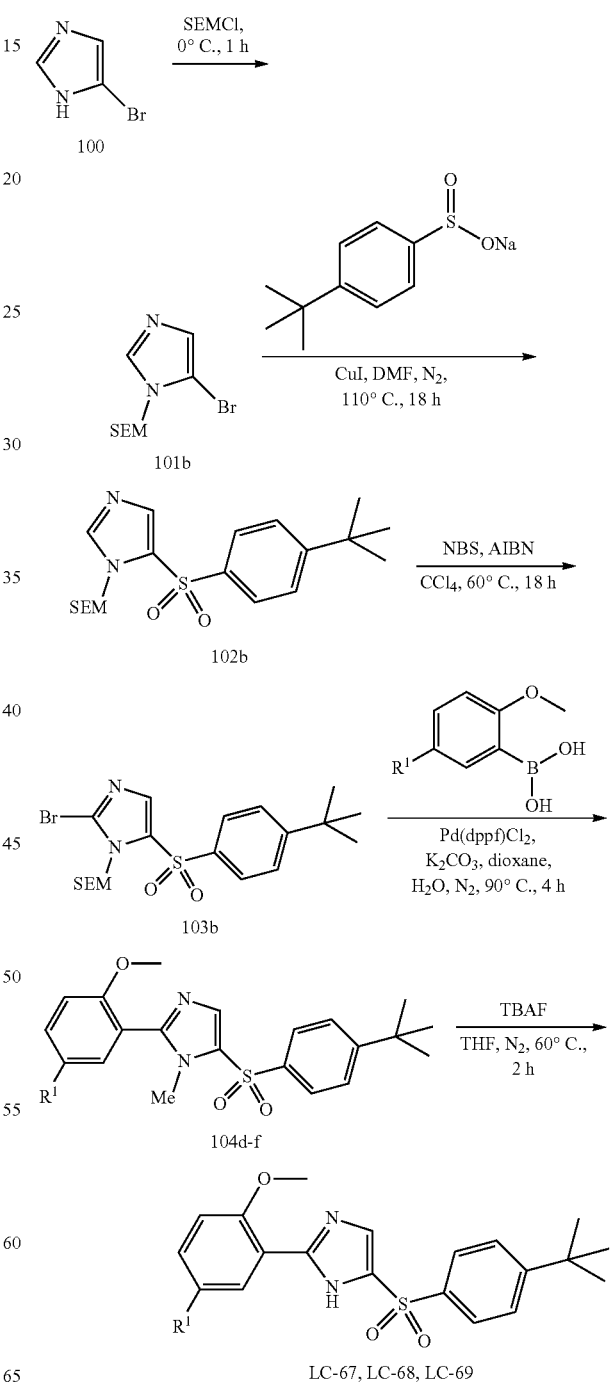

147 i. Preparation of 5-((4-(tert-butyl)phenyl)sulfonyl)-2-(2,5-dimethoxyphenyl)-1H-imidazole (LC-67)

(1) Synthesis of 102b

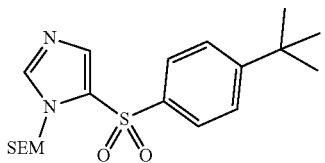 [SMILES: CC(C)(C)c1ccc(S(=O)(=O)c2cncn2COCC[Si](C)(C)C)cc1]

A solution of compound 101b[33] (2.76 g, 10 mmol), compound sodium 4-(tert-butyl)benzenesulfinate (2.2 g, 10 mmol) and CuI (1.9 g, 10 mmol) in DMF (50 mL) was heated at 110° C. for 18 hours under $N_2$. The reaction was then cooled down and filtered. $H_2O$ (100 mL) was added to the filtrate and the mixture was extracted with EtOAc (100 mL×3). The combined organic layers were dried with anhydrous $Na_2SO_4$ and concentrated with a Rotavapor. The residue was purified by silica gel chromatography (Petroleum Ether/EtOAc=10/1 to 2/1) to give the chemical 102b (551 mg, 14% yield). $^1$H NMR (CDCl$_3$, 400 MHz): δ (ppm) 7.98 (d, 2H, J=8.4 Hz), 7.77 (s, 1H), 7.65 (s, 1H), 7.55 (d, 2H, J=8.4 Hz), 5.31 (s, 2H), 3.52 (t, 2H, J=8.0 Hz), 1.34 (s, 9H), 0.92 (t, 2H, J=8.0 Hz), 0.00 (s, 9H). m/z 395 (M+H)$^+$.

(2) Synthesis of 103b

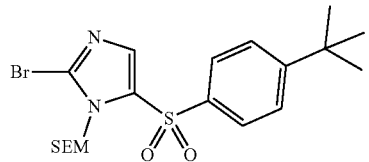 [SMILES: CC(C)(C)c1ccc(S(=O)(=O)c2cnc(Br)n2COCC[Si](C)(C)C)cc1]

A solution of compound 102b (394 mg, 1 mmol), NBS (354 g, 2 mmol) and AIBN (16.4 mg, 0.1 mmol) in CCl$_4$ (20 mL) was stirred at 60° C. for 18 hours. The mixture was concentrated with a Rotavapor and the residue was purified by preparative TLC (Petroleum Ether/EtOAc=2/1) to give compound 103b (206 mg, 44% yield). $^1$H NMR (CDCl$_3$, 400 MHz): δ (ppm) 7.96 (d, 2H, J=8.4 Hz), 7.78 (s, 1H), 7.54 (d, 2H, J=8.4 Hz), 5.28 (s, 2H), 3.56 (t, 2H, J=8.0 Hz), 1.33 (s, 9H), 0.93 (t, 2H, J=8.0 Hz), 0.00 (s, 9H). m/z 473 (M+H)$^+$.

(3) Synthesis of 104e

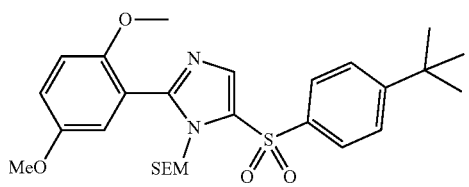 [SMILES: COc1ccc(OC)c(-c2ncc(S(=O)(=O)c3ccc(C(C)(C)C)cc3)n2COCC[Si](C)(C)C)c1]

148

A solution of compound 103b (94 mg, 0.2 mmol), 2,5-dimethoxyphenylboronic acid (73 mg, 0.4 mmol), Pd(dppf)Cl$_2$ (8 mg) and K$_2$CO$_3$ (138 mg, 1 mmol) in dioxane (3 mL) and H$_2$O (0.6 mL) was heated at 90° C. for 4 hr under N$_2$. After the reaction was cooled down to room temperature, H$_2$O (5 mL) was added and the mixture was extracted with EtOAc (5 mL×3). The combined organic layers were dried with anhydrous Na$_2$SO$_4$ and concentrated with a Rotavapor. The residue was purified by preparative TLC (Petroleum Ether/EtOAc=2/1) to give compound 104e (98 mg, 92% yield). m/z 531 (M+H)$^+$.

(4) Synthesis of LC-67

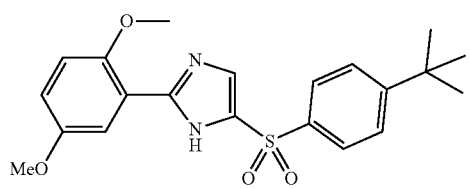 [SMILES: COc1ccc(OC)c(-c2ncc(S(=O)(=O)c3ccc(C(C)(C)C)cc3)[nH]2)c1]

A solution of compound 104e (98 mg, 0.184 mmol) and TBAF (500 mg) in THF (2 mL) was heated at 60° C. for 2 hours under N$_2$. After cooled down, the reaction was diluted with H$_2$O (10 mL) and extracted with EtOAc (30 mL×2). The combined organic layers were dried with anhydrous Na$_2$SO$_4$ and concentrated with a Rotavapor. The residue was purified by preparative HPLC to yield the compound LC-67 (68 mg, 92% yield). $^1$H NMR (CDCl$_3$, 400 MHz): δ (ppm) 7.98 (d, 2H, J=8.4 Hz), 7.85 (d, 1H, J=1.6 Hz), 7.74 (s, 1H), 7.49 (d, 2H, J=8.8 Hz), 6.89 (s, 2H), 3.94 (s, 3H), 3.81 (s, 3H), 1.28 (s, 9H). m/z 401 (M+H)$^+$.

ii. Preparation of 5-((4-(tert-butyl)phenyl)sulfonyl)-2-(2-methoxy-5-methylphenyl)-1H-imidazole (LC-68)

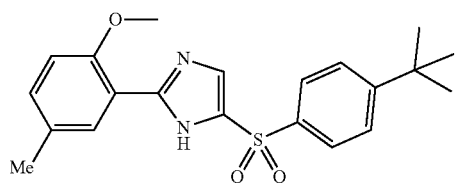 [SMILES: COc1ccc(C)cc1-c1ncc(S(=O)(=O)c2ccc(C(C)(C)C)cc2)[nH]1]

The preparation of compound LC-68 (34 mg, 48.1% yield) was similar to the preparation of compound LC-67 except that 2-methoxy-5-methyl-phenylboronic acid was used to replace the 2,5-dimethoxyphenylboronic acid in the preparation of compound LC-67. $^1$H NMR (CDCl$_3$, 400 MHz): δ (ppm) 10.70 (s, 1H), 8.15 (s, 1H), 7.98 (d, 2H, J=8.0 Hz), 7.73 (s, 1H), 7.49 (d, 2H, J=8.4 Hz), 7.12 (d, 1H, J=7.2 Hz), 6.86 (d, 1H, J=8.4 Hz), 3.95 (s, 3H), 2.30 (s, 3H), 1.28 (s, 9H). m/z 385 (M+H)$^+$.

iii. Preparation of 5-((4-(tert-butyl)phenyl)sulfonyl)-2-(5-chloro-2-methoxyphenyl)-1H-imidazole (LC-69)

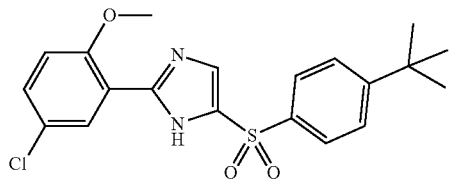 [SMILES: COc1ccc(Cl)cc1-c1ncc(S(=O)(=O)c2ccc(C(C)(C)C)cc2)[nH]1]

The preparation of compound LC-69 (55 mg, 74% yield) was similar to the preparation of compound LC-67 except that 2-methoxy-5-chloro-phenylboronic acid was used to replace the 2,5-dimethoxyphenylboronic acid in the preparation of compound LC-67. $^1$H NMR (CDCl$_3$, 400 MHz): δ (ppm) 10.68 (s, 1H), 8.32 (d, 1H, J=2.4 Hz), 7.98 (d, 2H, J=8.4 Hz), 7.75 (d, 1H, J=1.6 Hz), 7.50 (d, 2H, J=8.4 Hz), 7.24-7.28 (m, 1H), 6.90 (d, 1H, J=8.8 Hz), 3.98 (s, 3H), 1.29 (s, 9H). m/z 405 (M+H)$^+$.

u. Synthesis of 5-((4-(tert-butyl)phenyl)sulfonyl)-2-(2,5-dimethoxyphenyl)-4-methyl-1H-imidazole (LC-73)

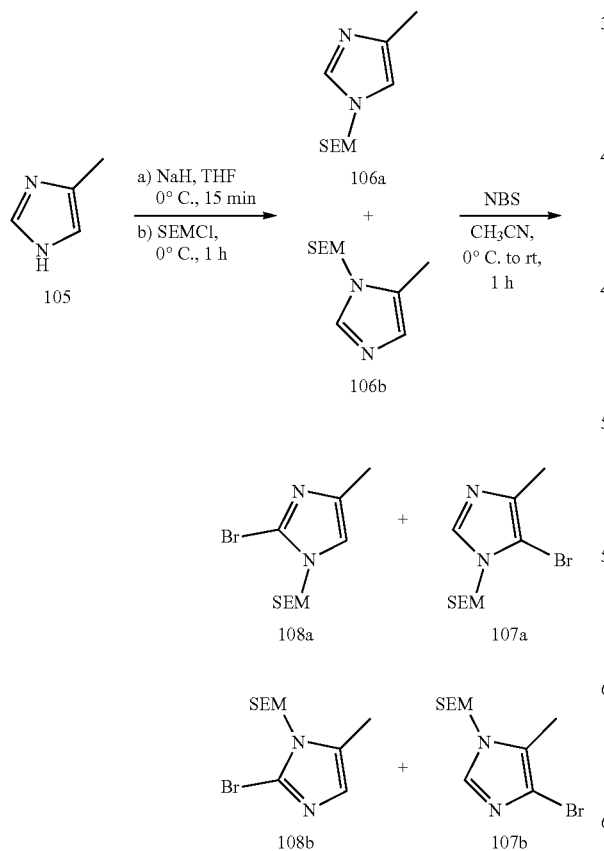

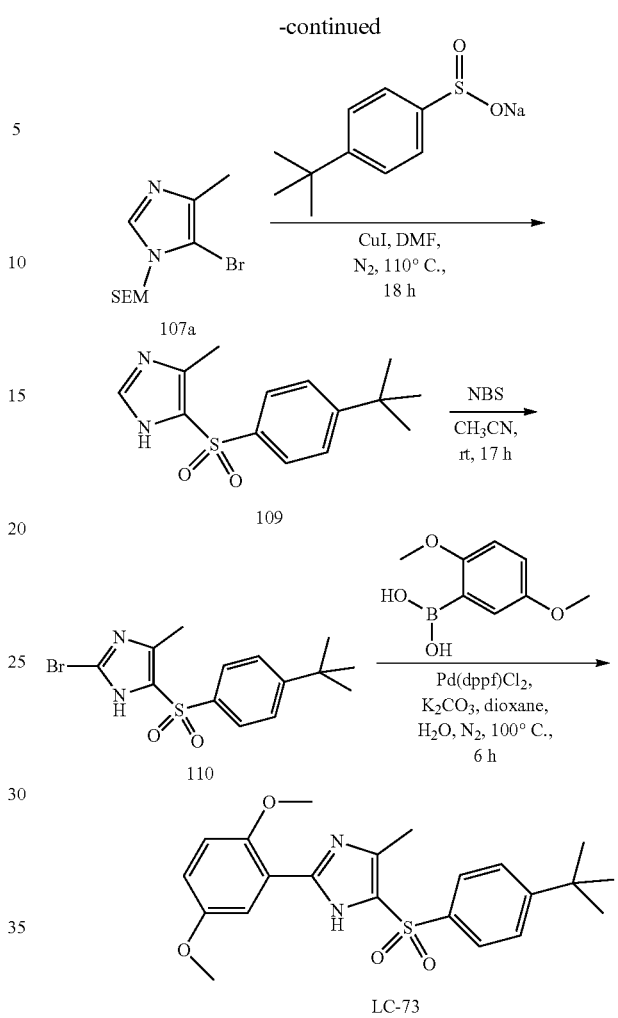

i. Preparation of 106a and 106b

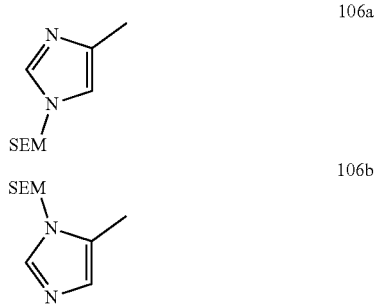

NaH (4.8 g, 0.12 mol) was added to a solution of compound 105 (8.2 g, 0.1 mol) in THF (100 mL) at 0° C. The mixture was stirred at 0° C. for 15 min and SEMCl (19.9 g, 0.12 mol) was added dropwise to the mixture. The reaction was stirred for another hour at 0° C. and then quenched with H$_2$O (50 mL) and extracted with EtOAc (100 mL×3). The combined organic layers were dried with anhydrous Na$_2$SO$_4$ and concentrated with a Rotavapor. The residue was purified by silica gel chromatography (Petroleum Ether/EtOAc=10/1 to 1/1) to give compound 106a and 106b (17.5 g, 83% yield). m/z 213 (M+H)⁺.

II. Preparation of 107a, 107b, 108a, and 108b

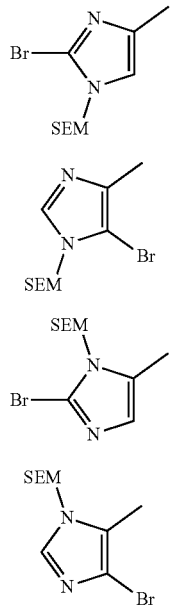

NBS (12 g, 67.9 mmol) in CH₃CN (100 mL) was added dropwise to compound 106a and 106b (16 g, 75.5 mmol) in CH₃CN (100 mL) at 0° C. The reaction was stirred at room temperature for 1 hour and then quenched with H₂O (200 mL) and extracted with EtOAc (100 mL×3). The combined organic layers were dried with anhydrous Na₂SO₄ and concentrated with a Rotavapor. The residue was purified by silica gel chromatography (Petroleum Ether/EtOAc=10/1 to DCM/MeOH=1/1) to give compound 107a, 107b (9.2 g, 42.0% yield) and 108a, 108b (1.3 g, 5.9% yield). ¹H NMR (CD₃OD, 400 MHz): δ (ppm) 7.45 (s, 1H), 5.22 (s, 2H), 3.47-3.55 (m, 2H), 2.27 (s, 2H), 0.91-0.96 (m, 2H), 0.02 (s, 9H). m/z 291 (M+H)⁺.

iii. Preparation of 109

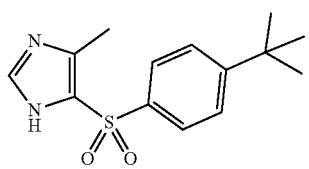 [SMILES: Cc1nc[nH]c1S(=O)(=O)c1ccc(C(C)(C)C)cc1]

A solution of compounds 107a and 107b (9.2 g, 31.7 mmol), sodium 4-(tert-butyl)benzenesulfinate (9.06 g, 41.2 mmol), and CuI (6.6 g, 34.9 mmol) in DMF (100 mL) was heated at 110° C. for 18 hr under N₂. After cooled down to room temperature, the reaction mixture was filtered and H₂O (100 mL) was added to the filtrate. The mixture was extracted with EtOAc (100 mL×3). The combined organic layers were dried with anhydrous Na₂SO₄ and concentrated with a Rotavapor. The residue was purified by silica gel chromatography (Petroleum Ether/EtOAc=10/1 to DCM/MeOH=15/1) to give compound 109 (100 mg, 1.14% yield). m/z 279 (M+H)⁺.

iv. Preparation of 110

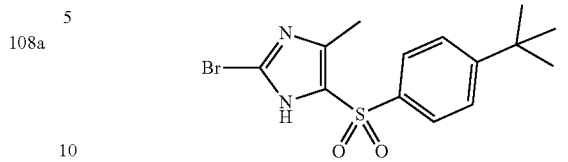

NBS (64 mg, 0.36 mmol) was added to compound 109 (100 mg, 0.36 mmol) in CH₃CN (3 mL) and the solution was stirred at room temperature for 17 hours. H₂O (5 mL) was then added to the reaction and the mixture was extracted with EtOAc (5 mL×3). The combined organic layers were dried with anhydrous Na₂SO₄ and concentrated with a Rotavapor. The residue was purified by preparative HPLC to give compound 110 (100 mg, 78.1% yield). m/z 257 (M+H)⁺.

v. Preparation of 5-((4-(tert-butyl)phenyl)sulfonyl)-2-(2,5-dimethoxyphenyl)-4-methyl-1H-imidazole (LC-73)

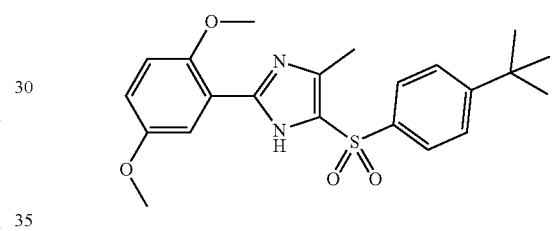

A solution of compound 110 (100 mg, 0.28 mmol), 2,5-dimethoxyphenylboronic acid (61 mg, 0.336 mmol), Pd(dppf)Cl₂ (10 mg) and K₂CO₃ (1.38 g, 4.26 mmol) in dioxane (3 mL) and H₂O (0.6 mL) was heated at 100° C. for 6 hours under N₂. After the reaction was cooled down to room temperature, H₂O (5 mL) was then added and the mixture was extracted with EtOAc (5 mL×3). The combined organic layers were dried with anhydrous Na₂SO₄ and concentrated with a Rotavapor. The residue was purified by preparative HPLC to give compound LC-73 (50 mg, 43.1% yield). ¹H NMR (CDCl₃, 400 MHz): δ (ppm) 7.88 (d, J=8.4 Hz, 2H), 7.76 (s, 1H), 7.44 (d, J=8.4 Hz, 2H), 6.85 (s, 2H), 3.90 (s, 3H), 3.75 (s, 3H), 2.55 (s, 3H), 1.24 (s, 9H). m/z 415 (M+H)⁺.

v. Synthesis of 5-((4-(tert-butyl)phenyl)sulfonyl)-2-(5-chloro-2-methoxyphenyl)-4-methyl-1H-imidazole (LC-75)

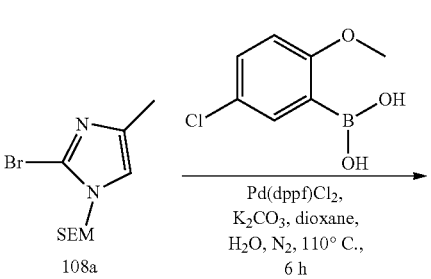

-continued

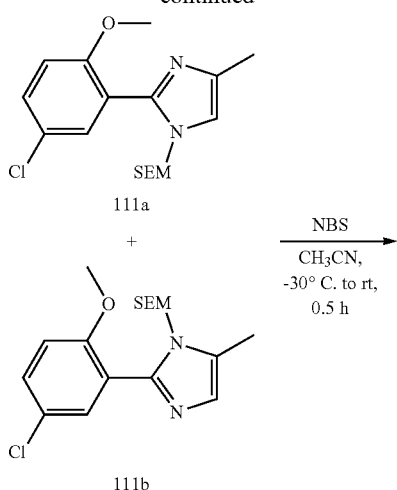
111a

+

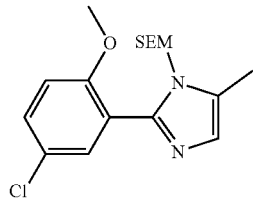

NBS
CH₃CN,
−30° C. to rt,
0.5 h
→

111b

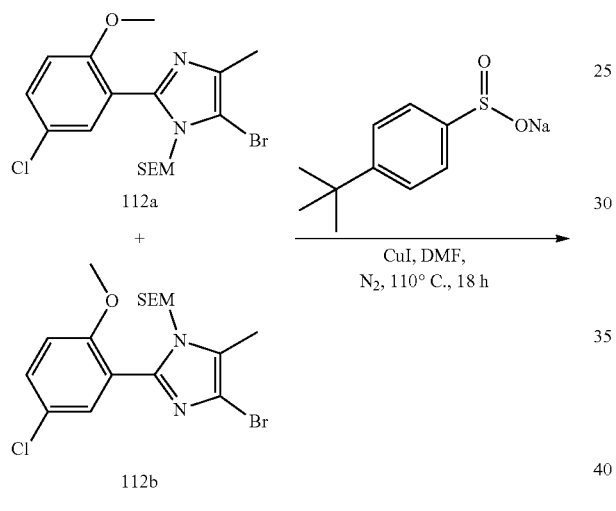

112a

+

112b

CuI, DMF,
N₂, 110° C., 18 h
→

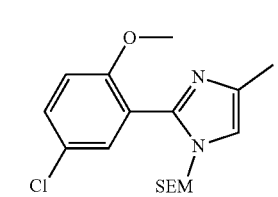

LC-75 i. Preparation of 111a and 111b

-continued

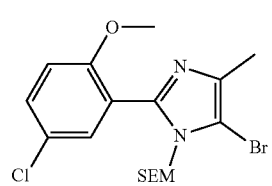
111b

A solution of compound 108a, 108b (1 g, 3.45 mmol), 2-methoxy-5-chlorophenylboronic acid (770 mg, 4.14 mmol), Pd(dppf)Cl₂ (100 mg) and K₂CO₃ (0.95 g, 6.9 mmol) in dioxane (10 mL) and H₂O (2 mL) was heated at 110° C. for 6 hours under N₂. After cooled down to the room temperature, the reaction mixture was added with H₂O (10 mL) and extracted with EtOAc (10 mL×3). The combined organic layers were dried with anhydrous Na₂SO₄ and concentrated with a Rotavapor. The residue was purified by preparative HPLC to give compound 111a and 111b (300 mg, 25% yield). m/z 353 (M+H)⁺.

ii. Preparation of 112a and 112b

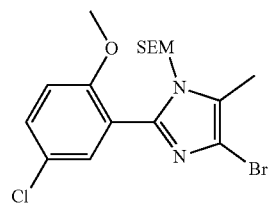

112a

112b

NBS (151 mg, 0.85 mmol) was added to a solution of 111a and 111b (300 mg, 0.85 mmol) in CH₃CN (5 mL) at −30° C. The reaction was then stirred at room temperature for 0.5 hour. The reaction was quenched with H₂O (5 mL) and the mixture was extracted with EtOAc (10 mL×3). The combined organic layers were dried with anhydrous Na₂SO₄ and concentrated with a Rotavapor. The residue was purified by preparative HPLC to give compound 112a and 112b (260 mg, 85.6% yield). m/z 358 (M+H)⁺.

iii. Preparation of 5-((4-(tert-butyl)phenyl)sulfonyl)-2-(5-chloro-2-methoxyphenyl)-4-methyl-1H-imidazole (LC-75)

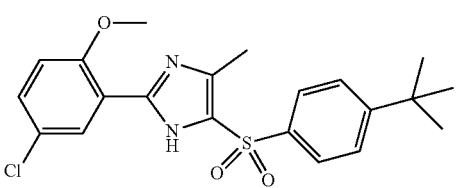 [SMILES: COc1ccc(Cl)cc1-c1nc(C)c(S(=O)(=O)c2ccc(C(C)(C)C)cc2)[nH]1]

A solution of compound 112a, 112b (260 mg, 0.73 mmol), sodium 4-(tert-butyl)benzenesulfinate (208 mg, 0.94 mmol), and CuI (153 mg, 0.8 mmol) in DMF (5 mL) was heated at 110° C. for 18 hr under $N_2$. After cooled down to the room temperature, the reaction was quenched with $H_2O$ (10 mL) and extracted with EtOAc (10 mL×3). The combined organic layers were dried with anhydrous $Na_2SO_4$ and concentrated with a Rotavapor. The residue was purified by preparative HPLC to give compound LC-75 (15 mg, 4.9% yield). $^1H$ NMR (CDCl$_3$, 400 MHz): δ (ppm) 10.21 (s, 1H), 8.24 (s, 1H), 7.91 (d, J=8.4 Hz, 2H), 7.44 (d, J=8.4 Hz, 2H), 7.17 (s, 1H), 6.83 (d, J=8.4 Hz, 1H), 3.90 (s, 3H), 2.60 (s, 3H), 1.24 (s, 9H). m/z 419 (M+H)$^+$.

w. Synthesis of 5-((4-(tert-butyl)phenyl)sulfonyl)-2-(2-methoxy-5-methylphenyl)-4-methyl-1H-imidazole (LC-74)

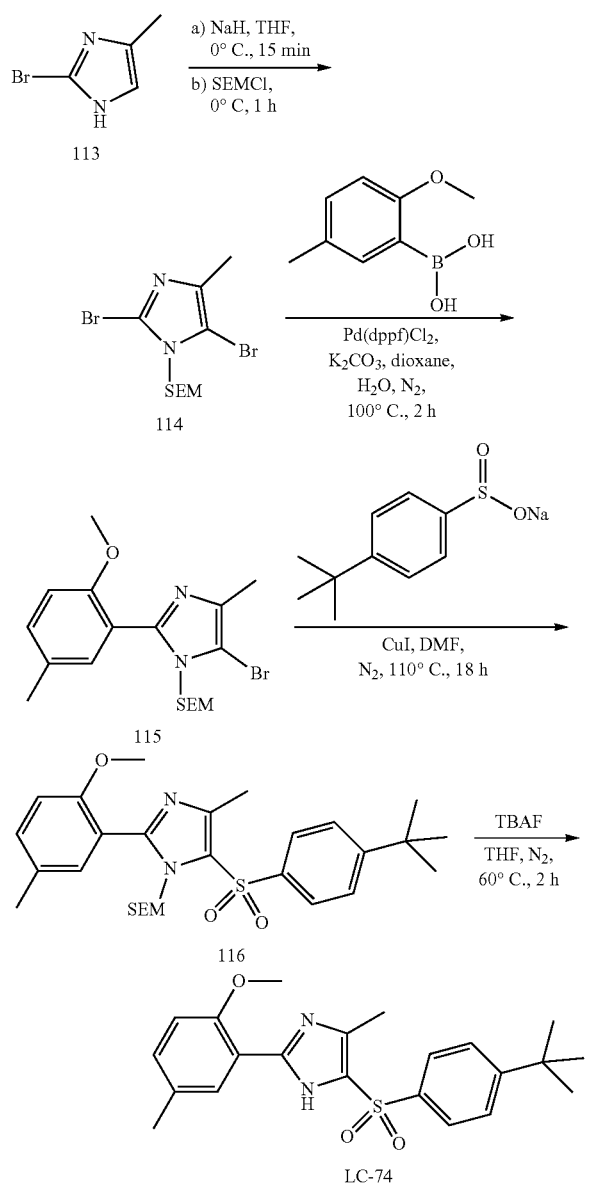

i. Preparation of 114

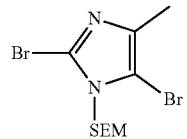

NaH (200 mg, 5 mmol) was added to a stirred solution of compound 113 (952 mg, 4 mmol) in THF (10 mL) at 0° C. and the reaction was stirred at 0° C. for 15 min. SEMCl (797 mg, 4.8 mmol) was added and the reaction was stirred for another hour at 0° C. The reaction was then quenched with $H_2O$ (30 mL) and extracted with EtOAc (30 mL×3). The combined organic layers were dried with anhydrous $Na_2SO_4$ and concentrated with a Rotavapor. The residue was purified by silica gel chromatography (Petroleum Ether/EtOAc=10/1 to 1/1) to give compound 114 (1.2 g, 82% yield). m/z 369 (M+H)$^+$.

ii. Preparation of 115

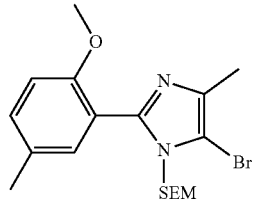 [SMILES: COc1ccc(C)cc1-c1nc(C)c(Br)n1COCC[Si](C)(C)C]

A solution of compound 114 (1.2 g, 3.3 mmol), 2-methoxy5-methyl-phenylboronic acid (664 mg, 4 mmol), Pd(dppf)Cl$_2$ (81.6 mg, 0.1 mmol) and K$_2$CO$_3$ (1.38 g, 10 mmol) in dioxane (15 mL) and H$_2$O (5 mL) was heated at 100° C. for 3 hr under N$_2$. After cooled down to room temperature, the reaction was quenched with H$_2$O (30 mL) and extracted with EtOAc (50 mL×2). The combined organic layers were dried with anhydrous Na$_2$SO$_4$ and concentrated with a Rotavapor. The residue was purified by preparative TLC (Petroleum Ether/EtOAc=5/1) to give compound 115 (450 mg, 33% yield). $^1H$ NMR (CDCl$_3$, 400 MHz): δ (ppm) 7.37 (s, 1H), 7.32 (d, 1H, J=8.4 Hz), 6.95 (d, 1H, J=8.4 Hz), 5.23 (s, 2H), 3.86 (s, 3H), 3.21 (t, 2H, J=8.4 Hz), 2.39 (s, 3H), 2.41 (s, 3H), 0.79 (t, 2H, J=8.4 Hz), 0.00 (s, 9H). m/z 411 (M+H)$^+$.

iii. Preparation of 116

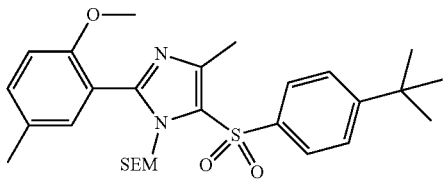 [SMILES: COc1ccc(C)cc1-c1nc(C)c(S(=O)(=O)c2ccc(C(C)(C)C)cc2)n1COCC[Si](C)(C)C]

A solution of compound 115 (410 mg, 1 mmol), sodium 4-(tert-butyl)benzenesulfinate (440 mg, 2 mmol), and CuI (190 mg, 1 mmol) in DMF (10 mL) was heated at 110° C.

for 18 hours under $N_2$. After cooled down to room temperature, the reaction was filtered. The filtrate was added with $H_2O$ (20 mL) and extracted with EtOAc (30 mL×3). The combined organic layers were dried with anhydrous $Na_2SO_4$ and concentrated with a Rotavapor. The residue was purified by preparative TLC (Petroleum Ether/EtOAc=2/1) to give compound 116 (25 mg, 5% yield). m/z 529 (M+H)⁺.

iv. Preparation of 5-((4-(tert-butyl)phenyl)sulfonyl)-2-(2-methoxy-5-methylphenyl)-4-methyl-1H-imidazole (LC-74)

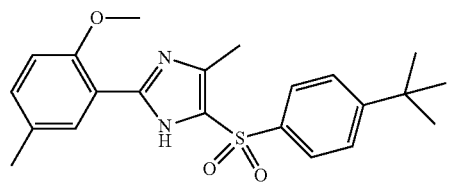 [SMILES: COc1ccc(C)cc1-c1nc(C)c(S(=O)(=O)c2ccc(C(C)(C)C)cc2)[nH]1]

A solution of compound 116 (25 mg, 0.05 mmol) and TBAF (500 mg) in THF (2 mL) was heated at 60° C. for 2 hours under $N_2$. After cooled down to the room temperature, the reaction was quenched with $H_2O$ (10 mL) and extracted with EtOAc (30 mL×2). The combined organic layers were dried with anhydrous $Na_2SO_4$ and concentrated with a Rotavapor. The residue was purified by preparative HPLC to give compound LC-74 (11 mg, 55% yield). $^1$H NMR (CDCl$_3$, 400 MHz): δ (ppm) 8.04 (s, 1H), 7.90 (d, 2H, J=8.4 Hz), 7.53 (d, 2H, J=8.8 Hz), 7.22 (s, 1H), 6.91 (d, 1H, J=8.8 Hz), 4.01 (s, 3H), 2.58 (s, 3H), 2.29 (s, 3H), 1.30 (s, 9H). m/z 399 (M+H)⁺.

x. General Synthesis of LC-76, LC-77, and LC-78

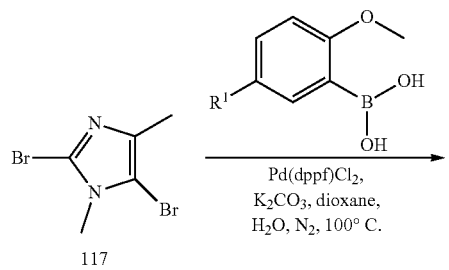

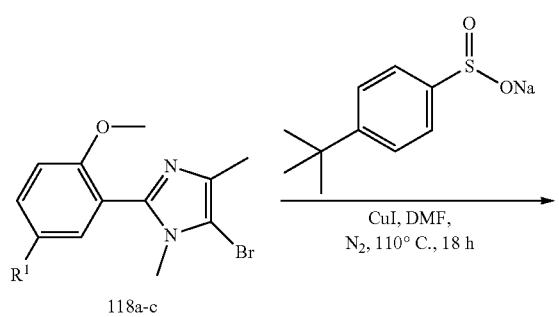

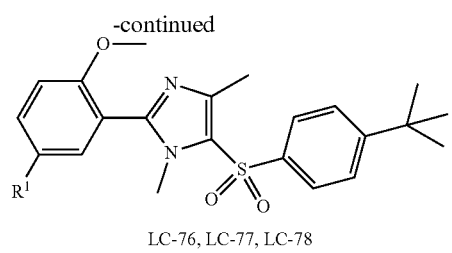

LC-76, LC-77, LC-78 i. Preparation of 5-((4-(tert-butyl)phenyl)sulfonyl)-2-(2,5-dimethoxyphenyl)-1,4-dimethyl-1H-imidazole (LC-76)

(1) Synthesis of 118a

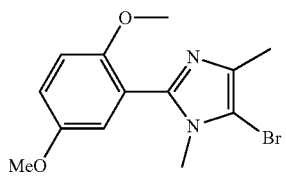 [SMILES: COc1ccc(OC)c(-c2nc(C)c(Br)n2C)c1]

A solution of compound 117 (1.0 g, 3.97 mmol), 2,5-dimethoxyphenylboronic acid (722 mg, 3.97 mmol), Pd(dppf)Cl$_2$ (100 mg) and $K_2CO_3$ (1.1 g, 7.94 mmol) in dioxane (10 mL) and $H_2O$ (2 mL) was heated at 100° C. for 3 hours under $N_2$. After cooled down to room temperature, the reaction was quenched with $H_2O$ (15 mL) and extracted with EtOAc (15 mL×3). The combined organic layers were dried with anhydrous $Na_2SO_4$ and concentrated with a Rotavapor. The residue was purified by preparative TLC (Petroleum Ether/EtOAc=2/1) to give compound 118a (500 mg, 40.6% yield). m/z 311 (M+H)⁺.

(2) Synthesis of LC-76

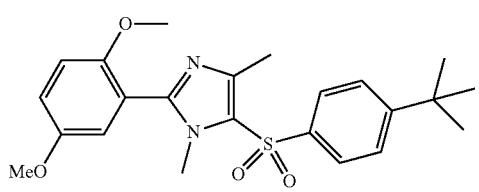 [SMILES: COc1ccc(OC)c(-c2nc(C)c(S(=O)(=O)c3ccc(C(C)(C)C)cc3)n2C)c1]

A solution of compound 118a (500 mg, 1.6 mmol), sodium 4-(tert-butyl)benzenesulfinate (704 mg, 3.2 mmol), and CuI (337 mg, 1.77 mmol) in DMF (6 mL) was heated at 110° C. for 18 hours under $N_2$. The reaction was cooled down to room temperature and filtered. The filtrate was added with $H_2O$ (10 mL) and extracted with EtOAc (10 mL×3). The combined organic layers were dried with anhydrous $Na_2SO_4$ and concentrated with a Rotavapor. The residue was purified by preparative HPLC to give compound LC-76 (100 mg, 14.6% yield). $^1$H NMR (CDCl$_3$, 400 MHz): δ (ppm) 7.85 (d, J=8.8 Hz, 2H), 7.61 (d, J=8.8 Hz, 2H), 6.93-7.13 (m, 3H), 3.76 (s, 3H), 3.74 (s, 3H), 3.65 (s, 3H), 2.75 (s, 3H), 1.34 (s, 9H). m/z 429 (M+H)⁺.

ii. Preparation of 5-((4-(tert-butyl)phenyl)sulfonyl)-2-(2-methoxy-5-methylphenyl)-1,4-dimethyl-1H-imidazole (LC-77)

(1) Synthesis of 118b

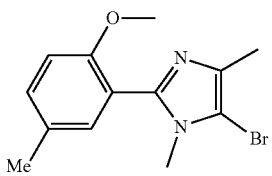 [SMILES: COc1ccc(C)cc1-c1nc(C)c(Br)n1C]

A solution of compound 117 (1.0 g, 3.97 mmol), 2-methoxy-5-methyl-phenylboronic acid (659 mg, 3.97 mmol), Pd(dppf)Cl$_2$ (100 mg) and K$_2$CO$_3$ (1.1 g, 7.94 mmol) in dioxane (10 mL) and H$_2$O (2 mL) was heated at 100° C. for 3 hours under N$_2$. After cooled down to room temperature, the reaction was quenched with H$_2$O (15 mL) and extracted with EtOAc (15 mL×3). The combined organic layers were dried with anhydrous Na$_2$SO$_4$ and concentrated with a Rotavapor. The residue was purified by preparative TLC (Petroleum Ether/EtOAc=2/1) to give compound 118b (400 mg, 34.2% yield). $^1$H NMR (CDCl$_3$, 400 MHz): δ (ppm) 7.23-7.24 (m, 1H), 7.18 (d, J=8.8 Hz, 1H), 6.83 (d, J=8.8 Hz, 1H), 3.77 (s, 3H), 3.38 (s, 3H), 2.28 (s, 3H), 2.22 (s, 3H). m/z 295 (M+H)$^+$.

(2) Synthesis of LC-77

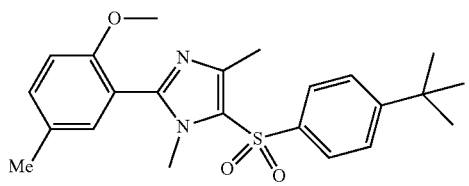 [SMILES: COc1ccc(C)cc1-c1nc(C)c(S(=O)(=O)c2ccc(C(C)(C)C)cc2)n1C]

A solution of compound 118b (400 mg, 1.36 mmol), sodium 4-(tert-butyl)benzenesulfinate (598 mg, 2.72 mmol), and CuI (284 mg, 1.5 mmol) in DMF (6 mL) was heated at 110° C. for 18 hours under N$_2$. The reaction was cooled down to room temperature and filtered. The filtrate was added with H$_2$O (10 mL) and extracted with EtOAc (10 mL×3). The combined organic layers were dried with anhydrous Na$_2$SO$_4$ and concentrated with a Rotavapor. The residue was purified by preparative HPLC to give compound LC-77 (80 mg, 14.3% yield). $^1$H NMR (CDCl$_3$, 400 MHz): δ (ppm) 7.80 (d, J=8.4 Hz, 2H), 7.56 (d, J=8.4 Hz, 2H), 7.30 (d, J=8.8 Hz, 1H), 7.19 (s, 1H), 6.84 (d, J=8.8 Hz, 1H), 3.71 (s, 3H), 3.60 (s, 3H), 2.70 (s, 3H), 2.22 (s, 3H), 1.29 (s, 9H). m/z 413 (M+H)$^+$.

iii. Preparation of 5-((4-(tert-butyl)phenyl)sulfonyl)-2-(5-chloro-2-methoxyphenyl)-1,4-dimethyl-1H-imidazole (LC-78)

(1) Synthesis of 118c

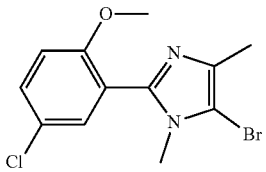 [SMILES: COc1ccc(Cl)cc1-c1nc(C)c(Br)n1C]

A solution of compound 117 (1.0 g, 3.97 mmol), 2-methoxy-5-chloro-phenylboronic acid (738 mg, 3.97 mmol), Pd(dppf)Cl$_2$ (100 mg) and K$_2$CO$_3$ (1.1 g, 7.94 mmol) in dioxane (10 mL) and H$_2$O (2 mL) was heated at 100° C. for 3 hours under N$_2$. After cooled down to room temperature, the reaction was quenched with H$_2$O (15 mL) and extracted with EtOAc (15 mL×3). The combined organic layers were dried with anhydrous Na$_2$SO$_4$ and concentrated with a Rotavapor. The residue was purified by preparative TLC (Petroleum Ether/EtOAc=2/1) to give compound 118c (500 mg, 40.0% yield). m/z 315 (M+H)$^+$.

(2) Synthesis of LC-78

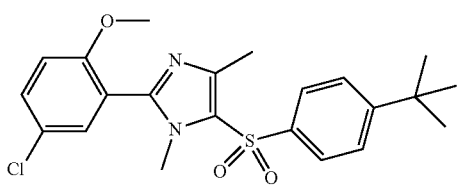 [SMILES: COc1ccc(Cl)cc1-c1nc(C)c(S(=O)(=O)c2ccc(C(C)(C)C)cc2)n1C]

A solution of compound 118c (500 mg, 1.6 mmol), sodium 4-(tert-butyl)benzenesulfinate (704 mg, 3.2 mmol), and CuI (337 mg, 1.77 mmol) in DMF (6 mL) was heated at 110° C. for 18 hours under N$_2$. The reaction was cooled down to room temperature and filtered. The filtrate was added with H$_2$O (10 mL) and extracted with EtOAc (10 mL×3). The combined organic layers were dried with anhydrous Na$_2$SO$_4$ and concentrated with a Rotavapor. The residue was purified by preparative HPLC to give compound LC-78 (150 mg, 21.7% yield). $^1$H NMR (CDCl$_3$, 400 MHz): δ (ppm) 7.85 (d, J=8.4 Hz, 2H), 7.60 (d, J=8.4 Hz, 2H), 7.49 (d, J=8.8 Hz, 1H), 7.38 (s, 1H), 6.94 (d, J=8.8 Hz, 1H), 3.78 (s, 3H), 3.63 (s, 3H), 2.72 (s, 3H), 1.34 (s, 9H). m/z 433 (M+H)$^+$.

y. General Synthesis of LC-79, LC-80, and LC-81

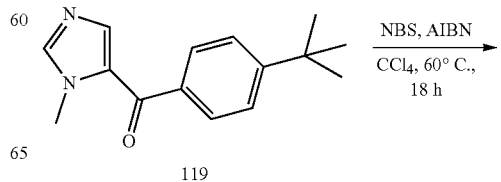

-continued

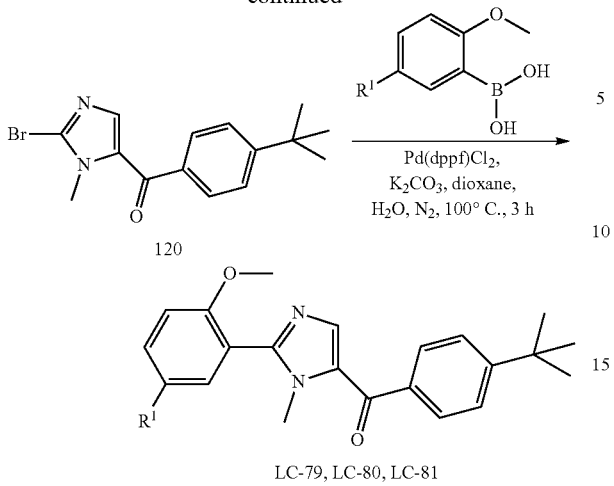

LC-79, LC-80, LC-81 i. Preparation of 120

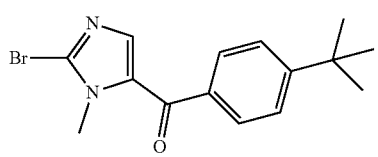 [SMILES: Cn1c(C(=O)c2ccc(C(C)(C)C)cc2)cnc1Br]

A solution of compound 119 (605 mg, 2.5 mmol), NBS (442 g, 2.5 mmol) and AIBN (16.4 mg, 0.1 mmol) in CCl$_4$ (20 mL) was stirred at 60° C. for 18 hours. The mixture was concentrated with a Rotavapor and the residue was purified by preparative TLC (Petroleum Ether/EtOAc=5/1) to give product 120 (488 mg, 61% yield). $^1$H NMR (CDCl$_3$, 400 MHz): δ (ppm) 8.18-8.20 (m, 2H), 7.47-4.49 (m, 2H), 7.06 (s, 1H), 4.02 (s, 3H), 1.32 (s, 9H). m/z 321 (M+H)$^+$.

ii. Preparation of (4-(tert-butyl)phenyl)(2-(2,5-dimethoxyphenyl)-1-methyl-1H-imidazol-5-yl)methanone (LC-79)

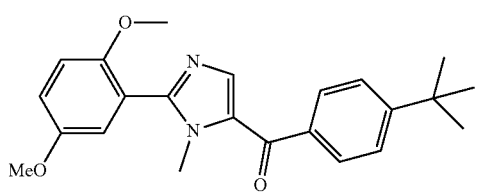 [SMILES: COc1ccc(OC)c(-c2ncc(C(=O)c3ccc(C(C)(C)C)cc3)n2C)c1]

A solution of compound 120 (160 mg, 0.5 mmol), 2,5-dimethoxyphenylboronic acid (182 mg, 1 mmol), Pd(dppf)Cl$_2$ (16 mg) and K$_2$CO$_3$ (276 mg, 2 mmol) in dioxane (5 mL) and H$_2$O (1 mL) was heated at 100° C. for 3 hours under N$_2$. H$_2$O (5 mL) was then added and the mixture was extracted with EtOAc (15 mL×3). The combined organic layers were dried with anhydrous Na$_2$SO$_4$ and concentrated with a Rotavapor. The residue was purified by preparative HPLC to give the product LC-79 (108 mg, 57% yield). $^1$H NMR (CDCl$_3$, 400 MHz): δ (ppm) 8.03 (d, 2H, J=8.0 Hz), 7.51 (d, 2H, J=8.4 Hz), 7.32 (s, 1H), 7.00-7.03 (m, 1H), 6.95 (d, 1H, J=8.8 Hz), 6.85 (d, 1H, J=2.8 Hz), 3.83 (s, 3H), 3.79 (d, 6H, J=3.6 Hz), 1.33 (s, 9H). m/z 379 (M+H)$^+$.

iii. Preparation of (4-(tert-butyl)phenyl)(2-(2-methoxy-5-methylphenyl)-1-methyl-1h-imidazol-5-yl)methanone (LC-80)

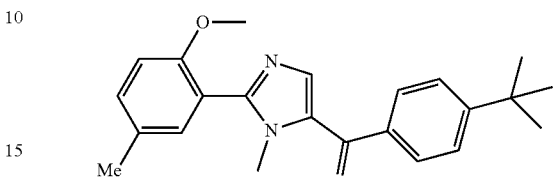

The preparation of compound LC-80 (56 mg, 30.9% yield) was similar to the preparation of compound LC-79 except that 2-methoxy-5-methyl-phenylboronic acid was used as the starting material to replace the 2,5-dimethoxyphenylboronic acid in the preparation of compound LC-79. $^1$H NMR (CDCl$_3$, 400 MHz): δ (ppm) 8.13 (d, 2H, J=8.4 Hz), 7.43 (d, 2H, J=8.4 Hz), 7.14-7.18 (m, 2H), 7.03 (d, 1H, J=1.2 Hz), 6.83 (d, 1H, J=8.4 Hz), 3.76 (s, 3H), 3.73 (s, 3H), 2.26 (s, 3H), 1.28 (s, 9H). m/z 363 (M+H)$^+$.

iv. Preparation of (4-(tert-butyl)phenyl)(2-(5-chloro-2-methoxyphenyl)-1-methyl-1H-imidazol-5-yl)methanone (LC-81)

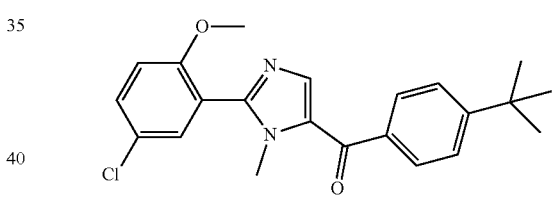

The preparation of compound LC-81 (77 mg, 40.3% yield) was similar to the preparation of compound LC-79 except that 2-methoxy-5-chloro-phenylboronic acid was used as the starting material to replace the 2,5-dimethoxyphenylboronic acid in the preparation of compound LC-79. $^1$H NMR (CDCl$_3$, 400 MHz): δ (ppm) 7.99 (d, 2H, J=8.4 Hz), 7.51 (d, 2H, J=8.0 Hz), 7.44-7.46 (m, 1H), 7.35 (s, 1H), 7.30 (d, 1H, J=2.4 Hz), 6.96 (d, 1H, J=9.2 Hz), 3.84 (s, 3H), 3.82 (s, 3H), 1.33 (s, 9H). m/z 383 (M+H)$^+$.

z. Synthesis of 2-(tert-butyl)-5-((1-(2,5-dimethoxyphenyl)-5-methyl-1H-1,2,3-triazol-4-yl)sulfonyl)phenol (LC-88)

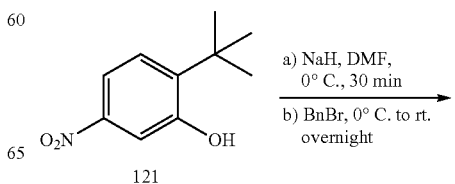

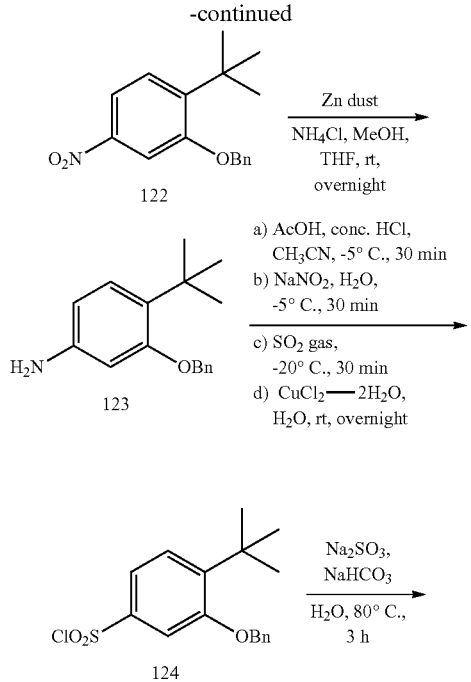

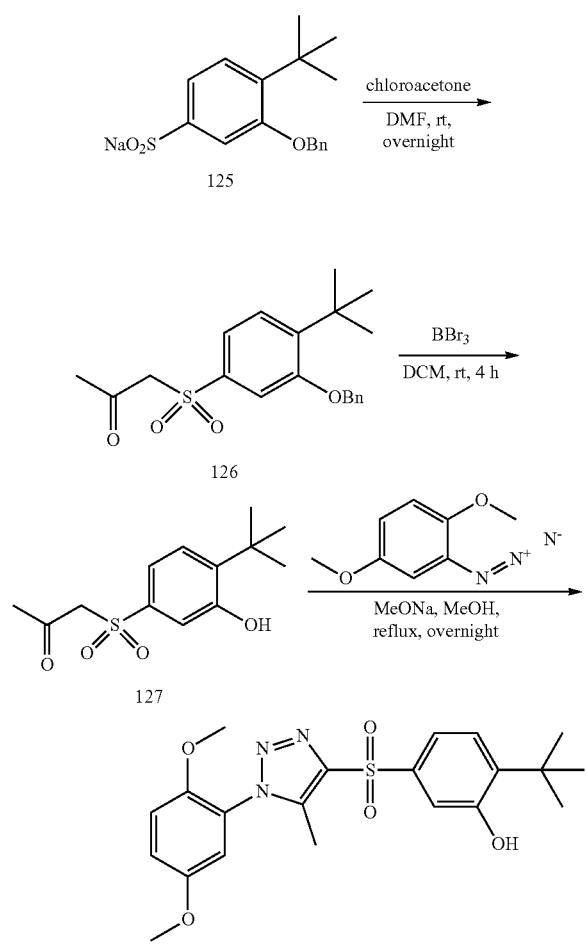

i. Preparation of 122

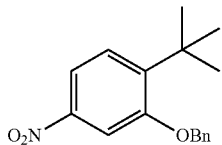

Sodium hydride (60% in mineral oil, 6.2 g, 0.155 mol) was added in portions to a solution of compound 121 (42.8 g, 0.15 mol) in DMF (250 mL) at 0° C. The reaction was stirred at 0° C. for 30 min. Benzyl bromide (26.5 g, 0.155 mol) was then added dropwise and the mixture was stirred at room temperature overnight. The reaction mixture was poured into water, and the aqueous layer was extracted with ethyl acetate twice. The combined organic layers were washed with brine, dried with anhydrous $Na_2SO_4$ and concentrated with a Rotavapor. The residue was purified by silica gel chromatography (Petroleum Ether/EtOAc=10/1) to give compound 122 (15 g, 39.5% yield). $^1$H NMR (CDCl$_3$, 400 MHz): δ (ppm) 7.78-7.75 (m, 2H), 7.48-7.33 (m, 6H), 5.18 (s, 2H), 1.40 (s, 9H).

ii. Preparation of 123

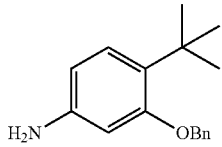

$NH_4Cl$ (21.4 g, 0.33 mol), followed by Zn dust (15 g, 0.38 mol) in portions was added to a solution of compound 122 (10.5 g, 0.037 mol) in MeOH (150 mL) and THF (150 mL) at room temperature. The reaction was stirred at room temperature overnight. The mixture was filtered and the filtrate was concentrated with a Rotavapor. The residue was purified by silica gel chromatography (Petroleum Ether/EtOAc=10/1 to 5/1) to give compound 123 (7 g, 74% yield). $^1$H NMR (CDCl$_3$, 400 MHz): δ (ppm) 7.45-7.26 (m, 5H), 7.09 (d, J=8.0 Hz, 1H), 6.32 (d, J=1.6 Hz, 1H), 6.28 (dd, J=8.0 Hz, 1.6 Hz, 1H), 5.07 (s, 2H), 3.55 (brs, 2H), 1.36 (s, 9H). m/z 256 (M+H)$^+$.

iii. Preparation of 124

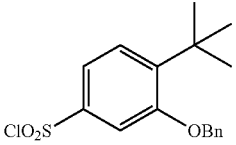

HOAc (12.5 mL) and then concentrated HCl (12.5 mL) were added to a solution of compound 123 (5.1 g, 0.02 mol) in acetonitrile (120 mL) at −5° C. The mixture was stirred at −5° C. for 30 min and a solution of sodium nitrite (1.63 g, 0.024 mol) in water (2.5 mL) was added dropwise in 10 minutes at −5° C. The reaction was stirred at −5° C. for 30 minutes and then cooled down to −20° C. The reaction was bubbled into SO₂ gas for 10 minutes, followed by the addition of a solution of CuCl₂·2H₂O (3.8 g, 0.022 mol) in water (3.5 mL) in one portion. The reaction was then stirred at room temperature overnight. The reaction mixture was quenched with water and then extracted with ethyl acetate (150 mL×3). The combined organic layers were dried with anhydrous Na₂SO₄ and concentrated with a Rotavapor. The residue was purified by silica gel chromatography (Petroleum Ether/EtOAc=10/1) to give compound 124 (3.3 g, 50% yield). ¹H NMR (CDCl₃, 400 MHz): δ (ppm) 7.60-7.34 (m, 8H), 5.18 (s, 2H), 1.40 (s, 9H).

iv. Preparation of 125

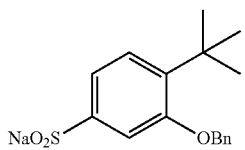

A solution of compound 124 (3.3 g, 0.01 mol), Na₂SO₃ (1.51 g, 0.012 mol) and NaHCO₃ (1.68 g, 0.02 mol) in water (40 mL) was heated at 80° C. for 3 hours. Water was removed with a Rotavapor and the residual water was further removed with toluene by azeotropic distillation to give crude compound 125 which was used directly for the next step without further purification.

v. Preparation of 126

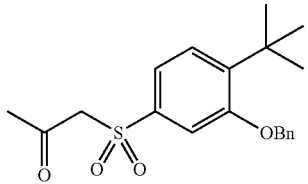

A solution of compound 125 (3.26 g, 0.01 mol) and chloroacetone (5.0 g, 0.05 mol) in DMF (40 mL) was stirred at room temperature overnight. The reaction mixture was poured into water and extracted with ethyl acetate three times. The organic layer was washed with brine, dried with anhydrous Na₂SO₄ and concentrated with a Rotavapor to give compound 126 which was used directly for the next step without further purification.

vi. Preparation of 127

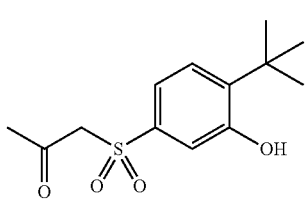 [SMILES: CC(=O)CS(=O)(=O)c1ccc(C(C)(C)C)c(O)c1]

BBr₃ (0.5 mL) was added to a solution of crude compound 126 in DCM (20 mL) at room temperature and the reaction was stirred at room temperature for 4 hours. The reaction was quenched with saturated NaHCO₃ aqueous solution and the mixture was extracted with DCM three times. The combined organic layer was washed with brine, dried with anhydrous Na₂SO₄ and concentrated with a Rotavapor. The residue was purified by silica gel chromatography (Petroleum Ether/EtOAc=10/1 to 4/1) to give compound 127 (720 mg, 26.7% yield for three steps). ¹H NMR (CDCl₃, 400 MHz): δ (ppm) 7.45 (d, J=8.4 Hz, 1H), 7.36 (dd, J=8.1 Hz, 1.8 Hz, 1H), 7.27 (d, J=2.1 Hz, 1H), 6.39 (s, 1H), 4.17 (s, 2H), 2.39 (s, 3H), 1.40 (s, 9H). m/z 292.8 (M+Na)⁺.

vii. Preparation of 2-(tert-butyl)-5-((1-(2,5-dimethoxyphenyl)-5-methyl-1H-1,2,3-triazol-4-yl)sulfonyl)phenol (LC-88)

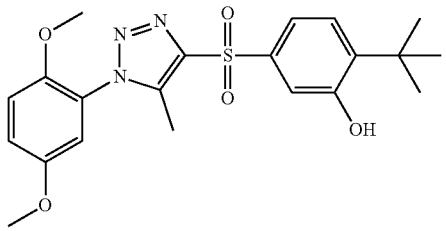 [SMILES: COc1ccc(OC)c(-n2nnc(S(=O)(=O)c3ccc(C(C)(C)C)c(O)c3)c2C)c1]

A solution of compound 127 (720 mg, 2.67 mmol), 2-azido-1,4-dimethoxybenzene³² (573 mg, 3.2 mmol) and NaOCH₃ (288 mg, 5.33 mmol) in CH₃OH (10 mL) was heated at reflux overnight. The reaction was cooled down to room temperature, quenched with H₂O (80 mL) and extracted with EtOAc (50 mL×3). The combined EtOAc solution was washed with brined, dried with anhydrous Na₂SO₄ and concentrated with a Rotavapor. The residue was purified by silica gel chromatography (Petroleum Ether/EtOAc=85/15 to 70/30) to give compound LC-88 (450 mg, 39% yield). ¹H NMR (DMSO-d₆, 400 MHz): δ (ppm) 10.34 (brs, 1H), 7.47-7.21 (m, 6H), 3.74 (s, 3H), 3.73 (s, 3H), 2.36 (s, 3H), 1.35 (s, 9H). m/z 432.2 (M+H)⁺.

aa. Synthesis of 2-(4-((4-(tert-butyl)-3-hydroxyphenyl)sulfonyl)-5-methyl-1H-1,2,3-triazol-1-yl)-4-methoxyphenol (LC-83)

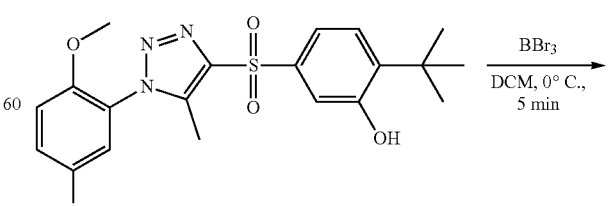

LC-88

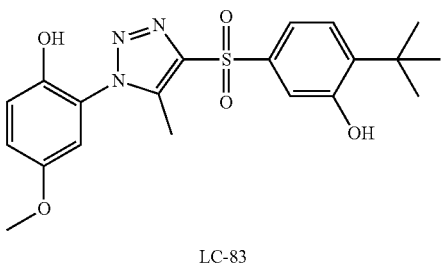

LC-83

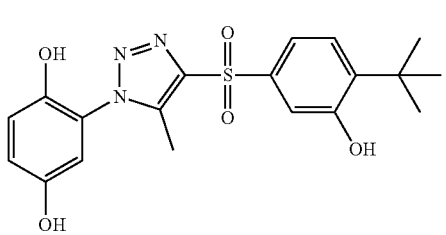 [SMILES: Cc1c(S(=O)(=O)c2ccc(C(C)(C)C)c(O)c2)nnn1-c1cc(O)ccc1O]

BBr₃ (115 mg, 0.46 mmol) was added to a solution of compound LC-88 (100 mg, 0.23 mmol) in anhydrous DCM (5 mL) at 0° C. and the reaction was stirred at this temperature for 5 min. The reaction mixture was quenched with saturated NaHCO₃ aqueous solution (20 mL) and extracted with DCM (30 mL×3). The combined organic layer was washed with brine, dried with anhydrous Na₂SO₄ and concentrated with a Rotavapor. The residue was purified by preparative HPLC to give compound LC-83 (46 mg, 47% yield). ¹H NMR (DMSO-d₆, 400 MHz): δ (ppm) 10.33 (brs, 1H), 10.07 (brs, 1H), 7.45-7.35 (m, 3H), 7.06-7.00 (m, 3H), 3.68 (s, 3H), 2.37 (s, 3H), 1.33 (s, 9H). m/z 418.2 (M+H)⁺.

bb. Synthesis of 2-(tert-butyl)-5-((1-(5-hydroxy-2-methoxyphenyl)-5-methyl-1H-1,2,3-triazol-4-yl)sulfonyl)phenol (LC-82)

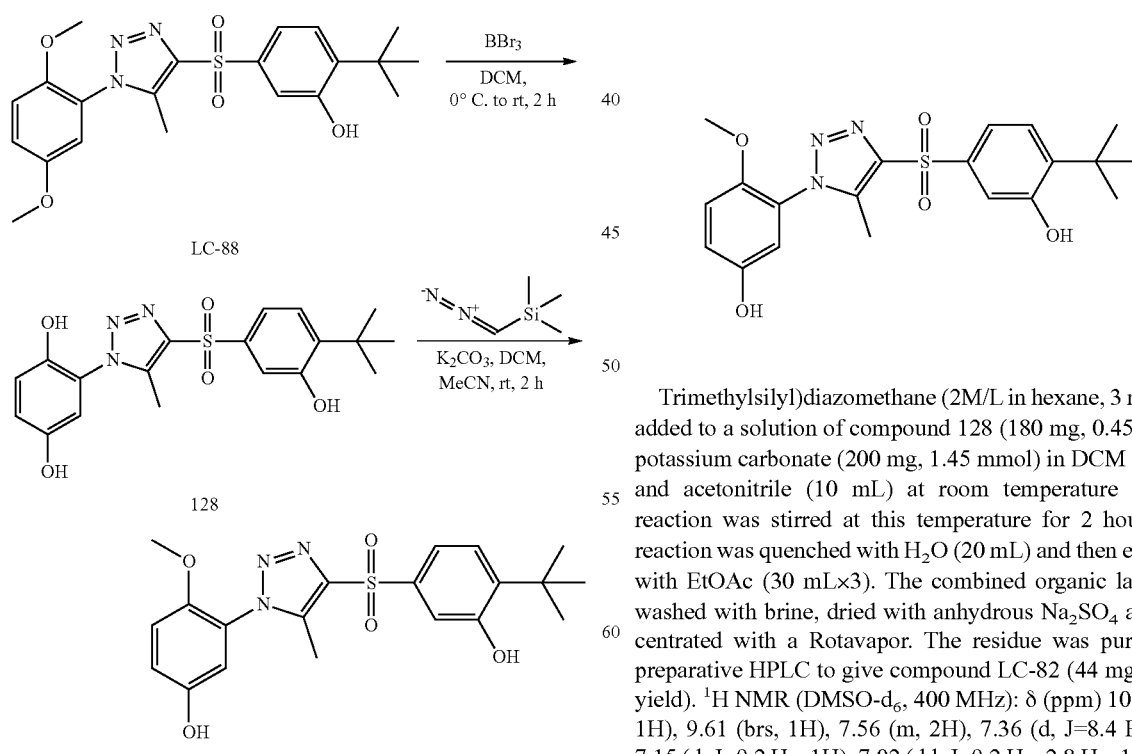

i. Preparation of 128

BBr₃ (783 mg, 3.1 mmol) was added to a solution of compound LC-88 (270 mg, 0.63 mmol) in anhydrous DCM (10 mL) at 0° C. and the reaction was then stirred at room temperature for 2 hour. The reaction mixture was quenched with saturated NaHCO₃ aqueous solution (20 mL) and extracted with DCM (30 mL×3). The combined organic layer was washed with brine, dried with anhydrous Na₂SO₄ and concentrated with a Rotavapor. The residue was purified by silica gel chromatography (Petroleum Ether/EtOAc=9/1 to 3/1) to give compound 128 (180 mg, 71% yield). ¹H NMR (DMSO-d₆, 400 MHz): δ (ppm) 10.30 (s, 1H), 9.77 (s, 1H), 9.35 (s, 1H), 7.44-7.34 (m, 3H), 6.92-6.85 (m, 2H), 6.73 (d, J=2.8 Hz, 1H), 2.36 (s, 3H), 1.33 (s, 9H). m/z 404.0 (M+H)⁺.

ii. Preparation of 2-(tert-butyl)-5-((1-(5-hydroxy-2-methoxyphenyl)-5-methyl-1H-1,2,3-triazol-4-yl)sulfonyl)phenol (LC-82)

Trimethylsilyl)diazomethane (2M/L in hexane, 3 mL) was added to a solution of compound 128 (180 mg, 0.45 mmol), potassium carbonate (200 mg, 1.45 mmol) in DCM (10 mL) and acetonitrile (10 mL) at room temperature and the reaction was stirred at this temperature for 2 hours. The reaction was quenched with H₂O (20 mL) and then extracted with EtOAc (30 mL×3). The combined organic layer was washed with brine, dried with anhydrous Na₂SO₄ and concentrated with a Rotavapor. The residue was purified by preparative HPLC to give compound LC-82 (44 mg, 23.7% yield). ¹H NMR (DMSO-d₆, 400 MHz): δ (ppm) 10.31 (brs, 1H), 9.61 (brs, 1H), 7.56 (m, 2H), 7.36 (d, J=8.4 Hz, 1H), 7.15 (d, J=9.2 Hz, 1H), 7.02 (dd, J=9.2 Hz, 2.8 Hz, 1H), 6.85 (J=2.8 Hz, 1H), 3.61 (s, 3H), 2.36 (s, 3H), 1.33 (s, 9H). m/z 418.2 (M+H)⁺.

cc. Synthesis of 5-(tert-butyl)-2-((1-(2,5-dimethoxyphenyl)-5-methyl-1H-1,2,3-triazol-4-yl)sulfonyl)phenol (LC-84)

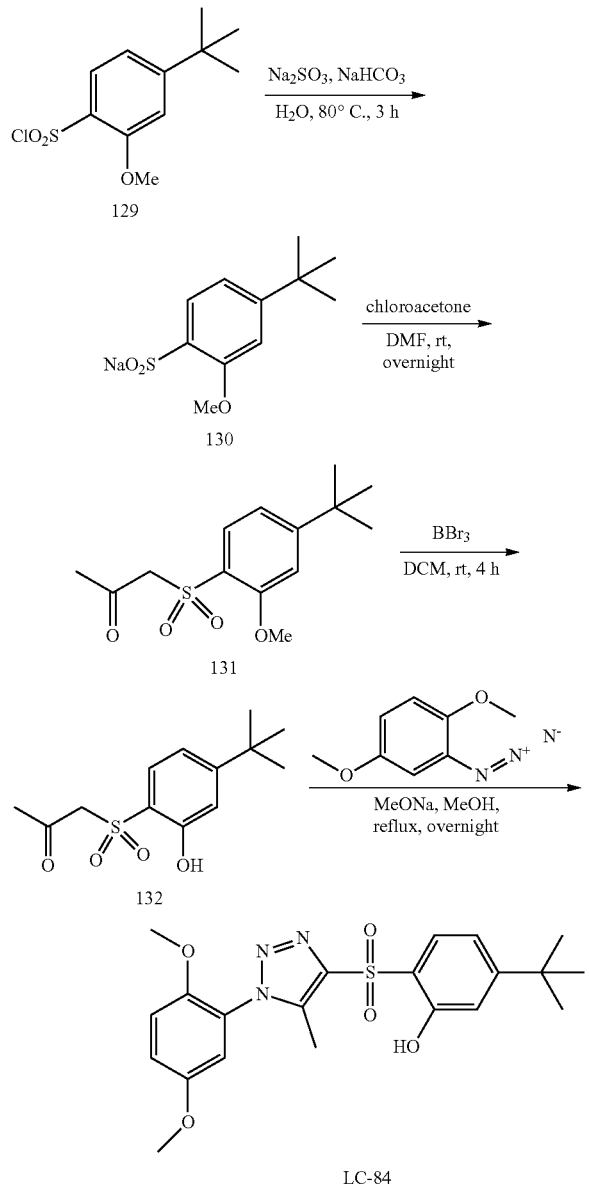

i. Preparation of 130

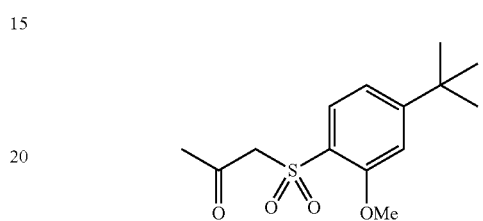

A solution of compound 129 (600 mg, 2.28 mmol), Na$_2$SO$_3$ (345 mg, 2.74 mmol) and NaHCO$_3$ (383 mg, 4.56 mmol) in H$_2$O (8 mL) was heated at 80° C. for 3 hours. The reaction was cooled down to room temperature. Water in the reaction mixture was removed with a Rotavapor and the residual water was further removed with toluene by azeotropic distillation to give crude compound 130 which was used directly for the next step without further purification.

ii. Preparation of 131

A solution of compound 130 (crude, from the above step) and chloroacetone (1.3 g, 14 mmol) in DMF (20 mL) was stirred at room temperature overnight. The reaction was quenched with H$_2$O (50 mL) and extracted with EtOAC (60 mL×3). The combined organic layer was washed with brine, dried with anhydrous Na$_2$SO$_4$ and concentrated with a Rotavapor. The residue was purified by silica gel chromatography (Petroleum Ether/EtOAc=4/0 to 4/1) to give compound 131 (350 mg, 56.7% yield). $^1$H NMR (CDCl$_3$, 400 MHz): δ (ppm) 7.81 (d, J=8.4 Hz, 1H), 7.11 (dd, J=8.1 Hz, 1.5 Hz, 1H), 7.01 (d, J=1.2 Hz, 1H), 4.34 (s, 2H), 3.97 (s, 3H), 2.38 (s, 3H), 1.32 (s, 9H).

iii. Preparation of 132

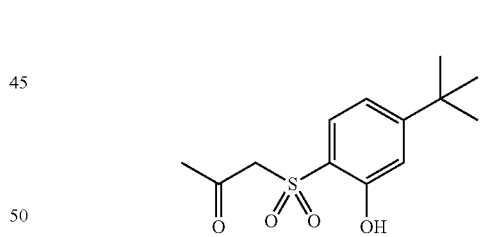

BBr$_3$ (0.3 mL) was added to a solution of compound 131 (330 mg, 1.16 mmol) in anhydrous DCM (5 mL) at room temperature and the reaction was then stirred at this temperature for 4 hours. The reaction mixture was quenched with saturated NaHCO$_3$ aqueous solution (20 mL) and extracted with DCM (30 mL×3). The combined organic layer was washed with brine, dried with anhydrous Na$_2$SO$_4$ and concentrated with a Rotavapor. The residue was purified by silica gel chromatography (Petroleum Ether/EtOAc=9/1 to 3/1) to give compound 132 (180 mg, 57.5% yield). $^1$H NMR (CDCl$_3$, 400 MHz): δ (ppm) 8.62 (brs, 1H), 7.54 (dd, J=8.1 Hz, 0.9 Hz 1H), 7.06-7.01 (m, 2H), 4.20 (s, 2H), 2.38 (s, 3H), 1.29 (s, 9H).

iv. Preparation of 5-(tert-butyl)-2-((1-(2,5-dimethoxyphenyl)-5-methyl-1H-1,2,3-triazol-4-yl)sulfonyl)phenol (LC-84)

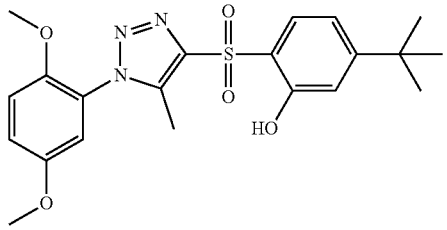 [SMILES: COc1ccc(OC)c(-n2nnc(S(=O)(=O)c3ccc(C(C)(C)C)cc3O)c2C)c1]

A solution of compound 132 (180 mg, 0.67 mmol), 2-azido-1,4-dimethoxybenzene[32] (143 mg, 0.8 mmol) and NaOCH$_3$ (108 mg, 2.0 mmol) in CH$_3$OH (4 mL) was heated at reflux overnight. The reaction was cooled down to room temperature, quenched with H$_2$O (30 mL) and extracted with EtOAc (20 mL×3). The combined EtOAc solution was washed with brined, dried with anhydrous Na$_2$SO$_4$ and concentrated with a Rotavapor. The residue was purified by silica gel chromatography (Petroleum Ether/EtOAc=85/15 to 70/30) to give compound LC-84 (80 mg, 27.7% yield). $^1$H NMR (CDCl$_3$, 400 MHz): δ (ppm) 9.05 (s, 1H), 10.07 (brs, 1H), 7.78 (d, J=8.4 Hz, 1H), 7.10-7.00 (m, 4H), 6.89 (d, J=6.8 Hz, 1H), 3.78 (s, 3H), 3.75 (s, 3H), 2.45 (s, 3H), 1.30 (s, 9H). m/z 432.2 (M+H)$^+$.

dd. Synthesis of 2-(4-((4-(tert-butyl)phenyl)sulfonyl)-5-methyl-1H-1,2,3-triazol-1-yl)benzene-1,4-diol (LC-85)

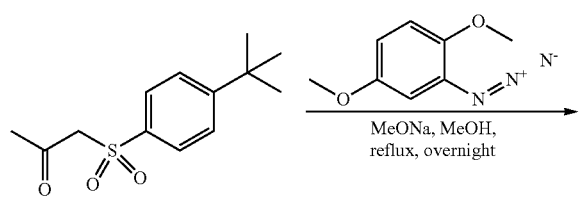

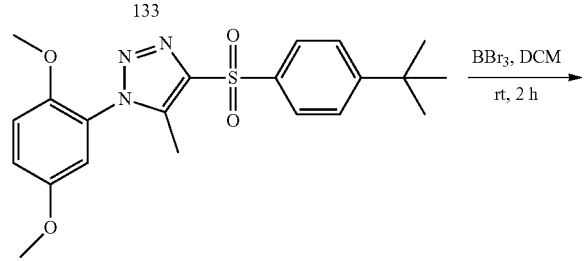

i. Preparation of 4-((4-(tert-butyl)phenyl)sulfonyl)-1-(2,5-dimethoxyphenyl)-5-methyl-1H-1,2,3-triazole (LC-1; 134)

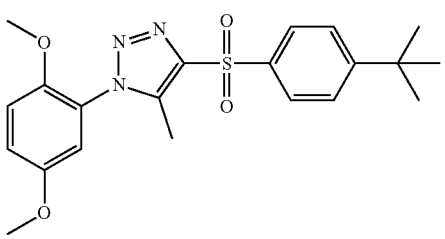 [SMILES: COc1ccc(OC)c(-n2nnc(S(=O)(=O)c3ccc(C(C)(C)C)cc3)c2C)c1]

A solution of compound 133 (1.0 g, 3.94 mmol), 2-azido-1,4-dimethoxybenzene[32] (540 mg, 3.0 mmol) and NaOCH$_3$ (810 mg, 15 mmol) in CH$_3$OH (10 mL) was heated at reflux overnight. The reaction was cooled down to room temperature, quenched with H$_2$O (30 mL) and extracted with EtOAc (20 mL×3). The combined EtOAc solution was washed with brined, dried with anhydrous Na$_2$SO$_4$ and concentrated with a Rotavapor. The residue was purified by silica gel chromatography (Petroleum Ether/EtOAc=85/15 to 70/30) to give compound 134 (LC-1, 380 mg, 30% yield). $^1$H NMR (CDCl$_3$, 400 MHz): δ (ppm) 8.06 (d, J=8.8 Hz, 2H), 7.58 (d, J=8.4 Hz, 2H), 7.09 (dd, J=9.2 Hz, 2.8 Hz, 1H), 7.02 (d, J=9.2 Hz, 1H), 6.88 (d, J=2.8 Hz, 1H), 3.77 (s, 3H), 3.74 (s, 3H), 2.46 (s, 3H), 1.56 (s, 9H). m/z 416.1 (M+H)$^+$.

ii. Preparation of 2-(4-((4-(tert-butyl)phenyl)sulfonyl)-5-methyl-1H-1,2,3-triazol-1-yl)benzene-1,4-diol (LC-85)

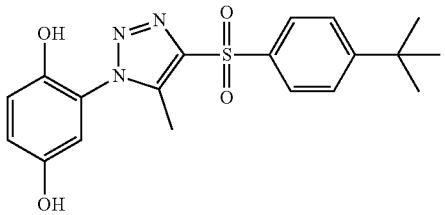 [SMILES: Cc1c(S(=O)(=O)c2ccc(C(C)(C)C)cc2)nnn1-c1cc(O)ccc1O]

BBr$_3$ (500 mg, 2 mmol) was added to a solution of compound 134 (400 mg, 0.96 mmol) in anhydrous DCM (10 mL) at room temperature and the reaction was then stirred at this temperature for 2 hours. The reaction mixture was quenched with saturated NaHCO$_3$ aqueous solution (20 mL) and extracted with DCM (30 mL×3). The combined organic layer was washed with brine, dried with anhydrous Na$_2$SO$_4$ and concentrated with a Rotavapor. The residue was purified by silica gel chromatography (Petroleum Ether/EtOAc=9/1 to 3/1) to give compound LC-85 (330 mg, 88% yield). $^1$H NMR (DMSO-d$_6$, 400 MHz): δ (ppm) 9.76 (brs, 1H), 9.34 (brs, 1H), 7.94 (d, J=8.0 Hz, 2H), 7.70 (d, J=8.4 Hz, 2H), 6.92 (m, 2H), 6.73 (d, J=2.4 Hz, 1H), 2.38 (s, 3H), 1.30 (s, 9H). m/z 388.2 (M+H)$^+$.

ee. Synthesis of 2-(4-((4-(tert-butyl)phenyl)sulfonyl)-5-methyl-1H-1,2,3-triazol-1-yl)-4-methoxyphenol (LC-86)

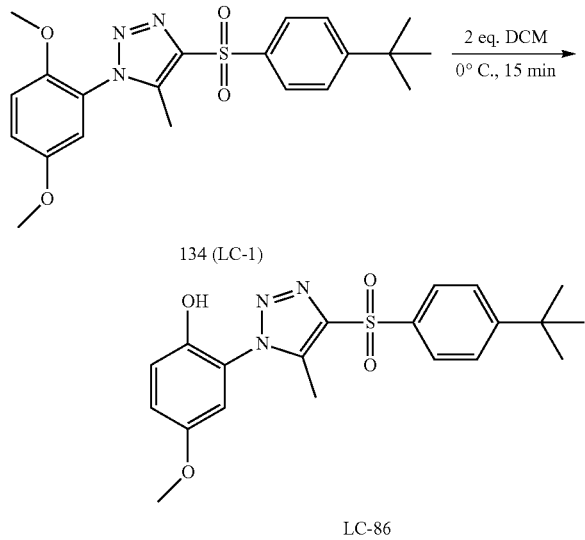

BBr$_3$ (225 mg, 0.9 mmol) was added to a solution of compound 134 (150 mg, 0.36 mmol) in anhydrous DCM (3 mL) at 0° C. and the reaction was then stirred at this temperature for 15 minutes. The reaction mixture was quenched with saturated NaHCO$_3$ aqueous solution (10 mL) and extracted with DCM (20 mL×3). The combined organic layer was washed with brine, dried with anhydrous Na$_2$SO$_4$ and concentrated with a Rotavapor. The residue was purified by preparative HPLC to give compound LC-86 (85 mg, 58.6% yield). $^1$H NMR (DMSO-d$_6$, 400 MHz): δ (ppm) 8.01 (d, J=8.4 Hz, 2H), 7.57 (d, J=8.4 Hz, 2H), 7.05 (d, J=8.0 Hz, 1H), 6.98 (dd, J=8.0 Hz, 3.2 Hz, 1H), 6.76 (d, J=3.2 Hz, 1H), 6.75 (brs, 1H), 3.75 (s, 3H), 2.55 (s, 3H), 1.32 (s, 9H). m/z 402.1 (M+H)$^+$.

ff. Synthesis of 3-(4-((4-(tert-butyl)phenyl)sulfonyl)-5-methyl-1H-1,2,3-triazol-1-yl)-4-methoxyphenol (LC-87)

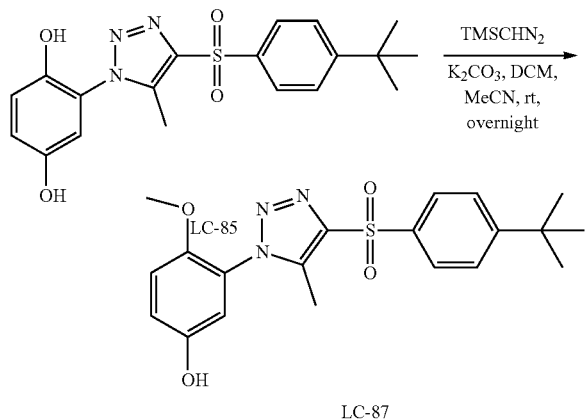

(Trimethylsilyl)diazomethane (1.5 mL, 2M/L in hexane) was added to a solution of compound LC-85 (150 mg, 0.39 mmol), potassium carbonate (200 mg, 1.45 mmol) in DCM (5 mL) and acetonitrile (5 mL) at room temperature. The reaction was stirred at this temperature overnight. The reaction was quenched with H$_2$O (20 mL) and extracted with EtOAc (30 mL×3). The combined organic layer was washed with brine, dried with anhydrous Na$_2$SO$_4$ and concentrated with a Rotavapor. The residue was purified by preparative HPLC to give compound LC-87 (35 mg, 24% yield). $^1$H NMR (DMSO-d$_6$, 400 MHz): δ (ppm) 9.56 (brs, 1H), 8.12 (d, J=8.4 Hz, 2H), 7.75 (d, J=8.4 Hz, 2H), 7.27 (d, J=8.8 Hz, 1H), 7.15 (d, J=8.4 Hz, 1H), 7.02 (s, 1H), 3.67 (s, 3H), 2.35 (s, 3H), 1.32 (s, 9H). m/z 402.1 (M+H)$^+$.

3. Biology Experimentals a. Materials and Methods

PXR binding assay kits, GeneBLAzer panel nuclear receptor cells, DMEM, phenol red-free DMEM, non-essential amino acids, sodium pyruvate, HEPES, hygromycin B, zeocin, penicillin and streptomycin were purchased from Invitrogen (Carlsbad, Calif.) (now ThermoFisher). Tissue culture flasks, 384-well low volume solid black plates, tissue culture-treated 384-well black clear bottom plates and tissue culture-treated poly-D-lysine-coated 384-well black clear bottom plates were purchased from Corning Life Sciences (Tewksbury Mass.). Tissue culture-treated 384-well white solid bottom plates and Steadylite HTS reagent were purchased from PerkinElmer Life Sciences (Hopkinton, Mass.). CellTiter Glo luminescent cell viability assay reagent was obtained from Promega (Madison, Wis.). FBS and charcoal/dextran-treated FBS were purchased from Hyclone (Logan, Utah). HepG2 cells were obtained from ATCC (Manassas, Va.). FuGENE 6 was purchased from Roche (Indianapolis, Ind.). DMSO, SR12813, rifampicin, 1α, 25-dihydroxyvitamin D3, dexamethasone, mifepristone, 9-cis-retinoic acid, GW4604, T0901317 and GW9662 were purchased from Sigma (St. Louis, Mo.). Staurosporine was purchased from LC Labs (Woburn, Mass.). Matrical Gel was purchased from BD (Franklin Lakes, N.J.).

b. PXR Binding Assay

The time-resolved fluorescence resonance transfer (TR-FRET) hPXR competitive binding assay was performed according to the manufacturer's instructions (Invitrogen) with minor modifications. Briefly, the binding assays were performed in 384-well low volume (20 μl per well) solid black plates with 5 nM GST-hPXR ligand-binding domain, 40 nM fluorescent-labeled hPXR ligand (Fluormore PXR Green, also referred to as a "tracer"), 5 nM terbium-labeled anti-GST antibody, and test compound at a variety of concentrations. DMSO (0.4%) was used as the negative control (0% inhibition) and a potent hPXR agonist, SR-12813 at 10 μM (with 0.4% DMSO) was used as the positive control (100% inhibition). The activities of individual chemicals tested at various concentrations (1-to-2 series dilutions for 16 concentration levels from 40 μM with 0.4% final DMSO concentration) were normalized to positive and negative controls to generate % Inhibition (PMID: 18784074).

In the reaction mixture, GST-hPXR forms a complex with the terbium-labeled anti-GST antibody and the tracer. Excitation of terbium (the donor) using a 340-nm excitation filter results in energy transfer to the fluorophore of the tracer. This energy transfer is detected by an increase in the fluorescence emission of the tracer at 520 nm and a decrease in the fluorescence emission of terbium at 495 nm. The FRET ratio was calculated by dividing the emission signal at 520 nm by the emission signal at 495 nm. A competitor compound such as SR-12813 replaces the tracer from the complex and decreases the FRET ratio accordingly. The reactions were incubated at 25° C. for 30 min before measuring the fluorescent emission of each well at 495 and 520 nm using a 340-nm excitation filter, 100-μs delay time, and 200-μs integration time, with a PHERAStar plate reader (BMG Labtech, Durham, N.C.). The curve-fitting software GraphPad Prism 4.0 (Graphpad Software, La Jolla, Calif.) was used to generate the dose response curves and determine the $IC_{50}$ values for individually tested compounds if applicable. SR-12813 has an $IC_{50}$ of 65 nM in this assay.

c. hPXR Tranxactivation Assays

The hPXR transactivation assays (PXR agonistic and antagonistic assays) were performed in the HepG2 cells stably expressing FLAG-hPXR and CYP3A4-luciferase reporter. Briefly, various concentrations (1-to-3 series dilutions for 10 concentration levels from 40 μM with 0.5% final DMSO concentration) of hPXR agonist rifampicin, various concentrations of tested chemicals alone or combined with 5 μM of rifampicin, were added to the wells of white 384-well tissue culture-treated plates with 5,000 cells in 25 μl of phenol red-free DMEM supplemented with 5% charcoal/dextran-treated FBS and incubated for 24 h at 37° C. before luciferase assay using Steadylite HTS (PerkinElmer Life Sciences). The luminescence signal was detected using an Envision plate reader (PerkinElmer Life Sciences). In the agonistic assays, DMSO (0.5% final concentration) was used as the negative control (0% activation) and rifampicin (10 μM in 0.5% DMSO) was used as the positive control (100% activation). In the antagonistic assays, rifampicin (5 μM with 0.5% final DMSO concentration) was used as the negative control (0% inhibition) and DMSO (0.5%) was used as the positive control (100% inhibition). The activities of individual chemicals tested at various concentrations were normalized to the corresponding positive and negative controls to generate % Activation in agonistic assays and % Inhibition in antagonistic assays. The curve-fitting software GraphPad Prism 4.0 (Graphpad Software, La Jolla, Calif.) was used to generate the dose response curves and determine the $IC_{50}$ (for hPXR antagonists) or $EC_{50}$ (for hPXR agonists) values for individually tested compounds if applicable. Rifampicin has an $IC_{50}$ of 1.18 μM in this assay.

d. HepG2 Cytotoxicity Assays

In the HepG2 cytotoxicity assays, various concentrations (1-to-3 series dilutions for 10 concentration levels from 40 μM in 0.5% final DMSO concentration) of testing compounds, staurosporine (1-to-3 series dilutions for 16 concentration levels from 56 μM with 0.5% final DMSO concentration, or 56 μM with 0.5% final DMSO concentration) or DMSO (0.5%) were added to the wells of white 384-well tissue culture-treated plates with 2,500 cells in 25 μl of phenol red-free DMEM supplemented with 10% FBS and incubated for 72 h at 37° C. before performing the cytotoxic assay with CellTiter Glo luminescent cell viability assay (Promega, Madison, Wis.). The luminescence signal was detected using an Envision plate reader (PerkinElmer Life Sciences). In the cytotoxic assay, DMSO (0.5%) was used as the negative control (0% Inhibition) and staurosporine (56 μM with 0.5% DMSO) was used as the positive control (100% Inhibition). The activities of individual chemicals tested at various concentrations were normalized to the positive and negative controls to generate % Inhibition. The curve-fitting software GraphPad Prism 4.0 (Graphpad Software, La Jolla, Calif.) was used to generate the dose response curves and determine the $IC_{50}$ values for individually tested compounds if applicable. Staurosporine has an $IC_{50}$ of 96 nM in this assay.

e. hCAR Transactivation Assays

In the hCAR transactivation assays, 5 million HepG2 cells were seeded into a T25 flask 24 h before transiently transfected with a plasmid:FuGENE 6 mixture (0.75 μg of pcDNA3-FLAG-hCAR, 2.25 μg of CYP2B6-2.2 kb, and 0.3 μg of pRL-TK). 24 h post-transfection, 5,000 cells in 25 μl of phenol red-free DMEM supplemented with 5% charcoal/dextran-treated FBS were seeded into each well of 384-well white culture plates and treated with compounds for another 24 h prior to Dual-Glo luciferase assay, using an Envision plate reader. Relative luciferase activity was determined by normalizing the firefly luciferase signal with the Renilla luciferase signal, and used to represent the "Relative activity of CAR". The curve-fitting software GraphPad Prism 4.0 (Graphpad Software, La Jolla, Calif.) was used to generate the dose response curves and determine the $IC_{50}$ values for tested compounds if applicable.

f. Human Vitamin D Receptor (hVDR) Transactivation Assays

Human vitamin D receptor (hVDR) transactivation assays were performed using VDR-UAS-bla HEK 293T cells (VDR cells, Invitrogen, Carlsbad, Calif.). Cells were maintained by following manufacturer's instruction. Briefly, VDR cells were maintained in matrigel-coated tissue culture flasks in DMEM supplemented with 10% dialyzed FBS, 0.1 mM non-essential amino acids, 1 mM sodium pyruvate, 25 mM HEPES, 80 μg/ml of hygromycin B, 80 μg/ml of zeocin, 100 units/ml penicillin and 100 μg/ml streptomycin. For VDR transactivation assay, various concentrations of VDR agonist 1α, 25-dihydroxyvitamin D3, various concentrations of testing compounds alone or combined with 2 nM of 1α, 25-dihydroxyvitamin D3, was added to the wells of black 384-well tissue culture-treated clear bottom plates with VDR cells (20,000 cells/well) in 30 μl of assay medium (phenol red-free DMEM supplemented with 2% charcoal/dextran-treated FBS, 0.1 mM non-essential amino acids, 1 mM sodium pyruvate, 100 units/ml penicillin and 100 μg/ml streptomycin). Assay medium containing DMSO without cells serves as background control. 24 h later, 6 μl/well of loading solution was added, followed by 90 minutes of incubation at room temperature in the dark before measuring the fluorescent emission at 460 and 535 nm (using excitation at 400 nm) with an Envision plate reader by using the bottom read mode. After subtraction of background, emission signal at 460 and 535 nm was used to determine the ratio of 460 nm/535 nm, and used to represent the activity of the "Relative activity of VDR". In the agonistic VDR assay, 100 nM 1α, 25-dihydroxyvitamin D3 and DMSO were used as positive (100% activation) and negative (0% activation) controls, respectively. In the antagonistic VDR assay, 2 nM 1α, 25-dihydroxyvitamin D3 and DMSO were used as corresponding negative (0% inhibition) and positive (100% inhibition) controls. The activities of individual chemicals tested at various concentrations were normalized to the corresponding positive and negative controls to generate % Activation in agonistic assays and % Inhibition in antagonistic assays. The curve-fitting software GraphPad Prism 4.0 (Graphpad Software, La Jolla, Calif.) was used to generate the dose response curves and determine the $EC_{50}$ (for agonists) or $IC_{50}$ (for antagonists) values for individually tested compounds if applicable. In the VDR assay, 1a, 25-dihydroxyvitamin D3 had an $EC_{50}$ of 0.4 nM.

g. Human Glucocorticoid Receptor (hGR) Transactivation Assays

Human glucocorticoid receptor (hGR) transactivation assays were performed using GR-UAS-bla HEK 293T cells (hGR cells, Invitrogen, Carlsbad, Calif.). Cells were maintained by following manufacturer's instruction. Briefly, hGR cells were maintained in matrigel-coated tissue culture flasks in DMEM supplemented with 10% dialyzed FBS, 0.1 mM non-essential amino acids, 25 mM HEPES, 150 µg/ml of hygromycin B, 80 µg/ml of zeocin, 100 units/ml penicillin and 100 µg/ml streptomycin. For GR transactivation assay, various concentrations of GR agonist dexamethasone, GR antagonist mifepristone, various concentrations of testing compounds alone or combined with 5 nM of dexamethasone, was added to the wells of black 384-well tissue culture-treated clear bottom plates with GR cells (20,000 cells/well) in 30 µl of assay medium (phenol red-free DMEM supplemented with 2% charcoal/dextran-treated FBS, 0.1 mM non-essential amino acids, 1 mM sodium pyruvate, 25 mM HEPES (pH 7.3), 100 units/ml penicillin and 100 µg/ml streptomycin). Assay medium containing DMSO without cells serves as background control. 24 h later, 6 µl/well of loading solution was added, followed by 120 minutes of incubation at room temperature in the dark before measuring the fluorescent emission at 460 and 535 nm (using excitation at 400 nm) with an Envision plate reader by using the bottom read mode. After subtraction of background, emission signal at 460 and 535 nm was used to determine the ratio of 460 nm/535 nm, and used to represent the activity of the "Relative activity of GR". In the agonistic GR assay, 100 nM dexamethasone and DMSO were served as positive (100% activation) and negative (0% activation) controls, respectively. In the antagonistic GR assay, 5 nM dexamethasone and 5 nM dexamethasone along with 100 nM mifepristone were used as corresponding negative (0% inhibition) and positive (100% inhibition) controls. The activities of individual chemicals tested at various concentrations were normalized to the corresponding positive and negative controls to generate % Activation in agonistic assays and % Inhibition in antagonistic assays. The curve-fitting software GraphPad Prism 4.0 (Graphpad Software, La Jolla, Calif.) was used to generate the dose response curves and determine the $EC_{50}$ (for agonists) or $IC_{50}$ (for antagonists) values for individually tested compounds if applicable. In the GR agonistic assay, dexamethasone had an $EC_{50}$ of 2.2 nM. In the GR antagonistic assay, mifepristone had an $IC_{50}$ of 6.8 nM.

h. Human Retinoid X Receptor Alpha (hRXRa) Transactivation Assays

Human retinoid X receptor alpha (hRXRα) transactivation assays were performed using RXR alpha-UAS-bla HEK 293T cells (RXRα cells, Invitrogen, Carlsbad, Calif.). Cells were maintained by following manufacturer's instruction. Briefly, RXRα cells were maintained in DMEM supplemented with 10% dialyzed FBS, 0.1 mM non-essential amino acids, 25 mM HEPES, 100 µg/ml of hygromycin B, 100 µg/ml of zeocin, 100 units/ml penicillin and 100 µg/ml streptomycin. For RXRα transactivation assay, various concentrations of RXRα agonist 9-cis-retinoic acid, various concentrations of testing compounds alone or combined with 100 nM of 9-cis-retinoic acid, was added to the wells of black 384-well tissue culture-treated clear bottom plates with RXRα cells (20,000 cells/well) in 30 µl of assay medium (phenol red-free DMEM supplemented with 2% charcoal/dextran-treated FBS, 0.1 mM non-essential amino acids, 1 mM sodium pyruvate, 100 units/ml penicillin and 100 µg/ml streptomycin). Assay medium containing DMSO without cells serves as background control. 24 h later, 6 µl/well of loading solution was added, followed by 75 minutes of incubation at room temperature in the dark before measuring the fluorescent emission at 460 and 535 nm (using excitation at 400 nm) with an Envision plate reader by using the bottom read mode. After subtraction of background, emission signal at 460 and 535 nm was used to determine the ratio of 460 nm/535 nm, and used to represent the activity of the "Relative activity of RXRα". In the agonistic RXRα assay, 10 µM 9-cis-retinoic acid and DMSO were used as positive (100% activation) and negative (0% activation) controls, respectively. In the antagonistic RXRα assay, 100 nM 9-cis-retinoic acid and DMSO were used as corresponding negative (0% inhibition) and positive (100% inhibition) controls. The activities of individual chemicals tested at various concentrations were normalized to the corresponding positive and negative controls to generate % Activation in agonistic assays and % Inhibition in antagonistic assays. The curve-fitting software GraphPad Prism 4.0 (Graphpad Software, La Jolla, Calif.) was used to generate the dose response curves and determine the $EC_{50}$ (for agonists) or $IC_{50}$ (for antagonists) values for individually tested compounds if applicable. In the RXRα assay, 9-cis-retinoic acid had an $EC_{50}$ of 13.3 nM.

i. Human Retinoid X Receptor Beta (hRXTb) Transactivation Assays

Human retinoid X receptor beta (hRXRβ) transactivation assays were performed using RXR beta-UAS-bla HEK 293T cells (RXRβ cells, Invitrogen, Carlsbad, Calif.). Cells were maintained by following manufacturer's instruction. Briefly, RXRβ cells were maintained in DMEM supplemented with 10% dialyzed FBS, 0.1 mM non-essential amino acids, 25 mM HEPES, 100 µg/ml of hygromycin B, 100 µg/ml of zeocin, 100 units/ml penicillin and 100 µg/ml streptomycin. For RXRβ transactivation assay, various concentrations of RXRβ agonist 9-cis-retinoic acid, various concentrations of testing compounds alone or combined with 100 nM of 9-cis-retinoic acid, was added to the wells of black 384-well tissue culture-treated clear bottom plates with RXRβ cells (25,000 cells/well) in 30 µl of assay medium (phenol red-free DMEM supplemented with 2% charcoal/dextran-treated FBS, 0.1 mM non-essential amino acids, 1 mM sodium pyruvate, 100 units/ml penicillin and 100 µg/ml streptomycin). Assay medium containing DMSO without cells serves as background control. 24 h later, 6 µl/well of loading solution was added, followed by 90 minutes of incubation at room temperature in the dark before measuring the fluorescent emission at 460 and 535 nm (using excitation at 400 nm) with an Envision plate reader by using the bottom read mode. After subtraction of background, emission signal at 460 and 535 nm was used to determine the ratio of 460 nm/535 nm, and used to represent the activity of the "Relative activity of RXRβ". In the agonistic RXRβ assay, 10 µM 9-cis-retinoic acid and DMSO were used as positive (100% activation) and negative (0% activation) controls, respectively. In the antagonistic RXRβ assay, 100 nM 9-cis-retinoic acid and DMSO were used as corresponding negative (0% inhibition) and positive (100% inhibition) controls. The activities of individual chemicals tested at various concentrations were normalized to the corresponding positive and negative controls to generate % Activation in agonistic assays and % Inhibition in antagonistic assays. The curve-fitting software GraphPad Prism 4.0 (Graphpad Software, La Jolla, Calif.) was used to generate the dose response curves and determine the $EC_{50}$ (for agonists) or $IC_{50}$ (for antagonists) values for individually tested compounds if applicable. In the RXRα assay, 9-cis-retinoic acid had an $EC_{50}$ of 7.6 nM.

j. Human Farnesoid X Receptor (hFXR) Transactivation Assays

Human Farnesoid X receptor (hFXR) transactivation assays were performed using FXR-UAS-bla HEK 293T cells (FXR cells, Invitrogen, Carlsbad, Calif.). Cells were maintained by following manufacturer's instruction. Briefly, FXR cells were maintained in DMEM supplemented with 10% dialyzed FBS, 0.1 mM non-essential amino acids, 25 mM HEPES, 100 µg/ml of hygromycin B, 100 µg/ml of zeocin, 100 units/ml penicillin and 100 µg/ml streptomycin. For FXR transactivation assay, various concentrations of FXR agonist GW4604, various concentrations of testing compounds alone or combined with 200 nM of GW4604, was added to the wells of black 384-well tissue culture-treated clear bottom plates with FXR cells (22,500 cells/well) in 30 µl of assay medium (phenol red-free DMEM supplemented with 2% charcoal/dextran-treated FBS, 0.1 mM non-essential amino acids, 1 mM sodium pyruvate, 100 units/ml penicillin and 100 µg/ml streptomycin). Assay medium containing DMSO without cells serves as background control. 24 h later, 6 µl/well of loading solution was added, followed by 90 minutes of incubation at room temperature in the dark before measuring the fluorescent emission at 460 and 535 nm (using excitation at 400 nm) with an Envision plate reader by using the bottom read mode. After subtraction of background, emission signal at 460 and 535 nm was used to determine the ratio of 460 nm/535 nm, and used to represent the activity of the "Relative activity of FXR". In the agonistic FXR assay, 10 µM GW4604 and DMSO were used as positive (100% activation) and negative (0% activation) controls, respectively. In the antagonistic FXR assay, 200 nM GW4604 and DMSO were used as corresponding negative (0% inhibition) and positive (100% inhibition) controls. The activities of individual chemicals tested at various concentrations were normalized to the corresponding positive and negative controls to generate % Activation in agonistic assays and % Inhibition in antagonistic assays. The curve-fitting software GraphPad Prism 4.0 (Graphpad Software, La Jolla, Calif.) was used to generate the dose response curves and determine the $EC_{50}$ (for agonists) or $IC_{50}$ (for antagonists) values for individually tested compounds if applicable. In the FXR assay, GW4604 had an $EC_{50}$ of 77.1 nM.

k. Human Liver X Receptor Alpha (hLXRa) Transactivation Assays

Human Liver X receptor alpha (hLXRα) transactivation assays were performed using LXR alpha-UAS-bla HEK 293T cells (LXRα cells, Invitrogen, Carlsbad, Calif.). Cells were maintained by following manufacturer's instruction. Briefly, LXRα cells were maintained in DMEM supplemented with 10% dialyzed FBS, 0.1 mM non-essential amino acids, 25 mM HEPES, 80 µg/ml of hygromycin B, 80 µg/ml of zeocin, 100 units/ml penicillin and 100 µg/ml streptomycin. For LXRα transactivation assay, various concentrations of LXRα agonist T0901317, various concentrations of testing compounds alone or combined with 300 nM of T0901317, was added to the wells of poly-D-lysine coated black 384-well tissue culture-treated clear bottom plates with LXRα cells (20,000 cells/well) in 30 µl of assay medium (phenol red-free DMEM supplemented with 2% charcoal/dextran-treated FBS, 0.1 mM non-essential amino acids, 1 mM sodium pyruvate, 100 units/ml penicillin and 100 µg/ml streptomycin). Assay medium containing DMSO without cells serves as background control. 24 h later, 6 µl/well of loading solution was added, followed by 90 minutes of incubation at room temperature in the dark before measuring the fluorescent emission at 460 and 535 nm (using excitation at 400 nm) with an Envision plate reader by using the bottom read mode. After subtraction of background, emission signal at 460 nm/535 nm was used to determine the ratio of 460 nm/535 nm, and used to represent the activity of the "Relative activity of LXR". In the agonistic LXRα assay, 2 µM T0901317 and DMSO were used as positive (100% activation) and negative (0% activation) controls, respectively. In the antagonistic LXRα assay, 300 nM T0901317 and DMSO were served as corresponding negative (0% inhibition) and positive (100% inhibition) controls. The activities of individual chemicals tested at various concentrations were normalized to the corresponding positive and negative controls to generate % Activation in agonistic assays and % Inhibition in antagonistic assays. The curve-fitting software GraphPad Prism 4.0 (Graphpad Software, La Jolla, Calif.) was used to generate the dose response curves and determine the $EC_{50}$ (for agonists) or $IC_{50}$ (for antagonists) values for individually tested compounds if applicable. In the LXRα assay, T0901317 had an $EC_{50}$ of 21.3 nM.

l. Human Liver X Receptor Beta (hLXRb) Transactivation Assays

Human Liver X receptor beta (hLXRβ) transactivation assays were performed using LXR beta-UAS-bla HEK 293T cells (LXRβ cells, Invitrogen, Carlsbad, Calif.). Cells were maintained by following manufacturer's instruction. Briefly, LXRβ cells were maintained in matrigel-coated tissue culture flasks in DMEM supplemented with 10% dialyzed FBS, 0.1 mM non-essential amino acids, 1 mM sodium pyruvate, 25 mM HEPES, 80 µg/ml of hygromycin B, 15 µg/ml of blasticidin, 100 units/ml penicillin and 100 µg/ml streptomycin. For LXRβ transactivation assay, various concentrations of LXRβ agonist T0901317, various concentrations of testing compounds alone or combined with 3 µM of T0901317, was added to the wells of poly-D-lysine coated black 384-well tissue culture-treated clear bottom plates with LXRβ cells (20,000 cells/well) in 30 µl of assay medium (phenol red-free DMEM supplemented with 2% charcoal/dextran-treated FBS, 0.1 mM non-essential amino acids, 1 mM sodium pyruvate, 100 units/ml penicillin and 100 µg/ml streptomycin). Assay medium containing DMSO without cells serves as background control. 24 h later, 6 µl/well of loading solution was added, followed by 90 minutes of incubation at room temperature in the dark before measuring the fluorescent emission at 460 and 535 nm (using excitation at 400 nm) with an Envision plate reader by using the bottom read mode. After subtraction of background, emission signal at 460 and 535 nm was used to determine the ratio of 460 nm/535 nm, and used to represent the activity of the "Relative activity of LXRβ". In the agonistic LXRβ assay, 20 µM T0901317 and DMSO were used as positive (100% activation) and negative (0% activation) controls, respectively. In the antagonistic LXRβ assay, 3 µM T0901317 and DMSO were used as corresponding negative (0% inhibition) and positive (100% inhibition) controls. The activities of individual chemicals tested at various concentrations were normalized to the corresponding positive and negative controls to generate % Activation in agonistic assays and % Inhibition in antagonistic assays. The curve-fitting software GraphPad Prism 4.0 (Graphpad Software, La Jolla, Calif.) was used to generate the dose response curves and determine the $EC_{50}$ (for agonists) or $IC_{50}$ (for antagonists) values for individually tested compounds if applicable. In the LXRβ assay, T0901317 had an $EC_{50}$ of 50.4 nM.

m. Human Peroxisome Proliferator-Activated Receptor Gamma (PPARΓ) Transactivation Assays Human peroxisome proliferator-activated receptor gamma (PPARγ) transactivation assays were performed using PPAR gamma-UAS-bla 293H cells (PPARγ cells, Invitrogen, Carlsbad, Calif.). Cells were maintained by following manufacturer's instruction. Briefly, PPARγ cells were maintained in matrigel-coated tissue culture flasks in DMEM supplemented with 10% dialyzed FBS, 0.1 mM non-essential amino acids, 1 mM sodium pyruvate, 25 mM HEPES, 100 µg/ml of hygromycin B, 500 µg/ml of geneticin, 100 units/ml penicillin and 100 µg/ml streptomycin. For PPARγ transactivation assay, various concentrations of PPARγ agonist rosiglitazone, antagonist GW9662, various concentrations of testing compounds alone or combined with 100 nM of rosiglitazone, was added to the wells of poly-D-lysine coated black 384-well tissue culture-treated clear bottom plates with PPARγ cells (25,000 cells/well) in 30 µl of assay medium (phenol red-free DMEM supplemented with 2% charcoal/dextran-treated FBS, 0.1 mM non-essential amino acids, 1 mM sodium pyruvate, 100 units/ml penicillin and 100 µg/ml streptomycin). Assay medium containing DMSO without cells serves as background control. 24 h later, 6 µl/well of loading solution was added, followed by 120 minutes of incubation at room temperature in the dark before measuring the fluorescent emission at 460 and 535 nm (using excitation at 400 nm) with an Envision plate reader by using the bottom read mode. After subtraction of background, emission signal at 460 and 535 nm was used to determine the ratio of 460 nm/535 nm, and used to represent the activity of the "Relative activity of PPARγ". In the agonistic PPARγ assay, 2.5 µM rosiglitazone and DMSO were used as positive (100% activation) and negative (0% activation) controls, respectively. In the antagonistic PPARγ assay, 100 nM rosiglitazone and 1 µM GW9662 along with 100 nM rosiglitazone were used as corresponding negative (0% inhibition) and positive (100% inhibition) controls. The activities of individual chemicals tested at various concentrations were normalized to the corresponding positive and negative controls to generate % Activation in agonistic assays and % Inhibition in antagonistic assays. The curve-fitting software GraphPad Prism 4.0 (Graphpad Software, La Jolla, Calif.) was used to generate the dose response curves and determine the $EC_{50}$ (for agonists) or $IC_{50}$ (for antagonists) values for individually tested compounds if applicable. In the PPARγ agonistic assay, rosiglitazone had an $EC_{50}$ of 5.0 nM. In the PPARγ antagonistic assay, GW9662 had an $IC_{50}$ of 240.8 nM.

4. Biological Characterization of Exemplary Compounds

The compounds in Table 1 below were synthesized and the indicated assays were carried out as described herein. The assays in Table 2 refer to the compound numbers used in Table 1, and the assays were carried out as described herein.

TABLE 1

| No. | Structure | $IC_{50}$ (binding)* | $IC_{50}$ (antag)* | $EC_{50}$ (agon)* | $IC_{50}$ (cyto)* |
|---|---|---|---|---|---|
| LC-1 | 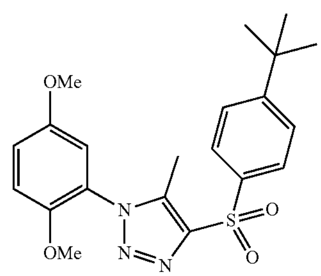 | 0.41 µM | 0.51 µM | NA** | NA |
| LC-2 | 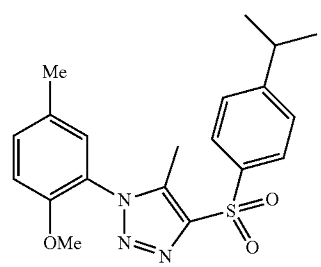 [SMILES: COc1ccc(C)cc1-n1nnc(S(=O)(=O)c2ccc(C(C)C)cc2)c1C] | 0.99 µM | 0.66 µM | NA | NA |
| LC-3 | 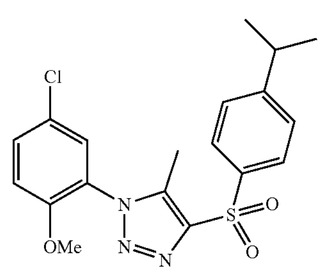 [SMILES: COc1ccc(Cl)cc1-n1nnc(S(=O)(=O)c2ccc(C(C)C)cc2)c1C] | 0.77 µM | 0.52 µM | NA | NA |

TABLE 1-continued

| No. | Structure | IC$_{50}$ (binding)* | IC$_{50}$ (antag)* | EC$_{50}$ (agon)* | IC$_{50}$ (cyto)* |
|---|---|---|---|---|---|
| LC-4 | 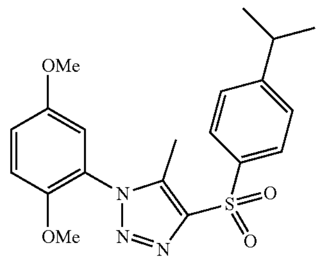 [SMILES: COc1ccc(OC)c(-n2nnc(S(=O)(=O)c3ccc(C(C)C)cc3)c2C)c1] | 1.18 μM | 0.63 μM | NA | NA |
| LC-5 | 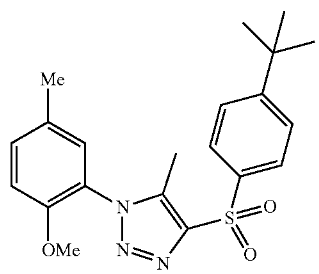 [SMILES: COc1ccc(C)cc1-n1nnc(S(=O)(=O)c2ccc(C(C)(C)C)cc2)c1C] | 0.64 μM | 0.08 μM | NA | NA |
| LC-6 | 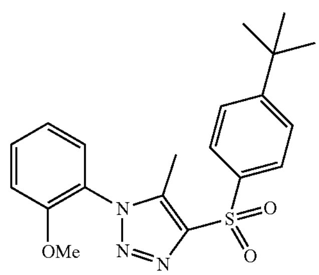 [SMILES: COc1ccccc1-n1nnc(S(=O)(=O)c2ccc(C(C)(C)C)cc2)c1C] | 1.05 μM | 0.39 μM | NA | NA |
| LC-7 | 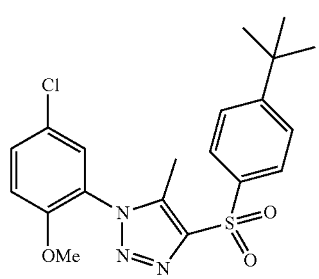 [SMILES: COc1ccc(Cl)cc1-n1nnc(S(=O)(=O)c2ccc(C(C)(C)C)cc2)c1C] | 0.38 μM | 0.13 μM | NA | NA |
| LC-8 | 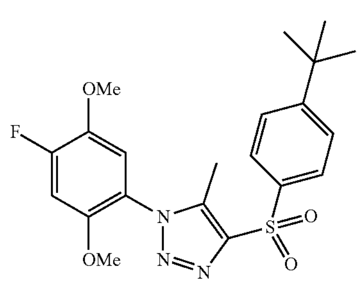 [SMILES: COc1cc(-n2nnc(S(=O)(=O)c3ccc(C(C)(C)C)cc3)c2C)c(OC)cc1F] | 0.01 μM | 1.52 μM | NA | NA |

TABLE 1-continued

| No. | Structure | IC$_{50}$ (binding)* | IC$_{50}$ (antag)* | EC$_{50}$ (agon)* | IC$_{50}$ (cyto)* |
|---|---|---|---|---|---|
| LC-9 | 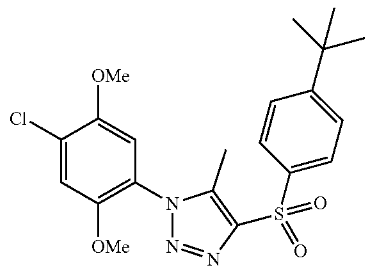 [SMILES: COc1cc(-n2nnc(S(=O)(=O)c3ccc(C(C)(C)C)cc3)c2C)c(OC)cc1Cl] | 0.39 μM | NA | 0.84 μM | NA |
| LC-10 | 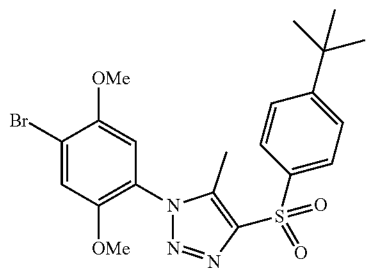 [SMILES: CCc1cc(OC)c(-n2nnc(S(=O)(=O)c3ccc(C(C)(C)C)cc3)c2C)cc1OC] | 0.08 μM | NA | 0.75 μM | NA |
| LC-11 | 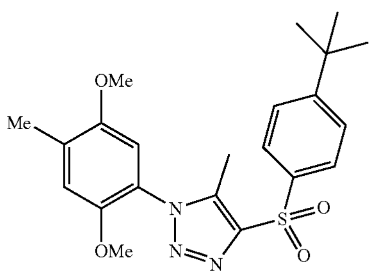 | 0.11 μM | NA | 0.88 μM | NA |
| LC-12 | 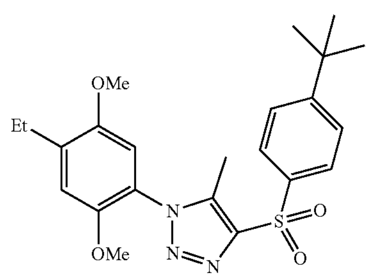 | 0.10 μM | NA | 0.78 μM | NA |
| LC-13 | 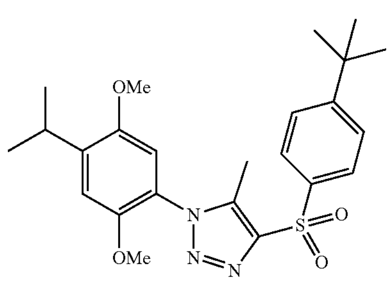 [SMILES: COc1cc(-n2nnc(S(=O)(=O)c3ccc(C(C)(C)C)cc3)c2C)c(OC)cc1C(C)C] | 0.07 μM | NA | 0.84 μM | NA |

TABLE 1-continued

| No. | Structure | IC$_{50}$ (binding)* | IC$_{50}$ (antag)* | EC$_{50}$ (agon)* | IC$_{50}$ (cyto)* |
|---|---|---|---|---|---|
| LC-14 | 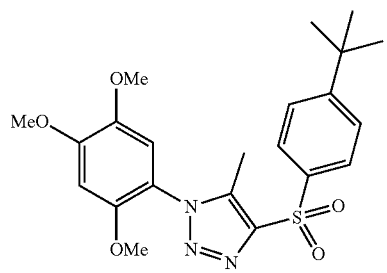 [SMILES: COc1cc(OC)c(-n2nnc(S(=O)(=O)c3ccc(C(C)(C)C)cc3)c2C)cc1OC] | 0.10 μM | NA | 7.2 μM | NA |
| LC-15 | 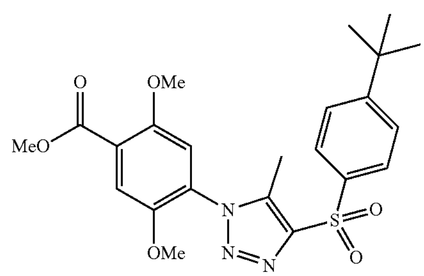 [SMILES: COC(=O)c1cc(OC)c(-n2nnc(S(=O)(=O)c3ccc(C(C)(C)C)cc3)c2C)cc1OC] | 10.9 μM | NA | 3.8 μM | NA |
| LC-16 | 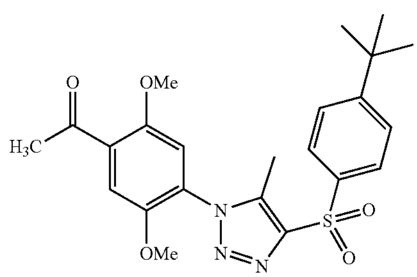 [SMILES: COc1cc(-n2nnc(S(=O)(=O)c3ccc(C(C)(C)C)cc3)c2C)c(OC)cc1C(C)=O] | 0.38 μM | NA | 1.2 μM | NA |
| LC-17 | 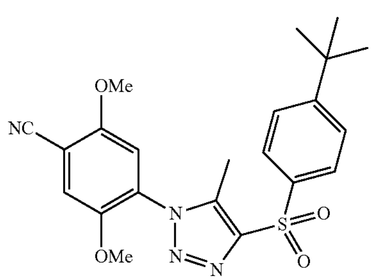 [SMILES: COc1cc(-n2nnc(S(=O)(=O)c3ccc(C(C)(C)C)cc3)c2C)c(OC)cc1C#N] | 0.03 μM | NA | 1.3 μM | NA |
| LC-18 | 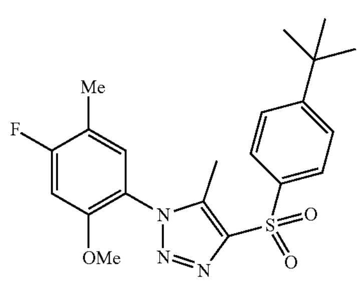 [SMILES: COc1cc(F)c(C)cc1-n1nnc(S(=O)(=O)c2ccc(C(C)(C)C)cc2)c1C] | 0.03 μM | 0.64 μM | NA | NA |

TABLE 1-continued

| No. | Structure | IC$_{50}$ (binding)* | IC$_{50}$ (antag)* | EC$_{50}$ (agon)* | IC$_{50}$ (cyto)* |
|---|---|---|---|---|---|
| LC-19 | 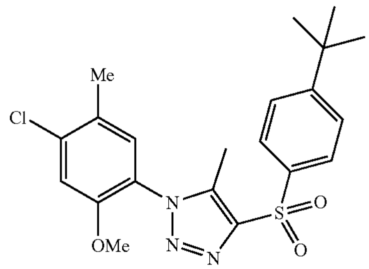 [SMILES: COc1cc(Cl)c(C)cc1-n1nnc(S(=O)(=O)c2ccc(C(C)(C)C)cc2)c1C] | 0.12 μM | 1.8 μM | NA | NA |
| LC-20 | 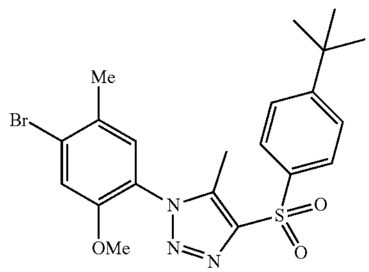 | 0.01 μM | NA | 0.91 μM | NA |
| LC-21 | 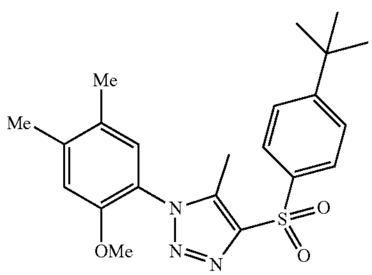 | 0.15 μM | 0.99 μM | NA | NA |
| LC-22 | 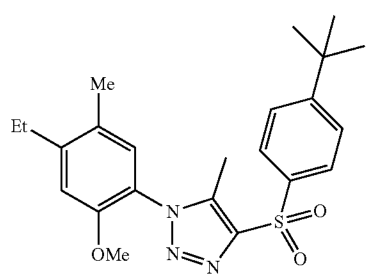 | 0.24 μM | NA | 0.75 μM | NA |
| LC-23 | 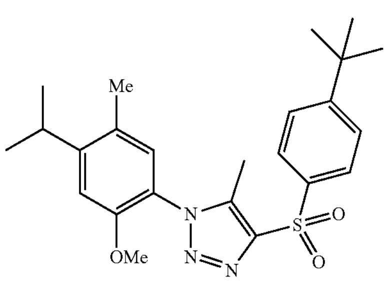 [SMILES: COc1cc(C(C)C)c(C)cc1-n1nnc(S(=O)(=O)c2ccc(C(C)(C)C)cc2)c1C] | 0.10 μM | NA | 0.73 μM | NA |

TABLE 1-continued

| No. | Structure | IC$_{50}$ (binding)* | IC$_{50}$ (antag)* | EC$_{50}$ (agon)* | IC$_{50}$ (cyto)* |
|---|---|---|---|---|---|
| LC-24 | 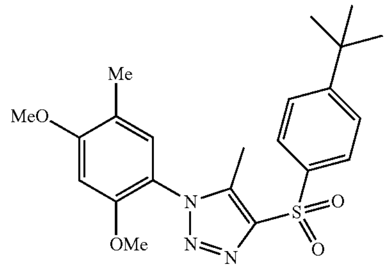 [SMILES: COc1cc(OC)c(-n2nnc(S(=O)(=O)c3ccc(C(C)(C)C)cc3)c2C)cc1C] | 0.34 μM | NA | 0.88 μM | NA |
| LC-25 | 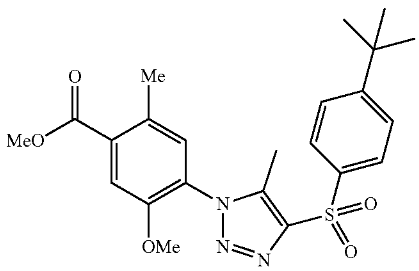 [SMILES: COC(=O)c1cc(OC)c(-n2nnc(S(=O)(=O)c3ccc(C(C)(C)C)cc3)c2C)cc1C] | 0.10 μM | NA | 1.7 μM | NA |
| LC-26 | 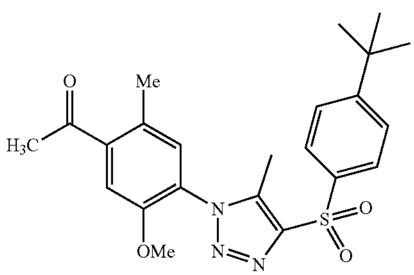 [SMILES: COc1cc(C(C)=O)c(C)cc1-n1nnc(S(=O)(=O)c2ccc(C(C)(C)C)cc2)c1C] | 0.07 μM | NA | 0.16 μM | 3.4 μM |
| LC-27 | 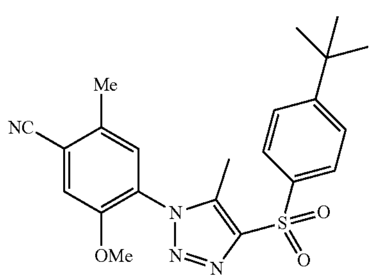 [SMILES: COc1cc(C#N)c(C)cc1-n1nnc(S(=O)(=O)c2ccc(C(C)(C)C)cc2)c1C] | 0.09 μM | NA | 1.9 μM | NA |
| LC-28 | 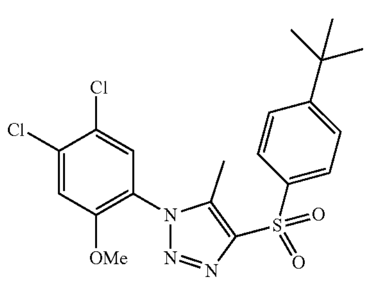 [SMILES: COc1cc(Cl)c(Cl)cc1-n1nnc(S(=O)(=O)c2ccc(C(C)(C)C)cc2)c1C] | 0.87 μM | 0.61 μM | NA | NA |

TABLE 1-continued

| No. | Structure | IC$_{50}$ (binding)* | IC$_{50}$ (antag)* | EC$_{50}$ (agon)* | IC$_{50}$ (cyto)* |
|---|---|---|---|---|---|
| LC-29 | 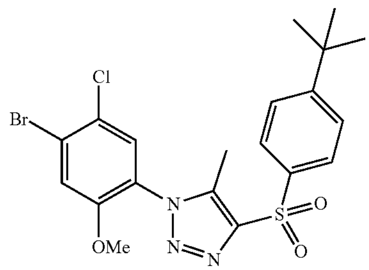 | 0.02 μM | NA | 0.53 μM | NA |
| LC-30 | 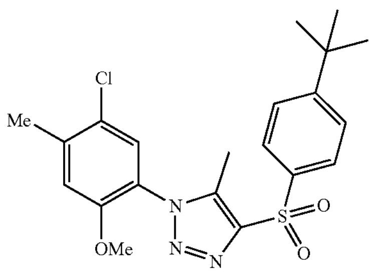 | 0.01 μM | 1.3 μM | NA | NA |
| LC-31 | 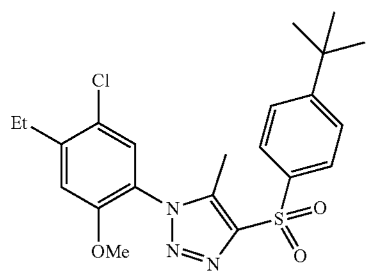 [SMILES: CCc1cc(OC)c(-n2nnc(S(=O)(=O)c3ccc(C(C)(C)C)cc3)c2C)cc1Cl] | 0.11 μM | NA | 0.76 μM | 14.8 μM |
| LC-32 | 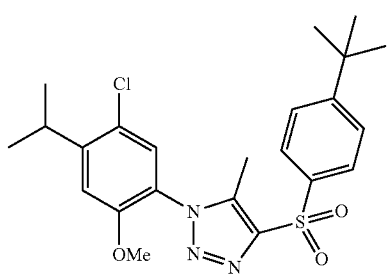 [SMILES: COc1cc(C(C)C)c(Cl)cc1-n1nnc(S(=O)(=O)c2ccc(C(C)(C)C)cc2)c1C] | 2.20 μM | NA | 3.4 μM | NA |
| LC-33 | 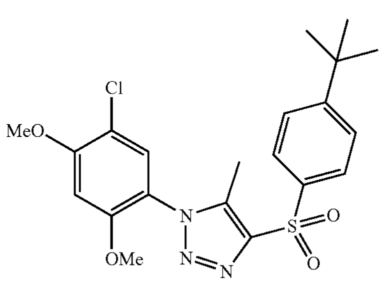 [SMILES: COc1cc(OC)c(-n2nnc(S(=O)(=O)c3ccc(C(C)(C)C)cc3)c2C)cc1Cl] | 0.85 μM | NA | 1.2 μM | NA |

TABLE 1-continued

| No. | Structure | IC$_{50}$ (binding)* | IC$_{50}$ (antag)* | EC$_{50}$ (agon)* | IC$_{50}$ (cyto)* |
|---|---|---|---|---|---|
| LC-34 | 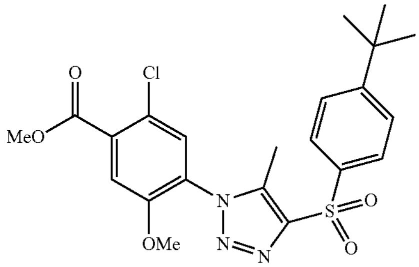 [SMILES: COC(=O)c1cc(OC)c(-n2nnc(S(=O)(=O)c3ccc(C(C)(C)C)cc3)c2C)cc1Cl] | 0.39 µM | NA | 1.6 µM | NA |
| LC-35 | 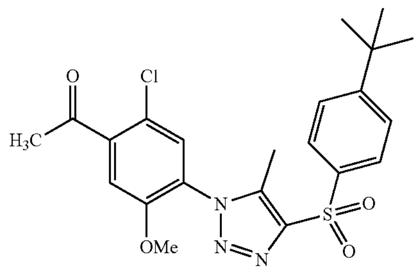 [SMILES: COc1cc(C(C)=O)c(Cl)cc1-n1nnc(S(=O)(=O)c2ccc(C(C)(C)C)cc2)c1C] | 0.01 µM | NA | 1.3 µM | 7.2 µM |
| LC-36 | 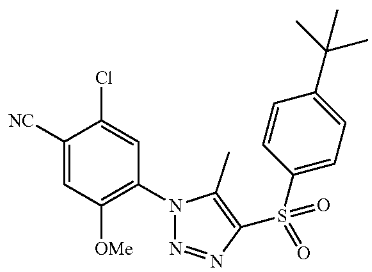 [SMILES: COc1cc(C#N)c(Cl)cc1-n1nnc(S(=O)(=O)c2ccc(C(C)(C)C)cc2)c1C] | 0.01 µM | NA | 2.4 µM | NA |
| LC-37 | 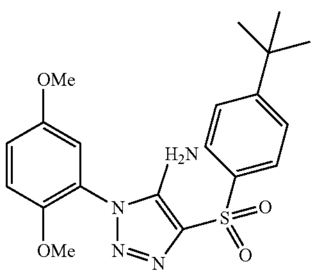 [SMILES: COc1ccc(OC)c(-n2nnc(S(=O)(=O)c3ccc(C(C)(C)C)cc3)c2N)c1] | 0.69 µM | NA | 4.1 µM | NA |
| LC-38 | 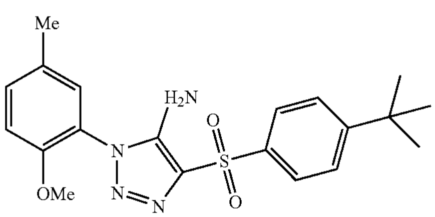 [SMILES: COc1ccc(C)cc1-n1nnc(S(=O)(=O)c2ccc(C(C)(C)C)cc2)c1N] | 0.30 µM | NA | 1.3 µM | NA |
| LC-39 | 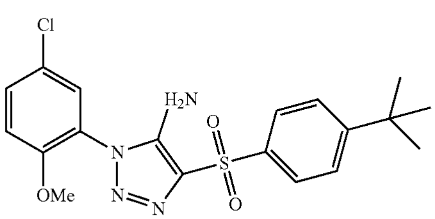 [SMILES: COc1ccc(Cl)cc1-n1nnc(S(=O)(=O)c2ccc(C(C)(C)C)cc2)c1N] | 0.29 µM | NA | 1.0 µM | 16.1 µM |

TABLE 1-continued

| No. | Structure | IC$_{50}$ (binding)* | IC$_{50}$ (antag)* | EC$_{50}$ (agon)* | IC$_{50}$ (cyto)* |
|---|---|---|---|---|---|
| LC-40 | 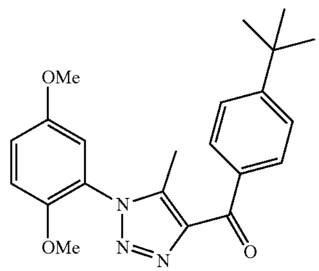 [SMILES: COc1ccc(OC)c(-n2nnc(C(=O)c3ccc(C(C)(C)C)cc3)c2C)c1] | 0.10 μM | 0.52 μM | NA | NA |
| LC-41 | 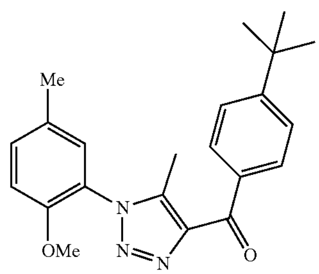 [SMILES: COc1ccc(C)cc1-n1nnc(C(=O)c2ccc(C(C)(C)C)cc2)c1C] | 0.99 μM | 0.67 μM | NA | NA |
| LC-42 | 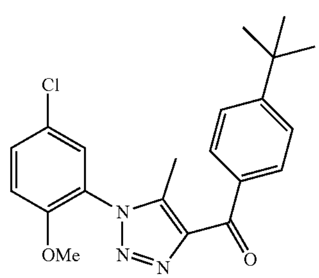 [SMILES: COc1ccc(Cl)cc1-n1nnc(C(=O)c2ccc(C(C)(C)C)cc2)c1C] | 0.06 μM | 0.93 μM | NA | NA |
| LC-43 | 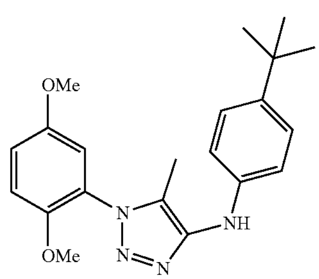 | 8.1 μM | NA | 1.5 μM | NA |
| LC-44 | 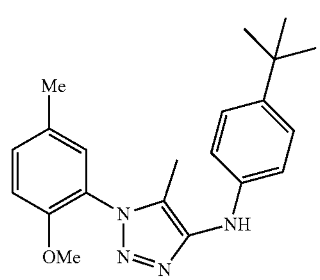 [SMILES: COc1ccc(C)cc1-n1nnc(Nc2ccc(C(C)(C)C)cc2)c1C] | 5.9 μM | NA | 1.2 μM | 22.5 μM |

TABLE 1-continued

| No. | Structure | IC$_{50}$ (binding)* | IC$_{50}$ (antag)* | EC$_{50}$ (agon)* | IC$_{50}$ (cyto)* |
|---|---|---|---|---|---|
| LC-45 | 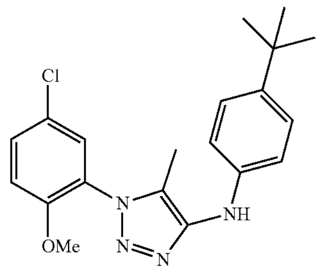 [SMILES: COc1ccc(Cl)cc1-n1nnc(Nc2ccc(C(C)(C)C)cc2)c1C] | 1.7 μM | NA | 1.1 μM | 30.7 μM |
| LC-46 | 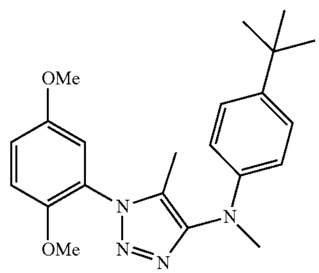 [SMILES: COc1ccc(OC)c(-n2nnc(N(C)c3ccc(C(C)(C)C)cc3)c2C)c1] | 0.28 μM | NA | 0.98 μM | NA |
| LC-47 | 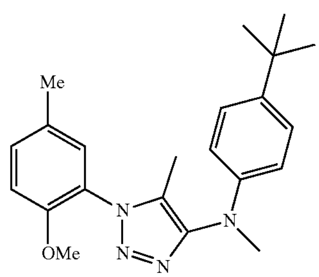 [SMILES: COc1ccc(C)cc1-n1nnc(N(C)c2ccc(C(C)(C)C)cc2)c1C] | 0.91 μM | NA | 0.73 μM | NA |
| LC-48 | 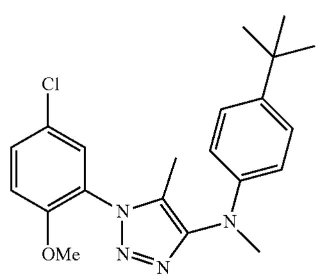 [SMILES: COc1ccc(Cl)cc1-n1nnc(N(C)c2ccc(C(C)(C)C)cc2)c1C] | 0.18 μM | NA | 0.70 μM | 33.8 μM |
| LC-49 | 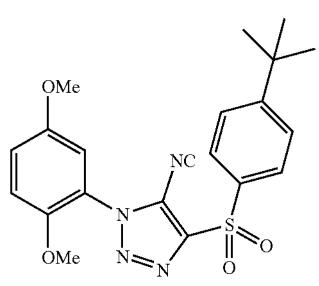 | 0.57 μM | 0.97 μM | NA | NA |

TABLE 1-continued

| No. | Structure | IC$_{50}$ (binding)* | IC$_{50}$ (antag)* | EC$_{50}$ (agon)* | IC$_{50}$ (cyto)* |
| --- | --- | --- | --- | --- | --- |
| LC-50 | 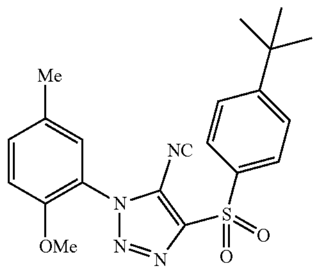 | 0.41 μM | NA | 0.18 μM | NA |
| LC-51 | 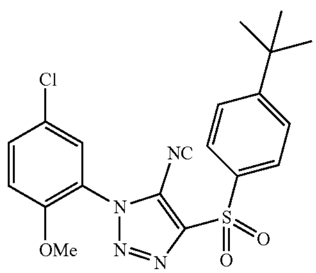 | 0.16 μM | NA | 0.14 μM | NA |
| LC-52 | 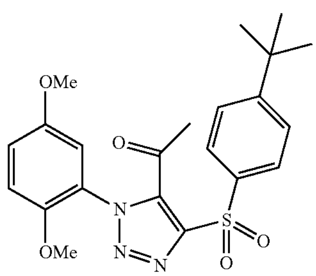 [SMILES: COc1ccc(OC)c(-n2nnc(S(=O)(=O)c3ccc(C(C)(C)C)cc3)c2C(C)=O)c1] | 0.46 μM | 1.4 μM | NA | NA |
| LC-53 | 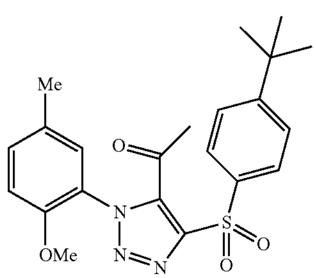 [SMILES: COc1ccc(C)cc1-n1nnc(S(=O)(=O)c2ccc(C(C)(C)C)cc2)c1C(C)=O] | 0.91 μM | 0.55 μM | NA | NA |
| LC-54 | 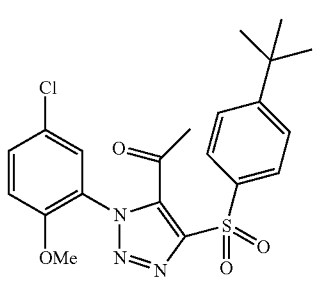 [SMILES: COc1ccc(Cl)cc1-n1nnc(S(=O)(=O)c2ccc(C(C)(C)C)cc2)c1C(C)=O] | 0.66 μM | NA | 0.53 μM | NA |

TABLE 1-continued

| No. | Structure | IC$_{50}$ (binding)* | IC$_{50}$ (antag)* | EC$_{50}$ (agon)* | IC$_{50}$ (cyto)* |
|---|---|---|---|---|---|
| LC-55 | 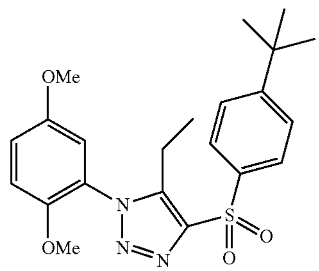 | 0.37 µM | 0.21 µM | NA | NA |
| LC-56 | 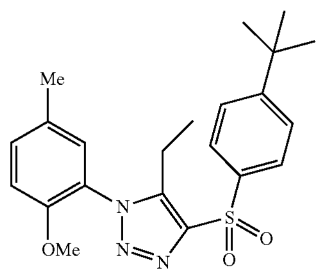 [SMILES: CCc1c(S(=O)(=O)c2ccc(C(C)(C)C)cc2)nnn1-c1cc(C)ccc1OC] | 0.91 µM | 0.66 µM | NA | NA |
| LC-57 | 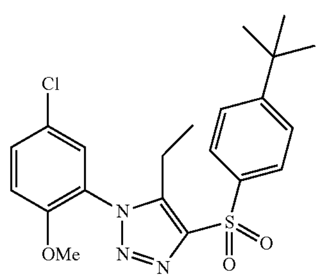 [SMILES: CCc1c(S(=O)(=O)c2ccc(C(C)(C)C)cc2)nnn1-c1cc(Cl)ccc1OC] | 0.84 µM | 0.39 µM | NA | NA |
| LC-58 | 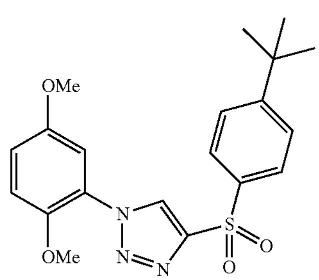 [SMILES: COc1ccc(OC)c(-n2cc(S(=O)(=O)c3ccc(C(C)(C)C)cc3)nn2)c1] | 0.45 µM | 2.4 µM | NA | NA |
| LC-59 | 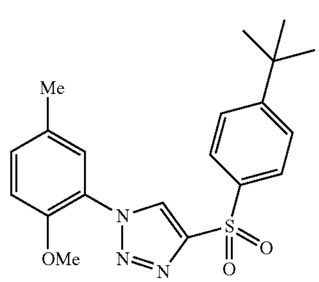 [SMILES: COc1ccc(C)cc1-n1cc(S(=O)(=O)c2ccc(C(C)(C)C)cc2)nn1] | 0.42 µM | 1.1 µM | NA | NA |

TABLE 1-continued

| No. | Structure | IC$_{50}$ (binding)* | IC$_{50}$ (antag)* | EC$_{50}$ (agon)* | IC$_{50}$ (cyto)* |
| --- | --- | --- | --- | --- | --- |
| LC-60 | 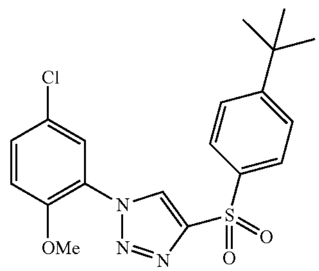 [SMILES: COc1ccc(Cl)cc1-n1cc(S(=O)(=O)c2ccc(C(C)(C)C)cc2)nn1] | 0.54 μM | 2.1 μM | NA | NA |
| LC-61 | 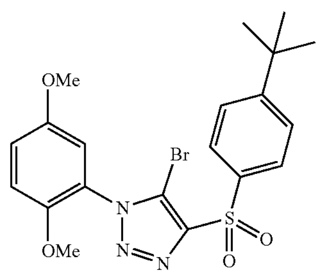 [SMILES: COc1ccc(OC)c(-n2nnc(S(=O)(=O)c3ccc(C(C)(C)C)cc3)c2Br)c1] | 0.06 μM | 0.25 μM | NA | NA |
| LC-62 | 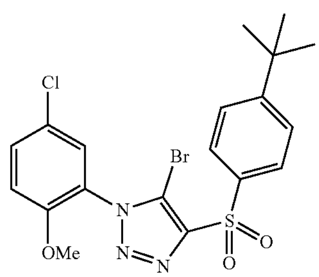 [SMILES: COc1ccc(Cl)cc1-n1nnc(S(=O)(=O)c2ccc(C(C)(C)C)cc2)c1Br] | 0.22 μM | 0.28 μM | NA | NA |
| LC-63 | 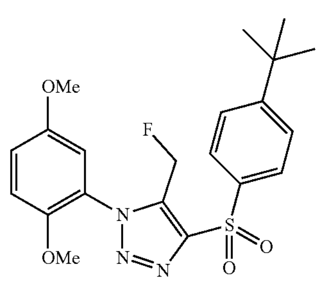 [SMILES: COc1ccc(OC)c(-n2nnc(S(=O)(=O)c3ccc(C(C)(C)C)cc3)c2CF)c1] | 2.0 μM | 0.44 μM | NA | NA |
| LC-64 | 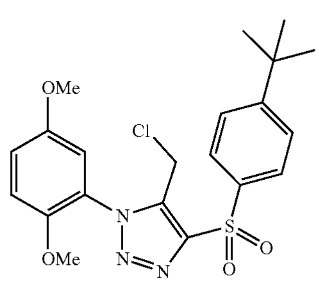 | 1.2 μM | 0.52 μM | NA | 7.9 μM |

TABLE 1-continued

| No. | Structure | IC$_{50}$ (binding)* | IC$_{50}$ (antag)* | EC$_{50}$ (agon)* | IC$_{50}$ (cyto)* |
|---|---|---|---|---|---|
| LC-65 | 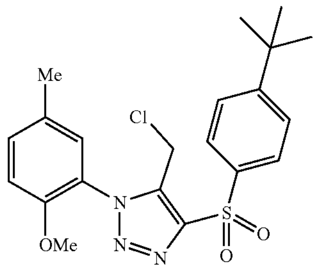 [SMILES: COc1ccc(C)cc1-n1nnc(S(=O)(=O)c2ccc(C(C)(C)C)cc2)c1CCl] | 1.1 µM | NA | 6.1 µM | 7.0 µM |
| LC-66 | 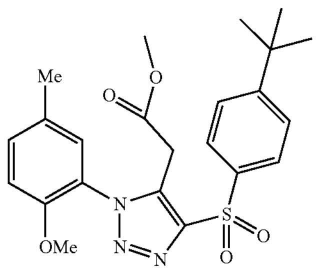 [SMILES: COC(=O)Cc1c(S(=O)(=O)c2ccc(C(C)(C)C)cc2)nnn1-c1cc(C)ccc1OC] | 0.48 µM | 0.26 µM | NA | NA |
| LC-67 | 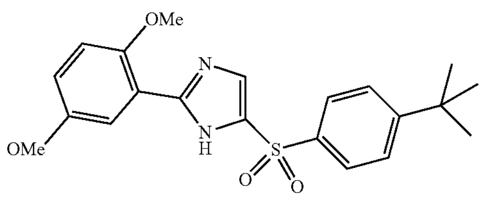 [SMILES: COc1ccc(OC)c(-c2ncc(S(=O)(=O)c3ccc(C(C)(C)C)cc3)[nH]2)c1] | 0.29 µM | NA | 1.7 µM | NA |
| LC-68 | 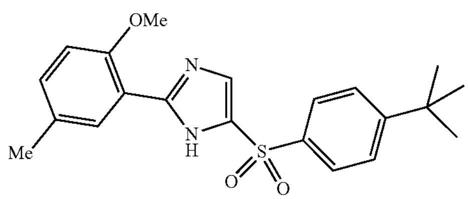 [SMILES: COc1ccc(C)cc1-c1ncc(S(=O)(=O)c2ccc(C(C)(C)C)cc2)[nH]1] | 86.5 nM | NA | 1.5 µM | NA |
| LC-69 | 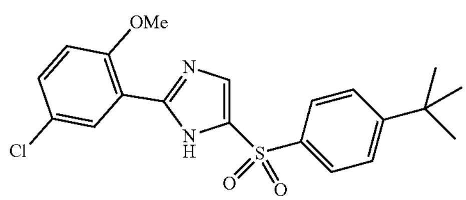 [SMILES: COc1ccc(Cl)cc1-c1ncc(S(=O)(=O)c2ccc(C(C)(C)C)cc2)[nH]1] | 12.3 nM | NA | 0.61 µM | NA |
| LC-70 | 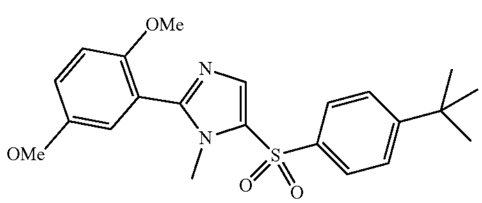 [SMILES: COc1ccc(OC)c(-c2ncc(S(=O)(=O)c3ccc(C(C)(C)C)cc3)n2C)c1] | 0.51 µM | 4.1 µM | NA | 15.3 µM |
| LC-71 | 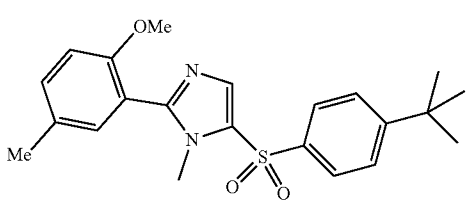 [SMILES: COc1ccc(C)cc1-c1ncc(S(=O)(=O)c2ccc(C(C)(C)C)cc2)n1C] | 0.02 µM | 13.9 µM | NA | 34.9 µM |

TABLE 1-continued

| No. | Structure | IC$_{50}$ (binding)* | IC$_{50}$ (antag)* | EC$_{50}$ (agon)* | IC$_{50}$ (cyto)* |
| --- | --- | --- | --- | --- | --- |
| LC-72 | 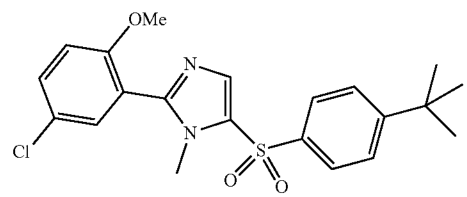 [SMILES: COc1ccc(Cl)cc1-c1ncc(S(=O)(=O)c2ccc(C(C)(C)C)cc2)n1C] | 0.69 μM | 7.6 μM | NA | 30.9 μM |
| LC-73 | 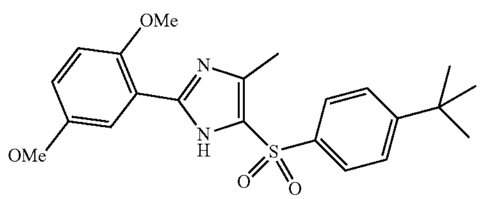 [SMILES: COc1ccc(OC)c(-c2nc(C)c(S(=O)(=O)c3ccc(C(C)(C)C)cc3)[nH]2)c1] | 0.02 μM | 6.6 μM | NA | NA |
| LC-74 | 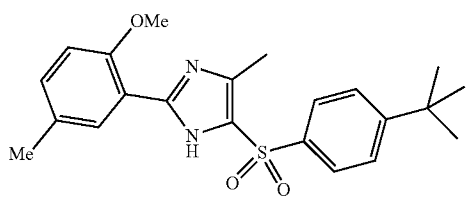 [SMILES: COc1ccc(C)cc1-c1nc(C)c(S(=O)(=O)c2ccc(C(C)(C)C)cc2)[nH]1] | 0.06 μM | 1.7 μM | NA | NA |
| LC-75 | 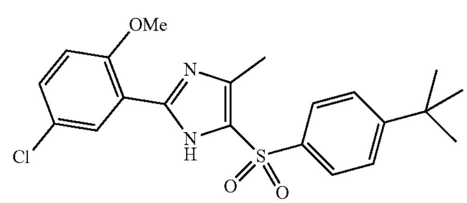 [SMILES: COc1ccc(Cl)cc1-c1nc(C)c(S(=O)(=O)c2ccc(C(C)(C)C)cc2)[nH]1] | 0.12 μM | NA | 0.92 μM | NA |
| LC-76 | 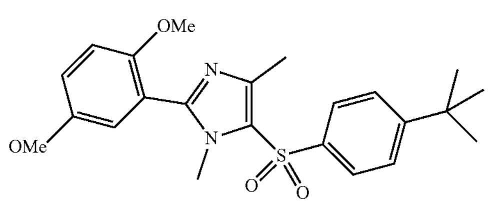 [SMILES: COc1ccc(OC)c(-c2nc(C)c(S(=O)(=O)c3ccc(C(C)(C)C)cc3)n2C)c1] | 0.14 μM | NA | 2.8 μM | NA |
| LC-77 | 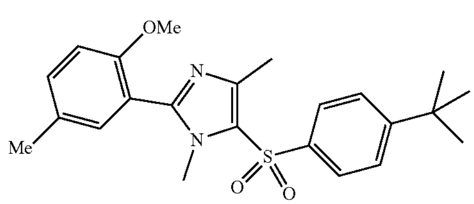 [SMILES: COc1ccc(C)cc1-c1nc(C)c(S(=O)(=O)c2ccc(C(C)(C)C)cc2)n1C] | 0.07 μM | NA | 0.79 μM | NA |
| LC-78 | 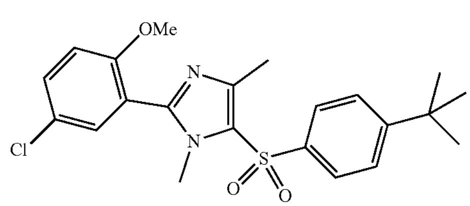 [SMILES: COc1ccc(Cl)cc1-c1nc(C)c(S(=O)(=O)c2ccc(C(C)(C)C)cc2)n1C] | 0.03 μM | NA | 1.4 μM | 24.4 μM |

TABLE 1-continued

| No. | Structure | IC$_{50}$ (binding)* | IC$_{50}$ (antag)* | EC$_{50}$ (agon)* | IC$_{50}$ (cyto)* |
|---|---|---|---|---|---|
| LC-79 | 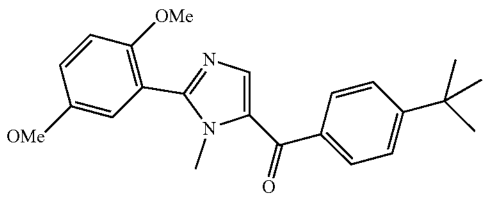 [SMILES: COc1ccc(OC)c(-c2ncc(C(=O)c3ccc(C(C)(C)C)cc3)n2C)c1] | 0.79 μM | 3.1 μM | NA | NA |
| LC-80 | 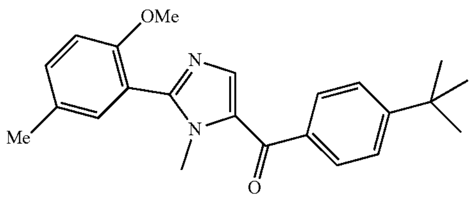 [SMILES: COc1ccc(C)cc1-c1ncc(C(=O)c2ccc(C(C)(C)C)cc2)n1C] | 0.69 μM | NA | 2.4 μM | NA |
| LC-81 | 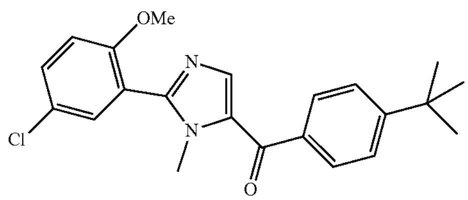 [SMILES: COc1ccc(Cl)cc1-c1ncc(C(=O)c2ccc(C(C)(C)C)cc2)n1C] | 6.4 μM | NA | 1.2 μM | NA |
| LC-82 | 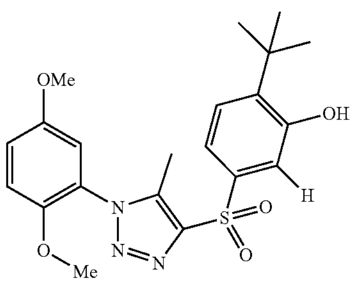 [SMILES: COc1ccc(OC)c(-n2nnc(S(=O)(=O)c3ccc(C(C)(C)C)c(O)c3)c2C)c1] | 0.04 μM | 17.2 μM | NA | 18.5 μM |
| LC-83 | 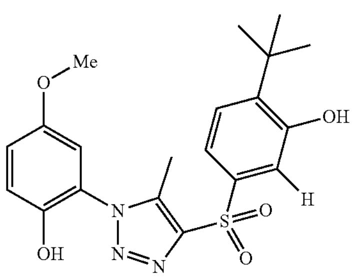 [SMILES: COc1ccc(O)c(-n2nnc(S(=O)(=O)c3ccc(C(C)(C)C)c(O)c3)c2C)c1] | 0.45 μM | NA | 5.0 μM | 16.2 μM |
| LC-84 | 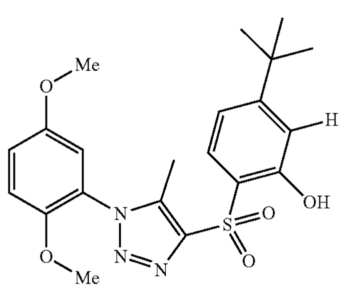 [SMILES: COc1ccc(OC)c(-n2nnc(S(=O)(=O)c3ccc(C(C)(C)C)cc3O)c2C)c1] | 0.03 μM | NA | 3.3 μM | 20.9 μM |

TABLE 1-continued

| No. | Structure | IC$_{50}$ (binding)* | IC$_{50}$ (antag)* | EC$_{50}$ (agon)* | IC$_{50}$ (cyto)* |
|---|---|---|---|---|---|
| LC-85 | 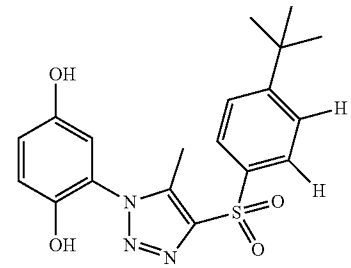 [SMILES: Cc1c(S(=O)(=O)c2ccc(C(C)(C)C)cc2)nnn1-c1cc(O)ccc1O] | 0.59 μM | 3.9 μM | NA | NA |
| LC-86 | 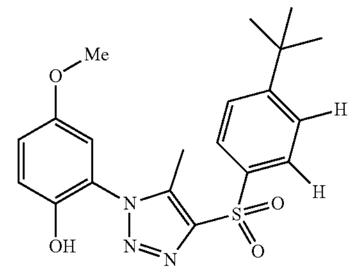 [SMILES: COc1ccc(O)c(-n2nnc(S(=O)(=O)c3ccc(C(C)(C)C)cc3)c2C)c1] | 0.24 μM | 0.18 μM | NA | 26.1 μM |
| LC-87 | 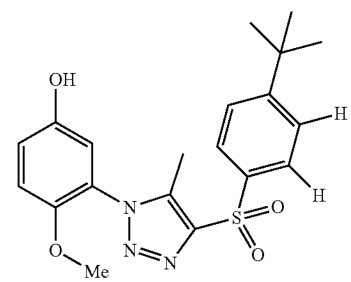 [SMILES: COc1ccc(O)cc1-n1nnc(S(=O)(=O)c2ccc(C(C)(C)C)cc2)c1C] | 0.04 μM | NA | 12.0 μM | NA |
| LC-88 | 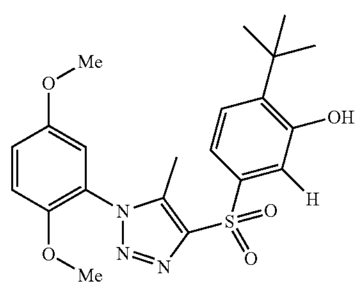 [SMILES: COc1ccc(OC)c(-n2nnc(S(=O)(=O)c3ccc(C(C)(C)C)c(O)c3)c2C)c1] | 0.10 μM | NA | 1.4 μM | 13.0 μM |

*IC$_{50}$ (binding) values were determined using the time-resolved fluorescence resonance transfer (TR-FRET) hPXR competitive binding assay described herein above; IC$_{50}$ (antag) and EC50 (agon) values were determined using the hPXR transactivation assay described herein above; and IC$_{50}$ (cyto) values were determined using the HepG2 cytotoxicity assay described herein above.
**"NA" indicates that the compound was not active in the indicated assay.

TABLE 2

| No. | CAR* | VDR* | GR* | RXRα* | RXRβ* |
|---|---|---|---|---|---|
| LC-1 | NA** | NA | NA | NA | NA |
| LC-8 | NT# | NA | NA | NA | NA |
| LC-18 | NT | NA | NA | NA | NA |
| LC-21 | NT | NA | NA | NA | NA |
| LC-28 | NT | NA | NA | NA | NA |
| LC-30 | NT | NA | NA | NA | NA |
| LC-40 | NT | NA | NA | NA | NA |
| LC-41 | NT | NA | NA | NA | NA |
| LC-42 | NT | NA | NA | NA | NA |
| LC-55 | NT | NA | NA | NA | NA |
| LC-56 | NT | NA | NA | NA | NA |
| LC-57 | NT | NA | NA | NA | NA |
| LC-58 | NT | NA | NA | NA | NA |
| LC-61 | NT | NA | NA | NA | NA |
| LC-62 | NT | NA | NA | NA | NA |
| LC-63 | NT | NA | NA | NA | NA |
| LC-64 | NT | 7.3 μM (Anta) | 5.6 μM (Anta) | 5.8 μM (Anta) | 4.1 μM (Anta) |
| LC-66 | NT | NA | NA | NA | 19.3 μM (Ag†) |
| LC-70 | NT | NA | 20.4 μM (Anta†) | 16.1 μM (Anta) | NA |
| LC-73 | NT | NA | 4.4 μM (Anta) | NA | NA |
| LC-85 | NT | NA | NA | NA | 31.0 μM (Anta) |

TABLE 2-continued

| No. | FXR* | LXRα* | LXRβ* | PPARγ* |
|---|---|---|---|---|
| LC-86 | NT | 24.2 μM (Anta) | 21.4 μM (Anta) | 20.6 μM (Anta) | 17.9 μM (Anta) |
| LC-1 | NA** | NA | NA | NA |
| LC-8 | NA | NA | NA | NA |
| LC-18 | NA | NA | NA | NA |
| LC-21 | NA | NA | NA | NA |
| LC-28 | NA | NA | NA | 14.4 μM (Anta) |
| LC-30 | NA | NA | NA | NA |
| LC-40 | NA | NA | NA | NA |
| LC-41 | NA | NA | NA | NA |
| LC-42 | NA | NA | NA | NA |
| LC-55 | NA | NA | NA | NA |
| LC-56 | NA | NA | NA | NA |
| LC-57 | NA | NA | NA | NA |
| LC-58 | NA | NA | NA | NA |
| LC-61 | NA | NA | NA | 12.8 μM (Anta†) |
| LC-62 | NA | NA | NA | 10.5 μM (Anta) |
| LC-63 | NA | NA | NA | NA |
| LC-64 | 6.3 μM (Anta) | 6.5 μM (Anta) | 4.1 μM (Anta) | 1.5 μM (Anta) |
| LC-66 | NA | NA | NA | NA |
| LC-70 | 14.3 μM (Anta) | NA | NA | 28.3 μM (Anta) |
| LC-73 | NA | NA | NA | NA |
| LC-85 | NA | NA | NA | 12.8 μM (Anta) |
| LC-86 | 21.9 μM (Anta) | 29.8 μM (Anta) | 18.9 μM (Anta) | 11.8 μM (Anta) |

*CAR indicates activity was determined using the hCAR transactivation assay described herein above:
"VDR" indicates activity was determined using the human vitamin Dreceptor transactivation assay described herein above;
"GR" indicates activity was determined using the human glucocorticoid receptor transactivation assay described herein above;
"RXRα" indicates activity was determined using the human retinoid Xreceptor alpha transactivation assay described herein above; and
"RXRβ" indicates activity was determined using the human retinoid X receptor beta transactivation assay described herein above.
*FXR indicates activity was determined using the human farnesoid X receptor transactivation assay described herein above;
"LXRα" indicates activity was determined using the human liver X receptor alpha transactivation assay described herein above;
"LXRβ" indicates activity was determined using the human liver X receptor beta transactivation assay described herein above; and
"PPARγ" indicates activity was determined using the human human peroxisome proliferator-activated receptor transactivation assay described herein above.
**NA indicates that the compound was not active in the indicated assay,
†Ag indicates the compound exhibited agonism in the indicated assay; and
"Anta" indicates that the compound exhibited antagonism in the indicated assay.

5. In Vivo Studies

All animal experiments were conducted in accordance with a protocol approved by the St. Jude Children's Research Hospital Institutional Animal Care and Use Committee. Male C57BL/6 mice (8-15 weeks old, Charles River Laboratories, Wilmington, Mass.) and humanized PXR (hPXR-tg) mice (in house) were housed at 22-23° C. with a 12 h light/dark cycle and free access to food and water in the St. Jude Animal Resources Center certified by the American Association for Accreditation of Laboratory Animal Care. All animals within an experiment were matched for age and body weight.

a. Hydrodynamic Injections, Treatment, and In Vivo Imaging.

In vivo delivery of CYP3A4-luc reporter gene and hPXR gene into mouse liver was performed using the hydrodynamic injection method as described (Liu et al., 1999, Schuetz et al., 2002 and Wang et al., 2013). Briefly, mice were given a rapid (5-10 s) tail vein injection of 25 μg of linearized CYP3A4-luc plasmid DNA with linearized hPXR plasmid DNA in sterile saline in a volume equal to 10% of body weight. Imaging for luciferase activity was performed 2-8 weeks after somatic gene transfer, during which the bioluminescence was stable in the mice. 15 mice were given injections of VivoGlo luciferin (150 mg/kg of body weight, i.p., Promega), anesthetized using 2.5% isoflurane, and imaged 10 min later in the Xenogen IVIS 200 system (Xenogen) to obtain a basal image. The mice were then received 3 rounds of sequential treatment intraperitoneally with vehicle control, 10 mg/kg RIF, or 10 mg/kg RIF plus 10 mg/kg RIF plus 150 mg/kg test compound (4-((4-(tert-butyl)phenyl)sulfonyl)-1-(2,5-dimethoxyphenyl)-5-methyl-1H-1,2,3-triazole) every 24 h for 2 days, respectively, with a washout period of 72-hour between two rounds of treatment. 10 hours after the last treatment of each round, the mice were imaged as described above. Uniform regions of interest were drawn around the liver, and total photon flux was analyzed with Living Image 3.2 software (Xenogen). The induction of CYP3A4-luc reporter activity was calculated using the imaging from the same mouse as follows: induction rate=total photon flux (after treatment)/total photon flux (before treatment).

hPXR-tg mice were generated previously (Xie et al., 2000). Five mice in each group were dosed orally with vehicle control or 10 mg/kg RIF, every 24 h for three days. Eight hours after the last dose, the animals were euthanized by C02 and liver tissues were harvested. A piece of each liver was preserved in RNAlater solution (Invitrogen) at 4° C. for mRNA isolation. The remaining tissue was instantly frozen in liquid nitrogen and stored at −80° C. for total protein extraction. 3-5 mice in each group were dosed orally with vehicle control, 10 mg/kg RIF or 10 mg/kg RIF plus 200 mg/kg test compound (4-((4-(tert-butyl)phenyl)sulfonyl)-1-(2,5-dimethoxyphenyl)-5-methyl-1H-1,2,3-triazole; intraperitoneally) every 24 h for three days. Eight hours after the last dose, the animals were euthanized by C02 and liver tissues were harvested. A piece of each liver was preserved in RNAlater solution (Invitrogen) at 4° C. for mRNA isolation. The remaining tissue was instantly frozen in liquid nitrogen and stored at −80° C. for total protein extraction.

b. Loss of Righting Reflex (LORR) Assay.

Mice were intraperitoneally injected with 250 mg/kg of 2,2,2-tribromoethanol, which is metabolically cleared only via mouse CYP3A11. After the mice lost their righting reflex, they were placed on their backs under a heat lamp. The duration of LORR was measured as the time from the start of LORR to recovery (i.e., when mice could right themselves after being placed on their backs twice within 1 min). A baseline LORR duration was established for each mouse at the administered dose of 2,2,2-tribromoethanol. After a 1-wk washout period, each mouse was administered orally with vehicle, 10 mg/kg RIF or 10 mg/kg RIF plus 200 mg/kg test compound (4-((4-(tert-butyl)phenyl)sulfonyl)-1-(2,5-dimethoxyphenyl)-5-methyl-1H-1,2,3-triazole; intraperitoneally) every 24 h for three days, and the righting reflex experiment was repeated at least 8 h after the last treatment. The paired Student's t-test was used to compare LORR duration between baseline and after treatment. A P value <0.05 was considered to indicate a significant difference between compared groups.

c. LC-MS/MS Analysis.

Midazolam and 1-OH midazolam were from BD Gentest. Midazolam-D4 maleate (internal standard, IS) was from Cerilliant; Paclitaxel and 3'-p-Hydroxypaclitaxel were from Sigma; and 6α-hydroxy Paclitaxel was from Cayman Chemical. 100 μl of reaction medium at each different time point was collected and 200 μl of acetonitrile containing IS was added. This solution was then vigorously mixed for 10 min and centrifuged at 10,000 rpm for 10 min. Calibration and quality control samples were prepared. 5 μl of the samples was injected onto a Waters Acquity UPLC BEH C18 column (2.1×50 mm, 1.7 μm), using a Waters Acquity UPLC system. Chromatographic separation was performed by gradient elution at a constant flow rate of 1 mL/min for 15 min. The gradient consisted of 0.1% formic acid water (mobile phase A) and methanol (mobile phase B). The gradient applied was 0.0 min, 90% A-10% B; 1.35 min, 80% A-20% B; 1.65 min, 5% A-95% B; and 1.95 min, 10% A-90% B. The eluate was directed to an AB SCIEX Triple Quad™ 6500 System mass spectrometer (Applied Biosystems Sciex, Foster, Calif.) equipped with an via electrospray ionization source. Mass transitions of m/z 326 to m/z 291 for MDZ, m/z 342 to m/z 324 for 1-OH MDZ, m/z 342 to m/z 325 for 4-OH MDZ, and m/z 330 to m/z 295 for D4-MDZ were monitored. Ionization was achieved at 3 kV and a temperature of 650° C. Nitrogen was applied as curtain, collision and drying gas at 60 psi. Declustering potentials, entrance potential and collision energy was as follows: 120 V, 12 V and 35 V for MDZ; 70 V, 12 V and 30 V for 1-OH MDZ; and 120 V, 12 V and 37 V for IS.

6. Prophetic Pharmaceutical Composition Examples

"Active ingredient" as used throughout these examples relates to one or more disclosed compounds or products of disclosed methods of making as described hereinbefore, or a pharmaceutically acceptable salt, solvate, or polymorph thereof. The following examples of the formulation of the compounds of the present invention in tablets, suspension, injectables and ointments are prophetic. Typical examples of recipes for the formulation of the invention are as given below.

Various other dosage forms can be applied herein such as a filled gelatin capsule, liquid emulsion/suspension, ointments, suppositories or chewable tablet form employing the disclosed compounds in desired dosage amounts in accordance with the present invention. Various conventional techniques for preparing suitable dosage forms can be used to prepare the prophetic pharmaceutical compositions, such as those disclosed herein and in standard reference texts, for example the British and US Pharmacopoeias, Remington's Pharmaceutical Sciences (Mack Publishing Co.) and Martindale The Extra Pharmacopoeia (London The Pharmaceutical Press), which is hereby incorporated by reference.

a. Pharmaceutical Composition for Oral Administration

A tablet can be prepared as follows:

| Component | Amount |
|---|---|
| Active ingredient | 10 to 500 mg |
| Lactose | 100 mg |
| Crystalline cellulose | 60 mg |
| Magnesium stearate | 5 |
| Starch (e.g. potato starch) | Amount necessary to yield total weight indicated below |
| Total (per capsule) | |

Alternatively, about 100 mg of a disclosed compound, 50 mg of lactose (monohydrate), 50 mg of maize starch (native), 10 mg of polyvinylpyrrolidone (PVP 25) (e.g. from BASF, Ludwigshafen, Germany) and 2 mg of magnesium stearate are used per tablet. The mixture of active component, lactose and starch is granulated with a 5% solution (m/m) of the PVP in water. After drying, the granules are mixed with magnesium stearate for 5 min. This mixture is molded using a customary tablet press (e.g. tablet format: diameter 8 mm, curvature radius 12 mm). The molding force applied is typically about 15 kN.

Alternatively, a disclosed compound can be administered in a suspension formulated for oral use. For example, about 100-5000 mg of the desired disclosed compound, 1000 mg of ethanol (96%), 400 mg of xanthan gum, and 99 g of water are combined with stirring. A single dose of about 10-500 mg of the desired disclosed compound according can be provided by 10 ml of oral suspension.

In these Examples, active ingredient can be replaced with the same amount of any of the compounds according to the present invention, in particular by the same amount of any of the exemplified compounds. In some circumstances it may be desirable to use a capsule, e.g. a filled gelatin capsule, instead of a tablet form. The choice of tablet or capsule will depend, in part, upon physicochemical characteristics of the particular disclosed compound used.

Examples of alternative useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. These alternative carriers can be substituted for those given above as required for desired dissolution, absorption, and manufacturing characteristics.

The amount of a disclosed compound per tablet for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

b. Pharmaceutical Composition for Injectable Use

A parenteral composition can be prepared as follows:

| Component | Amount |
|---|---|
| Active ingredient | 10 to 500 mg |
| Sodium carbonate | 560 mg* |
| Sodium hydroxide | 80 mg* |
| Distilled, sterile water | Quantity sufficient to prepare total volume indicated below. |
| Total (per capsule) | 10 ml per ampule |

*Amount adjusted as required to maintain physiological pH in the context of the amount of active ingredient, and form of active ingredient, e.g. a particular salt form of the active ingredient.

Alternatively, a pharmaceutical composition for intravenous injection can be used, with composition comprising about 100-5000 mg of a disclosed compound, 15 g polyethylenglycol 400 and 250 g water in saline with optionally up to about 15% Cremophor EL, and optionally up to 15% ethyl alcohol, and optionally up to 2 equivalents of a pharmaceutically suitable acid such as citric acid or hydrochloric acid are used. The preparation of such an injectable composition can be accomplished as follows: The disclosed compound and the polyethylenglycol 400 are dissolved in the water with stirring. The solution is sterile filtered (pore size 0.22 μm) and filled into heat sterilized infusion bottles under aseptic conditions. The infusion bottles are sealed with rubber seals.

In a further example, a pharmaceutical composition for intravenous injection can be used, with composition comprising about 10-500 mg of a disclosed compound, standard saline solution, optionally with up to 15% by weight of Cremophor EL, and optionally up to 15% by weight of ethyl alcohol, and optionally up to 2 equivalents of a pharmaceutically suitable acid such as citric acid or hydrochloric acid. Preparation can be accomplished as follows: a desired disclosed compound is dissolved in the saline solution with stirring. Optionally Cremophor EL, ethyl alcohol or acid are added. The solution is sterile filtered (pore size 0.22 μm) and filled into heat sterilized infusion bottles under aseptic conditions. The infusion bottles are sealed with rubber seals.

In this Example, active ingredient can be replaced with the same amount of any of the compounds according to the present invention, in particular by the same amount of any of the exemplified compounds.

The amount of a disclosed compound per ampule for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

Carriers suitable for parenteral preparations are, for example, water, physiological saline solution, etc. which can be used with tris(hydroxymethyl)aminomethane, sodium carbonate, sodium hydroxide or the like serving as a solubilizer or pH adjusting agent. The parenteral preparations contain preferably 50 to 1000 mg of a disclosed compound per dosage unit.

F. References

Pokhodylo, N. T.; Matiychuk, V. S.; Obushak, M. D. (Arylsulfonyl)acetones and -acetonitriles: new activated methylenic building blocks for synthesis of 1,2,3-triazoles. *Synthesis* 2009, 2321-2323.

Chen, J.; Lei, G.; Xu, W.; Jin, X.; Shao, M.; Tang, Y. Synthesis and crystal structure of isomerized butadiene (dicarbonyl)(ethoxyarylcarbene)iron complexes. *J. Organomet. Chem.* 1985, 286, 55-67.

Slocum, D. W.; Reece, T. L.; Sandlin, R. D.; Reinscheld, T. K.; Whitley, P. E. Metalations utilizing aryllithiums; ortho-functionalization of p-bromoanisole (pBrA). *Tetrahedron Lett.* 2009, 50, 1593-1595.

Bennett, M. J.; Betancort, J. M.; Boloor, A.; Kaldor, S. W.; Stafford, J. A.; Veal, J. M. Heterocyclic compounds as bromodomain inhibitors and their preparation. WO2015058160A1, 2015.

McKean, D. R.; Parrinello, G.; Renaldo, A. F.; Stille, J. K. Synthesis of functionalized styrenes via palladium-catalyzed coupling of aryl bromides with vinyl tin reagents. *J. Org. Chem.* 1987, 52, 422-4.

Beattie, D.; Beer, D.; Bradley, M. E.; Bruce, I.; Charlton, S. J.; Cuenoud, B. M.; Fairhurst, R. A.; Farr, D.; Fozard, J. R.; Janus, D.; Rosethorne, E. M.; Sandham, D. A.; Sykes, D. A.; Trifilieff, A.; Turner, K. L.; Wissler, E. An investigation into the structure-activity relationships associated with the systematic modification of the 12-adrenoceptor agonist indacaterol. *Bioorg. Med. Chem. Lett.* 2012, 22, 6280-6285.

Aalten, H. L.; Van Koten, G.; Grove, D. M.; Kuilman, T.; Piekstra, O. G.; Hulshof, L. A.; Sheldon, R. A. The copper catalyzed reaction of sodium methoxide with aryl bromides. A mechanistic study leading to a facile synthesis of anisole derivatives. *Tetrahedron* 1989, 45, 5565-78.

Rao, B. N.; Krishnakumari, B.; Pardhasaradhi, M. Dichlorobis(triphenylphosphine)palladium-catalyzed carbalkoxylation of aryl bromides. *J. Mol. Catal.* 1989, 50, L27-L29.

Maligres, P. E.; Waters, M. S.; Fleitz, F.; Askin, D. A highly catalytic robust palladium-catalyzed cyanation of aryl bromides. *Tetrahedron Lett.* 1999, 40, 8193-8195.

Ortiz-Marciales, M.; Tirado, L. M.; Colon, R.; Ufret, M. L.; Figueroa, R.; Lebron, M.; DeJesus, M.; Martinez, J.; Malave, T. N-tert-Butyldimethylsilyl imines as intermediates for the synthesis of amines and ketones. *Synth. Commun.* 1998, 28, 4067-4075.

Furuya, T.; Kaiser, H. M.; Ritter, T. Palladium-mediated fluorination of arylboronic acids. *Angew. Chem., Int. Ed.* 2008, 47, 5993-5996, S5993/1-S5993/78.

Hodgson, H. H.; Ratcliffe, J. Influence of water on the coupling power of diazotized amines and on diazo group elimination in aqueous ethanol-sulfuric acid media. *J. Chem. Soc.* 1949, S233-4.

Doyle, M. P.; Siegfried, B.; Dellaria, J. F., Jr. Alkyl nitrite-metal halide deamination reactions. 2. Substitutive deamination of arylamines by alkyl nitrites and copper(II) halides. A direct and remarkably efficient conversion of arylamines to aryl halides. *J. Org. Chem.* 1977, 42, 2426-31.

Rosenmund, K. W.; Struck, E. Halogen attached to a ring carbon atom and its replacement by other substituents. I. Replacement of the halogen by the carboxyl group. *Ber. Dtsch. Chem. Ges. B* 1919, 52B, 1749-56.

Mo, J.; Hyder, Z.; Xu, L.; Xiao, J. Ionic liquid-promoted regioselective catalysis by palladium. *Proc.—Electrochem. Soc.* 2006, 2004-24, 564-571.

Nahm, S.; Weinreb, S. M. N-Methoxy-N-methylamides as effective acylating agents. *Tetrahedron Lett.* 1981, 22, 3815-18.

Korwar, S.; Nguyen, T.; Ellis, K. C. Preparation and evaluation of deconstruction analogues of 7-deoxykalafungin as AKT kinase inhibitors. *Bioorg. Med. Chem. Lett.* 2014, 24, 271-274.

Poss, M. A.; Tortolani, D. R.; Dodd, D. S.; Mussari, C. P.; Tokarski, J. S.; Gavai, A. V.; Zhao, Y.; DeLucca, G. V.; O'Malley, D.; Norris, D. J.; Gill, P.; Quesnelle, C. A.; Han, W.-C. Preparation of carbazole compounds useful as bromodomain inhibitors. WO2014134232A1, 2014.

Hartwig, J. F.; Kawatsura, M.; Hauck, S. I.; Shaughnessy, K. H.; Alcazar-Roman, L. M. Transition metal-catalyzed process for preparing arylamines. U.S. Pat. No. 6,100,398A, 2000.

Chakrabarty, M.; Batabyal, A. An expedient synthesis of 5,11-dimethylindolo[3,2-b]carbazole, a potent ligand and the receptor for TCDD. *Synth. Commun.* 1996, 26, 3015-3023.

Peng, Y. Cu(I)-catalyzed coupling of arylsulfinic salts with aryl bromides. *J. Chem. Res.* 2014, 38, 447-449.

O'Connell, J. F.; Parquette, J.; Yelle, W. E.; Wang, W.; Rapoport, H. Convenient synthesis of methyl 1-methyl-2,4-dibromo-5-imidazolecarboxylate. *Synthesis* 1988, 767-71.

Sutherland, H. S.; Blaser, A.; Kmentova, I.; Franzblau, S. G.; Wan, B.; Wang, Y.; Ma, Z.; Palmer, B. D.; Denny, W. A.; Thompson, A. M. Synthesis and Structure-activity Relationships of Antitubercular 2-Nitroimidazooxazines Bearing Heterocyclic Side Chains. *J. Med. Chem.* 2010, 53, 855-866.

Recnik, L.-M.; Abd El Hameid, M.; Haider, M.; Schnuerch, M.; Mihovilovic, M. D. Selective sequential cross-coupling reactions on imidazole towards neurodazine and analogues. *Synthesis* 2013, 45, 1387-1405.

Kruse, L. I. Synthesis of 4-substituted indoles from o-nitrotoluenes. *Heterocycles* 1981, 16, 1119-24.

Shaginian, A.; Whitby, L. R.; Hong, S.; Hwang, I.; Farooqi, B.; Searcey, M.; Chen, J.; Vogt, P. K.; Boger, D. L. Design, Synthesis, and Evaluation of an α-Helix Mimetic Library Targeting Protein-Protein Interactions. *J. Am. Chem. Soc.* 2009, 131, 5564-5572.

Ikemoto, N.; Liu, J.; Brands, K. M. J.; McNamara, J. M.; Reider, P. J. Practical routes to the triarylsulfonyl chloride intermediate of a β3 adrenergic receptor agonist. *Tetrahedron* 2003, 59, 1317-1325.

Bouhlel, A.; Curti, C.; Dumetre, A.; Laget, M.; Crozet, M. D.; Azas, N.; Vanelle, P. Synthesis and evaluation of original amidoximes as antileishmanial agents. *Bioorg. Med. Chem.* 2010, 18, 7310-7320.

Neubert, A.; Barnes, D.; Kwak, Y.-S.; Nakajima, K.; Bebemitz, G. R.; Coppola, G. M.; Kirman, L.; Serrano-Wu, M. H.; Stams, T.; Topiol, S. W.; Vedananda, T. R.; Wareing, J. R. Organic arylthiadiazolidinetrione compounds as protein tyrosine phosphatase inhibitors and their preparation, pharmaceutical compositions and use in the treatment of diseases. WO2007115058A2, 2007.

El-Ayache, N. C.; Li, S.-H.; Warnock, M.; Lawrence, D. A.; Emal, C. D. Novel bis-arylsulfonamides and aryl sulfonimides as inactivators of plasminogen activator inhibitor-1 (PAI-1). *Bioorg. Med. Chem. Lett.* 2010, 20, 966-970.

Ito, Y.; Ishida, K.; Okada, S.; Murakami, M. The absolute stereochemistry of anachelins, siderophores from the cyanobacterium *Anabaena cylindrica*. *Tetrahedron* 2004, 60, 9075-9080.

Shrestha, J. P.; Fosso, M. Y.; Bearss, J.; Chang, C.-W. T. Synthesis and anticancer structure activity relationship investigation of cationic anthraquinone analogs. *Eur. J. Med. Chem.* 2014, 77, 96-102.

Abeywardane, A.; Farmer, B.; Farrow, N. A.; Gao, D. A.; Heim-Riether, A.; Keenan, L. L. S.; Mugge, I. A.; Taylor, S. J.; Xiong, Z.; Yu, Y.; Zhang, Q. Preparation of heteroaryl substituted indole compounds useful as MMP-13 inhibitors. WO2010045188A1, 2010.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for modulating pregnane X receptor activity in a mammal comprising the step of administering to the mammal a therapeutically effective amount of at least one compound having a structure represented by a formula:

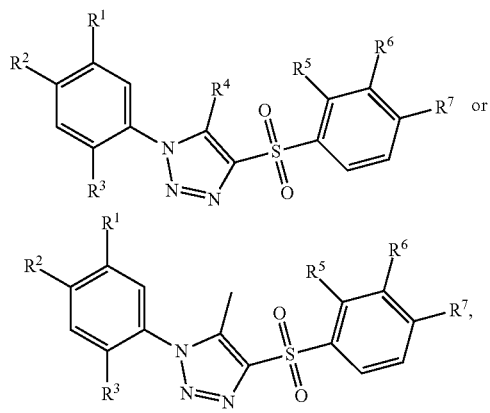

wherein $R^1$ is hydroxy, halogen, C1-C6 alkyl, C1-C6 alkoxy, and —(C1-C6)-OH; wherein $R^2$ is hydrogen, halogen, cyano, C1-C6 alkyl, C1-C6 alkoxy, C1-C6 monohaloalkyl, C1-C6 polyhaloalkyl, —CO$_2$H, —(C=O)H, —(C=O)-(C1-C6 alkyl), —(C=O)—O (C1-C6 alkyl); wherein $R^3$ is hydrogen, hydroxy, halogen, C1-C6 alkyl, C1-C6 alkoxy, and —(C1-C6)-OH; and wherein $R^4$ is methyl; or wherein $R^1$ is hydroxy, halogen, C1-C6 alkyl, C1-C6 alkoxy, and —(C1-C6)-OH; wherein $R^2$ is halogen, cyano, C1-C6 alkyl, C1-C6 alkoxy, C1-C6 monohaloalkyl, C1-C6 polyhaloalkyl, —CO$_2$H, —(C=O)H, —(C=O)-(C1-C6 alkyl), —(C=O)—O(C1-C6 alkyl); wherein $R^3$ is hydroxy, halogen, C1-C6 alkyl, C1-C6 alkoxy, and —(C1-C6)-OH; and wherein $R^4$ is hydrogen, cyano, halogen, C1-C6 alkyl, C1-C6 monohaloalkyl, C1-C6 polyhaloalkyl, —(C=O)-(C1-C6 alkyl), —(C=O)—O(C1-C6 alkyl), —(C1-C6 alkyl)-(C=O)-(C1-C6 alkyl), —(C1-C6 alkyl)-(C=O)—O (C1-C6 alkyl), Ar$^1$, or Cy$^1$;

wherein Ar$^1$ is monocyclic aryl or monocyclic heteroaryl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl;

wherein Cy$^1$ is C3-C8 cycloalkyl or C2-C7 heterocloalkyl substituted with 0, 1, 2, or 3 groups selected from halogen, hydroxy, cyano, amino, C1-C3 alkyl, C1-C3 hydroxyalkyl, C1-C3 monohaloalkyl, or C1-C3 polyhaloalkyl; and wherein $R^5$ is hydrogen, halogen, hydroxy, or C1-C3 alkyl;

wherein $R^6$ is hydrogen, halogen, hydroxy, or C1-C3 alkyl; and wherein $R^7$ is C1-C6 alkyl;

or a pharmaceutically acceptable salt thereof.

2. The method of claim 1, wherein the compound is:

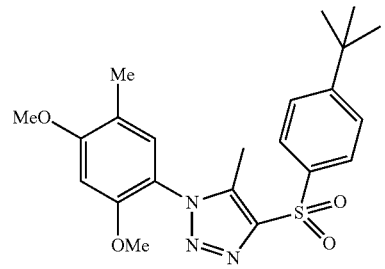

3. The method of claim 1, wherein the compound is:

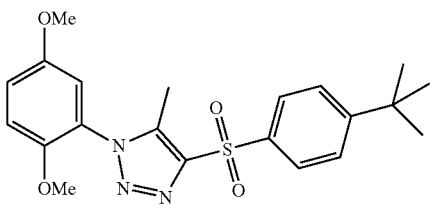

4. The method of claim 1, wherein the mammal is a human.

5. The method of claim 1, wherein $R^1$ is alkoxy and $R^3$ is alkoxy.

6. The method of claim 1, wherein $R^3$ is methoxy.

7. The method of claim 1, wherein $R^4$ is methyl.

8. The method of claim 1, wherein $R^7$ is tert-butyl.

9. The method of claim 1, wherein $R^1$ is hydroxy, halogen, methyl, ethyl, methoxy, or ethoxy; wherein $R^2$ is fluoro or methyl; wherein $R^3$ is hydroxy, halogen, methyl, ethyl, methoxy, or ethoxy; wherein $R^4$ is fluoro, chloro, bromo, cyano, methyl, ethyl, propyl, isopropyl, —CH$_2$F, —CH$_2$Cl, —(C=O)CH$_3$, or —CH$_2$(C=O)OCH$_3$, wherein $R^5$ is hydrogen, hydroxy, or methyl; wherein $R^6$ is hydrogen, hydroxy, or methyl; and wherein $R^7$ is propyl, isopropyl, n-butyl, tert-butyl, or sec-butyl.

10. The method of claim 1, wherein the compound has a structure represented by formula:

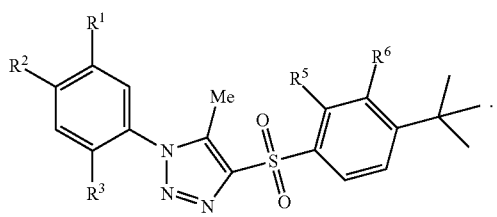

11. The method of claim 1, wherein the compound has a structure represented by formula:

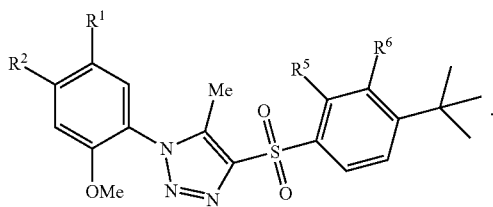

12. The method of claim 1, wherein the compound is selected from:

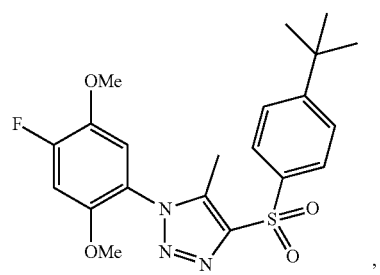

,

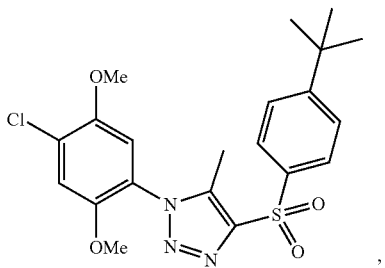

,

-continued

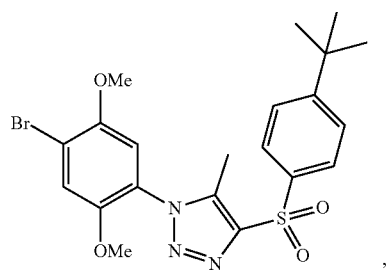

,

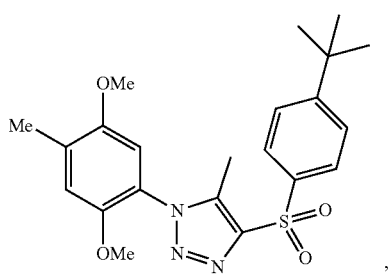

,

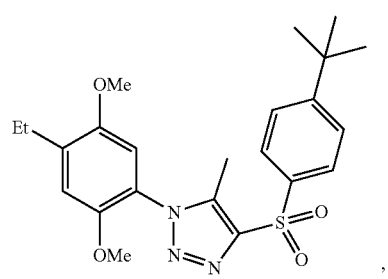

,

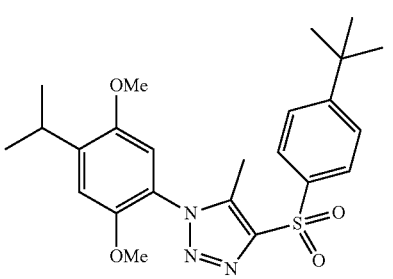

,

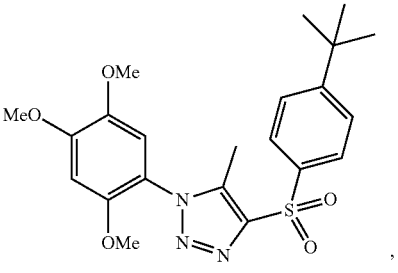

,

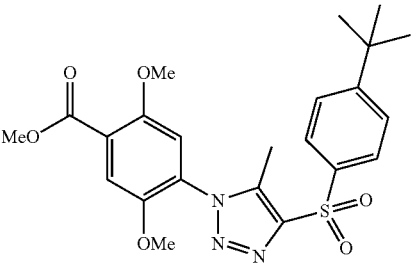

,

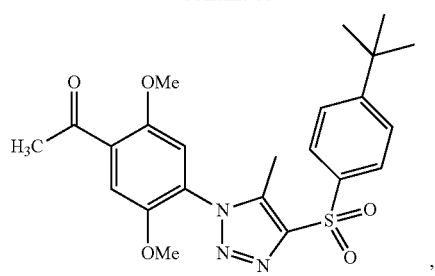
,
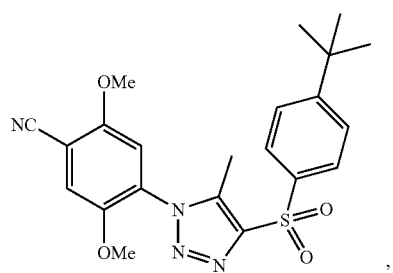
,
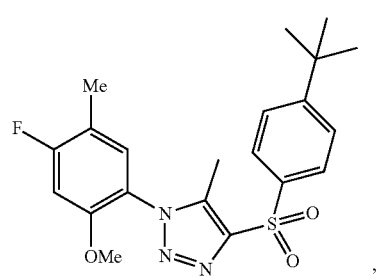
,
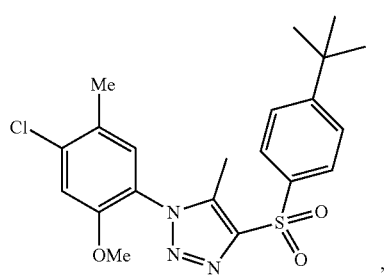
,
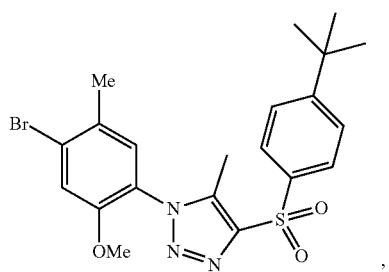
,
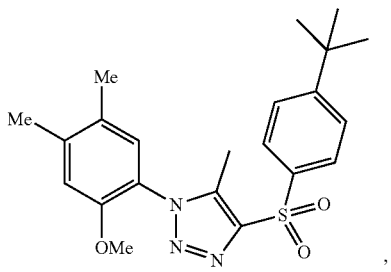
,
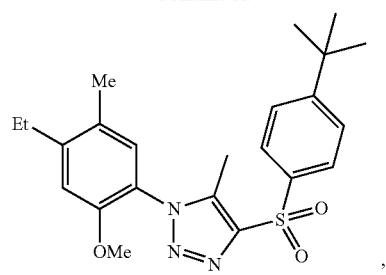
,
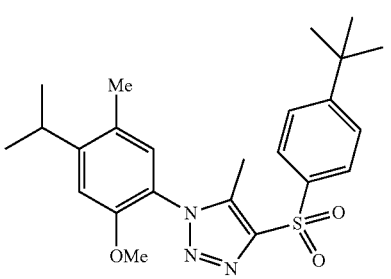
,
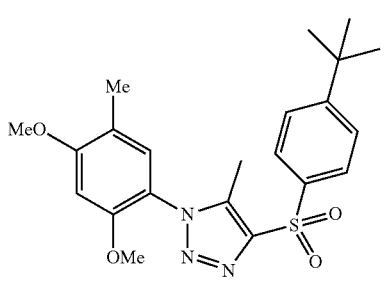
,
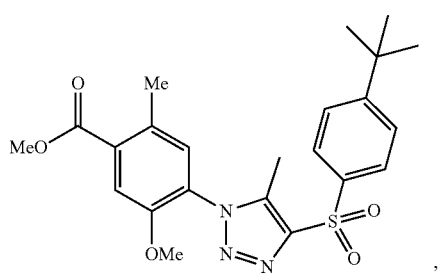
,
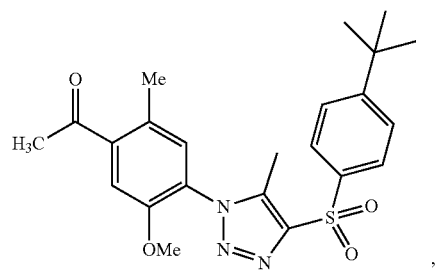
,
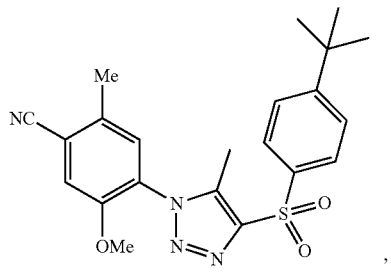
,

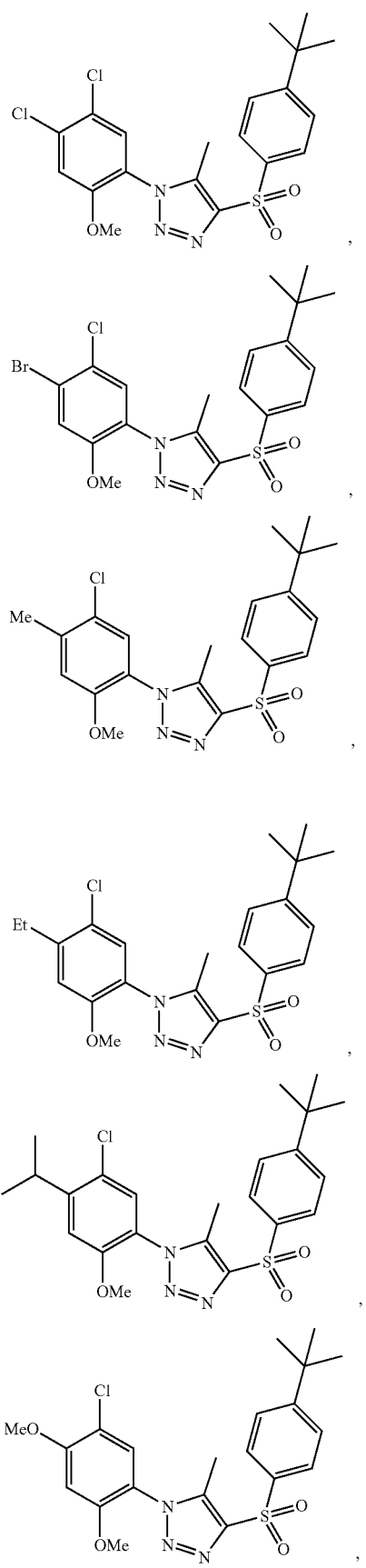
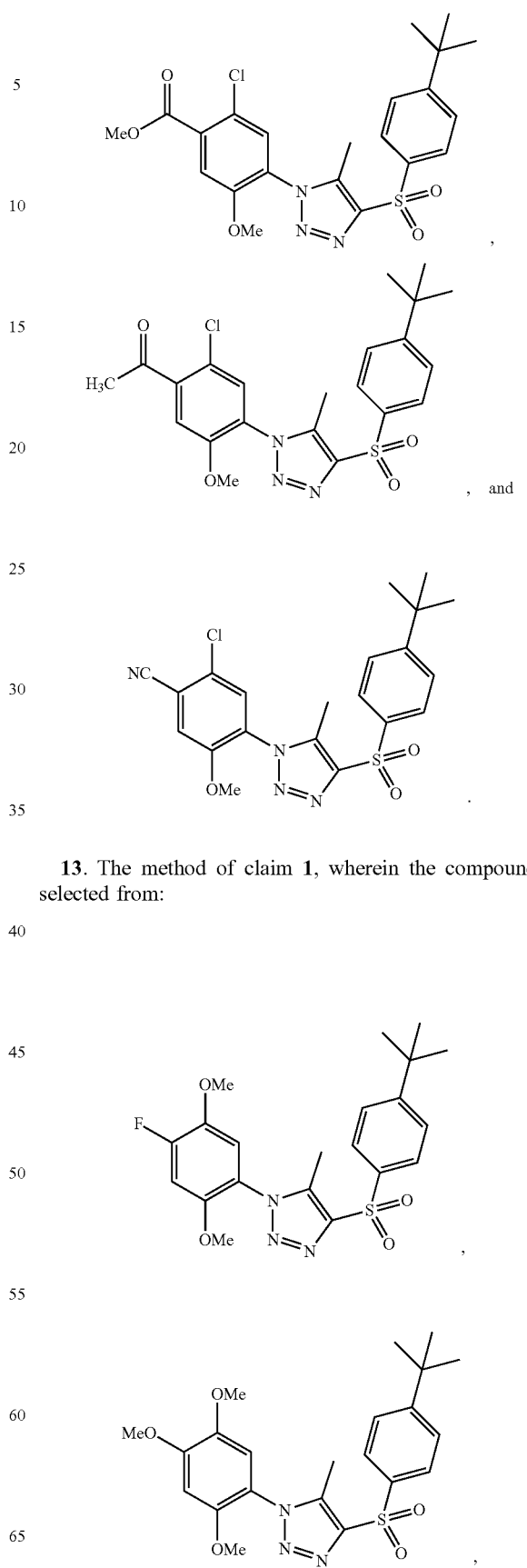
13. The method of claim 1, wherein the compound is selected from:

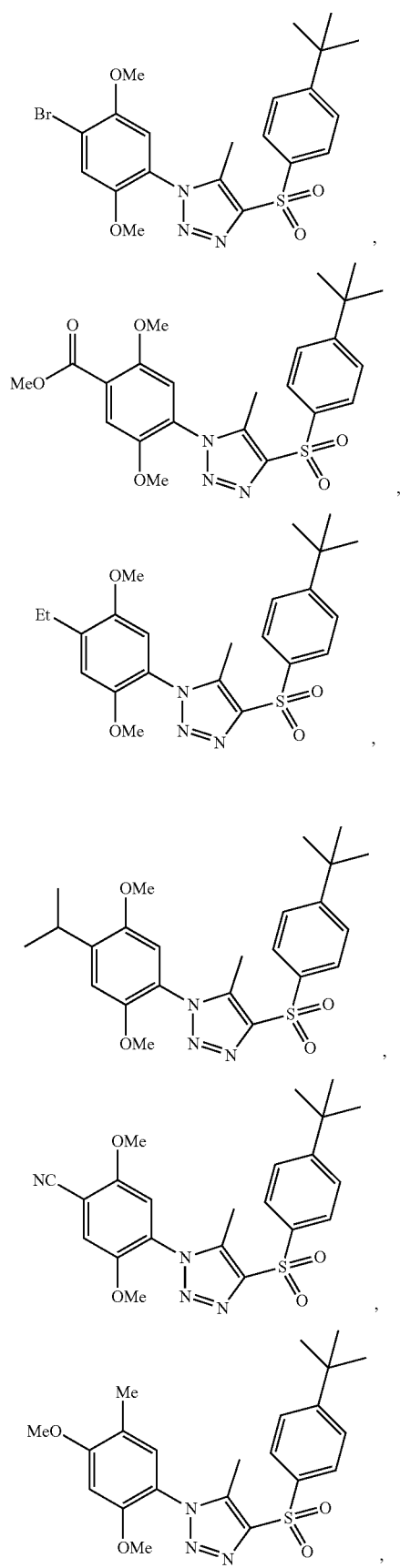
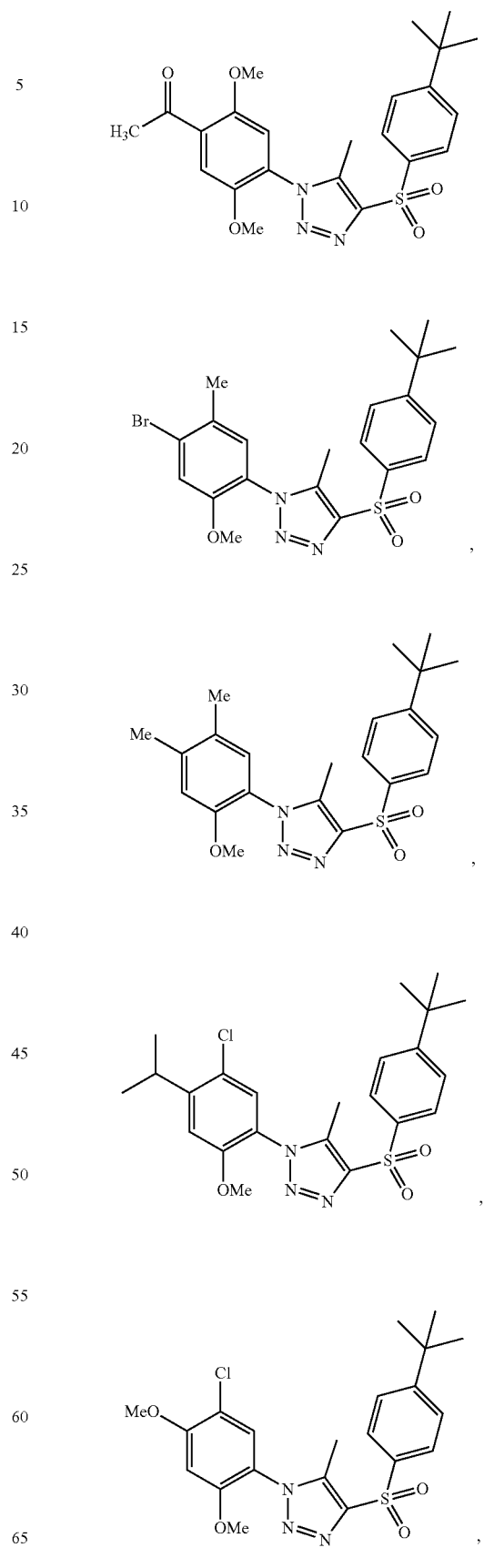

-continued
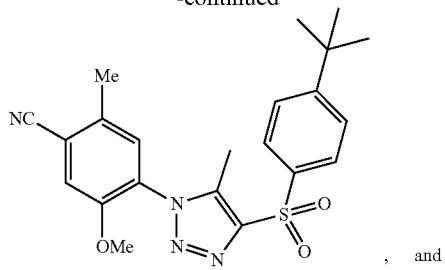
, and
14. The method of claim 1, wherein the compound is:
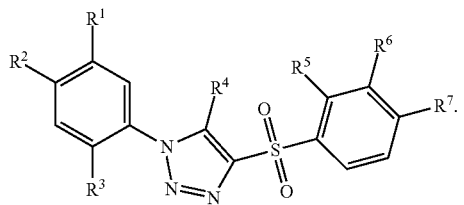
15. The method of claim 1, wherein the compound is:
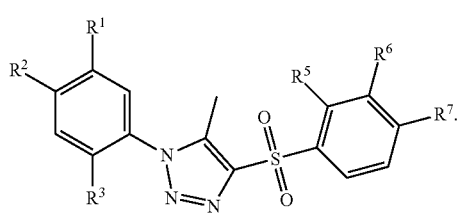
* * * * *